US012409149B2

(12) United States Patent
Niemelä

(10) Patent No.: US 12,409,149 B2
(45) Date of Patent: Sep. 9, 2025

(54) METHODS OF TARGETED DELIVERY TO A HOST USING A CARRIER

(71) Applicant: FINNCURE OY, Espoo (FI)

(72) Inventor: Erik Johan Niemelä, Helsinki (FI)

(73) Assignee: FINNCURE OY, Espoo (FI)

(*) Notice: Subject to any disclaimer, the term of this patent is extended or adjusted under 35 U.S.C. 154(b) by 0 days.

(21) Appl. No.: 19/007,447

(22) Filed: Dec. 31, 2024

(65) Prior Publication Data

US 2025/0213498 A1 Jul. 3, 2025

Related U.S. Application Data

(63) Continuation of application No. 18/544,302, filed on Dec. 18, 2023, now Pat. No. 12,194,157, which is a continuation-in-part of application No. 18/152,930, filed on Jan. 11, 2023, now Pat. No. 12,144,898, which is a continuation of application No. 17/684,341, filed on Mar. 1, 2022, now Pat. No. 11,564,892, which is a continuation-in-part of application No. PCT/FI2021/050259, filed on Apr. 9, 2021.

(60) Provisional application No. 63/433,755, filed on Dec. 19, 2022.

(30) Foreign Application Priority Data

Apr. 9, 2020 (FI) ..................................... 20205382
Feb. 19, 2021 (FI) ..................................... 20215182

(51) Int. Cl.

| | |
|---|---|
| ***A61K 31/7105*** | (2006.01) |
| ***A61K 9/00*** | (2006.01) |
| ***A61K 9/16*** | (2006.01) |
| ***A61K 9/50*** | (2006.01) |
| ***A61K 9/51*** | (2006.01) |
| ***A61K 31/56*** | (2006.01) |
| ***A61K 31/711*** | (2006.01) |
| ***A61K 33/30*** | (2006.01) |
| ***A61K 39/00*** | (2006.01) |
| ***A61K 39/145*** | (2006.01) |
| ***A61K 39/215*** | (2006.01) |
| ***A61K 47/62*** | (2017.01) |
| ***A61K 47/69*** | (2017.01) |
| ***C07K 14/08*** | (2006.01) |
| ***C07K 17/00*** | (2006.01) |
| ***C07K 17/02*** | (2006.01) |
| ***C07K 17/14*** | (2006.01) |

(52) U.S. Cl.

CPC ............ *A61K 9/5184* (2013.01); *A61K 9/007* (2013.01); *A61K 9/167* (2013.01); *A61K 9/5078* (2013.01); *A61K 9/5089* (2013.01); *A61K 9/51* (2013.01); *A61K 9/5192* (2013.01); *A61K 31/56* (2013.01); *A61K 31/7105* (2013.01); *A61K 31/711* (2013.01); *A61K 33/30* (2013.01); *A61K 39/145* (2013.01); *A61K 39/215* (2013.01); *A61K 47/62* (2017.08); *A61K 47/6929* (2017.08); *C07K 14/08* (2013.01); *C07K 17/00* (2013.01); *C07K 17/02* (2013.01); *C07K 17/14* (2013.01); *A61K 2039/544* (2013.01); *A61K 2039/6093* (2013.01)

(58) Field of Classification Search

CPC ...... A61K 2039/544; A61K 2039/6093; A61K 47/62; A61K 47/6929; A61K 9/167

See application file for complete search history.

(56) References Cited

U.S. PATENT DOCUMENTS

| | | | |
|---|---|---|---|
| 5,374,423 | A | 12/1994 | Klimpel et al. |
| 5,733,540 | A | 3/1998 | Lee |
| 6,146,632 | A | 11/2000 | Momin et al. |
| 6,372,227 | B1 | 4/2002 | Garcon et al. |
| 6,399,074 | B1 | 6/2002 | Roland |
| 6,544,518 | B1 | 4/2003 | Friede et al. |
| 6,866,847 | B1 | 3/2005 | Kelly-Aehle |
| 7,115,266 | B2 | 10/2006 | Bachmann |
| 7,393,525 | B2 | 7/2008 | Powell et al. |
| 7,541,039 | B2 | 6/2009 | Leenhouts et al. |
| 7,842,515 | B2 | 11/2010 | Zou et al. |
| 7,888,102 | B2 | 2/2011 | Van den Brink et al. |
| 7,951,423 | B2 | 5/2011 | Gräter |
| 8,058,069 | B2 | 11/2011 | Yaworski et al. |
| 8,278,036 | B2 | 10/2012 | Kariko et al. |

(Continued)

FOREIGN PATENT DOCUMENTS

| | | | |
|---|---|---|---|
| CN | 113549154 | A | 10/2021 |
| CN | 114617977 | A | 6/2022 |

(Continued)

OTHER PUBLICATIONS

Abagnale et al., "Surface topography enhances differentiation of mesenchymal stem cells towards osteogenic and adipogenic lineages", Biomaterials, pp. 316-326, vol. 61 (Aug. 2015).

(Continued)

*Primary Examiner* — Barry A Chestnut

(74) *Attorney, Agent, or Firm* — KNOBBE, MARTENS, OLSON & BEAR, LLP

(57) ABSTRACT

According to some embodiments, a method of providing treatment of a host comprises binding a carrier to cell structures of cells of the host to reduce a likelihood of an agent binding to said cell structures to at least partially inhibits the agent from binding to said cell structures, wherein the carrier comprises a core and a surface functionalized on the core, wherein the functionalized surface bind to target areas of cell structures of the host's cells, and wherein the carrier is to be used as targeted treatment for one or more disease, infections or allergic reactions caused by a disease-causing agent or source.

19 Claims, 9 Drawing Sheets

Specification includes a Sequence Listing.

(56) References Cited

U.S. PATENT DOCUMENTS

| | | | |
|---|---|---|---|
| 8,628,972 | B2 | 1/2014 | Tang et al. |
| 8,637,051 | B2 | 1/2014 | Clancy et al. |
| 8,652,640 | B2 | 2/2014 | Santore et al. |
| 8,658,093 | B2 | 2/2014 | Lau et al. |
| 8,691,966 | B2 | 4/2014 | Kariko et al. |
| 8,748,089 | B2 | 6/2014 | Kariko et al. |
| 8,835,108 | B2 | 9/2014 | Kariko et al. |
| 8,986,966 | B2 | 3/2015 | Toner et al. |
| 9,012,219 | B2 | 4/2015 | Kariko et al. |
| 9,066,894 | B2 | 6/2015 | Connaris et al. |
| 9,138,467 | B2 | 9/2015 | Szathmary et al. |
| 9,139,554 | B2 | 9/2015 | Hope et al. |
| 9,163,213 | B2 | 10/2015 | Kariko et al. |
| 9,250,238 | B2 | 2/2016 | Low et al. |
| 9,364,435 | B2 | 6/2016 | Yaworski et al. |
| 9,371,511 | B2 | 6/2016 | Kariko et al. |
| 9,404,127 | B2 | 8/2016 | Yaworski et al. |
| 9,422,517 | B2 | 8/2016 | Chen et al. |
| 9,428,547 | B2 | 8/2016 | Dryga et al. |
| 9,434,940 | B2 | 9/2016 | Dykes |
| 9,474,831 | B2 | 10/2016 | Boyden et al. |
| 9,476,812 | B2 | 10/2016 | Dryga et al. |
| 9,506,846 | B2 | 11/2016 | Rubner et al. |
| 9,518,272 | B2 | 12/2016 | Yaworski et al. |
| 9,551,704 | B2 | 1/2017 | Norvell |
| 9,561,263 | B2 | 2/2017 | Loibner et al. |
| 9,562,896 | B2 | 2/2017 | Esch et al. |
| 9,567,296 | B2 | 2/2017 | Payne et al. |
| 9,580,711 | B2 | 2/2017 | Payne et al. |
| 9,669,089 | B2 | 6/2017 | Thess et al. |
| 9,750,824 | B2 | 9/2017 | Kariko et al. |
| 9,758,795 | B2 | 9/2017 | Cullis et al. |
| 9,797,893 | B2 | 10/2017 | Azizoglu et al. |
| 9,814,769 | B2 | 11/2017 | Ghunaim et al. |
| 9,814,777 | B2 | 11/2017 | Manoharan et al. |
| 9,868,692 | B2 | 1/2018 | Benenato |
| 9,943,846 | B2 | 4/2018 | Cullis et al. |
| 9,950,065 | B2 | 4/2018 | Sahin et al. |
| 10,006,007 | B2 | 6/2018 | Kariko et al. |
| 10,041,091 | B2 | 8/2018 | Cullis et al. |
| 10,064,959 | B2 | 9/2018 | Schrum et al. |
| 10,100,102 | B2 | 10/2018 | Lai et al. |
| 10,131,899 | B2 | 11/2018 | Hansen et al. |
| 10,159,652 | B2 | 12/2018 | Walsh et al. |
| 10,166,298 | B2 | 1/2019 | Ansell et al. |
| 10,221,127 | B2 | 3/2019 | Du et al. |
| 10,227,302 | B2 | 3/2019 | Payne et al. |
| 10,232,055 | B2 | 3/2019 | Kariko et al. |
| 10,233,148 | B2 | 3/2019 | Payne et al. |
| 10,238,109 | B2 | 3/2019 | Hope |
| 10,253,348 | B2 | 4/2019 | Jung |
| 10,266,485 | B2 | 4/2019 | Benenato |
| 10,285,952 | B2 | 5/2019 | Zhang et al. |
| 10,350,320 | B2 | 7/2019 | Lee et al. |
| 10,383,950 | B2 | 8/2019 | Lehr et al. |
| 10,442,756 | B2 | 10/2019 | Benenato et al. |
| 10,485,884 | B2 | 11/2019 | Sahin et al. |
| 10,557,779 | B2 | 2/2020 | Astier et al. |
| 10,576,146 | B2 | 3/2020 | Sahin et al. |
| 10,577,403 | B2 | 3/2020 | De Fougerolles et al. |
| 10,653,780 | B2 | 5/2020 | Hope et al. |
| 10,661,273 | B2 | 5/2020 | Ok et al. |
| 10,702,600 | B1 | 7/2020 | Ciaramella et al. |
| 10,703,789 | B2 | 7/2020 | De Fougerolles et al. |
| 10,751,072 | B2 | 8/2020 | Kendall |
| 10,780,054 | B2 | 9/2020 | Ketterer et al. |
| 10,799,602 | B2 | 10/2020 | Baumhof |
| 10,813,988 | B2 | 10/2020 | Super et al. |
| 10,815,463 | B2 | 10/2020 | Chivukula et al. |
| 10,864,270 | B2 | 12/2020 | Lal et al. |
| 10,900,896 | B2 | 1/2021 | Spero et al. |
| 10,918,706 | B2 | 2/2021 | Putnam et al. |
| 11,045,555 | B2 | 6/2021 | Zink et al. |
| 11,105,820 | B2 | 8/2021 | Ratner et al. |
| 11,178,867 | B2 | 11/2021 | Zaltsman et al. |
| 11,203,623 | B2 | 12/2021 | Super et al. |
| 11,249,083 | B1 | 2/2022 | Huang et al. |
| 11,406,702 | B1 | 8/2022 | Bermudes |
| 11,564,892 | B2 | 1/2023 | Niemelä |
| 11,696,948 | B2 | 7/2023 | Hume et al. |
| 11,754,527 | B2 | 9/2023 | Krishnamoorthy et al. |
| 11,795,212 | B2 | 10/2023 | Ingber et al. |
| 12,144,898 | B2 | 11/2024 | Niemelä |
| 12,194,157 | B2 | 1/2025 | Niemelä |
| 2002/0028451 | A1 | 3/2002 | Abbott et al. |
| 2002/0086020 | A1 | 7/2002 | Lee |
| 2002/0110557 | A1 | 8/2002 | Boyd |
| 2003/0003441 | A1 | 1/2003 | Colston et al. |
| 2003/0170613 | A1 | 9/2003 | Straus |
| 2003/0172867 | A1 | 9/2003 | Shinnar et al. |
| 2003/0223938 | A1 | 12/2003 | Nagy et al. |
| 2004/0009167 | A1 | 1/2004 | Rider |
| 2004/0009937 | A1 | 1/2004 | Chen et al. |
| 2004/0033584 | A1 | 2/2004 | Lederberg |
| 2004/0058361 | A1 | 3/2004 | Maciver |
| 2004/0096960 | A1 | 5/2004 | Mehta et al. |
| 2004/0115210 | A1 | 6/2004 | Timmerman |
| 2004/0137428 | A1 | 7/2004 | Low |
| 2005/0048570 | A1 | 3/2005 | Weber et al. |
| 2005/0075298 | A1 | 4/2005 | Chen et al. |
| 2005/0113298 | A1 | 5/2005 | Farzan et al. |
| 2005/0130127 | A1 | 6/2005 | Rottier et al. |
| 2005/0203038 | A1 | 9/2005 | Dobie et al. |
| 2005/0214318 | A1 | 9/2005 | Karp |
| 2005/0249739 | A1 | 11/2005 | Marasco et al. |
| 2005/0260225 | A1 | 11/2005 | Goldberg et al. |
| 2005/0266433 | A1 | 12/2005 | Kapur et al. |
| 2006/0018797 | A1 | 1/2006 | Burnell et al. |
| 2006/0281074 | A1 | 12/2006 | Kulagina et al. |
| 2007/0009884 | A1 | 1/2007 | Stoughton et al. |
| 2007/0015179 | A1 | 1/2007 | Klapperich et al. |
| 2007/0116722 | A1 | 5/2007 | Agin et al. |
| 2007/0141078 | A1 | 6/2007 | D'Hondt et al. |
| 2007/0184120 | A1 | 8/2007 | Stutzenberger et al. |
| 2007/0207168 | A1 | 9/2007 | Daemmgen et al. |
| 2007/0218459 | A1 | 9/2007 | Miller et al. |
| 2007/0238681 | A1 | 10/2007 | Dobie et al. |
| 2007/0287147 | A1 | 12/2007 | Nagamune et al. |
| 2008/0044440 | A1 | 2/2008 | Dunkley |
| 2008/0044830 | A1 | 2/2008 | Tovar et al. |
| 2008/0103746 | A1 | 5/2008 | Jung et al. |
| 2008/0219959 | A1 | 9/2008 | Carbone et al. |
| 2008/0267943 | A1 | 10/2008 | Imboden et al. |
| 2008/0293079 | A1 | 11/2008 | Hauser et al. |
| 2008/0311590 | A1 | 12/2008 | Tan et al. |
| 2009/0156426 | A1 | 6/2009 | Schiestel et al. |
| 2009/0208501 | A1 | 8/2009 | Visintin et al. |
| 2009/0246796 | A1 | 10/2009 | Bernard et al. |
| 2009/0305230 | A1 | 12/2009 | Beattie et al. |
| 2010/0078020 | A1 | 4/2010 | Hyde et al. |
| 2010/0119535 | A1 | 5/2010 | Felgner et al. |
| 2010/0278846 | A1 | 11/2010 | Ferguson |
| 2010/0285972 | A1 | 11/2010 | Dubrow et al. |
| 2011/0117204 | A1 | 5/2011 | Szathmary et al. |
| 2011/0229579 | A1 | 9/2011 | Carbone et al. |
| 2011/0275912 | A1 | 11/2011 | Boyden et al. |
| 2012/0003711 | A1 | 1/2012 | Tseng et al. |
| 2012/0021034 | A1 | 1/2012 | Zink et al. |
| 2012/0039978 | A1 | 2/2012 | Moscana et al. |
| 2012/0135883 | A1 | 5/2012 | Lehmann |
| 2012/0184451 | A1 | 7/2012 | Singamaneni et al. |
| 2014/0030808 | A1 | 1/2014 | Sahin et al. |
| 2014/0100136 | A1 | 4/2014 | Clarizia et al. |
| 2014/0142028 | A1 | 5/2014 | Eckert et al. |
| 2014/0341975 | A1 | 11/2014 | Livneh |
| 2015/0064703 | A1 | 3/2015 | Super et al. |
| 2015/0072880 | A1 | 3/2015 | Calderwood et al. |
| 2015/0233919 | A1 | 8/2015 | Rodriguez et al. |
| 2015/0250897 | A1 | 9/2015 | Mattey et al. |
| 2015/0259668 | A1 | 9/2015 | Hansen et al. |
| 2016/0045591 | A1 | 2/2016 | Campos-Neto et al. |
| 2016/0222393 | A1 | 8/2016 | Bermudes |
| 2016/0256388 | A1 | 9/2016 | Galili et al. |
| 2016/0311877 | A1 | 10/2016 | Watters et al. |

(56) References Cited

U.S. PATENT DOCUMENTS

2016/0334312 A1 11/2016 Gaitas et al.
2016/0354462 A1 12/2016 Campos-Neto et al.
2017/0087237 A1 3/2017 Gunn et al.
2017/0253647 A1 9/2017 Martin et al.
2017/0273907 A1 9/2017 Haas et al.
2017/0281545 A1 10/2017 Gill et al.
2017/0362307 A1 12/2017 Ingber et al.
2018/0185516 A1 7/2018 Ansell et al.
2018/0237602 A1 8/2018 Ihalainen et al.
2018/0243336 A1 8/2018 Vanepps et al.
2018/0256747 A1 9/2018 Hawthorne et al.
2018/0263907 A1 9/2018 Hefesha et al.
2018/0296663 A1 10/2018 Hipp et al.
2018/0303925 A1 10/2018 Weissman et al.
2019/0002179 A1 1/2019 Rosqvist et al.
2019/0015501 A1 1/2019 Ciaramella et al.
2019/0022247 A1 1/2019 Ansell et al.
2019/0032087 A1 1/2019 Cullis et al.
2019/0077850 A1 3/2019 Ingber et al.
2019/0083602 A1 3/2019 Roos et al.
2019/0153428 A1 5/2019 Kariko et al.
2019/0224311 A1 7/2019 Connaris et al.
2019/0250100 A1 8/2019 Polland et al.
2019/0262469 A1 8/2019 Brinker et al.
2019/0270091 A1 9/2019 Kang et al.
2019/0274968 A1 9/2019 Weissman et al.
2019/0314496 A1 10/2019 Fotin-Mleczek et al.
2019/0321458 A1 10/2019 Sahin et al.
2019/0321570 A1 10/2019 Rubin
2019/0336608 A1 11/2019 Baumhof et al.
2019/0351048 A1 11/2019 Rauch
2020/0015567 A1 1/2020 Lau
2020/0038869 A1 2/2020 Devoe et al.
2020/0046830 A1 2/2020 Hooper et al.
2020/0046838 A1 2/2020 Ansell et al.
2020/0085852 A1 3/2020 Fotin-Mleczek
2020/0109113 A1 4/2020 Payne et al.
2020/0124602 A1 4/2020 Böse et al.
2020/0163878 A1 5/2020 Baumhof et al.
2020/0164038 A1 5/2020 De Fougerolles et al.
2020/0172472 A1 6/2020 Du
2020/0179526 A1 6/2020 Baumhof et al.
2020/0197508 A1 6/2020 Bihi et al.
2020/0206362 A1 7/2020 Besin et al.
2020/0246451 A1 8/2020 Mutzke et al.
2020/0283372 A1 9/2020 Du
2020/0297634 A1 9/2020 Karmali et al.
2020/0299345 A1 9/2020 Super et al.
2020/0300854 A1 9/2020 Cartwright et al.
2020/0345831 A1 11/2020 Thess et al.
2021/0002355 A1 1/2021 Lai et al.
2021/0024618 A1 1/2021 Lai et al.
2021/0061889 A1 3/2021 Lai et al.
2021/0113681 A1 4/2021 Nabel et al.
2021/0128651 A1 5/2021 Anselmo et al.
2021/0199656 A1 7/2021 Youngbull et al.
2021/0255178 A1 8/2021 Chang et al.
2021/0292384 A1 9/2021 Yu et al.
2021/0345617 A1 11/2021 Disegi
2021/0347858 A1 11/2021 Starzl
2021/0347859 A1 11/2021 Simplot et al.
2022/0008373 A1 1/2022 Loveless et al.
2022/0041660 A1 2/2022 Gleghorn et al.
2022/0088170 A1 3/2022 Volkmann et al.
2022/0127614 A1 4/2022 Lai et al.
2022/0162566 A1 5/2022 Rohwer et al.
2022/0232825 A1 7/2022 Joshi et al.
2022/0235118 A1 7/2022 Robinson et al.
2022/0249636 A1 8/2022 Hochrein et al.
2022/0280439 A1 9/2022 Niemelä
2022/0280635 A1 9/2022 Niemelä
2022/0290208 A1 9/2022 White et al.
2022/0411772 A1 12/2022 Liu
2023/0059344 A1 2/2023 Hinterberger et al.
2023/0114464 A1 4/2023 Kjaer et al.
2023/0151077 A1 5/2023 Marko-Varga et al.
2023/0158125 A1 5/2023 Fu et al.
2023/0172871 A1 6/2023 Niemelä
2023/0174611 A1 6/2023 Kolls et al.
2023/0181759 A1 6/2023 Ghobadi et al.
2023/0190922 A1 6/2023 Lauterbach et al.
2023/0203137 A1 6/2023 Weng et al.
2023/0203466 A1 6/2023 Seshagiri et al.
2023/0227537 A1 7/2023 Schepens et al.
2023/0233670 A1 7/2023 Hausmann et al.
2023/0235007 A1 7/2023 Yang et al.
2023/0257726 A1 8/2023 Glasgow et al.
2023/0263884 A1 8/2023 Schreiber et al.
2023/0265407 A1 8/2023 Jin et al.
2023/0270927 A1 8/2023 Varma et al.
2023/0272359 A1 8/2023 Torchia et al.
2023/0272400 A1 8/2023 Weng et al.
2023/0287090 A1 9/2023 Wang et al.
2023/0295023 A1 9/2023 Zhong et al.
2023/0346973 A1 11/2023 Arasoglu et al.
2023/0358740 A1 11/2023 Cartwright et al.
2023/0374114 A1 11/2023 Marasco et al.
2023/0374153 A1 11/2023 Bodie
2023/0406908 A1 12/2023 Mitteness et al.
2024/0009315 A1 1/2024 Schreiber et al.
2024/0019435 A1 1/2024 Varma et al.
2025/0057782 A1 2/2025 Niemelä

FOREIGN PATENT DOCUMENTS

CN 115991779 A 4/2023
CN 116120443 A 5/2023
CN 116490204 A 7/2023
EP 2090319 A2 8/2009
EP 3081937 A1 10/2016
EP 3906946 A1 11/2021
FI 20205382 5/2021
IN 202011016345 A 6/2020
IN 202011016346 A 6/2020
IN 201911005835 A 8/2020
KR 20140072985 A 6/2014
WO WO 86/07540 12/1986
WO WO 1997/018790 5/1997
WO WO 2003/031466 4/2003
WO WO 2003/063786 8/2003
WO WO 2005/020885 3/2005
WO WO 2006/066216 6/2006
WO WO 2007/010028 1/2007
WO WO 2007/044695 4/2007
WO WO 2008/150276 12/2008
WO WO 2008/154603 12/2008
WO WO 2009/023164 2/2009
WO WO 2009/086558 7/2009
WO WO 2010/044921 4/2010
WO WO 2010/085509 7/2010
WO WO 2011/036557 3/2011
WO WO 2011/053789 5/2011
WO WO 2013/030831 3/2013
WO WO 2013/059922 5/2013
WO WO 2013/087083 6/2013
WO WO 2014/153087 9/2014
WO WO 2015/043613 4/2015
WO WO 2015/054639 4/2015
WO WO 2015/164674 10/2015
WO WO 2016/023591 2/2016
WO WO 2016/118724 7/2016
WO WO 2016/118725 7/2016
WO WO 2016/156398 10/2016
WO WO 2017/009533 1/2017
WO WO 2017/021023 2/2017
WO WO 2017/032928 3/2017
WO WO 2017/070626 4/2017
WO WO 2017/165506 9/2017
WO WO 2018/100047 6/2018
WO WO 2018/129207 7/2018
WO WO 2019/241483 12/2019
WO WO 2019/241794 12/2019
WO WO 2020/002598 1/2020
WO WO 2020/012060 1/2020

(56) References Cited

FOREIGN PATENT DOCUMENTS

| | | |
|---|---|---|
| WO | WO 2020/097540 | 5/2020 |
| WO | WO 2020/097548 | 5/2020 |
| WO | WO 2021/032745 | 2/2021 |
| WO | WO 2021/089922 | 5/2021 |
| WO | WO 2021/142516 | 7/2021 |
| WO | WO 2021/195009 | 9/2021 |
| WO | WO 2021/205077 | 10/2021 |
| WO | WO 2021/205079 | 10/2021 |
| WO | WO 2021/206638 | 10/2021 |
| WO | WO 2021/209992 | 10/2021 |
| WO | WO 2021/211279 | 10/2021 |
| WO | WO 2021/222988 | 11/2021 |
| WO | WO 2021/226358 | 11/2021 |
| WO | WO 2021/231803 | 11/2021 |
| WO | WO 2021/233885 | 11/2021 |
| WO | WO 2021/234471 | 11/2021 |
| WO | WO 2021/247675 | 12/2021 |
| WO | WO 2021/255067 | 12/2021 |
| WO | WO 2022/043943 | 3/2022 |
| WO | WO 2022/058618 | 3/2022 |
| WO | WO 2022/086854 | 4/2022 |
| WO | WO 2022/090353 | 5/2022 |
| WO | WO 2023/044397 | 3/2023 |
| WO | WO 2023/056521 | 4/2023 |
| WO | WO 2023/081958 | 5/2023 |
| WO | WO 2023/245143 | 12/2023 |
| WO | WO 2025/054542 | 3/2025 |

OTHER PUBLICATIONS

Abagnale et al., "Surface Topography Guides Morphology and Spatial Patterning of Induced Pluripotent Stem Cell Colonies", Stem Cell Reports, pp. 654-666, vol. 9, Issue 2 (Aug. 8, 2017).

Abbott et al., "Metrics: Do metrics matter?", Nature, pp. 860-862, vol. 465 (Jun. 16, 2010).

Abdelkader et al., "Omics approaches for the assessment of biological responses to nanoparticles", Adv. Drug Delivery Rev., vol. 200, 114992 (Sep. 2023).

Abdellatif et al., "Approved and marketed nanoparticles for disease targeting and applications in COVID-19", Nanotechnology Reviews, vol. 10(1), pp. 1941-1977 (Oct. 2021).

Abdelmonem et al., "Charge and agglomeration dependent in vitro uptake and cytotoxicity of zinc oxide nanoparticles", J. Inorg. Biochem., vol. 153, pp. 334-338 (2015).

Abeywardhana et al., "In silico study of SARS-CoV-2 spike protein RBD and human ACE-2 affinity dynamics across variants and Omicron subvariants", J. Med. Virol., vol. 95(1), e28406 (Dec. 2022).

Abla et al., "Freeze-drying: A flourishing strategy to fabricate stable pharmaceutical and biological products", International Journal of Pharmaceutics, vol. 628, 122233 (Sep. 2022).

Abo-Zeid et al., "An investigation of rhinovirus infection on cellular uptake of poly (glycerol-adipate) nanoparticles", International Journal of Pharmaceutics, pp. 1-10, vol. 589 (Nov. 15, 2020).

Abumanhal-Masarweh, "Sodium bicarbonate nanoparticles modulate the tumor pH and enhance the cellular uptake of doxorubicin", Journal of Controlled Release, vol. 296, pp. 1-13 (Jan. 2019).

Achterberg et al., "The Nano-Scale Mechanical Properties of the Extracellular Matrix Regulate Dermal Fibroblast Function", Journal of Investigative Dermatology, pp. 1862-1872, vol. 134, Issue 7 (Jul. 1, 2014).

Adachi et al., "Heat shock proteins in neurodegenerative diseases: Pathogenic roles and therapeutic implications", International Journal of Hypothermia, pp. 647-654, vol. 25, Issue 8 (2009).

Adamo et al., "A Roadmap for Academic Health Centers to Establish Good Laboratory Practice-Compliant Infrastructure", Academic Medicine, pp. 279-284, vol. 87, No. 3 (Mar. 2012).

Adan et al., "Cell proliferation and cytotoxicity assays", Curr. Pharm. Biotechnol., vol. 17(14), pp. 1213-1221 (2016).

Addetia et al., "Structural changes in the SARS-CoV-2 spike E406W mutant escaping a clinical monoclonal antibody cocktail", Cell Reports, vol. 42(6), 112621 (Jun. 2023).

Afkhami et al., "Respiratory mucosal delivery of next-generation COVID-19 vaccine provides robust protection against both ancestral and variant strains of SARS-CoV-2", Cell, pp. 896-915, vol. 185, Issue 5 (Mar. 3, 2022).

Aggarwal, "Signalling pathways of the TNF superfamily: A double-edged sword", Nature Reviews Immunology, pp. 745-756, vol. 3 (Sep. 1, 2003).

Aghaei et al., "Double flow focusing microfluidic-assisted based preparation of methotrexate-loaded liposomal nanoparticles: Encapsulation efficacy, drug release and stability", Colloids and Surfaces A: Physicochemical and Engineering Aspects, vol. 614, 126166 (Jan. 2021).

Agrahari et al., "Facilitating the translation of nanomedicines to a clinical product: challenges and opportunities", Drug Discovery Today, vol. 23(5), pp. 974-991 (May 2018).

Ahmad et al., "Precision nanotoxicology in drug development: current trends and challenges in safetyand toxicity implications of customized multifunctional nanocarriers for drug-delivery applications", Pharmaceutics, vol. 14(11), 2463 (Nov. 2022).

Ahmad et al., "The Repurposed ACE2 Inhibitors: SARS-CoV-2 Entry Blockers of Covid-19", Top. Curr. Chem. (Cham), vol. 379(6), 40 (Oct. 2021).

Ahmed et al., "Detection of SARS-CoV-2 RNA in commercial passenger aircraft and cruise ship wastewater: a surveillance tool for assessing the presence of COVID-19 infected travellers", Journal of Travel Medicine, pp. 1-11, vol. 27, Issue 6 (2020).

Ahmed et al., "Preliminary Identification of Potential Vaccine Targets for the COVID-19 Coronavirus (SARS-CoV-2) Based on SARS-CoV Immunological Studies", Viruses, 12(3):254 (Feb. 25, 2020).

Akahata et al., "Safety and immunogenicity of SARS-CoV-2 self-amplifying RNA vaccine expressing an anchored RBD: A randomized, observer-blind phase 1 study", Cell Rep. Med., vol. 4(8), 101134 (Aug. 2023).

Åkerfelt et al., "Heat shock factors: integrators of cell stress, development and lifespan", Nature Reviews Molecular Cell Biology, pp. 1-25, vol. 11, Issue 8 (Aug. 2010).

Åkerlund et al., "Inflammation and (secondary) genotoxicity of Ni and NiO nanoparticles", Nanotoxicology, vol. 13(8), pp. 1060-1072 (2019).

Akram, "Inanimate surfaces as potential source of 2019-nCoV spread and their disinfection with biocidal agents", Virusdisease, pp. 94-96, vol. 31, Issue 2 (Apr.-Jun. 2020).

Al Awaidy et al., "Middle East Respiratory Syndrome Coronavirus (Mers-cov) in Oman: Current Situation and Going Forward", Oman Medical Journal, pp. 181-183, vol. 34, No. 3 (2019).

Alameh et al., "Lipid nanoparticles enhance the efficacy of mRNA and protein subunit vaccines byinducing robust T follicular helper cell and humoral responses", Immunity, vol. 54(12), pp. 2877-2892, (Dec. 2021).

Alastalo et al., "Formation of nuclear stress granules involves HSF2 and coincides with the nucleolar localization of Hsp70", Journal of Cell Science, pp. 3557-3570, vol. 116, Issue 17 (2003).

Albanese et al., "The effect of nanoparticle size, shape, and surface chemistry on biological systems", Annual Review of Biomedical Engineering, pp. 1-16, vol. 14 (2012).

Albano et al., "Overview of the mechanisms of oxidative stress: Impact in inflammation of the airway diseases", Antioxidants (Basel), vol. 11(11), 2237 (Nov. 2022).

Albini et al., "The SARS-CoV-2 receptor, ACE-2, is expressed on many different cell types:implications for ACE-inhibitor- and angiotensin II receptor blocker-based cardiovascular therapies", Internal and Emergency Medicine, pp. 759-766, vol. 15 (2020).

Al-Hallak et al., "Pulmonary delivery of inhalable nanoparticles: dry powder inhalers", Therapeutic Delivery, vol. 2(10), pp. 1313-1324 (2011).

Alharbi et al., "Assessment of the bacterial contamination of hand air dryer in washrooms", Saudi Journal of Biological Sciences, pp. 268-271, vol. 23 (2016).

(56) References Cited

OTHER PUBLICATIONS

Ali et al., "In silico investigations of heparin binding to SARS-CoV-2 variants with a focus at the RBD/ACE2 interface", Process Biochemistry, vol. 115, pp. 70-79 (Feb. 2022).
Ali et al., "Industrial perspective in ocular drug delivery", Advanced Drug Delivery Reviews, pp. 1258-1268, vol. 58, Issue 11 (Nov. 15, 2006).
Ali et al., "Microfluidics for development of lipid nanoparticles: paving the way for nucleic acids to the clinic", ACS Applied Bio Materials, vol. 6(9), pp. 3566-3576 (Dec. 2023).
Ali et al., "Preparation of hydrocortisone nanosuspension through a bottom-up nanoprecipitation technique using microfluidic reactors", International Journal of Pharmaceutics, vol. 375(1-2), pp. 107-113 (Apr. 2009).
Ali et al., "Sensing of COVID-19 antibodies in seconds via aerosol Jet nanoprinted reduced-graphene-oxide-coated 3D electrodes", Advanced Materials, vol. 33(7), 2006647 (Dec. 2021).
Alila et al., "Controlled surface modification of cellulose fibers by amino derivatives using N, N'-carbonyldiimidazole as activator", Carbohydrate Polymers, pp. 553-562, vol. 77, Issue 3 (2009).
Aljabali et al., "Nanomaterials and their impact on the immune system", Int. J. Mol. Sci., vol. 24(3), 2008 (Jan. 2023).
Allan et al., "Mechanisms of therapy-related carcinogenesis", Nature Reviews Cancer, pp. 943-955, vol. 5 (Nov. 18, 2005).
Almalki et al., "The relevant information about the severe acute respiratory syndrome coronavirus 2 (SARS-CoV-2) using the five-question approach (when, where, what, why, and how) and its impact on the environment", Environmental Science and Pollution Research, vol. 30(22), pp. 61430-61454 (Feb. 2022).
Alnaqbi et al., "HLA repertoire of 115 UAE nationals infected with SARS-CoV-2", Human Immunology,, pp. 1-9, vol. 83, Issue 1 (Jan. 2022 ).
Alphandery, "The Potential of Various Nanotechnologies for Coronavirus Diagnosis/Treatment Highlighted through a Literature Analysis", Bioconjugate Chemistry, pp. 1873-1882, vol. 31 (2020).
Altankov et al., "The role of surface zeta potential and substratum chemistry for regulation of dermalfibroblasts interaction", Materials Science & Engineering Technology, pp. 1120-1128, vol. 34, Issue 12 (Dec. 2003).
Altman et al., "Comparison of trypan blue dye exclusion and fluorometric assays for mammalian cell viability determinations", Biotechnol. Prog., vol. 9(6), pp. 671-674 (1993).
Alvandi et al., "Treatment and Diagnosis Roles of Nanoparticles Against SARS-CoV-2", Journal of Nanostructures, vol. 12(4), pp. 807-825 (Oct. 2022).
Amanat et al., "SARS-CoV-2 mRNA vaccination induces functionally diverse antibodies to NTD, RBD, and S2", Cell, vol. 184(15), pp. 3936-3948 (Jul. 2021).
Amidi et al., "Preparation and characterization of protein-loaded N-trimethyl chitosan nanoparticles as nasal delivery system", Journal of Controlled Release, vol. 111(1-2), pp. 107-116 (Dec. 2005).
Amidon et al., "A theoretical basis for a biopharmaceutic drug classification: the correlation of in vitro drug product dissolution and in vivo bioavailability", The AAPS Journal, pp. 894-898, vol. 16 (2014).
Amorim et al., "Effect assessment of engineered nanoparticles in solid media-Current insight and the way forward", Environ. Pollut., vol. 218, pp. 1370-1375 (2016).
Amraei et al., "Extracellular vimentin is an attachment factor that facilitates SARS-CoV-2 entry intohuman endothelial cells", Proceedings of the National Academy of Sciences, vol. 119(6), e2113874119 (Jan. 2022).
Amrhein et al., "Scientists rise up against statistical significance", Nature, Comments, pp. 305-307, vol. 567 (Mar. 21, 2019).
Anand et al., "Cancer is a Preventable Disease that Requires Major Lifestyle Changes". Pharmaceutical Research, pp. 2097-2116, vol. 25, No. 9 (Sep. 2008).
Ananthakrishnan et al., "The Forces Behind Cell Movement", International Journal of Biological Sciences, pp. 303-317, vol. 3, Issue 5 (2007).
Andar et al., "Microfluidic preparation of liposomes to determine particle size influence on cellular uptake mechanisms", Pharmaceutical Research, vol. 31, pp. 401-413 (2014).
Anderson et al., "A framework for the development of effective anti-metastatic agents", Nature Reviews | Clinical Oncology, pp. 185-204, vol. 16 (Mar. 2019).
Andersson et al., "Influences of Material Characteristics on Ibuprofen Drug Loading and Release Profiles from Ordered Micro- and Mesoporous Silica Matrices", Chemistry of Materials, pp. 4160-4167, vol. 16, Issue 21 (Oct. 19, 2004).
Anderton et al., "Cell death in chronic inflammation: breaking the cycle to treat rheumatic disease", Nat. Rev. Rheumatol., vol. 16(9), pp. 496-513 (Jul. 2020).
Anft et al., "COVID-19 progression is potentially driven by T cell immunopathogenesis", medRxiv 2020.04.28.20083089; doi: https://doi.org/10.1101/2020.04.28.20083089.
Angelova et al., "Rationalizing the design of polymeric biomaterials", Trends in Biotechnology, pp. 409-421, vol. 17, Issue 10 (Oct. 1, 1999).
Angsantikul et al., "Coating nanoparticles with gastric epithelial cell membrane for targeted antibiotic delivery against Helicobater pylori infection", Advanced Therapeutics, 1800016, in 20 pages, vol. 1 (Jun. 2018).
Ansari et al., "Evaluation of DNA interaction, genotoxicity and oxidative stress induced by iron oxide nanoparticles both in vitro and in vivo: attenuation by thymoquinone", Sci. Rep., vol. 9(1), 6912 (2019).
Anselmo et al., "Nanoparticles in the clinic: an update post COVID-19 vaccines", Bioengineering & Translational Medicine, vol. 6(3), e10246 (Aug. 2021).
Anton et al., "A new microfluidic setup for precise control of the polymer nanoprecipitation process and lipophilic drug encapsulation", Soft Matter, vol. 8(41), pp. 10628-10635 (May 2012).
Araf et al., "Omicron SARS-CoV-2: genomics, transmissibility, and responses to current COVID-19 vaccines", Journal of Medical Virology, vol. 94(5), pp. 1825-1832 (Jan. 2022).
Arakaki et al., "Detection of biomolecular interaction between biotin and streptavidin on a self-assembled monolayer using magnetic nanoparticles", Biotechnology and Bioengineering, vol. 88(4), pp. 543-546 (Nov. 2004).
Araujo et al., "In vivo dual-delivery of glucagon like peptide-1 (GLP-1) and dipeptidyl peptidase-4 (DPP4) inhibitor through composites prepared by microfluidics for diabetes therapy", Nanoscale, vol. 8(20), pp. 10706-10713 (Apr. 2016).
Araujo et al., "Microfluidic assembly of a multifunctional tailorable composite system designed for site specific combined oral delivery of peptide drugs", ACS Nano, vol. 9(8), pp. 8291-8302 (2015).
Arduino et al., "Microfluidic preparation and in vitro evaluation of iRGD-functionalized solid lipid nanoparticles for targeted delivery of paclitaxel to tumor cells", International Journal of Pharmaceutics, vol. 610 (Oct. 2021).
Arduino et al., "Preparation of cetyl palmitate-based PEGylated solid lipid nanoparticles by microfluidic technique", Acta Biomaterialia, pp. 566-578, vol. 121 (Feb. 2021).
Argyo et al., "Multifunctional Mesoporous Silica Nanoparticles as a Universal Platform for Drug Delivery", Chemistry of Materials, pp. 435-451, vol. 26, Issue 1 (2014).
Armstrong et al., "Transepithelial Invasion and Intramesenchymal Infiltration of the Chick Embryo Chorioallantois by Tumor Cell Lines", Cancer Research, pp. 1826-1837, vol. 42 (May 1982).
Arruebo et al., "Assessment of the Evolution of Cancer Treatment Therapies", Cancers, pp. 3279-3330, vol. 3 (2011).
Arts et al., "BCG Vaccination Protects against Experimental Viral Infection in Humans through the Induction of Cytokines Associated with Trained Immunity", Cell Host & Microbe, pp. 89-100, vol. 23, Issue 1 (Jan. 10, 2018).
Asati et al., "Surface-charge-dependent cell localization and cytotoxicity of cerium oxide nanoparticles", ACS Nano, vol. 4(9), pp. 5321-5331 (2010).
Aslan et al., "Controlled and reversible aggregation of biotinylated gold nanoparticles with streptavidin", The Journal of Physical Chemistry B, vol. 108(40), pp. 15631-15639 (May 2004).

(56) References Cited

OTHER PUBLICATIONS

Ataei et al., "Immunogenicity of different nanoparticle adjuvants containing recombinant RBD coronavirus antigen in animal model", Biotechnology and Applied Biochemistry, vol. 71(2), pp. 314-325 (Nov. 2023).
Atanasov et al., "Discovery and resupply of pharmacologically active plant-derived natural products: A review", Biotechnology Advances, pp. 1582-1614, vol. 33, Issue 8 (Dec. 2015).
Attarwala, "Role of antibodies in cancer targeting", Journal of Natural Science, Biology and Medicine, pp. 53-56, vol. 1, Issue 1 (Jul. 2010).
Aubry et al., "Annexin V used for measuring apoptosis in the early events of cellular cytotoxicity", Cytom.: J. Int. Soc. Anal. Cytol., vol. 37(3), pp. 197-204 (1999).
Augustine et al., "Cellular uptake and retention of nanoparticles: Insights on particle properties and interaction with cellular components", Mater. Today Commun., vol. 25, 101692 (Dec. 2020).
Awashra et al., "The toxicity of nanoparticles and their interaction with cells: an in vitro metabolomic perspective", Nanoscale Adv., vol. 5(10), pp. 2674-2723 (Jan. 2023).
Awoniyi, "The Petri-Dish Effect", Disaster Medicine and Public Health Preparedness, pp. e1-e2, vol. 14, Issue 3 (Jun. 2020).
A'Yun et al., "Dry heat induced whey protein-lactose conjugates largely improve the heat stability of O/W emulsions", International Dairy Journal, vol. 108, 2020, 104736.
Azizi et al., "Fabrication of protein-loaded PLGA nanoparticles: effect of selected formulation variables on particle size and release profile", Journal of Polymer Research, vol. 20, pp. 1-14 (Mar. 2013).
Badten et al., "Protein Nanoparticle-Mediated Delivery of Recombinant Influenza Hemagglutinin Enhances Immunogenicity and Breadth of the Antibody Response", ACS Infectious Diseases, vol. 9(2), pp. 239-252 (Dec. 2023).
Bae et al., "Targeted drug delivery to tumors: Myths, reality and possibility", Journal of Controlled Release, pp. 198-205, vol. 153, Issue 3 (Aug. 10, 2011).
Baer et al., "Provenance information as a tool for addressing engineered nanoparticle reproducibility challenges", Biointerphases, 04B401, vol. 11 (2016).
Baer, "Guide to Making XPS Measurements on nanparticles", Journal of Vacuum Science & Technology A, 031201, vol. 38 (2020).
Baer, "The Chameleon Effect: Characterization Challenges Due to the Variability of Nanoparticles and Their Surfaces", Frontiers in Chemistry, Article 145, pp. 1-7, vol. 6 (May 2018).
Bagnoli et al., "Cellular FLICE-inhibitory protein (c-FLIP) signalling: A key regulator of receptor-mediated apoptosis in physiologic context and in cancer", The International Journal of Biochemistry & Cell Biology, pp. 210-213, vol. 42, Issue 2 (Feb. 2010).
Bahuguna et al., "MTT assay to evaluate the cytotoxic potential of a drug", Bangladesh J. Pharmacol., vol. 12(2), pp. 115-118 (2017).
Bai et al., "In vivo protein corona formation: characterizations, effects on engineered nanoparticles' biobehaviors, and applications", Front. Bioeng. Biotechnol, vol. 9, 646708 (Mar. 2021).
Baker et al., "ChAdOx1 interacts with CAR and PF4 with implications for thrombosis with thrombocytopenia syndrome", Science Advances | Research Article, pp. 1-14, vol. 7, Issue 49 (Dec. 1, 2021).
Bali et al., "An overview of gene therapy in head and neck cancer", Indian Journal of Human Genetics, pp. 282-290, vol. 19, Issue 3 (Jul.-Sep. 2013).
Ballabh et al., "The blood-brain barrier: an overview: structure, regulation, and clinical implication", Neurobiology of Disease, pp. 1-13, vol. 16, Issue 1 (Jun. 2004).
Bally et al., "Improved size-tunable preparation of polymeric nanoparticles by microfluidic nanoprecipitation", Polymer, vol. 53(22), pp. 5045-5051 (2012).
Baltazar et al., "Acidic Nanoparticles Are Trafficked to Lysosomes and Restore an Acidic Lysosomal pH and Degradative Function to Compromised ARPE-19 Cells", PLOS | ONE, pp. 1-10, vol. 7, Issue 12 (Dec. 2012).
Banerjee et al., "Hypothesis testing, type I and type II errors", Industrial Psychiatry Journal, pp. 127-131, vol. 18, Issue 2 (Jul.-Dec. 2009).
Bangaru et al., "Structural analysis of full-length SARS-CoV-2 spike protein from an advanced vaccine candidate", Science, vol. 370(6520), pp. 1089-1094 (Dec. 2023).
Bao et al., "Engineering docetaxel-loaded micelles for non-small cell lung cancer: a comparative study of microfluidic and bulk nanoparticle preparation", RSC Advances, vol. 8(56), p. 31950-31966 (Sep. 2018).
Barbey et al., "Immunogenicity of a silica nanoparticle-based SARS-CoV-2 vaccine in mice", European Journal of Pharmaceutics and Biopharmaceutics, vol. 192, pp. 41-55 (Nov. 2023).
Barenholz, "Doxil®—The First FDA-approved nano-drug: Lessons learned", Journal of Controlled Release, pp. 117-134, vol. 160, Issue 2 (Jun. 10, 2012).
Barker et al., "Bioinformatic characterization of angiotensin-converting enzyme 2, the entry receptor for SARS-CoV2", PLoS One, in 29 pages, 15(10), e0240647 (2020).
Baron et al., "Amyotrophic lateral sclerosis-linked FUS/TLS alters stress granule assembly and dynamics", Molecular Neurodegeneration, pp. 1-18, vol. 8, Article No. 30, Research Article | Open Access, (Published Aug. 31, 2013).
Baron et al., "FULL-MDS: Fluorescent Universal Lipid Labeling for Microfluidic Diffusional Sizing", Analytical Chemistry, vol. 95(2), pp. 587-593 (Dec. 2022).
Barrick et al., "The role of high-throughput screening in ecotoxicology and engineered nanomaterials", Environ. Toxicol. Chem., vol. 36(7), pp. 1704-1714 (2017).
Bartrip, "History of asbestos related disease", Postgraduate Medical Journal, pp. 72-76, vol. 80(940) (Feb. 2004).
Bartsch et al., "The potential health care costs and resource use associated with COVID-19 in the United States", Health. Aff. (Millwood), vol. 39(6), 927-935 (Apr. 2020).
Barua et al., "Challenges associated with Penetration of Nanoparticles across Cell and Tissue Barriers: A Review of Current Status and Future Prospects", Nano Today, pp. 223-243, vol. 9, Issue 2 (Apr. 1, 2014).
Basnet et al., "Rhinoviruses and Their Receptors", Translating Basic Research Into Clinical Practice, Chest, vol. 155, pp. 1018-1025 (May 2019).
Bastard et al., "Autoantibodies against type I IFNs in patients with life-threatening COVID-19", Science, pp. 1-17, vol. 370, No. 6515 (Sep. 24, 2020).
Batista et al., "Minimizing disease spread on a quarantined cruise ship: A model of COVID-19 with asymptomatic infections", Mathematical Biosciences, pp. 1-11, vol. 329 (Nov. 2020, 108442).
Batlle et al., "Soluble angiotensin-converting enzyme 2: a potential approach for coronavirus infection therapy?", Clinical Science (London), pp. 543-545, vol. 134, No. 5 (Mar. 13, 2020).
Bazak et al., "Passive targeting of nanoparticles to cancer: A comprehensive review of the literature", Molecular and Clinical Oncology, pp. 904-908, vol. 2, Issue 6 (Nov.-Dec. 2014).
Bean et al., Treatment with ACE-inhibitors is associated with less severe disease with SARS-Covid-19 infection in a multi-site UK acute Hospital Trust, medRxiv 2020.04.07.20056788; doi: https://doi.org/10.1101/2020.04.07.20056788 (2020).
Beck et al., "A New Family of Mesoporous Molecular Sieves Prepared with Liquid Crystal Templates", Journal of the American Chemical Society, pp. 10834-10843, vol. 114 (1992).
Behbahanipour et al., "OligoBinders: Bioengineered Soluble Amyloid-like Nanoparticles to Bind and Neutralize SARS-CoV-2", ACS Applied Materials & Interfaces, vol. 15(9), pp. 11444-11457 (Dec. 2023).
Beigel et al., "Advances in respiratory virus therapeutics—A Meeting Report from the 6th ISIRV Antiviral Group Conference", Antiviral Research, vol. 167, pp. 45-67 (2019).
Belda-Iniesta, "Optimising SARS-CoV-2 vaccination schedules", The Lancet, vol. 398(10303), pp. 819-821 (Sep. 2021).

(56) References Cited

OTHER PUBLICATIONS

Belliveau et al., "Microfluidic synthesis of highly potent limit-size lipid nanoparticles for in vivo delivery of siRNA", Molecular Therapy-Nucleic Acids, vol. 1(8) (Aug. 2012).
Benet, "The Role of BCS (Biopharmaceutics Classification System) and BDDCS (Biopharmaceutics Drug Disposition Classification System) in Drug Development", Journal of Pharmaceutical Sciences, pp. 34-42, vol. 102, Issue 1 (Jan. 2013).
Berbekova et al., "A thematic analysis of crisis management in tourism: A theoretical perspective", Tourism Management, pp. 104342, vol. 86 (2021).
Bergelin et al., "S1P1 and VEGFR-2 form a signaling complex with extracellularly regulated kinase 1/2 and protein kinase C-alpha regulating ML-1 thyroid carcinoma cell migration", Endocrinology, pp. 2994-3005, vol. 151, Issue 7 (Jul. 1, 2010).
Bergman et al., "On the Complexity of Electrostatic Suspension Stabilization of Functionalized Silica Nanoparticles for Biotargeting and Imaging Applications", Journal of Nanomaterials, in 9 pages, vol. 2008, Research Article | Open Access, Article ID 712514, https://doi.org/10.1155/2008/712514 (Apr. 2008).
Berguer et al., "Covalent coupling of Spike's receptor binding domain to a multimeric carrier produces a high immune response against SARS-CoV-2", Scientific Reports, Argentinian AntiCovid Consortium, vol. 12, Article 692 (Jan. 2022).
Bergwerk et al., "Covid-19 Breakthrough Infections in Vaccinated Health Care Workers", The New England Journal of Medicine, pp. 1474-1484, vol. 385 (Oct. 14, 2021).
Bermejo et al., "PAMPA—a drug absorption in vitro model: 7. Comparing rat in situ, Caco-2, and PAMPA permeability of fluoroquinolones", European Journal of Pharmaceutical Sciences, vol. 21(4), pp. 429-441 (2004).
Bert et al., "Norovirus outbreaks on commercial cruise ships: A systematic review and new targets for the public health agenda", Food and Environmental Virology, pp. 67-74, vol. 6 (2014).
Bertoglio et al., "SARS-CoV-2 neutralizing human recombinant antibodies selected from pre-pandemic healthy donors binding at RBD-ACE2 interface", Nature Communications, vol. 12(1), Art. 1577 (Mar. 2021).
Bertoni et al., "pH and reactive oxygen species-sequential responsive nano-in-micro composite for targeted therapy of inflammatory bowel disease", Advanced Functional Materials, vol. 28(50) (2018).
Bettencourt et al., "Identification of antigens presented by MHC for vaccines against tuberculosis", npj Vaccines, in 14 pages, vol. 5, Article No. 2 (2020).
Beutler, "Natural Products as a Foundation for Drug Discovery", Current Protocols in Pharmacology, pp. 1-9, vol. 46, Issue 9 (2009).
Bhakta-Guha et al., "Hormesis: Decoding Two Sides of the Same Coin", Pharmaceuticals (Basel), pp. 865-883, vol. 8 (2015).
Bharti et al., "Mesoporous silica nanoparticles in target drug delivery system: A review", International Journal of Pharmaceutical Investigation, pp. 124-133, vol. 5, No. 3 (Jul. 2015).
Biamonti et al., "Nuclear stress bodies", Cold Spring Harbor Perspectives in Biology, pp. 1-12, vol. 2, Issue 6 (Jun. 2010).
Bian et al., "Colloidal crystals from microfluidics", Nano Micro Small, vol. 16(9) (Mar. 2020).
Bisht et al., "MoS 2 nanosheets effectively bind to the receptor binding domain of the SARS-CoV-2 spike protein and destabilize the spike-human ACE2 receptor interactions", Soft Matter, Royal Society of Chemistry, vol. 18(47), pp. 8961-8973 (Oct. 2022).
Blanco et al., "Development and characterization of protein-loaded poly (lactide-co-glycolide) nanospheres", European Journal of Pharmaceutics and Biopharmaceutics, vol. 43(3), pp. 287-294 (Jan. 1997).
Blanco-Melo et al., "Imbalanced Host Response to SARS-CoV-2 Drives Development of COVID-19", Cell, pp. 1036-1045, vol. 181, Issue 5 (May 28, 2020).
Blum et al., "Pathways of Antigen Processing", Annual Review of Immunology, pp. 443-473, vol. 31 (2013).
Blumenfeld et al., "Multiplexed reverse-transcriptase quantitative polymerase chain reaction using plasmonic nanoparticles for point-of-care COVID-19 diagnosis", Nature Nanotechnology, vol. 17(9), pp. 984-992 (Jul. 2022).
Blumenfeld, "Chemotherapy and fertility", Best Practice & Research Clinical Obstetrics & Gynaecology, pp. 379-390, vol. 26, Issue 3 (Jun. 2012).
Boatright et al., "A unified model for apical caspase activation", Molecular Cell, pp. 529-541, vol. 11, Issue 2 (Feb. 1, 2003).
Bobo et al., "Nanoparticle-Based Medicines: A Review of FDA-Approved Materials and Clinical Trials to Date", Pharmaceutical Research, pp. 2373-2387, vol. 33 (2016).
Bojkova et al., "Proteomics of SARS-CoV-2-infected host cells reveals therapy targets", Nature, pp. 469-472, vol. 583 (Jul. 16, 2020).
Boley et al., "Enhanced mucosal immune responses and reduced viral load in the respiratory tract of ferrets to intranasal lipid nanoparticle-based SARS-CoV-2 proteins and mRNA vaccines", Journal of Nanobiotechnology, vol. 21, Art. 60 (Feb. 2023).
Bollström et al., "Measuring solvent barrier properties of paper", Measurement Science and Technology, vol. 23, No. 1 (2012).
Bondarenko et al., "Toxicity of Ag, CuO and ZnO nanoparticles to selected environmentally relevant test organisms and mammalian cells in vitro: a critical review", Archives of Toxicology, pp. 1181-1200, vol. 87 (2013).
Borenfreund et al., "Comparisons of two in vitro cytotoxicity assays-the neutral red (NR) and tetrazolium MTT tests", Toxicol. In Vitro, vol. 2(1), pp. 1-6 (1988).
Boretti et al., "Zinc role in Covid-19 disease and prevention", Vacunas, doi: 10.1016/j.vacun.2021.08.003. (Available online Sep. 7, 2021.
Borra et al., "A simple method to measure cell viability in proliferation and cytotoxicity assays", Braz. Oral Res., vol. 23(3), pp. 255-262 (2009).
Borzenkov et al., "Fabrication of Inkjet-Printed Gold Nanostars Patterns with Photothermal Properties on Paper Substrate", ACS Applied Materials & Interfaces, pp. 9909-9916, vol. 8 (Mar. 31, 2016).
Borzenkov et al., "Photothermal effect of gold nanostars patterns inkjet-printed on coated paper substrates with different permeability", Beilstein Journal of Nanotechnology, pp. 1480-1485, vol. 7 (2016).
Bounous et al., "Comparison of MTT colorimetric assay and tritiated thymidine uptake for lymphocyte proliferation assays using chicken splenocytes", Avian Dis., vol. 36(4), pp. 1022-1027 (1992).
Bowe et al., "Acute and postacute sequelae associated with SARS-CoV-2 reinfection", Nature Medicine, vol. 28(11), pp. 2398-2405 (Nov. 2022).
Bowen, "Particle Size Distribution Measurement from Millimeters to Nanometers and from Rods to Platelets", Journal of Dispersion Science and Technology, pp. 631-662, vol. 23, No. 5 (Jan. 1, 2022).
Boyle et al., "Major histocompatibility complex class I-restricted alloreactive CD4 + T cells", Immunology, pp. 54-63, vol. 112, Issue 1 (2004).
Brandenburg et al., "G protein variation in respiratory syncytial virus group A does not correlate with clinical severity", Journal of Clinical Microbiology, pp. 3849-3852, vol. 38, Issue 10 (Oct. 1, 2000).
Brar et al., "Engineered nanoparticles in wastewater and wastewater sludge—Evidence and impacts", Waste Management, pp. 504-520, vol. 30, Issue 3 (Mar. 2010).
Braun et al., "Presence of SARS-CoV-2-reactive T cells in COVID-19 patients and healthy donors", medRxiv, doi: https://doi.org/10.1101/2020.04.17.20061440 (Posted Apr. 22, 2020).
Bray et al., "Global cancer statistics 2018: GLOBOCAN estimates of incidence and mortality worldwide for 36 cancers in 185 countries", CA: A Cancer Journal for Clinicians, pp. 394-424, vol. 68, Issue 6 (Nov./Dec. 2018).
Bremer-Hoffmann et al., "Identification of regulatory needs for nanomedicines", Journal of Interdisciplinary Nanomedicine, pp. 4-15, vol. 3, Issue 1 (Apr. 2018).

(56) References Cited

OTHER PUBLICATIONS

Brevet et al., "Mannose-targeted mesoporous silica nanoparticles for photodynamic therapy", Chemical Communications, pp. 1475-1477, vol. 12 (Mar. 28, 2009).
Brinker et al., "Sol-Gel Science: The Physics and Chemistry of Sol-Gel Processing", Academic Press (1990).
Brister et al., "NCBI Viral Genomes Resource", Nucleic Acids Research, pp. D571-D577, vol. 43, Database issue (Jan. 2015).
Brocklyn, "Regulation of cancer cell migration and invasion by sphingosine-1-phosphate", World Journal of Biological Chemistry, pp. 307-312, vol. 1, Issue 10 (Oct. 26, 2010).
Broggi et al., "Type III interferons disrupt the lung epithelial barrier upon viral recognition", Science, 2pgs. 706-712, vol. 369 (Aug. 7, 2020).
Brouwer et al., "Two-component spike nanoparticle vaccine protects macaques from SARS-CoV-2 infection", Cell, vol. 184(5), pp. 1188-1200 (Mar. 2021).
Broxmeyer, L., "Is cancer just an incurable infectious disease?", Medical Hypotheses, pp. 986-996, vol. 63, Issue 6 (2004).
Bruun et al., "Engineering a Rugged Nanoscaffold to Enhance Plug-and-Display Vaccination", ACS Nano, pp. 8855-8866, vol. 12 (2018).
Bu et al., "Structural basis for the Receptor Binding Specificity of Norwalk Virus", Journal of Virology, pp. 5340-5347, vol. 82, Issue 11 (Jun. 1, 2008) Virol, 2008, 82(11):5340-5347. doi:10.1128/JVI.00135-08.
Buffin et al., "Influenza A and B virus-like particles produced in mammalian cells are highly immunogenic and induce functional antibodies", Vaccine, pp. 6857-6867, vol. 37, Issue 46 (Oct. 31, 2019).
Bunyavanich et al., "Nasal Gene Expression of Angiotensin-Converting Enzyme 2 in Children and Adults", JAMA, pp. 2427-2429, vol. 323, No. 23 (Jun. 16, 2020).
Bushman et al., "Population impact of SARS-CoV-2 variants with enhanced transmissibility and/or partial immune escape", pp. 6229-6242, vol. 184, Issue 26 (Dec. 22, 2021).
Butterfield, "Cancer vaccines", BMJ, doi: 10.1136/bmj.h988 (Published online Apr. 22, 2015).
Cahn et al., "Biomaterials for intranasal and inhaled vaccine delivery", Nature Reviews Bioengineering, vol. 1(2), pp. 83-84 (Jan. 2023).
Cai et al., "Charged nanoparticles as protein delivery systems: a feasibility study using lysozyme as model protein", European Journal of Pharmaceutics and Biopharmaceutics, vol. 69(1), pp. 31-42 (2008).
Callaway, "Coronavirus Vaccine Trials Have Delivered Their First results—But Their Promise Is Still Unclear", Nature, pp. 363-364, vol. 581 (May 28, 2020).
Callaway, The Mutation That Helps Delta Spread Like Wildfire, Nature, pp. 472-473, vol. 596 (Aug. 26, 2021).
Calvo et al., "Novel hydrophilic chitosan-polyethylene oxide nanoparticles as protein carriers", Journal of Applied Polymer Science, vol. 63(1), pp. 125-132 (1997).
Campos et al., "Technological stability of solid lipid nanoparticles loaded with phenolic compounds: Drying process and stability along storage", Journal of Food Engineering, vol. 196, pp. 1-10 (2017).
Cánepa et al., "Development of a drug delivery system based on chitosan nanoparticles for oral administration of interferon-α", Biomacromolecules, vol. 18(10), pp. 3302-3309 (2017).
Cao et al., "Computer-aided nanotoxicology: risk assessment of metal oxide nanoparticles via nano-QSAR", Green Chem., vol. 22(11), pp. 3512-3521 (Apr. 2020).
Cao et al., "Microfluidic manufacturing of SN-38-loaded polymer nanoparticles with shear processing control of drug delivery properties", Molecular Pharmaceutics, vol. 16(1), pp. 96-107 (2019).
Cao et al., "Omicron escapes the majority of existing SARS-CoV-2 neutralizing antibodies", Nature, vol. 602(7898), pp. 657-663 (Dec. 2021).
Capretto et al., "Design, production and optimization of solid lipid microparticles (SLM) by a coaxial microfluidic device", Journal of Controlled Release, vol. 160(3), pp. 409-417 (2012).
Capretto et al., "Microfluidic and lab-on-a-chip preparation routes for organic nanoparticles and vesicular systems for nanomedicine applications", Advanced Drug Delivery Reviews, vol. 65(11-12), pp. 1496-1532 (2013).
Carcione et al., "A Simulation of a COVID-19 Epidemic Based on a Deterministic SEIR Model", Frontiers in Public Health, pp. 1-13, vol. 8, Article 230 (May 2020).
Cardona et al., "Current challenges in open-source bioimage informatics", Nature Methods, pp. 661-665, vol. 9 (2012).
Carlsson et al., "Indications that Stockholm has reached herd immunity, given limited restrictions, against several variants of SARS-CoV-2", medRxiv (Posted Jul. 13, 2021) doi: https://doi.org/10.1101/2021.07.07.21260167.
Carmeliet, "VEGF as a key mediator of angiogenesis in cancer", Oncology, pp. 4-10, vol. 69 Suppl. 3 (Nov. 2005).
Carpenter et al., "A call for bioimaging software usability", Nature Methods, pp. 666-670, vol. 9, Issue 7 (Jun. 28, 2012).
Carpino et al., "Comparison of the effects of 5- and 6-HOAt on model peptide coupling reactions relative to the cases for the 4- and 7-Isomers", Organic Letters, pp. 2253-2256, vol. 2, No. 15 (Jul. 27, 2000).
Carrilho et al., "Paper Microzone Plates", Analytical Chemistry, pp. 5990-5998, vol. 81, No. 20 (Jul. 2, 2009).
Carrillo-Conde et al., "Mannose-Functionalized "Pathogen-like" Polyanhydride Nanoparticles Target C-Type Lectin Receptors on Dendritic Cells", Molecular Pharmaceutics, pp. 1877-1886, vol. 8, Issue 5 (Sep. 1, 2011).
Caruana et al., "Diagnostic strategies for SARS-CoV-2 infection and interpretation of microbiological results", Clinical Microbiology and Infection, pp. 1178-1182, vol. 26, Issue 9 (Sep. 1, 2020).
Caruso et al., "Interrelated Mechanism by Which the Methide Quinone Celastrol, Obtained from the Roots of Tripterygium wilfordii, Inhibits Main Protease 3CLpro of COVID-19 and Acts as Superoxide Radical Scavenger", in 20 pages, vol. 21, Issue 23, 9266 (Dec. 1, 2020).
Casalino et al., "Shielding and Beyond: The Roles of Glycans in SARS-CoV-2 Spike Protein", Version 1. bioRxiv, Preprint, doi: 10.1101/2020.06.11.146522 (Jun. 11, 2020).
Cascão et al., "Celastrol: A Spectrum of Treatment Opportunities in Chronic Diseases", Frontiers in Medicine, pp. 1-18, vol. 4, Article 69 (Jun. 2017).
Cassano et al., "Comparing the CORAL and random forest approaches for modelling the in vitro cytotoxicity of silica nanomaterials", Altern. Lab. Anim., vol. 44(6), pp. 533-556 (2016).
Castedo et al., "Cell death by mitotic catastrophe: A molecular definition", Oncogene, pp. 2825-2837, vol. 23 (2004).
Castro et al., "Chitosan/poly (γ-glutamic acid) nanoparticles incorporating IFN-γ for immune response modulation in the context of colorectal cancer", Biomaterials Science, vol. 7(8), pp. 3386-3403 (Jun. 2019).
Cavalli et al., "Sterilization and freeze-drying of drug-free and drug-loaded solid lipid nanoparticles", International Journal of Pharmaceutics, vol. 148(1), pp. 47-54 (1997).
Cerdá et al., "Development of siRNA and Budesonide Dual-Loaded Hybrid Lipid-Polymer Nanoparticles by Microfluidics Technology as a Platform for Dual Drug Delivery to Macrophages: An in Vitro Mechanistic Study", Advanced Therapeutics, Article 2300048 (May 2023).
Chaiet et al., "The properties of streptavidin, a biotin-binding protein produced by Streptomycetes", Archives of Biochemistry and Biophysics, vol. 106 (1964).
Chaikittisilp et al., "Material evolution with nanotechnology, nanoarchitectonics, and materials informatics: what will be the next paradigm shift in nanoporous materials?", Adv. Mater., vol. 34(7), 2107212 (Oct. 2021).
Chambers et al., "Dissemination and growth of cancer cells in metastatic sites", Nature Reviews Cancer, pp. 563-572, vol. 2, Issue 8 (Aug. 2002).

(56) References Cited

OTHER PUBLICATIONS

Chan et al., "Stepwise ligand-induced self-assembly for facile fabrication of nanodiamond-gold nanoparticle dimers via noncovalent biotin-streptavidin interactions", Nano Letters, vol. 19(3), pp. 2020-2026 (2019).

Chandler et al., "SARS-CoV-2 exposure in wild white-tailed deer (Odocoileus virginianus)", Proceedings of the National Academy of Sciences of the United States of America, in 3 pages, vol. 118, No. 47 (2021).

Chang et al., "Co-axial capillaries microfluidic device for synthesizing size-and morphology-controlled polymer core-polymer shell particles", Lab on a Chip, vol. 9(20), pp. 3007-3011 (2009).

Chang et al., "Nanoparticle composite TPNT1 is effective against SARS-CoV-2 and influenza viruses", Scientific Reports, in 13 pages, vol. 11, Article No. 8692 (2021).

Chang et al., "A newly engineered A549 cell line expressing ACE2 and TMPRSS2 is highly permissive to SARS-CoV-2, including the Delta and Omicron variants", Viruses, vol. 14(7), 1369 (Jun. 2022).

Chappell et al., "Safety and immunogenicity of an MF59-adjuvanted spike glycoprotein-clamp vaccine for SARS-CoV-2: a randomised, double-blind, placebo-controlled, phase 1 trial", The Lancet Infectious Diseases, vol. 21(10), pp. 1383-1394 (Apr. 2021).

Charest et al., "Fabrication of substrates with defined mechanical properties and topological features for the study of cell migration" Macro-Molecular Bioscience, pp. 12-20, vol. 2 (2012).

Chatterjee et al., "Nanoparticle-mediated hyperthermia in cancer therapy", Therapeutic Delivery, pp. 1001-1014, 2(8) (2011).

Chauhan et al., "Nanotechnology for COVID-19: therapeutics and vaccine research", ACS Nano, vol. 14(7), pp. 7760-7782 (Jun. 2020).

Chavda et al., "Inhalable vaccines: can they help control pandemics?", Vaccines, vol. 10(8), 1309 (Aug. 2022).

Chavda et al., "Intranasal vaccines for SARS-CoV-2: From challenges to potential in COVID-19 management", Drug Discovery Today, vol. 26(11), pp. 2619-2636 (Nov. 2021).

Checa et al., "Reactive oxygen species: Drivers of physiological and pathological processes", J. Inflammation Res., vol. 13, pp. 1057-1073 (Aug. 2020).

Chen et al., "Acute toxicological effects of copper nanoparticles in vivo", Toxicology Letters, pp. 109-120, vol. 163, Issue 2 (May 25, 2006).

Chen et al., "Assembly of fluorescent polymer nanoparticles using different microfluidic mixers", Langmuir, vol. 38(26), pp. 7945-7955 (Jun. 2022).

Chen et al., "Biosafety in the preparation and processing of cytology specimens with potential coronavirus (COVID-19) infection", Cancer Cytopathology, pp. 309-316, doi: 10.1002/cncy.22280 (May 2020).

Chen et al., "Clinical characteristics of 113 deceased patients with coronavirus disease 2019: retrospective study", BMJ, vol. 368 (Mar. 2020).

Chen et al., "Computational prediction of the effect of amino acid changes on the binding affinity between SARS-CoV-2 spike RBD and human ACE2", Proceedings of the National Academy of Sciences, vol. 118(42), e2106480118 (Sep. 2021).

Chen et al., "Containing COVID-19 Among 627,386 Persons in Contact With the Diamond Princess Cruise Ship Passengers Who Disembarked in Taiwan: Big Data Analytics", Journal of Medical Internet Research, e19540, vol. 22, No. 5 (2020).

Chen et al., "Crystal Structure of the Receptor-Binding Domain from Newly Emerged Middle East Respiratory Syndrome Coronavirus", Journal of Virology, pp. 10777-10783, vol. 87, No. 19, (Oct. 2013).

Chen et al., "Development and Challenges of Antimicrobial Peptides for Therapeutic Applications", Antibiotics (Basel), in 20 pages, vol. 9, Issue 1 (Jan. 13, 2020).

Chen et al., "Development of lipid nanoparticle formulations of siRNA for hepatocyte gene silencing following subcutaneous administration", Journal of Controlled Release, vol. 196, pp. 106-112 (2014).

Chen et al., "Development of receptor binding domain (RBD)-conjugated nanoparticle vaccines with broad neutralization against SARS-CoV-2 delta and other variants", Advanced Science, vol. 9(11), 2105378 (Feb. 2022).

Chen et al., "Emerging coronaviruses: Genome structure, replication, and pathogenesis", Journal of Medical Virology, pp. 418-423, vol. 92 (2020).

Chen et al., "Establishment of pseudovirus infection mouse models for in vivo pharmacodynamics evaluation of filovirus entry inhibitors", Acta Pharmaceutica Sinica B, vol. 8(2), pp. 200-208 (2018).

Chen et al., "Inkjet Printed Conductive Tracks for Printed Electronics", ECS Journal of Solid State Science and Technology, pp. P3026-3033, vol. 4 (2015).

Chen et al., "Lipid nanoparticle-assisted miR29a delivery based on core-shell nanofibers improvestendon healing by cross-regulation of the immune response and matrix remodeling", Biomaterials, vol. 291, 121888 (Nov. 2022).

Chen et al., "mRNA Vaccines Against SARS-CoV-2 Variants Delivered by Lipid Nanoparticles Based on Novel lonizable Lipids", Advanced Functional Materials, vol. 32(39), 2204692 (Jul. 2022).

Chen et al., "Nanotechnology-based mRNA vaccines", Nat. Rev. Methods Primers, vol. 3(1), 63 (Aug. 2023).

Chen et al., "Physical and functional interaction between the α-and γ-secretases: a new model of regulated intramembrane proteolysis", Journal of Cell Biology, vol. 211(6), pp. 1157-1176 (2015).

Chen et al., "Probing the Dynamics of Doxorubicin-DNA Intercalation during the Initial Activation of Apoptosis by Fluorescence Lifetime Imaging Microscopy (Flim)", PLOS One, E44947, vol. 7, Issue 9 (Sep. 2012) in 8 pages, www.plosone.org.

Chen et al., "Rapid discovery of potent siRNA-containing lipid nanoparticles enabled by controlled microfluidic formulation", Journal of the American Chemical Society, vol. 134(16), pp. 6948-6951 (2012).

Chen et al., "Role of tannic acid against SARS-CoV-2 cell entry by targeting the interface region between S-protein-RBD and human ACE2", Frontiers in Pharmacology, vol. 13, 940628 (Aug. 2022).

Chen et al., "Scalable biomimetic SARS-CoV-2 nanovaccines with robust protective immune responses", Signal Transduction and Targeted Therapy, vol. 7(1), 96 (Mar. 2022).

Chen et al., "Shark nanobodies with potent SARS-CoV-2 neutralizing activity and broad sarbecovirus reactivity", Nature Communications, vol. 14(1), 580 (Feb. 2023).

Chen et al., "Sustained Delivery of SARS-CoV-2 RBD Subunit Vaccine Using a High Affinity Injectable Hydrogel Scaffold", Advanced Healthcare Materials, vol. 11(2), 2101714 (Nov. 2021).

Chen et al., "Synthetic virus-like particles prepared via protein corona formation enable effective vaccination in an avian model of coronavirus infection", Biomaterials, pp. 111-118, vol. 106 (Nov. 2016).

Chen et al., "Titanium dioxide nanoparticles induce emphysema-like lung injury in mice", The Faseb Journal, pp. 2393-2395, vol. 20 Issue 13 (2006).

Chen et al., "Treating cancer stem cells and cancer metastasis using glucose-coated gold nanoparticles", International Journal of Nanomedicine, pp. 2065-2077, vol. 10 (2015).

Cheng et al., "A pH-Responsive Cluster Metal-Organic Framework Nanoparticle for Enhanced Tumor Accumulation and Antitumor Effect", Advanced Materials, vol. 34(42), 2203915 (Aug. 2022).

Cheng et al., "Probabilistic risk assessment of gold nanoparticles after intravenous administration by integrating in vitro and in vivo toxicity with physiologically based pharmacokinetic modeling", Nanotoxicology, vol. 12(5), pp. 453-469 (2018).

Chiba et al., "Multivalent nanoparticle-based vaccines protect hamsters against SARS-CoV-2 after a single immunization", Communications Biology, vol. 4(1), 597 (May 2021).

Chilkoti et al., "Molecular origins of the slow streptavidin-biotin dissociation kinetics", Journal of the American Chemical Society, vol. 117(43), pp. 10622-10628 (1995).

Chivers et al., "A streptavidin variant with slower biotin dissociation and increased mechanostability", Nature Methods, vol. 7(5), pp. 391-393 (2010).

(56) References Cited

OTHER PUBLICATIONS

Chivers et al., "How the biotin-streptavidin interaction was made even stronger: investigation via crystallography and a chimaeric tetramer", Biochemical Journal, vol. 435(1), pp. 55-63 (2011).
Cho et al., "A bioluminescent cytotoxicity assay for assessment of membrane integrity using a proteolytic biomarker", Toxicol. In Vitro, vol. 22(4), pp. 1099-1106 (2008).
Choi et al., "Deep tumor penetration of doxorubicin-loaded glycol chitosan nanoparticles using high-intensity focused ultrasound", Pharmaceutics, vol. 12(10), 974 (Oct. 2020).
Choquet et al., "Ports closed to cruise ships in the context of COVID-19: What choices are there for coastal states?", Annals of Tourism Research, in 10 pages, vol. 86 (20021).
Chow et al., "Induction of heat shock proteins in differentiated human and rodent neurons by celastrol", Cell Stress & Chaperones, pp. 237-244, vol. 12, Issue 3 (2007).
Chowdhury et al., "Nanoparticles as an effective drug delivery system in COVID-19", Biomedicine & Pharmacotherapy, vol. 143 (Sep. 2021).
Chowell et al., "TCR contact residue hydrophobicity is a hallmark of immunogenic CD8+ T cell epitopes", The Proceedings of the National Academy of Sciences, pp. E1754-E1762, vol. 112, Issue 14 (Mar. 23, 2015).
Chu et al., "Physical distancing, face masks, and eye protection to prevent person-to-person transmission of SARS-CoV-2 and COVID-19: a systematic review and meta-analysis", The Lancet, pp. 1973-1987, vol. 395, Issue 10242 (Jun. 27, 2020.
Chu et al., "Respiratory viruses and virus-like particle vaccine development: How far have we advanced?", Viruses, vol. 15(2), 392 (Jan. 2023).
Chung et al., "COVID-19 vaccine frontrunners and their nanotechnology design", ACS Nano, vol. 14(10), pp. 12522-12537 (Oct. 2020).
Chung et al., "COVID-19 vaccines: The status and perspectives in delivery points of view", Advanced Drug Delivery Reviews, vol. 170 (Dec. 2020).
Chung et al., "The effect of surface charge on the uptake and biological function of mesoporous silica nanoparticles in 3T3-L1 cells and human mesenchymal stem cells", Biomaterials, pp. 2959-2966, vol. 28, Issue 19 (Jul. 2007).
Chung et al., "Viral nanoparticles for drug delivery, imaging, immunotherapy, and theranostic applications", Adv. Drug Delivery Rev., vol. 156, pp. 214-235 (Jun. 2020).
Clark et al., "Thyroid cancer: the case for total thyroidectomy", European Journal of Cancer, International Symposium on Controversies in the Management of Differentiated Thyroid Cancer, vol. 24, Issue 2, pp. 305-313 (Feb. 1, 1988).
Clementino et al., "The nasal delivery of nanoencapsulated statins—an approach for brain delivery", International Journal of Nanomedicine, vol. 11, pp. 6575-6590 (2016).
Codreanu et al., "Successful Control of an Onboard COVID-19 Outbreak Using the Cruise Ship as a Quarantine Facility, Western Australia, Australia", Emerging Infectious Diseases, pp. 1279-1287, vol. 27, No. 5 (May 2021).
Cohen et al., "Influenza A penetrates host mucus by cleaving sialic acids with neuraminidase", Virology Journal, in 13 pages, vol. 10:321 (2013).
Cohen et al., "Mosaic nanoparticles elicit cross-reactive immune responses to zoonotic coronaviruses in mice", Science, pp. 735-741, vol. 371, Issue 6530 (Jan. 12, 2021).
Cohen et al., "Mosaic RBD nanoparticles protect against challenge by diverse sarbecoviruses in animal models", Science, vol. 377(6606), eabq0839 (Aug. 2022).
Colleton et al., "Primary Human Immunodeficiency Virus Type 1-Specific CD8+ T-Cell Responses Induced by Myeloid Dendritic Cells", Journal of Virology, pp. 6288-6299, vol. 83, No. 12 (Jun. 2009).
Collins et al., "High throughput toxicity screening and intracellular detection of nanomaterials", Wiley Interdiscip. Rev. Nanomed. Nanobiotechnol., vol. 9(1), e1413 (2016).
Collins et al., "The comet assay: topical issues", Mutagenesis, vol. 23(3), pp. 143-151 (2008).
Collins et al., "The comet assay: what can it really tell US?", Mutat Res./Fundamental and Molecular Mechanisms of Mutagenesis, vol. 375(2), pp. 183-193 (1997).
Colson et al., "Culture and identification of a "Deltamicron" SARS-CoV-2 in a three cases cluster in southern France", in 26 pages, medRxiv, doi: https://doi.org/10.1101/2022.03.03.22271812 (2022).
Concu et al., "Probing the toxicity of nanoparticles: a unified in silico machine learning model based on perturbation theory", Nanotoxicology, vol. 11(7), pp. 891-906 (2017).
Condor et al., "Generation of SARS-CoV-2 spike pseudotyped virus for viral entry and neutralization assays: a 1-week protocol", Frontiers in Cardiovascular Medicine, vol. 7, 618651 (Jan. 2021).
Cooper, "The Development and Causes of Cancer", The Cell: A Molecular Approach, 2nd edition, Chapter 15, Sunderland (MA): Sinauer Associates Publisher (2000).
Copple et al., "Chemical tuning enhances both potency toward nrf2 and in vitro therapeutic index of triterpenoids", Toxicological Sciences, pp. 462-469, vol. 140, Issue 2 (Aug. 2014).
Corbett et al., "Immune Correlates of Protection by mRNA-1273 Immunization against SARS-CoV-2 Infection in Nonhuman Primates", bioRxiv., doi: https://doi.org/10.1101/2021.04.20.440647 (Posted Apr. 23, 2021).
Costa et al., "All-in-one microfluidic assembly of insulin-loaded pH-responsive nano-in-microparticles for oral insulin delivery", Biomaterials Science, vol. 8(12), pp. 3270-3277 (May 2020).
Costa et al., "Intranasal delivery of nanostructured lipid carriers, solid lipid nanoparticles and nanoemulsions: A current overview of in vivo studies", Acta Pharmaceutica Sinica B, vol. 11(4), pp. 925-940 (Mar. 2021).
Costa et al., "Modeling and comparison of dissolution profiles", European Journal of Pharmaceutical Sciences, pp. 123-133, vol. 13, Issue, Issue 2 (May 2001).
Costa et al., "One-step microfluidics production of enzyme-loaded liposomes for the treatment of inflammatory diseases", Colloids and Surfaces B: Biointerfaces, vol. 199, 111556 (Mar. 2021).
Cotto et al., "HSF1 granules: a novel stress-induced nuclear compartment of human cells", Journal of Cell Science, pp. 2925-2934, vol. 110, Issue 23 (Dec. 1997).
Covián et al., "BCG-Induced Cross-Protection and Development of Trained Immunity: Implication for Vaccine Design", Frontiers Immunology, Article 2806, vol. 10 (Nov. 2019).
Covid-19 Mental Disorders Collaborators, "Global prevalence and burden of depressive and anxiety disorders in 204 countries and territories in 2020 due to the Covid-19 pandemic", Lancet, vol. 398 (10312), pp. 6-12 (Nov. 2021).
Cox et al., "Application of high-throughput screening techniques to drug discovery", Prog. Med. Chem., vol. 37, pp. 83-133 (2000).
Crookes-Goodson et al., "Bio-directed synthesis and assembly of nanomaterials", Chemical Society Reviews, pp. 2403-2412, vol. 37 (2008).
Cross et al., "Who funded the research behind the Oxford-AstraZeneca COVID-19 vaccine?", BMJ Global Health, in 11 pgs., vol. 6 (Dec. 22, 2021).
Crux et al., "Human Leukocyte Antigen (HLA) and Immune Regulation: How do Classical and Non-Classical HLA Alleles Modulate Immune Response to Human Immunodeficiency Virus and Hepatitis C Virus Infections?", Frontiers in Immunology, Article 832 in 26 pages (Published Jul. 18, 2017).
Cruz-Cardenas et al., "A pseudovirus-based platform to measure neutralizing antibodies in Mexico using SARS-CoV-2 as proof-of-concept", Scientific Reports, vol. 12(1), 17966 (Oct. 2022).
Cui et al., "Development of a high-throughput platform for screening lipid nanoparticles for mRNA delivery", Nanoscale, vol. 14(4), pp. 1480-1491 (Jan. 2022).
Cui et al., "Mechanistic studies of an automated lipid nanoparticle reveal critical pharmaceutical properties associated with enhanced mRNA functional delivery in vitro and in vivo", Small, vol. 18(9), 2105832 (Dec. 2021).
Cui et al., "Super-soft hydrogel particles with tunable elasticity in a microfluidic blood capillary model", Advanced Materials, vol. 26(43), pp. 7295-7299 (2014).

(56) References Cited

OTHER PUBLICATIONS

D'Aoust et al., "The production of hemagglutinin-based virus-like particles in plants: a rapid, efficient and safe response to pandemic influenza", Plant Biotechnology Journal, Review Article, vol. 8(5), pp. 607-619 (2010).
Da Silva, "An overview of the impact of COVID-19 in the cruise industry with considerations for Florida", Transportation Research Interdisciplinary Perspectives, in 7 pages, vol. 10, 100391 (2021).
Dahl, "Coronavirus (Covid-19) outbreak on the cruise ship Diamond Princess", International Maritime Health, pp. 5-8, vol. 71, No. 1 (2020).
Dai et al., "A novel vehicle for local protein delivery to the inner ear: injectable and biodegradable thermosensitive hydrogel loaded with PLGA nanoparticles", Drug Development and Industrial Pharmacy, vol. 44(1), pp. 89-98 (2018).
Dai et al., "Viral targets for vaccines against COVID-19", Nature Reviews Immunology, vol. 21(2), pp. 73-82 (Dec. 2020).
Dalibera et al., "SARS-CoV-2 Nanovaccine Composed of Microfluidic-Produced Gold Nanoparticles Induces Neutralizing Immune Responses", ACS Applied Nano Materials, vol. 6(24), pp. 22774-22783 (Dec. 2023).
Dammes et al., "Conformation-sensitive targeting of lipid nanoparticles for RNA therapeutics", Nature Nanotechnology, vol. 16(9), pp. 1030-1038 (Jun. 2021).
Damoiseaux et al., "No time to lose-high throughput screening to assess nanomaterial safety", Nanoscale, vol. 3(4), pp. 1345-1360 (2011).
Đanić et al., "PAMPA model of gliclazide permeability: The impact of probiotic bacteria and bile acids" European Journal of Pharmaceutical Sciences, vol. 158, 105668 (Mar. 2021).
Daniell et al., "Debulking SARS-CoV-2 in saliva using angiotensin converting enzyme 2 in chewing gum to decrease oral virus transmission and infection", Molecular Therapy, pp. 1966-1978, vol. 30, Issue 5 (May 4, 2022).
Daoudi et al., "Ultra-sensitive and fast optical detection of the spike protein of the SARS-CoV-2 using AgNPs/SiNWs nanohybrid based sensors", Surfaces and Interfaces, vol. 27, 101454 (Dec. 2021).
Das et al., "Andrographolide induces anti-SARS-CoV-2 response through host-directed mechanism: an in silico study", Future Virology, vol. 17(9), pp. 651-673 (Jul. 2022).
Das et al., "Chapter 4—Production and physicochemical characterization of nanocosmeceuticals", In: Das MK, editor, In Nanocosmeceuticals; Academic Press, pp. 95-138 (Aug. 2022).
Dash et al., "Hemodynamic flow improves rat hepatocyte morphology, function, and metabolic activity in vitro", Am. J. Physiol. Cell Physiol., vol. 304(11), pp. C1053-C1063 (2013).
Day et al., "Multidisciplinary Approaches Identify Compounds that Bind to Human ACE2 or SARS-CoV- 2 Spike Protein as Candidates to Block SARS-CoV-2-ACE2 Receptor Interactions", ASM Journals, mBio, e03681-20, vol. 12, No. 2 (Mar./Apr. 2021).
D'Costa et al., "Genotoxicity assays: The micronucleus test and the single-cell gel electrophoresis assay", In: Meena SN and Naik MM, editor, In Advances in Biological Science Research; Elsevier, pp. 291-301 (2019).
De Carlo et al., "Negative staining and cryo-negative staining of macromolecules and viruses for TEM", Micron, vol. 42(2), pp. 117-131 (2011).
De Clercq et al., "Approved Antiviral Drugs over the Past 50 Years", Clinical Microbiology Reviews, pp. 695-747, vol. 29, No. 3 (2016).
De Silva et al., "Micro-Patterning of Animal Cells on PDMS Substrates in the Presence of Serum without Use of Adhesion Inhibitors", Biomedical Microdevices, pp. 219-222, vol. 6 (2004).
De Thonel et al., "Implication of Heat Shock Factors in Tumorigenesis: Therapeutical Potential", Cancers, pp. 1158-1181, vol. 3 (2011).
Debus et al., "Optimized preparation of pDNA/poly (ethylene imine) polyplexes using a microfluidic system", Lab on a Chip, vol. 12(14), pp. 2498-2506 (2012).
Dee et al., "Human Rhinovirus Infection Blocks Severe Acute Respiratory Syndrome Coronavirus 2 Replication Within the Respiratory Epithelium: Implications for COVID-19 Epidemiology", The Journal of Infectious Diseases, pp. 31-38, vol. 224, Issue 1 (Jul. 2021).
Del Agua et al., "Conducting Polymer Scaffolds Based on Poly(3,4-ethylenedioxythiophene) and Xanthan Gum for Live-Cell Monitoring", ACS Omega, pp. 7424-7431, vol. 3 (2018).
Del Pozo-Rodríguez et al., "Short-and long-term stability study of lyophilized solid lipid nanoparticles for gene therapy", European Journal of Pharmaceutics and Biopharmaceutics, vol. 71(2), pp. 181-189 (2009).
Delaugerre et al., "Prevention of SARS-CoV-2 transmission during a large, live, indoor gathering (SPRING): a non-inferiority, randomised, controlled trial", The Lancet, Infectious Diseases, pp. 341-348, vol. 22 (Mar. 2022).
Denesyuk et al., "NBCZone: Universal three-dimensional construction of eleven amino acids near the catalytic nucleophile and base in the superfamily of (chymo)trypsin-like serine fold proteases", International Journal of Biological Macromolecules, pp. 399-411, vol. 153 (2020).
Deng et al., "Lipid nanoparticle-encapsulated mRNA antibody provides long-term protection against SARS-CoV-2 in mice and hamsters", Cell Research, vol. 32(4), pp. 375-382 (Feb. 2022).
Deng et al., "Rational Development of a Polysaccharide-Protein-Conjugated Nanoparticle Vaccine Against SARS-CoV-2 Variants and *Streptococcus pneumoniae*", Advanced Materials, vol. 34(21), 2200443 (Mar. 2022).
Denisenko et al., "Mitotic catastrophe and cancer drug resistance: A link that must to be broken", Drug Resistance Updates, pp. 1-12, vol. 24 (2016).
Depellegrin et al., "The effects of COVID-19 induced lockdown measures on maritime settings of a coastal region", Science of the Total Environment, 140123, in 8 pages, vol. 740 (2020).
Derda et al., "Paper-supported 3D cell culture for tissue-based bioassays", The Proceedings of the National Academy of Sciences, pp. 18457-18462, vol. 106, No. 44 (Nov. 3, 2009).
Desai et al., "Design considerations for mesoporous silica nanoparticulate systems in facilitating biomedical applications", Mesoporous Biomater, pp. 16-43, vol. 1 (2014).
Desai et al., "Preparation, characterization and protein loading of hexanoyl-modified chitosan nanoparticles", Drug Delivery, vol. 13(5), pp. 375-381 (2006).
Desai, "Challenges in Development of Nanoparticle-Based Therapeutics", The AAPS Journal, pp. 282-295, vol. 14, No. 2 (Jun. 2012).
Desai, "Mesoporous Silica Nanoparticles as Versatile Intracellular Drug Delivery Platform", Thesis, Physical Chemistry Pharmaceutical Sciences Laboratory, Åbo Akademi University, (2016).
Devaux et al., "ACE2 receptor polymorphism: Susceptibility to SARS-CoV-2, hypertension, multi-organ failure, and COVID-19 disease outcome", Journal of Microbiology, Immunology and Infection, pp. 425-435, vol. 53, Issue 3 (Jun. 2020).
Dhawan et al., "Toxicity assessment of nanomaterials: methods and challenges", Anal. Bioanal. Chem., vol. 398(2), pp. 589-605 (2010).
Dheyab et al., "Focused role of nanoparticles against COVID-19: Diagnosis and treatment", Photodiagnosis and Photodynamic Therapy, vol. 34, 102287 (Apr. 2021).
Di Iorio et al., "Weak multivalent binding of influenza hemagglutinin nanoparticles at a sialoglycan-functionalized supported lipid bilayer", ACS Nano, vol. 13(3), pp. 3413-3423 (2019).
Diamond et al., "The Challenges of Vaccine Development against a New Virus during a Pandemic", Cell Host & Microbe, pp. 699-703, vol. 27, Issue 5 (2020).
Diao et al., "Human kidney is a target for novel severe acute respiratory syndrome coronavirus 2 infection", Nature Communications, vol. 12(1), 2506 (May 2021).
Dickey et al., "Design of a stabilized RBD enables potently neutralizing SARS-CoV-2 single-component nanoparticle vaccines", Cell Reports, vol. 42(3), 112266 (Mar. 2023).
Ding et al., "A review of drug release mechanisms from nanocarrier systems", Materials Science and Engineering: C, vol. 76, pp. 1440-1453 (2017).

(56) References Cited

OTHER PUBLICATIONS

Ding et al., "RBC-hitchhiking chitosan nanoparticles loading methylprednisolone for lung-targeting delivery", Journal of Controlled Release, vol. 341, pp. 702-715 (Jan. 2022).
Ding et al., "VE607 stabilizes SARS-CoV-2 Spike in the "RBD-up" conformation and inhibits viral entry", iScience, vol. 25(7), 104528 (Jun. 2022).
Discher et al., "Tissues cells feel and respond to the stiffness of their substrate", Science, pp. 1139-1143, vol. 310, Issue 5751 (Nov. 18, 2005).
Doerfler, "Adenoviral Vector DNA- and SARS-CoV-2 mRNA-Based Covid-19 Vaccines: Possible Integration into the Human Genome—Are Adenoviral Genes Expressed in Vector-based Vaccines?", Virus Research, 198466 in 7 pages, vol. 302 (2021).
Döhla et al., "SARS-CoV-2 in environmental samples of quarantined households". medRxiv 2020.05.28.20114041; doi: https://doi.org/10.1101/2020.05.28.20114041 (2020).
Dolgin, "mRNA flu shots move into trials", Nature Reviews, Drug Discovery, pp. 801-803, vol. 20 (Nov. 2021).
Dolgin, "Publisher Correction: Treg engineers take aim at autoimmunity", Nature Biotechnology, p. 131, vol. 40 (Jan. 2022).
Domènech et al., "Cruise Passengers' Spatial Behaviour and Expenditure Levels at Destination", Tourism Planning & Development, pp. 17-36, vol. 17, No. 1 (2020).
Dong et al., "An interactive web-based dashboard to track COVID-19 in real time", The Lancet Infectious Diseases, pp. 533-534, vol. 20, Issue 5 (May 1, 2020).
Donno et al., "Nanomanufacturing through microfluidic-assisted nanoprecipitation: Advanced analytics and structure-activity relationships", International Journal of Pharmaceutics, vol. 534(1-2), pp. 97-107 (2017).
Donofrio et al., "A simplified SARS-CoV-2 pseudovirus neutralization assay", Vaccines, vol. 9(4), 389 (Apr. 2021).
Dooley et al., "Pooling analysis of scanning probe images", Surface Science, pp. 206-220, vol. 406, Issues 1-3 (May 31, 1998).
Dos Anjos et al., "Impact of crystallinity and crystal size of nanostructured carbonated hydroxyapatite on pre-osteoblast in vitro biocompatibility", J. Biomed. Mater. Res., Part A, vol. 107(9), pp. 1965-1976 (2019).
Dou et al., "Cellular uptake and transport characteristics of chitosan modified nanoparticles in Caco-2 cell monolayers", International Journal of Biological Macromolecules, vol. 138, pp. 791-799 (2019).
Dou et al., Overview of Proteasome Inhibitor-Based Anti-cancer Therapies: Perspective onBortezomib and Second Generation Proteasome Inhibitors versus Future Generation Inhibitors of Ubiquitin-Proteasome System, Current Cancer Drug Targets, pp. 517-536, vol. 14, Issue 6 (2014).
Drozdetskiy et al., "JPred4: a protein secondary structure prediction server", Nucleic Acids Research, pp. W389-W394, vol. 43, Issue W1 (Jul. 1, 2015).
Duan et al., "Immunostimulatory nanomedicines synergize with checkpoint blockade immunotherapy to eradicate colorectal tumors", Nature Communications, vol. 10(1), 1899 (2019).
Duan et al., "Nanoparticle approaches against SARS-CoV-2 infection", Current Opinion in Solid State and Materials Science, vol. 25(6), 100964 (Oct. 2021).
Duarte et al., "Microfluidic production of perfluorocarbon-alginate core-shell microparticles for ultrasound therapeutic applications", Langmuir, vol. 30(41), pp. 12391-12399 (2014).
Dubey et al., "Heat shock proteins: a therapeutic target worth to consider", Veterinary World, pp. 46-51, vol. 8 (2015).
Dubois et al., "Colorimetric Method for Determination of Sugars and Related Substances", Analytical Chemistry, pp. 350-356, vol. 28, Issue 3 (Mar. 1, 1956).
Dubrez et al., "IAP proteins as targets for drug development in oncology", Onco Targets and Therapy, pp. 1285-1304, vol. 6 (2013).
Dufort et al., "Nebulized gadolinium-based nanoparticles: a theranostic approach for lung tumor imaging and radiosensitization", Small, vol. 11(2), pp. 215-221 (2015).
Duineveld, "The stability of ink-jet printed lines of liquid with zero receding contact angle on a homogeneous substrate", Journal of Fluid Mechanics, pp. 175-200, vol. 477 (2003).
Dundas et al., "Streptavidin-biotin technology: improvements and innovations in chemical and biological applications", Applied Microbiology and Biotechnology, vol. 97, pp. 9343-9353 (2013).
Durocher et al., "High-level and high-throughput recombinant protein production by transienttransfection of suspension-growing human 293-EBNA1 cells", Nucleic Acids Research, page e9, vol. 30, No. 2 (Jan. 15, 2002).
Dusinska et al., "Immunotoxicity, genotoxicity and epigenetic toxicity of nanomaterials: New strategies for toxicity testing?", Food Chem. Toxicol., vol. 109(1), pp. 797-811 (2017).
Eckelman et al., "The human anti-apoptotic proteins cIAP1 and cIAP2 bind but do not inhibit caspases", The Journal of Biological Chemistry, Enzyme Catalysis and Regulation, pp. 3254-3260, vol. 281, Issue 6 (Feb. 2006).
Edel et al., "Microfluidic routes to the controlled production of nanoparticles", Chemical Communications, Communication, pp. 1136-1137 (2002).
Edwards et al., "Academic Research in the 21st Century: Maintaining Scientific Integrity in a Climate of Perverse Incentives and Hypercompetition", Environmental Engineering Science, pp. 51-61, vol. 34, No. 1 (2017).
Egbuna et al., "Toxicity of nanoparticles in biomedical application: nanotoxicology", J. Toxicol., vol. 2021, pp. 1-21 (Jul. 2021).
El-Faham et al., "Novel Proton Acceptor Immonium-Type Coupling Reagents: Application in Solution and Solid-Phase Peptide Synthesis", Organic Letters, pp. 4475-4477, vol. 9, Issue 22 (2007).
Elia et al., "Design of SARS-CoV-2 hFc-conjugated receptor-binding domain mRNA vaccine delivered via lipid nanoparticles", ACS Nano, vol. 15(6), pp. 9627-9637 (Jan. 2021).
Elia et al., "Lipid nanoparticle RBD-hFc mRNA vaccine protects hACE2 transgenic mice against a lethal SARS-CoV-2 infection", Nano Letters, vol. 21(11), pp. 4774-4779 (May 2021).
Eliceiri et al., "Biological imaging software tools", Nature Methods, pp. 697-710, vol. 9 (2012).
Elmore, "Apoptosis: a review of programmed cell death" Toxicologic Pathology, pp. 495-516, vol. 35, Issue 4 (2007).
Elnakat et al., "Distribution, functionality and gene regulation of folate receptor isoforms: implications in targeted therapy", Advanced Drug Delivery, pp. 1067-1084, vol. 56, Issue 8 (Apr. 29, 2004).
Emami et al., "Drying Technologies for the Stability and Bioavailability of Biopharmaceuticals", Pharmaceutics, vol. 10, 131 in 22 pages (2018).
Engelking, Larry R., "Chapter 6—Enzyme Kinetics" Editor: Larry R. Engelking, Textbook of Veterinary Physiological Chemistry (Third Edition), pp. 32-38 (2015) ISBN 9780123919090.
Eshbach et al., "Receptor-Mediated Endocytosis in the Proximal Tubule", Annual Review of Physiology, pp. 425-448, vol. 79 (2017).
Esparza et al., "High affinity nanobodies block SARS-CoV-2 spike receptor binding domain interaction with human angiotensin converting enzyme", Scientific Reports, vol. 10, Article No. 22370, in 13 pages (2020).
Esposito et al., "Chemotherapy against cancer during pregnancy: A systematic review on neonatal outcomes", Medicine, pp. 1-6, vol. 95, Issue 38 (2016).
Etienne-Manneville, "Actin and microtubules in cell motility: which one is in control?", Traffic, pp. 470-477, vol. 5, Issue 7 (Jul. 2004).
Evers et al., "State-of-the-art design and rapid-mixing production techniques of lipid nanoparticles for nucleic acid delivery", Small Methods, vol. 2(9), 1700375 (2018).
Falconnet et al., "Surface engineering approaches to micropattern surfaces for cell-based assays". Biomaterials, pp. 3044-3063, vol. 27, Issue 16 (Jun. 2006).
Fan et al., "Acute respiratory distress syndrome advances in diagnosis and treatment", The Journal of the American Medical Association, pp. 698-710, vol. 319, Issue 7 (2018).
Fan et al., "Exosomes-based particles as inhalable COVID-19 vaccines", Biomedical Technology, vol. 4, pp. 24-27 (Dec. 2023).

(56) References Cited

OTHER PUBLICATIONS

Fan et al., "Neutralizing monoclonal antibodies elicited by mosaic RBD nanoparticles bind conserved sarbecovirus epitopes", Immunity, vol. 55(12), pp. 2419-2435 (Dec. 2022).
Fang et al., "How many infections of COVID-19 there will be in the 'Diamond Princess'-Predicted by a virus transmission model based on the simulation of crowd flow". arXi, 10616 (2002).
Fantini et al., "Structural dynamics of SARS-CoV-2 variants: A health monitoring strategy for anticipating Covid-19 outbreaks", The Journal of Infection, pp. 197-206, vol. 83, Issue 2 (Aug. 2021).
Faraji et al., "Nanoparticles in cellular drug delivery", Bioorganic & Medicinal Chemistry, vol. 17(8), pp. 2950-2962 (2009).
Farokhzad et al., "Impact of Nanotechnology on Drug Delivery", ACS Nano, pp. 16-20, Vo. 3, Issue 1 (2009).
Faulkner, "Towards a framework for tourism disaster management", Tourism Management, pp. 135-147, vol. 22, Issue 2 (Apr. 2001).
Feikin et al., "Estimating the Percentage of a Population Infected with SARS-CoV-2 Using the Number of Reported Deaths: A Policy Planning Tool", Pathogens, 838, in 11 pages, vol. 9 (2020).
Fenech, "Cytokinesis-block micronucleus cytome assay", Nat. Protoc., vol. 2(5), pp. 1084-1104 (2007).
Feng et al., "COVID-19 with Different Severities: A Multicenter Study of Clinical Features", American Journal of Respiratory and Critical Care Medicine, pp. 130-1388, vol. 201, No. 11 (Jun. 1, 2020).
Feng et al., "Multi-Epitope Vaccine Design Using an Immunoinformatic Approach for SARS-CoV-2", Pathogens, in 16 pages, vol. 10, Issue 6 (2021).
Feng et al., "Receptors for Respiratory Syncytial Virus Infection and Host Factors Regulating the Life Cycle of Respiratory Syncytial Virus", Frontiers in Cellular and Infection Microbiology, vol. 12, Article 858629 (Feb. 2022).
Fenton et al., "Multidimensional scaling and tourism research", Annals of Tourism Research, pp. 236-254, vol. 15, Issue 2 (1988).
Ferhan et al.m, "Lipid nanoparticle technologies for nucleic acid delivery: A nanoarchitectonics perspective", Advanced Functional Materials, vol. 32(37), 2203669 (Jun. 2022).
Fernandez et al., "Myxobacterial depsipeptide chondramides interrupt SARS-CoV-2 entry by targeting its broad, cell tropic spike protein", Journal of Biomolecular Structure and Dynamics, vol. 40(22), pp. 12209-12220 (Aug. 2021).
Fernando et al., "Cellular uptake and cytotoxicity of varying aspect ratios of gold nanorods in HeLa cells", ACS Appl. Bio Mater., vol. 3(3), pp. 1374-1384 (Feb. 2020).
Figueroa et al., "Real time monitoring and quantification of reactive oxygen species in breast cancer cell line MCF-7 by 2', 7'-dichlorofluorescin diacetate (DCFDA) assay", J. Pharmacol. Toxicol. Methods, vol. 94(1), pp. 26-33 (2018).
Finzi, "Treatment of SARS-CoV-2 with high dose oral zinc salts: A report on four patients", International Journal of Infectious Diseases, pp. 307-309, vol. 99 (Oct. 1, 2020).
Firth et al., "Using a real-world network to model localized COVID-19 control strategies", Nature Medicine, pp. 1616-1622, vol. 26 (Oct. 2020).
Fischer et al., "In vitro cytotoxicity testing of polycations: influence of polymer structure on cell viability and hemolysis", Biomaterials, vol. 24(7), pp. 1121-1131 (2003).
Fisher et al., "Community and Close Contact Exposures Associated with COVID-19 AmongSymptomatic Adults ≥18 Years in 11 Outpatient Health Care Facilities United States, 2020", Morbidity and Mortality Weekly Report, pp. 1258-1264, vol. 69, No. 36 (Sep. 11, 2020).
Fjodorova et al., "The way to cover prediction for cytotoxicity for all existing nano-sized metal oxides by using neural network method", Nanotoxicology, vol. 11(4), pp. 475-483 (2017).
Fleri et al., "The Immune Epitope Database and Analysis Resource in Epitope Discovery and Synthetic Vaccine Design", Frontiers in Immunology, pp. 1-16., vol. 8, Article 278 (Mar. 2017).
Flora et al., "26—Medical Countermeasures-Chelation Therapy" Handbook of Arsenic Toxicology, pp. 589-626, ISBN: 978-0-12-418688-0, Academic Press (2015).
Florindo et al., "Immune-mediated approaches against COVID-19", Nature Nanotechnology, pp. 630-645, vol. 15 (2020).
Floyd et al., "Profiling risk perceptions of tourists", Annals of Tourism Research, pp. 1051-1054, vol. 31, No. 4 ref. 6 (2004).
Fodor-Kardos et al., "Sustained in vitro interferon-beta release and in vivo toxicity of PLGA and PEG-PLGA nanoparticles", RSC Advances, vol. 10(27), p. 15893-15900 (Apr. 2020).
Fontana et al., "Biohybrid vaccines for improved treatment of aggressive melanoma with checkpoint inhibitor", ACS Nano, vol. 13(6), pp. 6477-6490 (2019).
Fontana et al., "Microfluidics as a cutting-edge technique for drug delivery applications", Journal of Drug Delivery Science and Technology, vol. 34, pp. 76-87 (2016).
Fontana et al., "Multistaged nanovaccines based on porous silicon@ acetalated dextran@ cancer cell membrane for cancer immunotherapy", Advanced Materials, vol. 29(7), 1603239 (2017).
Fontana et al., "Nuts and bolts: microfluidics for the production of biomaterials", Advanced Materials Technologies, vol. 4(6), 1800611 (2019).
Fontana et al., "Production of pure drug nanocrystals and nano co-crystals by confinement methods", Advanced Drug Delivery Reviews, vol. 131, pp. 3-21 (2018).
Food and Drug Administration, "Estimating the maximum safe starting dose in initial clinical trials for therapeutics in adult healthy volunteers" (2005).
Forbes et al., "Rapid and scale-independent microfluidic manufacture of liposomes entrapping protein incorporating in-line purification and at-line size monitoring", International Journal of Pharmaceutics, vol. 556, pp. 68-81 (2019).
Forigua et al., "Recent advances in the design of microfluidic technologies for the manufacture of drug releasing particles", Journal of Controlled Release, vol. 333, pp. 258-268 (May 2021).
Fosgerau et al., "Peptide therapeutics: current status and future directions", Drug Discovery Today, pp. 122-128, vol. 20, Issue 1 (Jan. 2015).
Fourches et al., "Computer-aided design of carbon nanotubes with the desired bioactivity and safety profiles", Nanotoxicology, vol. 10(3), pp. 374-383 (2016).
Franchi et al., "The inflammasome: a caspase-1-activation platform that regulates immune responses and disease pathogenesis", Nature Immunology, pp. 241-247, vol. 10 (2009).
Franco et al., "Limits and prospects of the "incremental approach" and the European legislation onthe management of risks related to nanomaterials", Regulatory Toxicology and Pharmacology, pp. 171-183, vol. 48, Issue 2 (Jul. 2007).
Freitas et al., "Spray-drying of solid lipid nanoparticles (SLNTM)", European Journal of Pharmaceutics and Biopharmaceutics, vol. 46(2), pp. 145-151 (1998).
Frey et al., "Nanovaccines Displaying the Influenza Virus Hemagglutinin in an Inverted Orientation Elicit an Enhanced Stalk-Directed Antibody Response", Advanced Healthcare Materials, vol. 12(13), 2202729 (Jan. 2023).
Frimat et al., "Plasma stencilling methods for patterning", Analytical and Bioanalytical Chemistry, pp. 601-609, vol. 395 (2009).
Fröhlich, "The role of surface charge in cellular uptake and cytotoxicity of medical nanoparticles", International Journal of Nanomedicine, pp. 5577-5591, vol. 7 (2012).
Fu et al., "Mechanisms of nanotoxicity: Generation of reactive oxygen species", J. Food Drug Anal., vol. 22(1), pp. 64-75 (2014).
Fu et al., "Recent progress on metal-based nanomaterials: fabrications, optical properties, and applications in ultrafast photonics", Adv. Funct. Mater., vol. 31(49), 2107363 (Sep. 2021).
Fu et al., "Tagged extracellular vesicles with the RBD of the viral spike protein for delivery of antiviral agents against SARS-COV-2 infection", Journal of Controlled Release, vol. 335, pp. 584-595 (Jul. 2021).
Fu et al., "The absorption, distribution, excretion and toxicity of mesoporous silica nanoparticles in mice following different exposure routes", Biomaterials, pp. 2565-2575, vol. 34, Issue 10 (Mar. 2013).

(56) References Cited

OTHER PUBLICATIONS

Fubini et al., "Physico-chemical features of engineered nanoparticles relevant to their toxicity", Nanotoxicology, vol. 4(4), pp. 347-363 (2010).
Fuentes-Prior et al., "The protein structures that shape caspase activity, specificity, activation and inhibition", Biochemical Journal, pp. 201-232, vol. 384 (2004).
Fujiwara et al., "Anthracycline Antibiotics", Critical Reviews in Biotechnology, pp. 133-157, vol. 3, Issue 2 (1985).
Funke et al., "Natural killer cells in HIV-1 infection: a double-edged sword", AIDS Reviews, pp. 67-76, vol. 13, Issue 2 (Apr.-Jun. 2011).
Gabizon et al., "Prolonged circulation time and enhanced accumulation in malignant exudates of doxorubicin encapsulated in polyethylene-glycol coated liposomes", Cancer Res., vol. 54(4), pp. 987-992 (1994).
Gaebler et al., "Evolution of antibody immunity to SARS-CoV-2", Nature, vol. 591(7851), pp. 639-644 (Mar. 2021).
Gaikwad et al., "Antibody-Dependent Complement Responses toward SARS-CoV-2 Receptor-Binding Domain Immobilized on "Pseudovirus-like" Nanoparticles", ACS Nano, (May 4, 2022) acsnano.2c02794.
Gajewicz et al., "Addressing a bottle neck for regulation of nanomaterials: quantitative read-across (Nano-QRA) algorithm for cases when only limited data is available", Environ. Sci.: Nano, vol. 4(2), pp. 346-358 (2016).
Gajewicz et al., "Novel approach for efficient predictions properties of large pool of nanomaterials based on limited set of species: nano-read-across", Nanotechnology, vol. 26(1), 015701 (2014).
Gajewicz et al., "Towards understanding mechanisms governing cytotoxicity of metal oxides nanoparticles: Hints from nano-QSAR studies", Nanotoxicology, vol. 9(3), pp. 313-325 (2014).
Gajewicz, "Development of valuable predictive read-across models based on "real-life" (sparse) nanotoxicity data", Environ. Sci.: Nano, vol. 4(6), pp. 1389-1403 (2017).
Gale et al., "Hydrogel-Based Slow Release of a Receptor-Binding Domain Subunit Vaccine Elicits Neutralizing Antibody Responses Against SARS-CoV-2", Advanced Materials, vol. 33(51), 2104362 (Oct. 2021).
Gallo et al., "The central role of the nasal microenvironment in the transmission, modulation, and clinical progression of SARS-CoV-2 infection", Mucosal Immunology, pp. 305-316, vol. 14 (2021).
Galluzzi et al., "Molecular definitions of cell death subroutines: recommendations of the Nomenclature Committee on Cell Death 2012", Cell Death and Differentiation, pp. 107-120, vol. 19 (2012).
Galluzzi et al., "Non-apoptotic functions of apoptosis-regulatory proteins", EMBO Reports, pp. 322-330, vol. 13, No. 4 (2012).
Galm et al., "Antitumor Antibiotics: Bleomycin, Enediynes, and Mitomycin", Chemical Reviews, pp. 739-758, vol. 105, Issue 2 (2005).
Galvao et al., "Unexpected low-dose toxicity of the universal solvent DMSO", The FASEB Journal, pp. 1317-1330, vol. 28, Issue 3 (Mar. 2014).
Gao et al., "Ancestral SARS-CoV-2-specific T cells cross-recognize the Omicron variant", Nature Medicine, pp. 472-476, vol. 28 (Mar. 2022).
Gao et al., "Development of an inactivated vaccine candidate for SARS-CoV-2", Science, pp. 77-81, vol. 369 (2020).
Gao, G. F., "Science-based COVID-19 vaccine development", National Science Review, vol. 8(10), nwab193 (Nov. 2021).
Gary-Bobo et al., "Cancer therapy improvement with mesoporous silica nanoparticles combiningtargeting, drug delivery and PDT", International Journal of Pharmaceutics, pp. 509-515, vol. 423-Issue 2 (Feb. 28, 2012) 10.1016/j.ijpharm.2011.11.045.
Gatoo et al., "Physicochemical properties of nanomaterials: implication in associated toxic manifestations", BioMed Res. Int., vol. 2014, 498420 (2014).
Gaviria et al., "A network analysis of COVID-19 mRNA vaccine patents", Nature Biotechnology, pp. 546-548, vol. 39 (2021).
Ge et al., "Celastrol causes apoptosis and cell cycle arrest in rat glioma cells", Neurological Research, pp. 94-100, vol. 32, Issue 1: Neuromyology II (2010).
Ge et al., "Low-cost, abundant, binary sulfides as promising thermoelectric materials", Materials Today, pp. 227-239, vol. 19, Issue 4 (May 2016).
Geng et al., "Novel virus-like nanoparticle vaccine effectively protects animal model from SARS-CoV-2 infection", PLoS Pathogens, vol. 17(9), e1009897 (Sep. 2021).
Geng et al., "Thio-glucose bound gold nanoparticles enhance radio-cytotoxic targeting of ovarian cancer", Nanotechnology, 285101, vol. 22, No. 28 (2011).
George et al., "Use of a high-throughput screening approach coupled with in vivo zebrafish embryo screening to develop hazard ranking for engineered nanomaterials", ACS Nano, vol. 5(3), pp. 1805-1817 (2011).
Gerlowski et al., "Microvascular permeability of normal and neoplastic tissues", Microvascular Research, pp. 288-305, vol. 31, Issue 3 (May 1986).
Ghaffari et al., "Inhibition of H1N1 influenza virus infection by zinc oxide nanoparticles: another emerging application of nanomedicine", Journal of Biomedical Science, in 10 pages, 26:70 (2019) https://doi.org/10.1186/s12929-019-0563-4.
Gholizadeh et al., "Therapeutic and diagnostic applications of nanoparticles in the management of COVID-19: a comprehensive overview", Virology Journal, vol. 19(1), 206 (Dec. 2022).
Gialeli et al., "Roles of matrix metalloproteinases in cancer progression and their pharmacological targeting", The FEBS Journal, pp. 16-27, vol. 278, Issue 1 (Jan. 2011).
Giang et al., "Prodrug applications for targeted cancer therapy", The American Association of Pharmaceutical Scientists Journal, pp. 899-913, vol. 16, No. 5 (Sep. 2014).
Gil et al., "Nanopharmacy: Inorganic nanoscale devices as vectors and active compounds", Pharmacological Research, pp. 115-125, vol. 62, Issue 2 (Aug. 2010).
Gilleron et al., "Image-based analysis of lipid nanoparticle-mediated siRNA delivery, intracellular trafficking and endosomal escape", Nature Biotechnology, vol. 31(7), pp. 638-646 (2013).
Gilstrap et al., "Initiation, Continuation, or Withdrawal of Angiotensin-Converting Enzyme Inhibitors/Angiotensin Receptor Blockers and Outcomes in Patients Hospitalized With Heart Failure With Reduced Ejection Fraction", Journal of the American Heart Association,in 21 pages, vol. 6, Issue 2 (Feb. 2, 2017).
Ginex et al., "ost-directed FDA-approved drugs with antiviral activity against SARS-CoV-2 identified by hierarchical in silico/in vitro screening methods", Pharmaceuticals, vol. 14(4), 332 (Apr. 2021).
Giorello et al., "Microfluidic Platforms for the Production of Nanoparticles at Flow Rates Larger Than One Liter Per Hour", Advanced Materials Technologies, vol. 7(9), 2101588 (Mar. 2022).
Giri et al., "Targeted novel surface-modified nanoparticles for interferon delivery for the treatment of hepatitis B", Acta Biochim Biophys Sin, vol. 43(11), 877-883 (2011).
Godbey et al., "Size matters: molecular weight affects the efficiency of poly(ethylenimine) as a gene delivery vehicle", Journal of Biomedical Materials Research, pp. 268-275, vol. 45, Issue 3 (Jun. 5, 1999).
Goel et al., "Synthesis and biomedcal application of copper sulfide nanoparticles: from sensors to theranostics", Small, pp. 631-645, vol. 10, Issue 4 (Feb. 26, 2014).
Goel et al., "VEGF targets the tumour cell", Nature Reviews Cancer, pp. 871-882, vol. 13 (2013).
Gole et al., "Biotin-streptavidin-induced aggregation of gold nanorods: tuning rod-rod orientation", Langmuir, vol. 21(23), pp. 10756-10762 (2005).
Golstein et al., "Cell death by necrosis: towards a molecular definition", Trends in Biochemical Sciences, pp. 37-43, vol. 32, Issue 1 (Jan. 1, 2007).
Gong et al., "Nanomaterials for T-cell cancer immunotherapy", Nat. Nanotechnol., vol. 16(1), pp. 25-36 (Jan. 2021).
Goñi, "The basic structure and dynamics of cell membranes: An update of the Singer-Nicolson model" Biochimica et Biophysica Acta, pp. 1467-1476, vol. 1838, Issue 6 (Jun. 2014).
González et al., "Extremely high thermal stability of streptavidin and avidin upon biotin binding", Biomolecular Engineering, vol. 16(1-4), pp. 67-72 (1999).

(56) References Cited

OTHER PUBLICATIONS

Gonzalez et al., "Genotoxicity of engineered nanomaterials: a critical review", Nanotoxicology, vol. 2(4), pp. 252-273 (2009).
González et al., "Interaction of biotin with streptavidin: thermostability and conformational changes upon binding", Journal of Biological Chemistry, vol. 272(17), pp. 11288-11294 (1997).
González et al., "Intranasal delivery of interferon-β-loaded nanoparticles induces control of neuroinflammation in a preclinical model of multiple sclerosis: A promising simple, effective, non-invasive, and low-cost therapy", Journal of Controlled Release, vol. 331, pp. 443-459 (Mar. 2021).
Gonzalez et al., "Towards a new paradigm in nano-genotoxicology: facing complexity of nanomaterials' cellular interactions and effects", Basic Clin. Pharmacol. Toxicol., vol. 121, pp. 23-29 (2016).
González Ordóñez et al., "Risk of venous thromboembolism associated with the insertion/deletion polymorphism in the angiotensin-converting enzyme gene", Blood Coagulation and Fibrinolysis, pp. 485-490, vol. 11, Issue 5 (Jul. 2000).
Gonzalez-Hernandez et al., "Preclinical immunogenicity and protective efficacy of a SARS-CoV-2RBD-based vaccine produced with the thermophilic filamentous fungal expression system Thermothelomyces heterothallica C1", Frontiers in Immunology, vol. 14, 1204834 (Jun. 2023).
González-Martínez et al., "Efficient capture of recombinant SARS-CoV-2 receptor-binding domain (RBD) with citrate-coated magnetic iron oxide nanoparticles", Nanoscale, vol. 15(17), pp. 7854-7869 (May 2023).
Gonzalez-Rodriguez et al., "Dynamics of Receptor-Mediated Nanoparticle Internalization into Endothelial Cells", . PLoS One, in 23 pages, vol. 10, Issue 4 (2015) e0122097. doi: 10.1371/journal.pone.0122097.
Goodsell, "The molecular perspective: methotrexate", Stem Cells, pp. 314-315, vol. 17, Issue 5 (1999).
Gordon et al., "A SARS-CoV-2 protein interaction map reveals targets for drug repurposing", Nature, vol. 583(7816), pp. 459-468 (Apr. 2020).
Gordon et al., "Immortality, but not oncogenic transformation, of primary human cells leads to epigenetic reprogramming of DNA methylation and gene expression", Nucleic Acids Research, pp. 3529-3541, vol. 42, Issue 6 (Apr. 1, 2014).
Gorshkov et al., "Quantum Dot-Conjugated SARS-CoV-2 Spike Pseudo-Virions Enable Tracking of Angiotensin Converting Enzyme 2 Binding and Endocytosis", ACS Nano, pp. 12234-12247, vol. 14 (2020).
Gottesman et al., "Multidrug resistance in cancer: role of ATP-dependent transporters", Nature Reviews Cancer, pp. 48-58, vol. 2 (2002).
Gould et al., "Contributing Factors in Restaurant-Associated Foodborne Disease Outbreaks, FoodNetSites, 2006 and 2007", Journal of Food Protection, pp. 1824-1828, vol. 76, Issue 11 (Nov. 1, 2013).
Gouveia et al., "Good manufacturing practices for medicinal products for human use", Journal of Pharmacy & BioAllied Sciences, pp. 87-96, vol. 7, Issue 2 (2015).
Graham et al., "Processing tissue and cells for transmission electron microscopy in diagnostic pathology and research", Nature Protocols, vol. 2(10), pp. 2439-2450 (2007).
Graverini et al., "Solid lipid nanoparticles for delivery of andrographolide across the blood-brain barrier: in vitro and in vivo evaluation", Colloids and Surfaces B: Biointerfaces, vol. 161, pp. 302-313 (2018).
Graziano et al., "Norovirus Attachment and Entry", Viruses, in 13 pages, vol. 11 (2019).
Greaney et al., "Complete Mapping of Mutations to the SARS-CoV-2 Spike Receptor-Binding Domain that Escape Antibody Recognition", Cell Host & Microbe, pp. 44-57.E9, vol. 29, Issue 1 (Jan. 13, 2021).
Greaney et al., "Mapping mutations to the SARS-CoV-2 RBD that escape binding by different classes of antibodies", Nature Communications, vol. 12(1), 4196 (Jul. 2021).
Greenwood et al., "Chemistry of the Elements, 2nd Edition", Butterworth-Heinemann, (Nov. 11, 1997) Paperback ISBN: 9780750633659.
Grenha et al., "Microencapsulated chitosan nanoparticles for lung protein delivery", European Journal of Pharmaceutical Sciences, vol. 25(4-5), pp. 427-437 (2005).
Grey et al., "Wound assessment", BMJ, pp. 285-288, vol. 332 (2006).
Griffiths et al., "IGF1R is an entry receptor for respiratory syncytial virus", Nature, pp. 615-619, vol. 583 (2020).
Grifoni et al., "A Sequence Homology and Bioinformatic Approach Can Predict Candidate Targets for Immune Responses to SARS-CoV-2", Cell Host & Microbe, pp. 671-680, vol. 27, Issue 4 (Apr. 8, 2020).
Grifoni et al., "Targets of T Cell Responses to SARS-CoV-2 Coronavirus in Humans with COVID-19 Disease and Unexposed Individuals", Cell, pp. 1489-1501, vol. 181, Issue 7 (Jun. 25, 2020).
Gross et al., "Biotinylated streptavidin surface coating improves the efficacy of a PLGA microparticle-based cancer vaccine", Bioconjugate Chemistry, vol. 31(9), pp. 2147-2157 (Sep. 2020).
Grubmüller et al., "Ligand binding: molecular mechanics calculation of the streptavidin-biotin rupture force", Science, vol. 271(5251), pp. 997-999 (1996).
Gu et al., "One dose of COVID-19 nanoparticle vaccine REVC-128 protects against SARS-CoV-2 challenge at two weeks post-immunization", Emerging Microbes & Infections, vol. 10(1), pp. 2016-2029 (Oct. 2021).
Guan et al., "Advances in SARS-CoV-2 receptor-binding domain-based COVID-19 vaccines", Expert Review of Vaccines, vol. 22(1), pp. 422-439 (May 2023).
Gudmundsdottir et al., "Inactivation of SARS-CoV-2 and HCoV-229E in vitro by ColdZyme® a medical device mouth spray against the common cold", Journal of Medical Virology, pp. 1792-1795, vol. 93, Issue 3 (Mar. 2021).
Guerrini et al., "Characterization of nanoparticles-based vaccines for COVID-19", Nature Nanotechnology, vol. 17(6), pp. 570-576 (Jun. 2022).
Guerrini et al., "Monitoring anti-PEG antibodies level upon repeated lipid nanoparticle-based COVID-19 vaccine administration", International Journal of Molecular Sciences, vol. 23(16), 8838 (Aug. 2022).
Guertler et al., "The WST survival assay: an easy and reliable method to screen radiation-sensitive individuals", Radiation Protection Dosimetry, pp. 487-490, vol. 143, Issue 2-4 (Feb. 2011).
Guimaraes et al., "Ionizable lipid nanoparticles encapsulating barcoded mRNA for accelerated in vivo delivery screening", Journal of Controlled Release, vol. 316, pp. 404-417 (2019).
Gumbiner, "Cell Adhesion: The Molecular Basis of Tissue Architecture and Morphogenesis", Cell, pp. 345-357, vol. 84, Issue 3 (Feb. 9, 1996).
Guo et al., "Fundamentals and Applications of Nanomaterials", ISBN:-13: 978-1-59693-262-3, Artech House Publishers, Norwood, MA (2009).
Guo et al., "Nanoparticles escaping RES and Endosome: challenges for siRNA delivery for cancer therapy", Journal of Nanomaterials, vol. 2011, 742895 (2011).
Gupta et al., "Platforms, advances, and technical challenges in virus-like particles-based vaccines", Front. Immunol., vol. 14, 1123805 (Feb. 2023).
Gurunathan et al., "Antiviral Potential of Nanoparticles—Can Nanoparticles Fight Against Coronaviruses?", Nanomaterials, in 29 pages. 1645, vol. 10, Issue 9 (2020).
Gutkin et al., "RNA delivery with a human virus-like particle", Nature Biotechnology, pp. 1514-1515, vol. 39 (2021).
Guy et al., "Rapid repurposing of drugs for COVID-19", Science, vol. 368(6493), pp. 829-830 (May 2020).
Gyrd-Hansen et al., "IAPs: from caspase inhibitors to modulators of NF-kappaB, inflammation and cancer", Nature Reviews Cancer, pp. 561-574, vol. 10 (2010).
Ha, "Dietary Salt Intake and Hypertension", Electrolyte Blood Press, pp. 7-18, vol. 12 (2014).
Haabeth et al., "An mRNA SARS-CoV-2 Vaccine Employing Charge-Altering Releasable Transporters with a TLR-9 Agonist

(56) References Cited

OTHER PUBLICATIONS

Induces Neutralizing Antibodies and T Cell Memory", ACS Central Science, pp. 1191-1204, vol. 7 (2021).
Hadjadj et al., "Impaired type I interferon activity and inflammatory responses in severe COVID-19 patients", Science, pp. 718-724, vol. 369, Issue 6504 (Jul. 13, 2020).
Haghi et al., "Advanced Nanotube and Nanofiber Materials", Nanotechnology Science and Technology, Novinka, ISBN: 978-1-62081-170-2 (Jul. 2012).
Halfmann et al., "Multivalent S2-based vaccines provide broad protection against SARS-CoV-2 variants of concern and pangolin coronaviruses", EBioMedicine, vol. 86 (Dec. 2022).
Halfmann et al., "Potent neutralization of SARS-CoV-2 including variants of concern by vaccines presenting the receptor-binding domain multivalently from nanoscaffolds", Bioengineering & Translational Medicine, vol. 6(3), e10253 (Aug. 2021).
Haller et al., "Microfluidic vortex enhancement for on-chip sample preparation", Micromachines, vol. 6(2), pp. 239-251 (Feb. 2015).
Halwani, "Development of pharmaceutical nanomedicines: From the bench to the market", Pharmaceutics, vol. 14(1), 106 (Jan. 2022).
Hamblett et al., "A streptavidin-biotin binding system that minimizes blocking by endogenous biotin", Bioconjugate Chemistry, vol. 13(3), pp. 588-598 (2002).
Hamdallah et al., "Microfluidics for pharmaceutical nanoparticle fabrication: The truth and the myth", International Journal of Pharmaceutics, vol. 584, 119408 (Jun. 2020).
Hamdi et al., "Investigating the Internalization and COVID-19 Antiviral Computational Analysis of Optimized Nanoscale Zinc Oxide", ACS Omega, pp. 6848-6860, vol. 6 (2021).
Hammerstedt et al., "Commercialization of basic research from within the university and return of value to the public", Animal Reproduction Science, pp. 158-178, vol. 105, 1-2 (2008).
Han et al., "Computational Design of ACE2-Based Peptide Inhibitors of SARS-CoV-2", ACS Nano, pp. 5143-5147, vol. 14 (2020).
Han et al., "Ligand-tethered lipid nanoparticles for targeted RNA delivery to treat liver fibrosis", Nature Communications, vol. 14(1), 75 (Jan. 2023).
Han et al., "Protein-modified hollow copper sulfide nanoparticles carrying indocyanine green for photothermal and photodynamic therapy", Journal of Materials Chemistry B, pp. 105-112, Issue 1 (2016).
Han et al., "Receptor binding and complex structures of human ACE2 to spike RBD from omicron and delta SARS-CoV-2", Cell, vol. 185(4), pp. 630-640 (Feb. 2022).
Hanafy et al., "Silymarin/curcumin loaded albumin nanoparticles coated by chitosan as muco-inhalable delivery system observing anti-inflammatory and anti COVID-19 characterizations in oleic acid triggered lung injury and in vitro COVID-19 experiment", International Journal of Biological Macromolecules, vol. 198, pp. 101-110 (Dec. 2022).
Hanahan et al., "The Hallmarks of Cancer", Cell, pp. 57-70, vol. 100, Issue 1 (Jan. 7, 2000).
Handy et al., "The ecotoxicology of nanoparticles and nanomaterials: current status, knowledge gaps, challenges, and future needs", Ecotoxicology, pp. 315-325, vol. 17 (2008).
Hanke et al., "An alpaca nanobody neutralizes SARS-CoV-2 by blocking receptor interaction", nature Communications, in 9 pages, vol. 11:4420 (2020).
Hansjosten et al., "Microscopy-based high-throughput assays enable multi-parametric analysis to assess adverse effects of nanomaterials in various cell lines", Arch. Toxicol., vol. 92(2), pp. 633-649 (2017).
Hao et al., "In vitro degradation behavior of silica nanoparticles under physiological conditions", Journal of Nanoscience and Nanotechnology, pp. 6346-6354, vol. 12, No. 8 (2012).
Haq et al., "Molecular Understanding of ACE-2 and HLA-Conferred Differential Susceptibility to COVID-19: Host-Directed Insights Opening New Windows in COVID-19 Therapeutics", Journal of Clinical Medicine, vol. 12(7), 2645 (Apr. 2023).
Harada et al., "Photocatalytic Properties of TiO2 Composites Immobilized with Gold Nanoparticle Assemblies Using the Streptavidin-Biotin Interaction", Langmuir, vol. 32(25), pp. 6459-6467 (2016).
Harndahl et al., Peptide-MHC class I stability is a better predictor than peptide affinity of CTL immunogenicity, European Journal of Immunology, pp. 1405-1416, vol. 42, Issue 6 (2012).
Hartig, "Basic Image Analysis and Manipulation in ImageJ", Current Protocols in Molecular Biology, pp. 1-14, Chapter14 (2013).
Hartung, "Rebooting the Generally Recognized as Safe (GRAS) Approach for Food Additive Safety in the US", Altex, pp. 3-25, vol. 35, No. 1 (2018).
Harvey et al., "SARS-CoV-2 variants, spike mutations and immune escape", Nature Reviews Microbiology, pp. 409-424, vol. 19 (Jul. 2021).
Haseda et al., "Microfluidic-prepared DOTAP nanoparticles induce strong T-cell responses in mice", PloS One, vol. 15(1), e0227891 (Jan. 2020).
Hasnidawani et al., "Synthesis of ZnO Nanostructures Using Sol-Gel Method", Procedia Chemistry, pp. 211-216, vol. 19 (2016).
Hatmal et al., "Comprehensive Structural and Molecular Comparison of Spike Proteins of SARS-CoV-2, SARS-CoV and MERS-CoV, and Their Interactions with ACE2" Cells, in 37 pages, 2638, vol. 9 (2020).
Hattori et al., "Human ACE2 Genetic Polymorphism Affecting SARS-CoV and SARS-CoV-2 Entry into Cells", Microbiology Spectrum, vol. 10(4), e00870-22 (Jul. 2022).
He et al., "A competitive panning method reveals an anti-SARS-CoV-2 nanobody specific for an RBD-ACE2 binding site", Vaccines, vol. 11(2), 371 (Feb. 2023).
He et al., "In vivo biodistribution and urinary excretion of mesoporous silica nanoparticles: effects of particle size and PEGylation", Small, pp. 271-280, vol. 7, Issue 2 (2011).
He et al., "Liposomes and liposome-like nanoparticles: From anti-fungal infection to the COVID-19 pandemic treatment", Asian Journal of Pharmaceutical Sciences, vol. 17, pp. 817-837 (Nov. 2022).
He et al., "Single-component, self-assembling, protein nanoparticles presenting the receptor binding domain and stabilized spike as SARS-CoV-2 vaccine candidates", Science Advances, in 17 pages, vol. 7, eabf1591, (Mar. 19, 2021).
He et al., "Temporal dynamics in viral shedding and transmissibility of COVID-19", Nature Medicine, pp. 672-675, vol. 26 (2020).
He et al., "The three-stage in vitro degradation behavior of mesoporous silica in simulated body fluid", Microporous and Mesoporous Materials, pp. 314-320, vol. 131 (2010).
Heida et al., "Development of an inhalable antiviral powder formulation against respiratory syncytial virus", Journal of Controlled Release, vol. 357, pp. 264-273 (May 2023).
Heida et al., "Inhaled vaccine delivery in the combat against respiratory viruses: a 2021 overview of recent developments and implications for COVID-19", Expert Review of Vaccines, vol. 21(7), pp. 957-974 (Aug. 2021).
Herranz-Blanco et al., "Microfluidics platform for glass capillaries and its application in droplet and nanoparticle fabrication", International Journal of Pharmaceutics, vol. 516(1-2), 100-105 (2017).
Herranz-Blanco et al., "Microfluidic assembly of multistage porous silicon-lipid vesicles for controlled drug release", Lab on a Chip, vol. 14(6), pp. 1083-1086 (2014).
Herranz-Blanco et al., "On-chip self-assembly of a smart hybrid nanocomposite for antitumoral applications", Advanced Functional Materials, vol. 25(10), pp. 1488-1497 (2015).
Heskin et al., "Caution required with use of ritonavir-boosted PF-07321332 in COVID-19 management", The Lancet, pp. 21-22, vol. 399, Issue 10319 (Jan. 1, 2022).
Heus et al., "Importance of intellectual property generated by biomedical research at universities andacademic hospitals", Journal of Clinical and Translational Research, pp. 250-259, vol. 3, Issue 2 (2017).
Heymann, Data sharing and outbreaks: best practice exemplified, The Lancet, pp. 469-470, vol. 3955, Issue 10223 (Feb. 15, 2020).
Hilgendorf et al., "The retinoblastoma protein induces apoptosis directly at the mitochondria", Genes & Development, pp. 1003-1015, vol. 27 (2013).

(56) References Cited

OTHER PUBLICATIONS

Hillaireau et al., "Nanocarriers' entry into the cell: relevance to drug delivery", Cellular and Molecular Life Sciences, pp. 2873-2896, vol. 66 (2009).
Hillen et al., "Structure of replicating SARS-CoV-2 polymerase", Nature, pp. 154-156, vol. 584 (Aug. 6, 2020).
Hillman et al., "Axitinib improves radiotherapy in murine xenograft lung tumors", Translational Oncology, vol. 7(3), pp. 400-409 (Jun. 2014).
Hoffmann et al., "SARS-CoV-2 Cell Entry Depends on ACE2 and TMPRSS2 and Is Blocked by a Clinically Proven Protease Inhibitor", Cell, pp. 271-280, vol. 181, Issue 2 (2020).
Hoffmann et al., "SARS-CoV-2 variants B. 1.351 and P. 1 escape from neutralizing antibodies", Cell, pp. 2384-2393, vol. 184, Issue 9 (Apr. 29, 2021).
Hoffmann et al., "Silica-based mesoporous organic-inorganic hybrid materials", Angewandte Chemie International Edition, A Journal of the German Chemical Society, pp. 3216-3251, vol. 45, Issue 20 (May 12, 2006).
Holland et al., "Cruising through a pandemic: The impact of COVID-19 on intentions to cruise", Transportation Research Interdisciplinary Perspectives, in 15 pages, 100328, vol. 9 (2021).
Holland, "Risk perceptions of health and safety in cruising", AIMS Geosciences, pp. 422-436, vol. 6, Issue 4 (2020).
Holmberg et al., "Formation of nuclear HSF1 granules varies depending on stress stimuli", Cell Stress & Chaperones, pp. 219-228, vol. 5, Issue 3 (2000).
Holmberg et al., "The biotin-streptavidin interaction can be reversibly broken using water at elevated temperatures", Electrophoresis, vol. 26(3), pp. 501-510 (2005).
Homer-Vanniasinkam et al., "The continuing challenges of translational research: clinician-scientists' perspective", Cardiology Research and Practice, vol. 2012, Article ID 246710, in 5 pages (2012).
Hongmei, "Extrinsic and Intrinsic Apoptosis Signal Pathway Review", Ntuli, T. M. , editor. Apoptosis and Medicine [Internet]. London: IntechOpen; 2012 [cited Jun. 22, 2022]. Available from: https://www.intechopen.com/chapters/38236 doi: 10.5772/50129.
Horejs, "From lipids to lipid nanoparticles to mRNA vaccines", Nature Review Materials, pp. 1075-1076, vol. 6 (2021).
Hortobagyi, "Overview of treatment results with trastuzumab (Herceptin) in metastatic breast cancer", Seminars in Oncology, pp. 43-47, vol. 28, Supplement 18 (Dec. 2001).
Hosseini et al., "Cholesterol-rich lipid-mediated nanoparticles boost of transfection efficiency, utilized for gene editing by CRISPR-Cas9", International Journal of Nanomedicine, pp. 4353-4366, vol. 14 (2019).
Hou et al., "Lipid nanoparticles for mRNA delivery", Nature Reviews Materials, vol. 6(12), pp. 1078-1094 (Dec. 2021).
Hou et al., "SARS-CoV-2 Reverse Genetics Reveals a Variable Infection Gradient in the Respiratory Tract", Cell, pp. 429-446, vol. 182, Issue 2 (Jul. 23, 2020).
Housman et al., "Drug Resistance in Cancer: An Overview", pp. 1769-1792, vol. 6, Issue 3 (2014).
Howarth et al., "A monovalent streptavidin with a single femtomolar biotin binding site", Nature Methods, vol. 3(4), pp. 267-273 (2006).
Hu et al., "Development of cell-based pseudovirus entry assay to identify potential viral entry inhibitors and neutralizing antibodies against SARS-CoV-2", Genes & Diseases, vol. 7(4), pp. 551-557 (Dec. 2020).
Hu et al., "Recent advances of cocktail chemotherapy by combination drug delivery systems", Advanced Drug Delivery Reviews, pp. 19-34, vol. 98 (2016).
Hu et al., "Shape controllable microgel particles prepared by microfluidic combining external ionic crosslinking", Biomicrofluidics, vol. 6(2) (May 2012).
Hu et al., "Single dose of bivalent H5 and H7 influenza virus-like particle protects chickens against highly pathogenic H5N1 and H7N9 avian influenza viruses", Front. Vet. Sci., vol. 8, 774630 (Nov. 2021).
Huanca et al., "In silico analysis applied to the study of cytotoxicity in natural products", Chem. Proc., vol. 12(1), 69 (Nov. 2022).
Huang et al., "Applications of nanoparticle drug delivery systems for the reversal of multidrug resistance in cancer", Oncology Letters, pp. 11-15, vol. 12, Issue 1 (Jul. 2016).
Huang et al., "Copper Sulfide Nanoparticles with Phospholipid-PEG Coating for In Vivo Near-Infrared Photothermal Cancer Therapy", Chemistry, an Asian Journal, pp. 370-376, vol. 10, Issue 2 (Feb. 2015).
Huang et al., "Modularized viromimetic polymer nanoparticle vaccines (VPNVaxs) to elicit durable and effective humoral immune responses", National Science Review, vol. 11, nwad310 (Dec. 2023).
Huang et al., "Nanotechnology-based strategies against SARS-CoV-2 variants", Nature Nanotechnology, vol. 17(10), pp. 1027-1037 (Oct. 2022).
Huang et al., "Nasal nanovaccines for SARS-CoV-2 to address COVID-19", Vaccines, vol. 10(3), 405 (Mar. 2022).
Huang et al., "Novel Peptide Inhibitors of Angiotensin-converting Enzyme 2*", Journal of Biological Chemistry, pp. 15532-15540, vol. 278, Issue 18 (May 2003).
Huang et al., "Relationship between particle size and lung retention time of intact solid lipid nanoparticle suspensions after pulmonary delivery", Journal of Controlled Release, vol. 325, pp. 206-222 (Sep. 2020).
Huang et al., "SARS-CoV-2 RBD neutralizing antibody induction is enhanced by particulate vaccination", Advanced Materials, vol. 32(50), 2005637 (Oct. 2020).
Huang et al., "Taking Account of Asymptomatic Infections in Modeling the Transmission Potential of the COVID-19 Outbreak on the Diamond Princess Cruise Ship", medRxiv, 2020.04.22, 20074286; doi: https://doi.org/10.1101/2020.04.22.20074286.
Huang et al., "The investigation of mRNA vaccines formulated in liposomes administrated in multiple routes against SARS-CoV-2", Journal of Controlled Release, vol. 335, pp. 449-456 (Jul. 2021).
Huang et al., "The promotion of human malignant melanoma growth by mesoporous silica nanoparticles through decreased reactive oxygen species", Biomaterials, pp. 6142-6153, vol. 31, Issue 24 (Aug. 2010).
Huang et al., "The Toxicity of Nanoparticles Depends on Multiple Molecular and Physicochemical Mechanisms", International Journal of Molecular Sciences, in 13 pages, vol. 18, 2702 (2017).
Huang et al., "Zinc oxide nanoparticles induce eosinophilic airway inflammation in mice", Journal of Hazardous Materials, vol. 297, pp. 304-312 (2015).
Huennekens, "The methotrexate story: a paradigm for development of cancer chemotherapeutic agents", Advances in Enzyme Regulation, pp. 397-419, vol. 34 (1994).
Humphrey et al., "VMD: Visual molecular dynamics", Journal of Molecular Graphics, pp. 33-38, vol. 14, Issue 1 (Feb. 1996).
Hung et al., "Alternating droplet generation and controlled dynamic droplet fusion in microfluidic device for CdS nanoparticle synthesis", Lab on a Chip, vol. 6(2), pp. 174-178 (Jan. 2006).
Hung et al., "Microfluidic devices for the synthesis of nanoparticles and biomaterials", Journal of Medical and Biological Engineering, vol. 27(1) (Jan. 2007).
Huo et al., "Neutralization of SARS-CoV-2 by Destruction of the Prefusion Spike", Cell Host & Microbe, pp. 445-454, vol. 28, Issue 3 (Sep. 9, 2020).
Hussain et al., "Acylation of Cellulose with N, N'-Carbonyldiimidazole-Activated Acids in the Novel Solvent Dimethyl Sulfoxide/Tetrabutylammonium Fluoride", Macromolecular Rapid Communications, pp. 916-920, vol. 25, Issue 9 (May 2004).
Hussain et al., "PEGylation: a promising strategy to overcome challenges to cancer-targeted nanomedicines: a review of challenges to clinical transition and promising resolution", Drug Delivery Transl. Res., vol. 9, pp. 721-734 (2019).
Huzair et al., "Biotechnology and the transformation of vaccine innovation: The case of the hepatitis B vaccines 1968-2000", Stud. Hist. Philos. Biol. Biomed. Sci., vol. 64, pp. 11-21 (2017).
Hystad et al., "Towards a destination tourism disaster management framework: Long-term lessons from a forest fire disaster", Tourism Management, pp. 151-162, vol. 29, Issue 1 (Feb. 2008).

(56) References Cited

OTHER PUBLICATIONS

Ianevski et al., "Potential antiviral options against SARS-CoV-2 infection", Viruses, vol. 12(6), 642 (Jun. 2020).
Idakwo et al., "A review on machine learning methods for in silico toxicity prediction", J. Environ. Sci. Health C, vol. 36(4), pp. 169-191 (2019).
Idris et al., "A SARS-CoV-2 targeted siRNA-nanoparticle therapy for COVID-19", Molecular Therapy, vol. 29(7), pp. 2219-2226 (Jul. 2021).
Ihalainen et al., "Paper-supported nanostructured ultrathin gold film electrodes—Characterization and functionalization", Applied Surface Science, pp. 321-329, vol. 329 (Feb. 2015).
Ihalainen et al., "Topographical, chemical, thermal and electrostatic properties of latex films", Colloids and Surfaces A Physicochemical and Engineering Aspects, pp. 320-330, vol. 354 (2010).
Ikuma et al., "When nanoparticles meet biofilms—interactions guiding the environmental fate and accumulation of nanoparticles", Frontiers in Microbiology, in 6 pages, vol. 6, Article 591 (2015).
Ilinskaya et al., "Understanding the immunogenicity and antigenicity of nanomaterials: Past, present and future", Toxicol. Appl. Pharmacol., vol. 299, pp. 70-77 (2016).
Imperiale et al., "Oral pharmacokinetics of a chitosan-based nanodrug delivery system of interferon alpha", Polymers, vol. 11(11), 1862 (2019).
Inglese et al., "Quantitative high-throughput screening: a titration-based approach that efficiently identifies biological activities in large chemical libraries", Proc. Natl. Acad. Sci., vol. 103(31), pp. 11473-11478 (2006).
International Search Report and Written Opinion issued in PCT/FI2021/050259 on Jul. 2, 2021.
International Search Report and Written Opinion issued in PCT/FI2021/050261 on Jul. 22, 2021.
Irmler et al., " Inhibition of death receptor signals by cellular FLIP", Nature, pp. 190-195, vol. 388 (Jul. 10, 1997).
Ishizuka et al., "Quantitating T Cell Cross-Reactivity for Unrelated Peptide Antigens", The Journal of Immunology, pp. 4337-4345, vol. 183, Issue 7 (Oct. 1, 2009).
Itani et al., "Optimizing use of theranostic nanoparticles as a life-saving strategy for treating COVID-19 patients", Theranostics, vol. 10(13), 5932 (May 2020).
Ito et al., "The cruise industry and the COVID-19 outbreak", Transportation Research Interdisciplinary Perspectives, 100136, in 11 pages, vol. 5 (May 2020).
Ivanova et al., "A bioassay for the simultaneous measurement of metabolic activity, membrane integrity, and lysosomal activity in cell cultures", Anal. Biochem., vol. 379(1), pp. 16-19 (2008).
Izquierdo et al., "Overexpression of the ABC transporter TAP in multidrug-resistant human cancer cell lines", British Journal of Cancer, pp. 1961-1967, vol. 74 (1996).
Jackson et al., "Mechanisms of SARS-CoV-2 entry into cells", Nature reviews Molecular cell biology, vol. 23(1), pp. 3-20 (Jan. 2022).
Jacob et al., "The Impact of Research Grant Funding on Scientific Productivity", Journal of Public Economics, pp. 1168-1177, vol. 95 (2011).
Jacobs et al., "Human rhinoviruses", Clinical Microbiology Reviews, pp. 135-162, vol. 26, Issue 1 (Jan. 2013).
Jafri et. al., "Roles of telomeres and telomerase in cancer, and advances in telomerase-targeted therapies", Genome Medicine, Article No. 69, in 18 pages, vol. 8 (2016).
Jagannathan et al., "Safety and efficacy of inhaled interferon-β1a (SNG001) in adults with mild-to-moderate COVID-19: a randomized, controlled, phase II trial", EClinicalMedicine, vol. 65, 102250 (Oct. 2023).
Jahn et al., "Preparation of nanoparticles by continuous-flow microfluidics", Journal of Nanoparticle Research, vol. 10, pp. 925-934 (2008).
Jain, "The Handbook of Nanomedicine Third Edition", ISBN: 978-1-4939-6965-4 (Jan. 2017).
Jain, "Understanding barriers to drug delivery: high resolution in vivo imaging is key", Clinical Cancer Research, pp. 1605-1606, vol. 5, Issue 7 (1999).
Jaradat et al., "Microfluidic paclitaxel-loaded lipid nanoparticle formulations for chemotherapy", International Journal of Pharmaceutics, vol. 628, 122320 (Nov. 2022).
Järnström et al., "Roughness of pigment coatings and its influence on gloss", Applied Surface Science, pp. 5741-5749, vol. 254, Issue 18 (Jul. 15, 2008).
Javadi et al., "Evaluating the immunogenicity of gold nanoparticles conjugated RBD with Freund's adjuvant as a potential vaccine against SARS-CoV-2", Microbial Pathogenesis, vol. 170, 105687 (Jul. 2022).
Jawad et al., "Computational Design of Miniproteins as SARS-CoV-2 Therapeutic Inhibitors. International Journal of Molecular", Sciences, vol. 23(2), 838 (Jan. 2022).
Jearanaiwitayakul et al., "Intranasal administration of RBD nanoparticles confers induction of mucosal and systemic immunity against SARS-CoV-2", Vaccines, vol. 9(7), 768 (Jul. 2021).
Jensen et al., "Miniaturized Plate Readers for Low-Cost, High-Throughput Phenotypic Screening", Journal of Laboratory Automation, pp. 51-55, vol. 20, Issue 1 (2015).
Jerome et al., "Measurement of CTL-induced cytotoxicity: the caspase 3 assay", Apoptosis, vol. 8(6), pp. 563-571 (2003).
Jeyanathan et al., "Immunological considerations for COVID-19 vaccine strategies", Nature Reviews Immunology, vol. 20(10), pp. 615-632 (Oct. 2020).
Ji et al., "Designed synthesis of CeO2 nanorods and nanowires for studying toxicological effects of high aspect ratio nanomaterials", ACS Nano, vol. 6(6), pp. 5366-5380 (2012).
Ji et al., "Machine learning models for predicting cytotoxicity of nanomaterials", Chem. Res. Toxicol., vol. 35(2), pp. 125-139 (Jan. 2022).
Jiang et al., "A bacterial extracellular vesicle-based intranasal vaccine against SARS-CoV-2 protects against disease and elicits neutralizing antibodies to wild-type and Delta variants", Journal of extracellular vesicles, vol. 11(3), e12192 (Feb. 2022).
Jiang et al., "Bacterial toxicity comparison between nano- and micro-scaled oxide particles", Environmental Pollution, pp. 1619-1625, vol. 157, Issue 5 (May 2009).
Jiang et al., "SARS-CoV-2 Spike Impairs DNA Damage Repair and Inhibits V(D)J Recombination In Vitro", Viruses, 2056 in 10 pages, vol. 13 (2021).
Jiao et al., "SARS-CoV-2 Protein Nanoparticle Vaccines Formed In Situ From Lyophilized Lipids", Small, vol. 20(9), 2304534 (Oct. 2023).
Jin et al., "Engineered Lipid Nanoparticles for the Treatment of Pulmonary Fibrosis by Regulating Epithelial-Mesenchymal Transition in the Lungs", Advanced Functional Materials, vol. 33(7), 2209432 (Dec. 2023).
Jing et al., "SARS-CoV-2 infection causes immunodeficiency in recovered patients by downregulating CD19 expression in B cells via enhancing B-cell metabolism", Signal Transduction and Targeted Therapy, Article No. 345, vol. 6 (2021).
Jo et al., "Design and Fabrication of Streptavidin-Functionalized, Fluorescently Labeled Polymeric Nanocarriers", Langmuir, pp. 15783-15794, vol. 34, Issue 51 (2018).
Jo et al., "Natural Product Celastrol Destabilizes Tubulin Heterodimer and Facilitates Mitotic Cell Death Triggered by Microtubule-Targeting Anti-Cancer Drugs", PLoS One, e10318 in 12 pages, vol. 5, Issue 4 (Apr. 2010).
Johansson et al., "SARS-CoV-2 Transmission From People Without COVID-19 Symptoms", JAMA Network Open, e2035057 in 8 pages, vol. 4, Issue 1 (2021).
Johnson et al., "NCBI Blast: a better web interface", Nucleic Acids Rsearch, pp. W5-W9, vol. 36 (2008).
Jolly et al., "In vivo binding of active heat shock transcription factor 1 to human chromosome 9 heterochromatin during stress", The Journal of Cell Biology, pp. 775-781, vol. 156, No. 5 (Mar. 4, 2002).
Jorgensen et al., "Comparison of simple potential functions for simulating liquid water", AIP The Journal of Chemical Physics, pp. 926-935, vol. 79, Issue 2 (1983).

(56) References Cited

OTHER PUBLICATIONS

Joyce et al., "A SARS-CoV-2 ferritin nanoparticle vaccine elicits protective immune responses in nonhuman primates", Science Translational Medicine, vol. 14(632), eabi5735 (Feb. 2022).
Joyce et al., "SARS-CoV-2 ferritin nanoparticle vaccines elicit broad SARS coronavirus immunogenicity", Cell Reports, 110143, vol. 37, Issue 12 (Dec. 21, 2021) DOI:https://doi.org/10.1016/j.celrep.2021.110143.
Jung et al., "Development of human-derived, three-dimensional respiratory epithelial tissue constructs with perfusable microvasculature on a high-throughput microfluidics screening platform", Biofabrication, vol. 14(2), 025012 (Feb. 2022).
Justus et al., "In vitro cell migration and invasion assays", Journal of Visualized Experiments, 51046, vol. 88 (Jun. 1, 2014) doi: 10.3791/51046.
Juvonen et al., "Biocompatibility of printed paper-based arrays for 2-D cell cultures", Acta Biomaterialia, pp. 6704-6710, vol. 9, Issue 5 (May 2013).
Juvonen et al., "Enhanced protein adsorption and patterning on nanostructured latex-coated paper", Colloids and SurfacesB: Biointerfaces, pp. 261-269, vol. 118 (Jun. 1, 2014).
Juvonen et al., "Protein and bacterial interactions with nanostructured polymer coatings", Colloids and Surfaces B: Biointerfaces, pp. 527-535, vol. 136 (Dec. 1, 2015).
Kain et al., "The chick embryo as an expanding experimental model for cancer and cardiovascular research", Developmental Dynamics, pp. 216-228, vol. 243, Issue 2 (Feb. 2014).
Kalathiya et al., "Multivalent display of SARS-CoV-2 spike (RBD domain) of COVID-19 to nanomaterial, protein ferritin nanocages", Biomolecules, vol. 11(2), 297 (Feb. 2021).
Kalepua et al., "Insoluble drug delivery strategies: review of recent advances and business prospects", Acta Pharmaceutica Sinica B, pp. 442-453, vol. 5, Issue 5 (Sep. 2015).
Kalhori et al., "FTY720 (Fingolimod) attenuates basal and sphingosine-1-phosphate-evoked thyroid cancer cell invasion", Endocrine-Related Cancer, pp. 457-468, vol. 23, Issue 5 (2016).
Kalil et al., "Influenza virus-related critical illness: pathophysiology and epidemiology", Critical Care, Article No. 258, vol. 23 (2019) https://doi.org/10.1186/s13054-019-2539-x.
Kalkeri et al., "SARS-CoV-2 spike pseudoviruses: a useful tool to study virus entry and address emerging neutralization escape phenotypes", Microorganisms, vol. 9(8), 1744 (Sep. 2021).
Kalluri et al., "The basics of epithelial-mesenchymal transition", Journal of Clinical Investigation, pp. 1420-1428, vol. 119, No. 6 (Jun. 2009).
Kamyshny et al., "Metal-based Inkjet Inks for Printed Electronics", The Open Applied Physics Journal, pp. 19-36, vol. 4 (2011).
Kanekiyo et al., "Mosaic nanoparticle display of diverse influenza virus hemagglutinins elicits broad B cell responses", Nature Immunology, pp. 362-372, vol. 20 (2019).
Kanekiyo et al., "Rational Design of an Epstein-Barr Virus Vaccine Targeting the Receptor-Binding Site", Cell, pp. 1090-1100, vol. 162 (Aug. 27, 2015).
Kang et al., "Rapid Development of SARS-CoV-2 Spike Protein Receptor-Binding Domain Self-Assembled Nanoparticle Vaccine Candidates", ACS Nano, pp. 2738-2752, vol. 15 (2021).
Kang et al., "Rapid development of SARS-CoV-2 receptor binding domain-conjugated nanoparticle vaccine candidate", bioRxiv, pp. 1-52 (2020).
Kankaanpää et al., "BiolmageXD: an open, general-purpose and high-throughput image-processing platform", Nature Methods, pp. 683-689, vol. 9 (2012).
Känkänen et al., "Microfluidic preparation and optimization of sorafenib-loaded poly (ethylene glycol-block-caprolactone) nanoparticles for cancer therapy applications", Journal of Colloid and Interface Science, vol. 633, pp. 383-395 (Nov. 2022).
Kanojia et al., "Developments in the formulation and delivery of spray dried vaccines", Human Vaccines & Immunotherapeutics, pp. 2364-2378, vol. 13, No. 10 (2017).
Kapoor et al., "Post-Translational Modifications Optimize the Ability of SARS-CoV-2 Spike for Effective Interaction with Host Cell Receptors", bioRxiv, https://doi.org/10.1101/2021.12.02.470852 (2021).
Kapur et al., "Establishing quantitative structure-property relationships (QSPR) of diesel samples by proton-NMR & multiple linear regression (MLR) analysis", Energy Fuels, vol. 15(4), pp. 943-948 (2001).
Kar et al., "Evaluating the cytotoxicity of a large pool of metal oxide nanoparticles to *Escherichia coli*:Mechanistic understanding through In Vitro and In Silico studies", Chemosphere, vol. 264(1), 128428 (Feb. 2021).
Kar et al., "Periodic table-based descriptors to encode cytotoxicity profile of metal oxide nanoparticles: A mechanistic QSTR approach", Ecotoxicol. Environ. Saf., vol. 107, pp. 162-169 (2014).
Karaman et al., "Shape engineering vs organic modification of inorganic nanoparticles as a tool for enhancing cellular internalization", Nanoscale Research Letters, pp. 1-14, vol. 7:358 (2012).
Karim et al., "Omicron SARS-CoV-2 variant: a new chapter in the COVID-19 pandemic", The Lancet, vol. 398(10317), pp. 2126-2128 (Dec. 2021).
Karjalainen et al., "A Raft-derived, Pak1-regulated Entry Participates in alpha2beta1 Integrin-dependent Sorting to Caveosomes", Molecular Biology of the Cell, pp. 2857-2869, vol. 19, No. 7 (Jul. 2008).
Karlsson et al., "Copper Oxide Nanoparticles Are Highly Toxic: A Comparison between Metal Oxide Nanoparticles and Carbon Nanotubes", Chemical Rsearch in Toxicology, pp. 1726-1732, vol. 21, No. 9 (2008).
Karlsson et al., "Size-dependent toxicity of metal oxide particles—A comparison between nano- and micrometer size", Toxicology Letters, pp. 112-118, vol. 188, Issue 2 (Jul. 24, 2009).
Karnik et al., "Microfluidic platform for controlled synthesis of polymeric nanoparticles", Nano Letters, vol. 8(9), pp. 2906-2912 (Jun. 2008).
Katsoularis et al., "Risk of acute myocardial infarction and ischaemic stroke following COVID-19 in Sweden: a self-controlled case series and matched cohort study", The Lancet, pp. 599-607, vol. 398, Issue 10300 (Aug. 14, 2021).
Kaufmann et al., "Host-directed therapies for bacterial and viral infections", Nature Reviews Drug Discovery, vol. 17(1), pp. 35-56 (Jan. 2018).
Kaur et al., "COVID-19 Vaccine: A comprehensive status report", Virus Research, 198114, in 12 pages, vol. 288 (Oct. 15, 2020).
Kaur et al., "Formulation of Biocompatible Vancomycin Conjugated Gold Nanoparticles for Enhanced Antibacterial Efficacy", 2022, ES Energy & Environment, pp. 34-44, vol. 15 (2022).
Kaur et al., "In vitro studies on radiosensitization effect of glucose capped gold nanoparticles in photonand ion irradiation of Hela cells", Nuclear Instruments and Methods in Physics Research B, pp. 7-11, vol. 301 (Apr. 2013).
Kayala et al., "Learning to Predict Chemical Reactions", Journal of Chemical Information and Modeling, pp. 2209-2222, vol. 51, Issue 9 (2011).
Kehrer et al., "Free radicals and related reactive species as mediators of tissue injury and disease: implications for health", Crit. Rev. Toxicol., vol. 45(9), pp. 765-798 (2015).
Keller et al., "TMPRSS2, a novel host-directed drug target against SARS-CoV-2", Signal Transduction and Targeted Therapy, vol. 7(1), 251 (Jul. 2022).
Kennedy et al., "Evaluation of Folate Conjugate Uptake and Transport by the Choroid Plexus of Mice", Pharmaceutical Research, pp. 714-719, vol. 20 (2003).
Kenny et al., "Distinct receptor binding domain IgG thresholds predict protective host immunity across SARS-CoV-2 variants and time", Part A Study Group Mallon Patrick, Nature Communications, vol. 14(1), 7015 (Nov. 2023).
Kerdsakundee et al., "Multifunctional nanotube-mucoadhesive poly (methyl vinyl ether-co-maleic acid)@ hydroxypropyl methylcellulose acetate succinate composite for site-specific oral drug delivery", Advanced Healthcare Materials, vol. 6(20), 1700629 (2017).
Kermi et al., "Regulation of DNA Replication in Early Embryonic Cleavages", Genes, 8, 42 in 21 pages, (2017) doi:10.3390/genes8010042.

(56) References Cited

OTHER PUBLICATIONS

Kerr et al., "Apoptosis: a basic biological phenomenon with wide-ranging implications in tissue kinetics", British Journal of Cancer, pp. 239-257, vol. 26, Issue 4 (Aug. 1972).
Ketabi et al., "Comparison of PEG interferon loaded and non-loaded iron oxide nanoparticles on hepatitis C virus replication in cell culture system", Iranian Journal of Virology, vol. 11(3), pp. 19-26 (2017).
Kettiger et al., "Comparative safety evaluation of silica-based particles", Toxicology in Vitro, pp. 355-363, vol. 30, Issue 1, Part B (Dec. 25, 2015).
Keum et al., "Biomimetic lipid Nanocomplexes incorporating STAT3-inhibiting peptides effectively infiltrate the lung barrier and ameliorate pulmonary fibrosis", Journal of Controlled Release, vol. 332, pp. 160-170 (Apr. 2021).
Khan et al., "Inkjet-Printed Flexible Gold Electrode Arrays for Biolelectronic Interfaces", Advanced Functional Materials, pp. 1004-1013, vol. 26, Issue 7 (Feb. 16, 2016).
Khan et al., "Visualizing in deceased COVID-19 patients how SARS-CoV-2 attacks the respiratory and olfactory mucosae but spares the olfactory bulb", Cell, pp. 5932-5949, vol. 184, Issue 24 (Nov. 24, 2021).
Khanna et al., "Nanotoxicity: an interplay of oxidative stress, inflammation and cell death", Nanomaterials, vol. 5(3), pp. 1163-1180 (2015).
Kheirvari et al., "Virus-like particle vaccines and platforms for vaccine development", Viruses, vol. 15, 1109 (May 2023).
Kianpour et al., "Nanoparticles for coronavirus control", Nanomaterials, vol. 12(9), 1602 (May 2022).
Kim et al., "Binding of human ACE2 and RBD of omicron enhanced by unique interaction patterns among SARS-CoV-2 variants of concern", Journal of Computational Chemistry, vol. 44(4), pp. 594-601 (Nov. 2022).
Kim et al., "Development of Spike Receptor-Binding Domain Nanoparticles as a Vaccine Candidate against SARS-CoV-2 Infection in Ferrets", Microbial Pathogenesis, e00230-21, in 13 pages, Research Article, vol. 12, No. 2 (Mar. 2, 2010).
Kim et al., "Discriminative cytotoxicity assessment based on various cellular damages", Toxicol. Lett., vol. 184(1), pp. 13-17 (2009).
Kim et al., "Droplet microfluidics for producing functional microparticles", Langmuir, vol. 30(6), pp. 1473-1488 (2014).
Kim et al., "Effects of COVID-19 on preferences for private dining facilities in restaurants", Journal of Hospitality and Tourism, pp. 67-70, vol. 45 (2020).
Kim et al., "Geraniin inhibits the entry of SARS-CoV-2 by blocking the interaction between spike protein RBD and human ACE2 receptor", International Journal of Molecular Sciences, vol. 22(16), 8604 (Aug. 2021).
Kim et al., "Lethal effect of adriamycin on the division cycle of HeLa cells", Cancer Research, pp. 323-325, vol. 32, Issue 2 (Feb. 1972).
Kim et al., "Mass production and size control of lipid-polymer hybrid nanoparticles through controlled microvortices", Nano Letters, vol. 12(7), pp. 3587-3591 (Jun. 2012).
Kim et al., "Microfluidic preparation of monodisperse polymeric microspheres coated with silica nanoparticles", Scientific Reports, vol. 8(1), 8525 (Jun. 2018).
Kim et al., "Post microtextures accelerate cell proliferation and osteogenesis", Acta Biomaterialia, pp. 160-169, vol. 6, Issue 1 (Jan. 2010).
Kim et al., "The Recent Progress in Quantitative Medical Image Analysis for Computer Aided Diagnosis Systems", Healthcare Informatics Research, pp. 143-149, vol. 17, Issue 3 (2011).
Kim et al., "The role of surface functionality in determining nanoparticle cytotoxicity", Acc. Chem. Res., vol. 46(3), pp. 681-691 (2013).
Kim et al., "Type I and III interferon responses in SARS-CoV-2 infection", Experimental & Molecular Medicine, vol. 53(5), pp. 750-760 (May 2021).
Kimbrell, "Governance of nanotechnology and nanomaterials: principles, regulation, and renegotiating the social contract", Journal of Law, Medicine & Ethics, pp. 706-723, vol. 37, Issue 4 (2009).
Kimura et al., "Development of a microfluidic-based post-treatment process for size-controlled lipidnanoparticles and application to siRNA delivery", ACS Applied Materials & Interfaces, vol. 12(30), pp. 34011-34020 (Jul. 2020).
Kimura et al., "Development of the iLiNP device: fine tuning the lipid nanoparticle size within 10 nm for drug delivery", ACS Omega, vol. 3(5), pp. 5044-5051 (2018).
Kimura et al., "Three-dimensional, symmetrically assembled microfluidic device for lipid nanoparticle production", RSC Advances, vol. 11(3), pp. 1430-1439 (Jan. 2021).
Kinaret et al., "Inhalation and oropharyngeal aspiration exposure to rod-like carbon nanotubes inducesimilar airway inflammation and biological responses in mouse lungs", ACS Nano, vol. 11(1), pp. 291-303 (2017).
King et al., "Efficacy and breadth of adjuvanted SARS-CoV-2 receptor-binding domain nanoparticle vaccine in macaques", Proceedings of the National Academy of Sciences, vol. 118(38), e2106433118 (Sep. 2021).
Kiseleva et al., "COVID-19 Shuts Doors to Flu but Keeps Them Open to Rhinoviruses", Biology,733 in 22 pages, vol. 10 (2021).
Kiss et al., "Structural analysis of respiratory syncytial virus reveals the position of M2-1 between the matrix protein and the ribonucleoprotein complex", Journal of Virology, pp. 7602-7617, vol. 88, No. 13 (Jul. 2014).
Kleandrova et al., "Computational tool for risk assessment of nanomaterials: Novel QSTR-perturbation model for simultaneous prediction of ecotoxicity and cytotoxicity of uncoated and coated nanoparticles under multiple experimental conditions", Environ. Sci. Technol., vol. 48(24), pp. 14686-14694 (2014).
Kleanthous et al., "Scientific rationale for developing potent RBD-based vaccines targeting COVID-19", NPJ Vaccines, vol. 6(1), 128 (Oct. 2021).
Klein et al., "Degradation of lipid based drug delivery formulations during nebulization", Chemical Physics, vol. 547, 111192 (Jul. 2021).
Koehler et al., "Defining and managing COVID-19-associated pulmonary aspergillosis: the 2020 ECMM/ISHAM consensus criteria for research and clinical guidance", The Lancet, pgs. E149-E162, vol. 21, Issue 6 (Jun. 1, 2021).
Koenig et al., "Structure-guided multivalent nanobodies block SARS-CoV-2 infection and suppress mutational escape", Science, 371, 691 in 17 pages (2021).
Kohl et al., "Genotoxicity of nanomaterials: Advanced in vitro models and high throughput methods for human hazard assessment—A review", Nanomaterials (Basel), vol. 10(10), 1911 (Sep. 2020).
Kohyama et al., "Efficient induction of cytotoxic T lymphocytes specific for severe acute respiratorysyndrome (SARS)-associated coronavirus by immunization with surface-linked liposomal peptides derived from a non-structural polyprotein 1a", Antiviral Research, pp. 168-177, vol. 84, Issue 2 (Nov. 2009).
Kojima et al., "Protective immunity after recovery from SARS-CoV-2 infection", The Lancet, pp. 12-14, vol. 22, Issue 1 (Jan. 1, 2022).
Koletsas et al., "Thyroid transcription factor-1 expression in invasive and non-invasive urothelial carcinoma", Hippokratia, pp. 154-157, vol. 21 (2017).
Komuro et al., "Inkjet printed (bio)chemical sensing devices", Analytical and Bioanalytical Chemistry, pp. 5785-5805, vol. 405 (2013).
Kong et al., "Enhancement of radiation cytotoxicity in breast-cancer cells by localized attachment of gold nanoparticles", Small, pp. 1537-1543, vol. 4, Issue 9 (2008).
Kong et al., "Inhibition of multidrug resistance of cancer cells by co-delivery of DNA nanostructuresand drugs using porous silicon nanoparticles@giant liposomes", Advanced Functional Materials, vol. 25(22), pp. 3330-3340 (2015).
Konno et al., "SARS-CoV-2 ORF3b is a potent interferon antagonist whose activity is further increased by a naturally occurring elongation variant", Cell Reports, vol. 32, Issue 12, pp. 1-16 (2020).

(56) References Cited

OTHER PUBLICATIONS

Konrath et al., "Nucleic acid delivery of immune-focused SARS-CoV-2 nanoparticles drives rapid and potent immunogenicity capable of single-dose protection", Cell Reports, vol. 38(5) (Feb. 2022).
Korber et al., "Tracking Changes in SARS-CoV-2 Spike: Evidence that D614G Increases Infectivity of the COVID-19 Virus", Cell, pp. 812-827, vol. 182, Issue 4 (2020).
Kotzabasaki et al., "QSAR modeling of the toxicity classification of superparamagnetic iron oxide nanoparticles (SPIONs) in stem-cell monitoring applications: an integrated study from data curation to model development", RSC Adv., vol. 10(9), pp. 5385-5391 (Feb. 2020).
Kou et al., "The endocytosis and intracellular fate of nanomedicines: Implication for rational design", Asian Journal of Pharmaceutical Sciences, pp. 1-10, vol. 8, Issue 1 (Feb. 2013).
Kovalishyn et al., "QSPR modeling for predicting toxicity of nanomaterials", Nanocon (2015).
Krakowiak et al., "Hsf1 and Hsp70 constitute a two-component feedback loop that regulates the yeast heat shock response", Elife, e31668 in 17 pages, vol. 7 (Feb. 2, 2018).
Kramer et al., "In vitro cell migration and invasion assays", Mutation Research/Reviews in Mutation Research, pp. 10-24, vol. 752, Issue 1 (Jan.-Mar. 2013).
Krammer, "SARS-CoV-2 vaccines in development", Nature, pp. 516-527, vol. 586 (2020).
Krause et al., "Rapid Microfluidic Immunoassays of Cancer Biomarker Proteins Using DisposableInkjet-Printed Gold Nanoparticles Arrays", ChemistryOpen Communications, pp. 141-145, vol. 2, Issue 4 (Aug. 2013).
Kresge et al., "Ordered mesoporous molecular sieves synthesized by a liquid-crystal template mechanism", Nature, pp. 710-712, vol. 359 (1992).
Kreyling et al., "Nanoparticles in the lung", Nature Biotechnology, vol. 28(12), pp. 1275-1276 (Dec. 2010).
Krile et al., "Forecasting the operational activities of the sea passenger terminal using intelligent technologies", Transport Problems, pp. 27-36, vol. 13, Issue 1 (Mar. 2018).
Kristó et al., "Preparation and investigation of core-shell nanoparticles containing human interferon-α", International Journal of Pharmaceutics, vol. 573, 118825 (Jan. 2020).
Kroemer G, et al., "Classification of cell death: recommendations of the Nomenclature Committee on Cell Death 2009", Cell Death & Differentiation, pp. 3-11, vol. 16 (2009).
Krogh et al., "Predicting transmembrane protein topology with a hidden markov model: application to complete genomes", Journal of Molecular Biology, pp. 567-580, vol. 305, Issue 3 (Jan. 19, 2001).
Kroll et al., "Current in vitro methods in nanoparticle risk assessment: Limitations and challenges", pp. 370-377, vol. 72, Issue 2 (Jun. 2009).
Kroll et al., "Cytotoxicity screening of 23 engineered nanomaterials using a test matrix of ten cell lines and three different assays" Particle and Fibre Toxicology, 8:9 in 19 pages (2011).
Krysko et al., "Apoptosis and necrosis: Detection, discrimination and phagocytosis", Methods, pp. 205-221, vol. 44, Issue 3 (Mar. 2008).
Krzysztońn et al., "Microfluidic self-assembly of folate-targeted monomolecular siRNA-lipid nanoparticles", Nanoscale, vol. 9(22), pp. 7442-7453 (2017).
Ku et al., "Copper Sulfide Nanoparticles as a New Class of Photoacoustic Contrast Agent for Deep Tissue Imaging at 1064 nm", ACS Nano, pp. 7489-7496, vol. 6, Issue 8 (2012).
Kuba et al., "A crucial role of angiotensin converting enzyme 2 (ACE2) in SARS coronavirus-induced lung injury", Nat. Med. Vol. 11(8), pp. 875-879 (2005).
Kue et al., "Small Molecules for Active Targeting in Cancer", Medicinal Research Reviews, pp. 494-575, vol. 36, Issue 3 (May 2016).
Kularatne et al., "Targeting of Nanoparticles: Folate Receptor", In: Grobmyer, S., Moudgil, B. (eds)Cancer Nanotechnology. Methods in Molecular Biology, pp. 249-265, vol. 624. Humana Press. https://doi.org/10.1007/978-1-60761-609-2_17.
Kumar et al., "Host-directed antiviral therapy", Clinical Microbiology Reviews, vol. 33(3) (Jul. 2020).
Kumar et al., "Synthesis and conjugation of ZnO nanoparticles with bovine serum albumin for biological applications", Applied Nanoscience, pp. 141-144, vol. 3 (2013).
Kumaravel et al., "Comet assay measurements: a perspective", Cell Biol. Toxicol., vol. 25, pp. 53-64 (2009).
Kura et al., "Outbreak of Legionnaires disease on a cruise ship linked to spa-bath filter stones contaminated with Legionella pneumophila serogroup 5", Epidemiology & Infection, pp. 385-391, vol. 134 (2006).
Kuster et al., "SARS-CoV2: should inhibitors of the renin-angiotensin system be withdrawn in patients with COVID-19?" European Heart Journal, pp. 1801-1803, vol. 41 (May 14, 2020).
Kusumoputro et al., "Potential nanoparticle applications for prevention, diagnosis, and treatment of COVID-19", View, vol. 1(4), 20200105 (Sep. 2020).
Kuthati et al., "Functionalization of mesoporous silica nanoparticles for targeting, biocompatibility, combined cancer therapies and theragnosis", Journal of Nanoscience and Nanotechnology, pp. 2399-2430, vol. 13 (2013).
Kwon et al., "Silica-based mesoporous nanoparticles for controlled drug delivery", Journal of Tissue Engineering, First Published Sep. 3, 2013, Research Article, https://doi: 10.1177/2041731413503357.
Kyte et al., "A simple method for displaying the hydropathic character of a protein", Journal of Molecular Biology, pp. 105-132, vol. 157, Issue 1 (May 5, 1982).
Labouta et al., "Meta-analysis of nanoparticle cytotoxicity via data-mining the literature", ACS Nano, vol. 13(2), pp. 1583-1594 (2019).
Lai, "Toward toxicity testing of nanomaterials in the 21st century: a paradigm for moving forward", Wiley Interdiscip. Rev.: Nanomed. Nanobiotechnol., vol. 4(1), pp. 1-15 (2011).
Lainšček et al., "A nanoscaffolded spike-RBD vaccine provides protection against SARS-CoV-2 with minimal anti-scaffold response", Vaccines, vol. 9(5), 431 (Apr. 2021).
Lam et al., "SARS-CoV-2 spike protein predicted to form complexes with host receptor proteinorthologues from a broad range of mammals", Scientific Reports, Article No. 16471, in 14 pages, vol. 10 (2020).
Lamas-Barreiro et al., "Angiotensin II suppression in SARS-CoV-2 infection: a therapeuticapproach", Nefrologia (Engl Ed). May-Jun. 2020; 40(3):213-216. English, Spanish. doi: 10.1016/j.nefro.2020.04.006. Epub Apr. 30, 2020. PMID: 32456945; PMCID: PMC7190491.
Lampinen et al., "Modular vaccine platform based on the norovirus-like particle", Journal of Nanobiotechnology, vol. 19(1), Art. 25 (Jan. 2021).
Lampinen et al., "SpyTag/SpyCatcher display of influenza M2e peptide on norovirus-like particle provides stronger immunization than direct genetic fusion", Frontiers in Cellular and Infection Microbiology, vol. 13, Art. 1216364 (Jun. 2023).
Lan et al., "Structural insights into the binding of SARS-CoV-2, SARS-CoV, and hCoV-NL63 spike receptor-binding domain to horse ACE2", Structure, vol. 30 (10), pp. 1432-1442 (Oct. 2022).
Lan et al., "Structural insights into the SARS-CoV-2 Omicron RBD-ACE2 interaction", Cell Research, vol. 32(6), pp. 593-595 (Apr. 2022).
Lan et al., "Structure of the SARS-CoV-2 spike receptor-binding domain bound to the ACE2 receptor", Nature, vol. 581(7807), pp. 215-220 (May 2020).
Landry et al., "Tumor-stroma interactions differentially alter drug sensitivity based on the origin of stromal cells", Molecular Systems Biology, e8322 in 15 pages, vol. 14, Issue 8, (Aug. 1, 2018).
Lane, "The unseen world: reflections on Leeuwenhoek (1677) 'Concerning little animals'", Philosophical Transactions of the Royal Society B, vol. 370, Issue 1666 (Apr. 19, 2015).
LÅngstedt et al., "Customer perceptions of COVID-19 countermeasures on passenger ships during the pandemic", Transportation Research Interdisciplinary Perspectives, 1005182, vol. 13 (2022).

(56) References Cited

OTHER PUBLICATIONS

Larsen et al., "Large-scale validation of methods for cytotoxic T-lymphocyte epitope prediction", BMC Bioinformatics, in 12 pages, 8:424 (2007).
Larsen et al., "Modeling the Onset of Symptoms of COVID-19", Frontiers in Public Health, Article 473 in 14 pages, vol. 8 (Aug. 13, 2020).
Lauster et al., "Phage capsid nanoparticles with defined ligand arrangement block influenza virus entry", Nature Nanotechnology, pp. 373-379, vol. 15 (2020).
Law et al., "SARS-COV-2 recombinant Receptor-Binding-Domain (RBD) induces neutralizing antibodies against variant strains of SARS-CoV-2 and SARS-CoV-1", Vaccine, vol. 39(40), pp. 5769-5779 (Aug. 2021).
Law et al., "Systems virology: host-directed approaches to viral pathogenesis and drug targeting", Nature Reviews Microbiology, vol. 11(7), pp. 455-466 (Jul. 2013).
Lawanprasert et al., "Inhalable SARS-CoV-2 Mimetic Particles Induce Pleiotropic Antigen Presentation", Biomacromolecules, pp. 1158-1168, vol. 23 (2022).
Le Bourhis, "Glass—Mechanics and Technology", 2nd Edition, Wiley-VCH, in 391 pages (2008).
Le Bourhis, "Glass—Mechanics and Technology, 2nd Edition", in 30 pgs., Wiley-VCH, Weinheim, Germany (2008) ISBN: 978-3-527-31549-9.
Le et al., "An experimental and computational approach to the development of ZnO nanoparticles that are safe by design", Small, vol. 12(26), pp. 3568-3577 (2016).
Leak, "Heat shock proteins in neurodegenerative disorders and aging", Journal of Cell Communication and Signaling, pp. 293-310, vol. 8 (2014).
Leamon et al., "Folate-mediated targeting: from diagnostics to drug and gene delivery", Drug Discovery Today, pp. 44-51, vol. 6, Issue 1 (Jan. 1, 2001).
Leamon et al., "Folate-targeted chemotherapy", Advanced Drug Delivery Reviews, pp. 1127-1141, vol. 56, Issue 8 (Apr. 29, 2004).
Lebre et al., "Nanosafety: an evolving concept to bring the safest possible nanomaterials to society and environment", Nanomaterials, vol. 12(11), 1810 (May 2022).
Ledford, "'Killer' Immune Cells Still Recognize Omicron Variant", Nature, p. 307, vol. 601 (Jan. 20, 2022).
Lee et al., "Identification of entry inhibitors against delta and omicron variants of SARS-CoV-2", International Journal of Molecular Sciences, vol. 23(7), 4050 (Apr. 2022).
Lee et al., "Mosaic RBD nanoparticles induce intergenus cross-reactive antibodies and protect against SARS-CoV-2 challenge", Proceedings of the National Academy of Sciences, vol. 120(4), e2208425120 (Jan. 2023).
Lee et al., "Multiscale modeling of dendrimers and their interactions with bilayers and polyelectrolytes", Molecules, pp. 423-438, vol. 14 (2009).
Lee et al., "Nano spray drying: a novel method for preparing protein nanoparticles for protein therapy", International Journal of Pharmaceutics, vol. 403(1-2), pp. 192-200 (2011).
Lee et al., "Oncogenes and Tumor Suppressor Genes", Cold Spring Harbor Perspectives in Biology, 2010, 2(10): a003236.
Lee et al., "Sensing discrete streptavidin-biotin interactions with atomic force microscopy", Langmuir, vol. 10(2), pp. 354-357 (1994).
Lee et al., "T cell-specific siRNA delivery using antibody-conjugated chitosan nanoparticles", Bioconjugate Chemistry, vol. 23(6), pp. 1174-1180 (2012).
Lee et al., "Three-Dimensional Cell Culture Matrices: State of the Art", Tissue Engineering Part B: Reviews, pp. 61-86, vol. 14, Issue 1 (Mar. 10, 2008).
Lee et al., "Uniform mesoporous dye-doped silica nanoparticles decorated with multiple magnetitenanocrystals for simultaneous enhanced magnetic resonance imaging, fluorescence imaging, and drug delivery", Journal of the American Chemical Society, pp. 552-557, vol. 132 (2010).
Legrand et al., "Pathophysiology of COVID-19-associated acute kidney injury", Nature Reviews Nephrology, vol. 17(11), pp. 751-764 (Nov. 2021).
Lehnert et al., "Cell behaviour on micropatterned substrata: limits of extracellular matrix geometry for spreading and adhesion", Journal of Cell Science, pp. 41-52, vol. 117 Part 1 (Jan. 1, 2004).
Lei et al., "Neutralization of SARS-CoV-2 spike pseudotyped virus by recombinant ACE2-Ig", Nature Communications, vol. 11(1), 2070 (Apr. 2020).
Leigh et al., "Resolution of inflammation in immune and nonimmune cells by interleukin-19", Am. J. Physiol. Cell Physiol., vol. 319(3), pp. C457-C464 (Aug. 2020).
Leikauf et al., "Mechanisms of ultrafine particle-induced respiratory health effects", Exp. Mol. Med., vol. 52(3), pp. 329-337 (Mar. 2020).
Leone et al., "CORAL: Predictive models for cytotoxicity of functionalized nanozeolites based on quasi-SMILES", Chemosphere, vol. 210, pp. 52-56 (2018).
Leong et al., "On the issue of transparency and reproducibility in nanomedicine", Nature Nanotechnology, pp. 629-635, vol. 14 (2019).
León-Núñez et al., "IgY Antibodies as Biotherapeutics in Biomedicine", Antibodies, vol. 11(4), 62 (Sep. 2022).
Lerman et al., "The Evolution of Polystyrene as a Cell Culture Material", Tissue Engineering Part B, pp. 359-372, vol. 24 (2018).
Letko et al., "Functional assessment of cell entry and receptor usage for SARS-CoV-2 and other lineage B betacoronaviruses", Nature Microbiology, pp. 562-569, vol. 5 (2020).
Leung et al., "Lipid nanoparticles containing siRNA synthesized by microfluidic mixing exhibit anelectron-dense nanostructured core", The Journal of Physical Chemistry C, vol. 116(34), pp. 18440-18450 (2012).
Leung et al., "Microfluidic assisted nanoprecipitation of PLGA nanoparticles for curcumin delivery to leukemia jurkat cells", Langmuir, vol. 34(13), pp. 3961-3970 (2018).
Leung et al., "Microfluidic mixing: a general method for encapsulating macromolecules in lipid nanoparticle systems", The Journal of Physical Chemistry B, vol. 119(28), pp. 8698-8706 (2015).
Levin et al., "Waning Immune Humoral Response to BNT162b2 Covid-19 Vaccine over 6 Months", New England Journal of Medicine, pp. E84(1)-e84(11), vol. 385:24 (Dec. 9, 2021).
Lewinski et al., "Cytotoxicity of nanoparticles", Small, vol. 4(1), pp. 26-49 (2008).
Lewis et al., "Continuous synthesis of copolymer particles in microfluidic reactors", Macromolecules, vol. 38(10), pp. 4536-4538 (2005).
Li et al., "A synthetic nanobody targeting RBD protects hamsters from SARS-CoV-2 infection", Article No. 4635, vol. 12 (2021).
Li et al., "Activation of topoisomerase II-mediated excision of chromosomal DNA loops during oxidative stress", Genes & Development, pp. 1553-1560, vol. 13 (1999).
Li et al., "Antitumor activity of celastrol nanoparticles in a xenograft retinoblastoma tumor mode", International Journal of Nanomedicine, pp. 2389-2398, vol. 7 (2012).
Li et al., "Antiviral and anti-inflammatory treatment with multifunctional alveolar macrophage-like nanoparticles in a surrogate mouse model of COVID-19", Advanced Science, vol. 8(13), 2003556 (May 2021).
Li et al., "Association of Renin-Angiotensin System Inhibitors With Severity or Risk of Death in Patients With Hypertension Hospitalized for Coronavirus Disease 2019 (COVID-19) Infection in Wuhan, China", JAMA Cardiology, pp. 825-830, vol. 5 (2020).
Li et al., "Breadth of SARS-CoV-2 neutralization and protection induced by a nanoparticle vaccine", Nature Communications, vol. 13(1), 6309 (Oct. 2022).
Li et al., "Cell-mimicking nanodecoys neutralize SARS-CoV-2 and mitigate lung injury in a non-human primate model of COVID-19" Nature Nanotechnology, pp. 942-951, vol. 16 (Aug. 2021).
Li et al., "Combinatorial design of nanoparticles for pulmonary mRNA delivery and genome editing", Nature Biotechnology, vol. 41, pp. 1410-1415 (Oct. 2023).
Li et al., "Copper sulfide nanoparticles for photothermal ablation of tumor cells", Nanomedicine, pp. 1161-1171, vol. 5 (2010).

(56) References Cited

OTHER PUBLICATIONS

Li et al., "Differential efficiencies to neutralize the novel mutants B. 1.1. 7 and 501Y. V2 by collectedsera from convalescent COVID-19 patients and RBD nanoparticle-vaccinated rhesus macaques", Cellular & Molecular Immunology, vol. 18(4), pp. 1058-1060 (Feb. 2021).
Li et al., "Effects of Surface Roughness of Hydroxyapatite on Cell Attachment and Proliferation", Journal of Biotechnology & Biomaterials, 2:150. doi: 10.4172/2155-952X.1000150.
Li et al., "Enhanced transfection efficiency and targeted delivery of self-assembling h-R3-dendriplexes in EGFR-overexpressing tumor cells", Oncotarget, vol. 6(28), 26177 (Jul. 2015).
Li et al., "Enhancing the immunogenicity of lipid-nanoparticle mRNA vaccines by adjuvanting the ionizable lipid and the mRNA", Nature Biomedical Engineering (Sep. 2023).
Li et al., "Enzyme-Catalyzed One-Step Synthesis of Ionizable Cationic Lipids for Lipid Nanoparticle-Based mRNA COVID-19 Vaccines", ACS Nano, vol. 16(11), pp. 18936-18950 (Nov. 2022).
Li et al., "Epitope-based peptide vaccines predicted against novel coronavirus disease caused by SARS-CoV-2", Virus Research, 198082, vol. 288 (Oct. 15, 2020).
Li et al., "Glucose-Conjugated Chitosan Nanoparticles for Targeted Drug Delivery and Their Specific Interaction with Tumor Cells", Frontiers of Materials Sciences, pp. 363-372, vol. 8 (Dec. 2014).
Li et al., "Hierarchical structured and programmed vehicles deliver drugs locally to inflamed sites of intestine", Biomaterials, vol. 185, pp. 322-332 (2018).
Li et al., "High drug-loaded microspheres enabled by controlled in-droplet precipitation promote functional recovery after spinal cord injury", Nature Communications, vol. 13(1), 1262 (Mar. 2022).
Li et al., "Inkjet printing for biosensor fabrication: combining chemistry and technology for advanced manufacturing", Lab on a Chip, pp. 2538-2558, vol. 15 (2015).
Li et al., "Microfluidic assembly of a nano-in-micro dual drug delivery platform composed of halloysite nanotubes and a pH-responsive polymer for colon cancer therapy", Acta Biomaterialia, vol. 48, pp. 238-246 (2017).
Li et al., "Mucin-controlled drug release from mucoadhesive phenylboronic acid-rich nanoparticles", International Journal of Pharmaceutics, vol. 479(1), pp. 261-264 (2015).
Li et al., "Self-assembling nanoparticle vaccines displaying the receptor binding domain of SARS-CoV-2elicit robust protective immune responses in rhesus monkeys", Bioconjugate Chemistry, vol. 32(5), pp. 1034-1046 (Jan. 2021).
Li et al., "Sulfonate-modified phenylboronic acid-rich nanoparticles as a novel mucoadhesive drug delivery system for vaginal administration of protein therapeutics: improved stability, mucin-dependent release and effective intravaginal placement", International Journal of Nanomedicine, vol. 11, pp. 5917-5930 (2016).
Li et al., "Surface coating-dependent cytotoxicity and degradation of graphene derivatives: Towards the design of non-toxic, degradable nano-graphene", Small, vol. 10(8), pp. 1544-1554 (2013).
Li et al., "The Horizon of Materiobiology: A Perspective on Material-Guided Cell Behaviors and Tissue Engineering", Chemical Reviews. pp. 4376-4421, vol. 117 (2017).
Li et al., "The MERS-CoV Receptor DPP4 as a Candidate Binding Target of the SARS-CoV-2 Spike", iScience, 101160, vol. 23, Issue 6 (Jun. 26, 2020).
Li et al., "Transmission Routes Analysis of SARS-CoV-2: A Systematic Review and Case Report", . Frontiers in Cell and Developmental Biology, vol. 8, Article 618 (Jul. 2020).
Li et al., "Yak interferon-alpha loaded solid lipid nanoparticles for controlled release", Research in Veterinary Science, vol. 88(1), pp. 148-153 (2010).
Li et al., "A comprehensive review of the global efforts on COVID-19 vaccine development", ACS Central Science, vol. 7(4), pp. 512-533 (Mar. 2021).
Lian et al., "Heterogeneous multi-compartmental DNA hydrogel particles prepared via microfluidic assembly for lymphocyte-inspired precision medicine", Nanoscale, vol. 13(48), pp. 20531-20540 (Dec. 2021).
Liang et al., "Design of a mutation-integrated trimeric RBD with broad protection against SARS-CoV-2", Cell Discovery, vol. 8, Art. 17 (Feb. 2022).
Liang et al., "Pulmonary Delivery of Biological Drugs", Pharmaceutics, 2020, 12(11):1025. https://doi.org/10.3390/pharmaceutics12111025.
Liang et al., "Solid lipid nanoparticle induced apoptosis of macrophages via a mitochondrial-dependent pathway in vitro and in vivo", International Journal of Nanomedicine, vol. 14, pp. 3283-3295 (2019).
Liao et al., "Interactions of Zinc Oxide Nanostructures with Mammalian Cells: Cytotoxicity and Photocatalytic Toxicity", International Journal of Molecular Sciences, 21(17):6305 (2020) doi: 10.3390/ijms21176305.
Liao et al., "Safety and immunogenicity of a recombinant interferon-armed RBD dimer vaccine (V-01)for COVID-19 in healthy adults: a randomized, double-blind, placebo-controlled, Phase I trial", Emerging Microbes & Infections, vol. 10(1), pp. 1589-1597 (Aug. 2021).
Liberti et al., "The Warburg Effect: How Does it Benefit Cancer Cells?" Trends in Biochemical Sciences, Opinion Special Issue: Mitochondria & Metabolism, pp. 211-218, vol. 41, Issue 3 (2016).
Lidén, "The European Commission Tries to Define Nanomaterials", Annals of Occupational Hygeine, pp. 1-5, vol. 55 (2011).
Lim et al., "SARS-CoV-2 infects macrophages in coronary atherosclerotic plaques", Nature Reviews Cardiology, vol. 20, pp. 795-797 (Dec. 2023).
Lin et al., "Celastrol Inhibits Dopaminergic Neuronal Death of Parkinson's Disease through Activating Mitophagy", Antioxidants, (Basel), Dec. 31, 2019, 9(1):37. doi: 10.3390/antiox9010037.
Lin et al., "Antiviral nanoparticles for sanitizing surfaces: A roadmap to self-sterilizing against COVID-19", Nano Today, vol. 40, 101267 (Aug. 2021).
Lin et al., "Aspect ratio plays a role in the hazard potential of CeO2 nanoparticles in mouse lung and zebrafish gastrointestinal tract", ACS Nano, vol. 8(5), pp. 4450-4464 (2014).
Lin et al., "Association of HLA class I with severe acute respiratory syndrome coronavirus infection", BMC Medical Genetics, pp. 1-7, 4:9 (2003).
Liong et al., "Multifunctional Inorganic Nanoparticles for Imaging, Targeting, and Drug Delivery", ACS Nano, pp. 889-896, vol. 2 (2008).
Liu et al., "A nano-in-nano vector: merging the best of polymeric nanoparticles and drug nanocrystals", Advanced Functional Materials, vol. 27(9), 1604508 (2017).
Liu et al., "A Versatile and Robust Microfluidic Platform Toward High Throughput Synthesis of Homogeneous Nanoparticles with Tunable Properties", Advanced Materials, pp. 2298-2304, vol. 27 (2015) https://doi.org/10.1002/adma.201405408.
Liu et al., "Aerodynamic analysis of SARS-CoV-2 in two Wuhan hospitals", Nature, pp. 557-560, vol. 582 (2020).
Liu et al., "An emergency responding mechanism for cruise epidemic prevention-taking COVID-19 as an example", Marine Policy, 2020, 119:104093. doi: 10.1016/j.marpol.2020.104093.
Liu et al., "An IgM-like inhalable ACE2 fusion protein broadly neutralizes SARS-CoV-2 variants", Nature Communications, vol. 14(1), 5191 (Aug. 2023).
Liu et al., "Analysis of model PM2.5-induced inflammation and cytotoxicity by the combination of avirtual carbon nanoparticle library and computational modeling", Ecotoxicol. Environ. Saf., vol. 191, 110216 (Mar. 2020).
Liu et al., "Anti-hypertensive Angiotensin II receptor blockers associated to mitigation of diseaseseverity in elderly COVID-19 patients", 2020, medRxiv, doi: https://doi.org/10.1101/2020.03.20.20039586.
Liu et al., "Atomic structure of a rhinovirus C, a virus species linked to severe childhood asthma", Proceedings of the National Academy of Sciences of the United States of America, pp. 8997-9002, vol. 113, No. 32 (Jul. 11, 2016).

(56) References Cited

OTHER PUBLICATIONS

Liu et al., "Biodegradable spheres protect traumatically injured spinal cord by alleviating the glutamate-induced Excitotoxicity", Advanced materials, vol. 30(14), 1706032 (2018).
Liu et al., "Broad-spectrum antiviral activity of Spatholobus suberectus Dunn against SARS-CoV-2, SARS-CoV-1, H5N1, and other enveloped viruses", Phytotherapy Research, vol. 36(8), pp. 3232-3247 (Aug. 2022).
Liu et al., "Classification nanoSAR development for cytotoxicity of metal oxide nanoparticles", Small, vol. 7(8), pp. 1118-1126 (2011).
Liu et al., "Close-loop dynamic nanohybrids on collagen-ark with in situ gelling transformation capabilityfor biomimetic stage-specific diabetic wound healing", Materials Horizons, Royal Society of Chemistry, vol. 6(2), pp. 385-393 (2019).
Liu et al., "Core/shell nanocomposites produced by superfast sequential microfluidic nanoprecipitation", Nano Letters, vol. 17(2), pp. 606-614 (Jan. 2017).
Liu et al., "Current developments and applications of microfluidic technology toward clinical translation of nanomedicines", Advanced Drug Delivery Reviews, vol. 128, pp. 54-83 (2018).
Liu et al., "Design Strategies for and Stability of MRNA-Lipid Nanoparticle COVID-19 Vaccines", Polymers, vol. 14(19), 4195 (Oct. 2022).
Liu et al., "Development of an LNP-encapsulated mRNA-RBD vaccine against SARS-CoV-2 and its variants", Pharmaceutics, vol. 14(5), 1101 (May 2022).
Liu et al., "Development of high-drug-loading nanoparticles", ChemPlusChem, vol. 85(9), pp. 2143-2157 (Aug. 2020).
Liu et al., "Lipid nanovesicles by microfluidics: manipulation, synthesis, and drug delivery", Advanced Materials, vol. 31(45), 1804788 (2019).
Liu et al., "Microfluidic Assembly of Monodisperse Multistage pH-Responsive Polymer/Porous Silicon Composites for Precisely Controlled Multi-Drug Delivery", Small, vol. 10(10), pp. 2029-2038 (2014).
Liu et al., "Microfluidic assisted one-step fabrication of porous silicon@ acetalated dextran nanocomposites for precisely controlled combination chemotherapy", Biomaterials, vol. 39, pp. 249-259 (2015).
Liu et al., "Microfluidic nanoparticles for drug delivery", Nano Micro Small, vol. 18(36), 2106580 (Apr. 2022).
Liu et al., "Microfluidic templated mesoporous silicon-solid lipid microcomposites for sustained drug delivery", ACS Applied Materials & Interfaces, vol. 5(22), pp. 12127-12134 (2013).
Liu et al., "Microfluidic-assisted fabrication of carriers for controlled drug delivery", Royal Society of Chemistry, Lab on a Chip, vol. 17(11), pp. 1856-1883 (2017).
Liu et al., "Microfluidics for production of particles: mechanism, methodology, and applications", Nano Micro Small, vol. 16(9), 1904673 (Nov. 2019).
Liu et al., "Multifunctional nanohybrid based on porous silicon nanoparticles, gold nanoparticles, andacetalated dextran for liver regeneration and acute liver failure theranostics", Advanced Materials, vol. 30(24), 1703393 (2018).
Liu et al., "On-chip preparation of calcium alginate particles based on droplet templates formed by using a centrifugal microfluidic technique", Journal of Colloid and Interface Science, vol. 466, pp. 20-27 (2016).
Liu et al., "Potential inhibitors against 2019-nCoV coronavirus M protease from clinically approved medicines", Journal of Genetics and Genomics, pp. 119-121, vol. 47 (2020).
Liu et al., "Promoting cardiac repair through simple engineering of nanoparticles with exclusivetargeting capability toward myocardial reperfusion injury by thermal resistant microfluidic platform", Advanced Functional Materials, vol. 32(36), 2204666 (Jun. 2022).
Liu et al., "Renal clearable inorganic nanoparticles: a new frontier of bionanotechnology", Materials Today, pp. 477-486, vol. 16, Issue 12 (Dec. 2013).
Liu et al., "Retracted: Preparation of bioactive interferon alpha-loaded polysaccharide nanoparticlesusing a new approach of temperature-induced water phase/water-phase emulsion", International Journal of Nanomedicine, vol. 7, pp. 4841-4848 (2012).
Liu et al., "SARS-CoV-2 tetrameric RBD protein blocks viral infection and induces potent neutralizing antibody response", Frontiers in Immunology, vol. 13, 960094 (Oct. 2022).
Liu et al., "Structural insights into the binding of hepatitis B virus core peptide to HLA-A2 alleles: Towards designing better vaccines", European Journal of Immunology, pp. 2097-2106, vol. 41 (2011).
Liu et al., "The Main Anticancer Bullets of the Chinese Medicinal Herb, Thunder God Vine", Molecules, pp. 5283-5297, vol. 16 (2011).
Liu et al., "Tourism crisis management: Can the Extended Parallel Process Model be used tounderstand crisis responses in the cruise industry?", Tourism Management, pp. 310-321, vol. 55 (Aug. 2016).
Liu et al., "Two-Step Self-Assembly of Hierarchically-Ordered Nanostructures", Journal of Materials Chemistry A, pp. 11688-11699, vol. 3, Issue 22 (2015).
Liu et al., "Vimentin contributes to epithelial-mesenchymal transition cancer cell mechanics by mediating cytoskeletal organization and focal adhesion maturation", Oncotarget, pp. 15966-15983, vol. 6 (2018).
Liu et al., "COVID-19: The first documented coronavirus pandemic in history", Biomed. J., vol. 43(4), pp. 328-333 (May 2020).
Liu, "The history of monoclonal antibody development—Progress, remaining challenges and future innovations", Annals of Medicine and Surgery, pp. 113-116, vol. 3, Issue 4 (Dec. 2014).
Locasale et al., "Altered metabolism in cancer", BMC Biology, Article No. 88 (2010).
Loetchutinat et al., "Spectrofluorometric determination of intracellular levels of reactive oxygen species in drug-sensitive and drug-resistant cancer cells using the 2?, 7 ?-dichlorofluorescein diacetate assay", Radiat. Phys. Chem., vol. 72(2-3), pp. 323-331 (2005).
Lokman et al., "Chick chorioallantoic membrane (CAM) assay as an in vivo model to study the effectof newly identified molecules on ovarian cancer invasion and metastasis", International Journal of Molecular Sciences, pp. 9959-9970, vol. 13 (2012).
London et al., "Rosetta FlexPepDock web server—High resolution modeling of peptide-protein interactions", Nucleic Acids Research, W249-W253, vol. 39 (2011).
Lone et al., "Microfluidic synthesis of Janus particles by UV-directed phase separation", Chemical Communications, vol. 47(9), pp. 2634-2636 (2011).
Long et al., "Novel Ionizable Lipid Nanoparticles for SARS-CoV-2 Omicron mRNA Delivery", Advanced Healthcare Materials, vol. 12(13), 2202590 (Jan. 2023).
Looi, "How are covid-19 symptoms changing?", The BMJ, vol. 380, p. 3 (Jan. 2023).
López-Alonso et al., "Carbodiimide EDC Induces Cross-Links That Stabilize RNase A C-Dimeragainst Dissociation: EDC Adducts Can Affect Protein Net Charge, Conformation, and Activity", Bioconjugate Chemistry, pp. 1459-1473, vol. 20 (2009).
López-Sagaseta et al., "Self-assembling protein nanoparticles in the design of vaccines", Computational and Structural Biotechnology Journal, pp. 58-68, vol. 14 (2015).
Lou et al., "Delivery of self-amplifying mRNA vaccines by cationic lipid nanoparticles: The impact of cationic lipid selection", Journal of Controlled Release, vol. 325, pp. 370-379 (Sep. 2020).
Loveridge et al., "The Sphingosine Kinase 1 Inhibitor 2-(p-hydroxyanilino)-4-(p-chlorophenyl)thiazole Induces Proteasomal Degradation of Sphingosine Kinase 1 in Mammalian Cells", Journal of Biological Chemistry, Signal Transduction, pp. 38841-38852, vol. 285, Issue 50 (Dec. 2010).
Lu et al., "COVID-19 Outbreak Associated with Air Conditioning in Restaurant, Guangzhou, China, 2020", Emerging Infectious Diseases, pp. 1628-1631, vol. 26 (2020).
Lu et al., "Size Effect on Cell Uptake in Well-Suspended, Uniform Mesoporous Silica Nanoparticles", Small, pp. 1408-1413, vol. 5 (2009).
Lu et al., "The impact of spike N501Y mutation on neutralizing activity and RBD binding of SARS-CoV-2 convalescent serum", EBioMedicine, vol. 71, 103554 (Sep. 2021).

(56) References Cited

OTHER PUBLICATIONS

Luan et al., "Computer-aided nanotoxicology: assessing cytotoxicity of nanoparticles under diverse experimental conditions by using a novel QSTR-perturbation approach", Nanoscale, vol. 6(18), pp. 10623-10630 (2014).
Lucas et al., "Protein deposition from dry powder inhalers: fine particle multiplets as performance modifiers", Pharmaceutical Research, pp. 562-569, vol. 15 (1998).
Lund et al., "Definition of supertypes for HLA molecules using clustering of specificity matrices", Immunogenetics, pp. 797-810, vol. 55 (2004).
Lunenfeld et al., "The clinical consequences of an ageing world and preventive strategies", Best Practice & Research Clinical Obstetrics & Gynaecology, pp. 643-659, vol. 27, Issue 5 (Oct. 2013).
Luo et al., "Controllable preparation of particles with microfluidics", Particuology, vol. 9(6), pp. 545-558 (2011).
Luong et al., "Chemistry of biotin-streptavidin and the growing concern of an emerging biotin interference in clinical immunoassays", ACS Omega, vol. 5(1), pp. 10-18 (Dec. 2019).
Lupala et al., "Mutations on RBD of SARS-CoV-2 Omicron variant result in stronger binding to human ACE2 receptor", Biochemical and Biophysical Research Communications, vol. 590, pp. 34-41 (Dec. 2021).
Luu et al., "Pannexin-1 channel opening is critical for COVID-19 pathogenesis", iScience, Dec. 17, 2021, 24(12):103478.
Lv et al., "Human papilloma virus DNA-biomarker analysis for cervical cancer: signal enhancement bygold nanoparticle-coupled tetravalent streptavidin-biotin strategy", International Journal of Biological Macromolecules, vol. 134, pp. 354-360 (2019).
Lyngse et al., "SARS-CoV-2 Omicron VOC Transmission in Danish Households", medRxiv, Dec. 27, 2021, 21268278; doi: https://doi.org/10.1101/2021.12.27.21268278.
Ma et al., "Intranasal vaccination with recombinant receptor-binding domain of MERS-CoV spike proteininduces much stronger local mucosal immune responses than subcutaneous immunization: Implication for designing novel mucosal MERS vaccines", Vaccine, pp. 2100-2108, vol. 32 (2014).
Ma et al., "Nanoparticle vaccines based on the receptor binding domain (RBD) and heptad repeat (HR)of SARS-CoV-2 elicit robust protective immune responses", Immunity, vol. 53(6), pp. 1315-1330 (Dec. 2020).
Ma et al., "SARS-CoV-2 Spike Stem Protein Nanoparticles Elicited Broad ADCC and Robust Neutralization against Variants in Mice", Small, vol. 18(25), 2200836 (May 2022).
Ma et al., "Selective killing of Shiga toxin-producing *Escherichia coli* with antibody-conjugated chitosannanoparticles in the gastro-intestinal tract", ACS Applied Materials & Interfaces, vol. 12(16), pp. 18332-18341 (Apr. 2020).
Ma et al., "Expression of SARS-CoV-2 receptor ACE2 and TMPRSS2 in human primary conjunctival and pterygium cell lines and in mouse cornea", Eye, vol. 34(7), pp. 1212-1219 (May 2020).
Maacha et al., "Evaluation of Tumor Cell Invasiveness In Vivo: The Chick Chorioallantoic membrane Assay", Methods in Molecular Biology, pp. 71-77, vol. 1749 (2018).
Määttänen et al., "A low-cost paper-based inkjet-printed platform for electrochemical analyses", Sensors and Actuators B: Chemical, pp. 153-162, vol. 177 (2013).
Määttänen et al., "Hierarchically structured self-supported latex films for flexible and semi-transparent electronics", Applied Surface Science, pp. 37-44, vol. 364 (2016).
Määttänen et al., "Printed paper-based arrays as substrates for biofilm formation" AMB Express, pp. 32-44, vol. 4, Article No. 32 (2014).
Mabrouk et al., "Advanced materials for SARS-CoV-2 vaccines", Advanced Materials, vol. 34(12), 2107781 (Dec. 2021).
Mabrouk et al., "Lyophilized, thermostable Spike or RBD immunogenic liposomes induce protective immunity against SARS-CoV-2 in mice", Science Advances, vol. 7(49), eabj1476 (Dec. 2021).
Maeki et al., "A strategy for synthesis of lipid nanoparticles using microfluidic devices with a mixer structure", RSC Advances, vol. 5(57), pp. 46181-46185 (2015).
Maeki et al., "Advances in microfluidics for lipid nanoparticles and extracellular vesicles and applications in drug delivery systems", Advanced Drug Delivery Reviews, vol. 128, pp. 84-100 (2018).
Maeki et al., "Mass production system for RNA-loaded lipid nanoparticles using piling up microfluidic devices", Applied Materials Today, vol. 31, 101754 (Apr. 2023).
Maeki et al., "Microfluidic technologies and devices for lipid nanoparticle-based RNA delivery", Journal of Controlled Release, vol. 344, pp. 80-96 (Feb. 2022).
Maestra et al., "Inhibition of the Cell Uptake of Delta and Omicron SARS-CoV-2 Pseudoviruses by N-Acetylcysteine Irrespective of the Oxidoreductive Environment", Cells, vol. 11(20), Art. 3313 (Oct. 2022).
Mafham et al., "What is the association of COVID-19 with heart attacks and strokes?", The Lancet, pp. 561-563, vol. 398, Issue 10300 (2021).
Magdolenova et al., "Impact of agglomeration and different dispersions of titanium dioxidenanoparticles on the human related in vitro cytotoxicity and genotoxicity", J. Environ. Monit., vol. 14(2), pp. 455-464 (2012).
Maghsoodi, "Role of Solvents in Improvement of Dissolution Rate of Drugs: Crystal Habit and Crystal Agglomeration", Advanced Pharmaceutical Bulletin, pp. 13-18, vol. 5, Issue 1 (2015).
Mahajan et al., "Antiviral strategies targeting host factors and mechanisms obliging +ssRNA viral pathogens", Bioorganic & Medicinal Chemistry, vol. 46, 116356 (Aug. 2021).
Mahmud et al., "Advances in nanomaterial-based platforms to combat COVID-19: Diagnostics, preventions, therapeutics, and vaccine developments", ACS Applied Bio Materials, vol. 5(6), pp. 2431-2460 (May 2022).
Maier et al., "ff14SB: Improving the Accuracy of Protein Side Chain and Backbone Parameters from ff99SB", Journal of Chemical Theory and Computation, pp. 3696-3713, vol. 11, Issue 8 (2015).
Mainzer, "Interdisciplinarity and innovation dynamics. On convergence of research, technology, economy, and society", Poiesis & Praxis, pp. 275-289, vol. 7 (2011).
Majdoul et al., "Lessons in self-defence: inhibition of virus entry by intrinsic immunity", Nature Reviews Immunology, vol. 22(6), pp. 339-352 (Oct. 2021).
Majumder et al., "Recent developments on therapeutic and diagnostic approaches for COVID-19", The AAPS Journal, vol. 23(1), 14 (Jan. 2021).
Mäkelä et al., "Intranasal inhibitor blocks Omicron and other variants of SARS-CoV-2", bioRxiv, 2021, 12.28 474326; doi: https://doi.org/10.1101/2021.12.28.474326.
Makled et al., "Nebulized solid lipid nanoparticles for the potential treatment of pulmonary hypertension via targeted delivery of phosphodiesterase-5-inhibitor", Int. J. Pharm. vol. 517, pp. 312-321 (2017).
Malabadi et al., "Vaccine development for coronavirus (SARS-CoV-2) disease (Covid-19): Lipid nanoparticles", International Journal of Research and Scientific Innovations, vol. 8, Issue 3, pp. 189-195 (Jan. 2021).
Malatesta et al., "Transmission electron microscopy as a powerful tool to investigate the interaction of nanoparticles with subcellular structures", International Journal of Molecular Sciences, vol. 22(23), 12789 (Nov. 2021).
Malhotra et al., "Classical chemotherapy: mechanisms, toxicities and the therapeutic window", Cancer Biology & Therapy, pp. 1-3, vol. 2, Suppl. 1 (Published online: Mar. 1, 2003).
Mallapaty, "Antibody tests suggest that coronavirus infections vastly exceed official counts", Nature, Apr. 17, 2020; Update Apr. 19, 2020; Correction Apr. 22, 2020, doi: https://doi.org/10.1038/d41586-020-01095-0.
Mamaeva et al., "Inhibiting Notch Activity in Breast Cancer Stem Cells by Glucose Functionalized Nanoparticles Carrying γ-secretase Inhibitors", Molecular Therapy, pp. 926-936, vol. 24, Issue 5 (2016).

(56) References Cited

OTHER PUBLICATIONS

Mamaeva et al., "Mesoporous silica nanoparticles as drug delivery systems for targeted inhibition of Notch signaling in cancer", Molecular Therapy, pp. 1538-1546, vol. 19, Issue 8 (2011).
Mandon et al., "Three-dimensional HepaRG spheroids as a liver model to study human genotoxicity in vitro with the single cell gel electrophoresis assay", Sci. Rep., vol. 9(1), 10548 (2019).
Mani et al., "Targeting DPP4-RBD interactions by sitagliptin and linagliptin delivers a potential host-directed therapy against pan-SARS-CoV-2 infections", International Journal of Biological Macromolecules, vol. 245, 125444 (Jun. 2023).
Manke et al., "Mechanisms of nanoparticle-induced oxidative stress and toxicity", BioMed Res. Int., vol. 2013, 942916 (2013).
Manshian et al., "The in vitro micronucleus assay and kinetochore staining: methodology and criteria for the accurate assessment of genotoxicity and cytotoxicity", In: Manshian BB, Singh N and Doak SH, editor, In Genotoxicity Assessment: Methods and Protocols; Springer, pp. 269-289 (2013).
Mao et al., "Design and application of nanoparticles as vaccine adjuvants against human corona virus infection", Journal of Inorganic Biochemistry, vol. 219, 111454 (Mar. 2021).
Maponga et al., "Persistent SARS-CoV-2 Infection with Accumulation of Mutations in a Patient with Poorly Controlled HIV Infection" in 12 pages, (Posted Jan. 21, 2022) Available at SSRN: https://ssrn.com/abstract=4014499 or http://dx.doi.org/10.2139/ssrn.4014499.
Maranda et al., "Safety and efficacy of inhaled IBIO123 for mild-to-moderate COVID-19: a randomised, double-blind, dose-ascending, placebo-controlled, phase 1/2 trial", The Lancet Infectious Diseases, vol. 24(1), pp. 25-35 (Aug. 2023).
Marcussen, "Visualizing the network of cruise destinations in the Baltic Sea—a multidimensional scaling approach", Scandinavian Journal of Hospitality and Tourism, pp. 1-15, vol. 17 (2016).
Marei et al., "Potential of antibody-drug conjugates (ADCs) for cancer therapy", Cancer Cell Int., vol. 22, 255 (2022).
Marks et al., "The MTT cell viability assay for cytotoxicity testing in multidrug-resistant human leukemic cells", Leuk. Res., vol. 16(12), pp. 1165-1173 (1992).
Marrison et al., "Ptychography—a label free, high-contrast imaging technique for live cells using quantitative phase information", Scientific Reports, vol. 3, Article No. 2369, in 7 pages (2013).
Martin et al., "Surface Functionalization of Nanomaterials with Dendritic Groups: Toward Enhanced Binding to Biological Targets" Journal of the American Chemical Society, pp. 734-741, vol. 131 (2009).
Martinez et al., "Diagnostics for the Developing World: Microfluidic Paper-Based Analytical Devices", Analytical Chemistry, pp. 3-10, vol. 82 (2010).
Martins et al., "Microfluidic nanoassembly of bioengineered chitosan-modified FcRn-targeted poroussilicon nanoparticles@ hypromellose acetate succinate for oral delivery of antidiabetic peptides", ACS Applied Materials & Interfaces, vol. 10(51), pp. 44354-44367 (2018).
Martins et al., "Using microfluidic platforms to develop CNS-targeted polymeric nanoparticles for HIV therapy", European Journal of Pharmaceutics and Biopharmaceutics, vol. 138, pp. 111-124 (2019).
Mary et al., "Rationale for COVID-19 Treatment by Nebulized Interferon-β-1b-Literature Review and Personal Preliminary Experience", Frontiers in Pharmacology, Hypothesis and Theory Article (Nov. 30, 2020) doi: 10.3389/fphar.2020.592543.
Masoomi Nomandan et al., "In silico design of refined ferritin-SARS-CoV-2 glyco-RBD nanoparticle vaccine", Frontiers in Molecular Biosciences, vol. 9, 976490 (Sep. 2022).
Masre et al., "Classical and alternative receptors for SARS-CoV-2 therapeutic strategy", Reviews in Medical Virology, vol. 31(5), pp. 1-9 (Dec. 2020).
Matsumura et al., "A new concept for macromolecular therapeutics in cancer chemotherapy:mechanism of tumoritropic accumulation of proteins and the antitumor agent smancs", Cancer Research, pp. 6387-6392, vol. 46 (1986).
Matsuura-Sawada et al., "Microfluidic Platform Enabling Efficient On-Device Preparation of Lipid Nanoparticles for Formulation Screening", ACS Applied Engineering Materials, vol. 1(1), pp. 278-286 (Nov. 2022).
Mayer et al., "Hsp70 chaperones: Cellular functions and molecular mechanism", Cellular and Molecular Life Sciences, pp. 670-684, vol. 62 (2005).
Maynard, "Don't define nanomaterials", Nature, p. 31, vol. 475 (Jul. 7, 2011).
Mazzu-Nascimento et al., "Towards low-cost bioanalytical tools for sarcosine assays for diagnostics", Analytical Methods, pp. 7312-7318, vol. 8 (2016).
McCallum et al., "SARS-CoV-2 immune evasion by the B.1.427/B.1.429 variant of concern", Science, pp. 648-654, vol. 373 (2021).
McCallum et al., "Structure-guided covalent stabilization of coronavirus spike glycoprotein trimers in the closed conformation", Nature Structural & Molecular Biology, pp. 942-949, vol. 27 (2020).
McCraw et al., "Structural analysis of influenza vaccine virus-like particles reveals a multicomponent organization", Scientific Reports, Article No. 10342 Vol. 8 (2018).
McKay et al., "Self-amplifying RNA SARS-CoV-2 lipid nanoparticle vaccine candidate induces high neutralizing antibody titers in mice", Nature communications, vol. 11(1), 3523 (Jul. 2020).
McKechnie et al., "The Innate Immune System: Fighting on the Front Lines or Fanning the Flames of COVID-19?" Cell Host & Microbe, pp. 863-869, vol. 27 (2020).
McLachlan, "The angiotensin-converting enzyme 2 (ACE2) receptor in the prevention and treatment of COVID-19 are distinctly different paradigms", Clinical Hypertenion, in 3 pages, 26:14 (2020).
McManus et al., "Co-encapsulation by Flash NanoPrecipitation of Insulin, Trypsin Inhibitor and Caprate Permeabilization Enhancer for Oral Administration", Nanomed, vol. 3, pp. 710-723 (Dec. 2020).
McNerney, "Diagnostics for Developing Countries", Diagnostics, pp. 200-209, vol. 5 (2015).
McQuaid et al., "Uptake of severe acute respiratory syndrome coronavirus 2 spike protein mediatedby angiotensin converting enzyme 2 and ganglioside in human cerebrovascular cells", Frontiers in Neuroscience, vol. 17, 1117845 (Feb. 2023).
Medhi et al., "Nanoparticle-Based Strategies to Combat COVID-19", ACS Applied Nano Materials, pp. 8557-8580, vol. 3 (2020).
Meena et al., "RBD decorated PLA nanoparticle admixture with aluminum hydroxide elicit robust andlong lasting immune response against SARS-CoV-2", European Journal of Pharmaceutics and Biopharmaceutics, vol. 176, pp. 43-53 (May 2022).
Meijerman et al., "Combined action and regulation of phase II enzymes and multidrug resistance proteins in multidrug resistance in cancer", Cancer Treatment Reviews, pp. 505-520, vol. 34 (2008).
Mejías et al., "Dimercaptosuccinic acid-coated magnetite nanoparticles for magnetically guided in vivo delivery of interferon gamma for cancer immunotherapy", Biomaterials, vol. 32(11), pp. 2938-2952 (2011).
Mendillo et al., "HSF1 Drives a Transcriptional Program Distinct from Heat Shock to Support Highly Malignant Human Cancers", Cell, pp. 549-562, vol. 150, Issue 3 (2012).
Menezes Dos Reis et al., "Immunometabolic Signature during Respiratory Viral Infection: A Potential Target for Host-Directed Therapies", Viruses, vol. 15(2), 525 (Feb. 2023).
Meng et al., "A predictive toxicological paradigm for the safety assessment of nanomaterials", ACS Nano, vol. 3(7), pp. 1620-1627 (2009).
Meng et al., "Anti-Entry Activity of Natural Flavonoids against SARS-CoV-2 by Targeting Spike RBD. Viruses", vol. 15(1), 160 (Jan. 2023).
Meng et al., "Inhalation delivery of dexamethasone with iSEND nanoparticles attenuates the COVID-19 cytokine storm in mice and nonhuman primates", Science Advances, vol. 9, Issue 24, eadg3277 (Jun. 2023).

(56) References Cited

OTHER PUBLICATIONS

Meng et al., "Intracellular drug release nanosystems", Materials Today, vol. 15(10), pp. 436-442 (2012).
Meng et al., "Renin-angiotensin system inhibitors improve the clinical outcomes of COVID-19 patients with hypertension", Emerging Microbes & Infections, pp. 757-760, vol. 9, Issue 1 (2020).
Merad et al., "Pathological inflammation in patients with COVID-19: a key role for monocytes and macrophages", Nature Reviews Immunology, pp. 355-362, vol. 20 (2020).
Mesárošová et al., "The role of reactive oxygen species in the genotoxicity of surface-modified magnetite nanoparticles", Toxicol. Lett., vol. 226(3), pp. 303-313 (2014).
Micheau et al., "NF-kappaB signals induce the expression of c-FLIP", Molecular and Cellular Biology, pp. 5299-5305, vol. 21, No. 16 (2001).
Migliorini et al., "Association between HLA genotypes and COVID-19 susceptibility, severity and progression: a comprehensive review of the literature", European Journal of Medical Research, 26(1):84, in 9 pages (2021).
Mikolajczyk et al., "Evaluating the toxicity of TiO2-based nanoparticles to Chinese hamster ovary cells and *Escherichia coli*: a complementary experimental and computational approach", Beilstein J. Nanotechnol., vol. 8, pp. 2171-2180 (2017).
Mikolajczyk et al., "Nano-QSAR modeling for ecosafe design of heterogeneous TiO2-based nano-photocatalysts", Environ. Sci.: Nano, vol. 5(5), pp. 1150-1160 (2018).
Milighetti et al., "Large clones of pre-existing T cells drive early immunity against SARS-COV-2 and LCMV infection", iScience, vol. 26(6) (May 2023).
Miller et al., "c-Myc and cancer metabolism", Clinical Cancer Research, pp. 5546-5553, vol. 18 (2012).
Miller et al., "Risk factors for metastatic disease at presentation with osteosarcoma: an analysis of the SEER database", The Journal of Bone and Joint Surgery, in 8 pages, 95(13): e89 (2013).
Miluzio et al., "Mapping of functional SARS-CoV-2 receptors in human lungs establishes differences in variant binding and SLC1A5 as a viral entry modulator of hACE2", EBioMedicine, vol. 87, 104390 (Dec. 2022).
Min et al., "Antibodies and vaccines target RBD of SARS-CoV-2", Frontiers in Molecular Biosciences, vol. 8, 671633 (Apr. 2021).
Mizuno et al., "Formation of monodisperse hierarchical lipid particles utilizing microfluidic droplets in a nonequilibrium state", Langmuir, vol. 31(8), pp. 2334-2341 (2015).
Moens et al., "The role of mitogen-activated protein kinase-activated protein kinases (MAPKAPKs) in inflammation", Genes (Basel), vol. 4(2), pp. 101-133 (2013).
Moghaddam et al., "Enhanced Cellular Uptake of Nanoparticles by Increasing the Hydrophobicity of Poly(lactic Acid) through Copolymerization with Cell-Membrane-Lipid Components", Chemical COmmunications, pp. 14605-14608, vol. 51, Issue 78 (2015).
Mohapatra et al., "Omicron (B.1.1.529 variant of SARS-CoV-2); an emerging threat: current global scenario", Journal of Medical Virology, vol. 94(5), 1780 (Jan. 2022).
Mohsen et al., "Virus-like particle vaccinology, from bench to bedside", Cellular & Molecular Immunology, vol. 19(9), pp. 993-1011 (Aug. 2022).
Molinaro et al., "Design and development of biomimetic nanovesicles using a microfluidic approach", Advanced Materials, vol. 30(15), 1702749 (2018).
Molinaro et al., "In Vitro Study of the Anti-inflammatory and Antifibrotic Activity of Tannic Acid-Coated Curcumin-Loaded Nanoparticles in Human Tenocytes", ACS Applied Materials & Interfaces, vol. 15(19), pp. 23012-23023 (May 2023).
MØller, "The comet assay: ready for 30 more years", Mutagenesis, vol. 33(1), pp. 1-7 (2018).
Monsé et al., "Concentration-dependent systemic response after inhalation of nano-sized zinc oxide particles in human volunteers", Particle and Fibre Toxicology, in 11 pages (2018) https://doi.org/10.1186/s12989-018-0246-4.
Monsigny et al., "Colorimetric determination of neutral sugars by a resorcinol sulfuric acid micromethod", Analytical Biochemistry, pp. 525-530, vol. 175, Issue 2 (1988).
Monteil et al., "Inhibition of SARS-CoV-2 Infections in Engineered Human Tissues Using Clinical-Grade Soluble Human ACE2", Cell, pp. 905-913, vol. 181, Issue 4 (2020).
Moore et al., "Vaccination and non-pharmaceutical interventions for COVID-19: a mathematical modelling study", The Lancet, pp. 793-802, vol. 21, Issue 6 (2021).
Morand et al., "Biodiversity and COVID-19: A report and a long road ahead to avoid another pandemic", One Earth, pp. 920-923, vol. 4 (2021).
Morawaska et al., "How can airborne transmission of COVID-19 indoors be minimised?", Environment International, 105832, in 7 pages, vol. 142 (Sep. 2020).
Morawska et al., "The physics of respiratory particle generation, fate in the air, and inhalation", Nat. Rev. Phys., vol. 4(11), pp. 723-734 (Aug. 2022).
Morimoto, "Regulation of the heat shock transcriptional response: cross talk between a family ofheat shock factors, molecular chaperones, and negative regulators", Genes and Development, pp. 3788-3796, vol. 12 (1998).
Moros et al., "Monosaccharides versus PEG-functionalized NPs: Influence in the cellular uptake", ACS Nano, vol. 6(2), pp. 1565-1577 (2012).
Morris et al., "Redox regulation of the immune response", Cell. Mol. Immunol., vol. 19(10), pp. 1079-1101 (Sep. 2022).
Mortera et al., "Cell-induced intracellular controlled release of membrane impermeable cysteine froma mesoporous silica nanoparticle-based drug delivery system", Chemical Communications, pp. 3219-3221, Issue 22 (2009).
Mosadegh et al., "Three-dimensional model for cardiac ischemia", Advanced Healthcare Materials, pp. 1036-1043, vol. 3, Issue 7 (Jul. 2014).
Mosesso et al., "In vitro cytogenetic assays: chromosomal aberrations and micronucleus tests", In:Dhawan A and Bajpayee M, editor, In Genotoxicity Assessment: Methods and Protocols; Springer, pp. 79-104 (2019).
Mosselhy et al., "COVID-19 pandemic: what about the safety of anti-coronavirus nanoparticles?", Nanomaterials, vol. 11(3), 796 (Mar. 2021).
Moubarak et al., "The death receptor antagonist FLIP-L interacts with Trk and is necessary for neurite outgrowth induced by neurotrophins", The Journal of Neuroscience, pp. 6094-6105, vol. 30(17) (Apr. 28, 2010).
Moulahoum et al., "How should diagnostic kits development adapt quickly in COVID 19-like pandemic models? Pros and cons of sensory platforms used in COVID-19 sensing", Talanta, 121534, in 11 pages, vol. 222 (2021).
Mu et al., "Predicting toxic potencies of metal oxide nanoparticles by means of nano-QSARs", Nanotoxicology, vol. 10(9), pp. 1207-1214 (2016).
Mühlfeld et al., "Visualization and quantitative analysis of nanoparticles in the respiratory tract by transmission electron microscopy", Particle and Fibre Toxicology, vol. 4(1) (2007).
Muhsin et al., "Effects of Chemical Conjugation of l-Leucine to Chitosan on Dispersibility and Controlled Release of Drug from a Nanoparticulate Dry Powder Inhaler Formulation", Molecular Pharmaceutics, pp. 1455-1466, vol. 13 (2016).
Mukherjee et al., "Preparation, characterization and in-vitro evaluation of sustained release protein-loaded nanoparticles based on biodegradable polymers", International Journal of Nanomedicine, vol. 3(4), pp. 487-496 (2008).
Muller et al., "The determination and interpretation of the therapeutic index in drug development" Nature Reviews Drug Discovery, pp. 751-761, vol. 11 (2012).
Mulligan et al., "Phase I/II study of COVID-19 RNA vaccine BNT162b1 in adults", Nature, vol. 586, pp. 589-593 (Aug. 2020).
Mulpuru et al., "Immunoinformatic based identification of cytotoxic T lymphocyte epitopes from the Indian isolate of SARS-CoV-2", Scientific Reports, 11:4516, in 9 pages (2021).

(56) References Cited

OTHER PUBLICATIONS

Münter et al., "Investigating generation of antibodies against the lipid nanoparticle vector following COVID-19 vaccination with an mRNA vaccine", Molecular Pharmaceutics, vol. 20, pp. 3356-3366 (Jul. 2023).
Muralidharan et al., "Inhalable nanoparticulate powders for respiratory delivery", Nanomedicine: Nanotechnology, Biology and Medicine, pp. 1189-1199, vol. 11, Issue 5 (Jul. 2015).
Murrell et al., "Forcing cells into shape: the mechanics of actomysin contractility", Nature Reviews Molecular Cell Biology, pp. 486-498, vol. 16 (2015).
Myers, "Why bioimage informatics matters", Nature Methods, pp. 659-660, 9:7 (Jun. 28, 2012).
Myhre et al., "Evaluation of the probes 2?, 7 ?-dichlorofluorescin diacetate, luminol, and lucigenin as indicators of reactive species formation", Biochem. Pharmacol., vol. 65(10), pp. 1575-1582 (2003).
Nadim et al., "COVID-19-associated acute kidney injury: consensus report of the 25th Acute Disease Quality Initiative (ADQI) Workgroup", Nature reviews nephrology, vol. 16(12), pp. 747-764 (Oct. 2020).
Nagase et al., "Apoptosis Induction in HL-60 cells and Inhibition of Topoisomerase II by Triterpene Celastrol", Bioscience Biotechnology Biochemistry, pp. 1883-1887, vol. 67, Issue 9 (2003).
Nagata, "Apoptosis and Clearance of Apoptotic Cells", Annual Review of Immunology, pp. 489-517, vol. 36 (2018).
Nakagawa et al., "Mechanisms of coronavirus nsp1-mediated control of host and viral gene expression", Cells, vol. 10 (2), 300 (Feb. 2021).
Nakajima et al., "Mechanism of Amide Formation by Carbodiimide for Bioconjugation in Aqueous Media", Bioconjugate Chemistry, pp. 123-130, vol. 6 (1995).
Nakamura et al., "Direct synthesis of monodispersed thiol-functionalized nanoporous silica spheresand their application to a colloidal crystal embedded with gold nanoparticles" Journal of Materials Chemistry, pp. 3726-3732, Issue 35 (2007).
Nakamura et al., "The effect of size and charge of lipid nanoparticles prepared by microfluidic mixingon their lymph node transitivity and distribution", Molecular Pharmaceutics, vol. 17(3), pp. 944-953 (Jan. 2020).
Nakanishi et al., "Genetic instability in cancer cells by impaired cell cycle checkpoints", Cancer Science, pp. 984-989, vol. 97, Issue 10 (Oct. 2006).
Nam et al., "Cellular uptake mechanism and intracellular fate of hydrophobically modified glycol chitosan nanoparticles", Journal of Controlled Release, pp. 259-267, vol. 135, Issue 3 (May 5, 2009).
Namiot et al., "Nanoparticles in Clinical Trials: Analysis of Clinical Trials, FDA Approvals and Use for COVID-19 Vaccines", International Journal of Molecular Sciences, vol. 24, 787 (Jan. 2023).
Nanishi et al., "Carbohydrate fatty acid monosulphate: oil-in-water adjuvant enhances SARS-CoV-2 RBD nanoparticle-induced immunogenicity and protection in mice", NPJ Vaccines, vol. 8(1) (Feb. 2023).
Narni-Mancinelli et al., "Clues that natural killer cells help to control COVID", Nature, pp. 226-227, vol. 600 (Dec. 9, 2021).
Nasr et al., "PAMAM dendrimers as aerosol drug nanocarriers for pulmonary delivery vianebulization", International Journal of Pharmaceutics, pp. 242-250, vol. 461, Issues 1-2 (Jan. 30, 2014).
Nature Methods, "The quest for quantitative microscopy", p. 627, vol. 9, No. 7 (Jul. 2012).
Nature Review Materials, "Let's talk about lipid nanoparticles", Nat. Rev. Mater., Editorial, vol. 6(2), pp. 99-99 (Feb. 2021).
Nature, "COVID research: a year of scientific milestones", doi: https://doi.org/10.1038/d41586-020-00502-w (May 5, 2021).
Neerukonda et al., "Establishment of a well-characterized SARS-CoV-2 lentiviral pseudovirus neutralization assay using 293T cells with stable expression of ACE2 and TMPRSS2", PloS One, vol. 16(3), e0248348 (Mar. 2021).
Negahdaripour et al., "Harnessing self-assembled peptide nanoparticles in epitope vaccine design", Biotechnology Advances, pp. 575-596, vol. 35 (2017).
Nel et al., "A multi-stakeholder perspective on the use of alternative test strategies for nanomaterial safety assessment", ACS Nano, vol. 7(8), pp. 6422-6433 (2013).
Nel et al., "Nanomaterial toxicity testing in the 21st century: Use of a predictive toxicological approach and high-throughput screening", Acc. Chem. Res., vol. 46(3), pp. 607-621 (2012).
Nel, "Implementation of alternative test strategies for the safety assessment of engineered nanomaterials", J. Intern. Med., vol. 274(6), pp. 561-577 (2013).
Neufurth et al., "The inorganic polymer, polyphosphate, blocks binding of SARS-CoV-2 spike protein to ACE2 receptor at physiological concentrations", Biochemical Pharmacology, 114215 in 10 pages, vol. 182 (Dec. 2020).
Ng et al., "Immunogenetics in SARS: A case-control study", Hong Kong Medical Journal, pp. 29-33, vol. 16, No. 5, Supplement 4 (Oct. 2010).
Ng et al., "Memory T cell responses targeting the SARS coronavirus persist up to 11 years post-infection", Vaccine, pp. 2008-2014, vol. 34, Issue 17 (Apr. 12, 2016).
Ng et al., "Paper-based cell culture platform and its emerging biomedical applications", Materials Today, pp. 32-44, vol. 20, Issue 1 (Jan.-Feb. 2017).
Nguyen et al., "Protein-based antigen presentation platforms for nanoparticle vaccines", NPJ Vaccines, vol. 6, Article No. 70 (2021).
Nguyen et al., "Diagnosis and Treatment of Patients with Thyroid Cancer", American Health & Drug Benefits, pp. 30-40, vol. 8, No. 1 (Feb. 2015).
Nguyen et al., "Human Leukocyte Antigen Susceptibility Map for Severe Acute Respiratory Syndrome Coronavirus 2", Journal of Virology, e00510-20 in 12 pages, vol. 94, Issue 13 (Jul. 2020).
Nguyen et al., "Metastasis: from dissemination to organ-specific colonization", Nature Reviews Cancer, pp. 274-284, vol. 9 (2009).
Nguyen et al., "Sialic acid-containing glycolipids mediate binding and viral entry of SARS-CoV-2", Nature Chemical Biology, vol. 18(1), pp. 81-90 (Nov. 2021).
Nicoletti et al., "A rapid and simple method for measuring thymocyte apoptosis by propidium iodide staining and flow cytometry", Journal of Immunological Methods, pp. 271-279, vol. 139, Issue 2 (Jun. 3, 1991).
Nie et al., "Development of in vitro and in vivo rabies virus neutralization assays based on a high-titer pseudovirus system", Scientific Reports, vol. 7(1), 42769 (2017).
Nie et al., "Establishment and validation of a pseudovirus neutralization assay for SARS-CoV-2", Emerging Microbes & Infections, vol. 9(1), pp. 680-686 (Mar. 2020).
Nie et al., "Optimization and proficiency testing of a pseudovirus-based assay for detection of HIV-1 neutralizing antibody in China", Journal of Virological Methods, vol. 185(2), pp. 267-275 (2012).
Nie et al., "Quantification of SARS-CoV-2 neutralizing antibody by a pseudotyped virus-based assay", Nat. Protoc., vol. 15(11), pp. 3699-3715 (Sep. 2020).
Niemelä et al., "Managing passenger flows for seaborne transportation during COVID-19 pandemic", Journal of Travel Medicine, pp. 1-4, vol. 28, 7 (2021).
Niemelä et al., "Nanoparticles carrying fingolimod and methotrexate enables targeted induction of apoptosis and immobilization of invasive thyroid cancer", European Journal of Pharmaceutics and Biopharmaceutics, pp. 1-9, vol. 148 (Mar. 2020).
Niemelä et al., "Quantitative bioimage analytics enables measurement of targeted cellular stress response induced by celastrol-loaded nanoparticles", Cell Stress and Chaperones, pp. 735-748, vol. 24 (2019).
Niemelä et al., "Sugar-decorated mesoporous silica nanoparticles as delivery vehicles for the poorly soluble drug celastrol enables targeted induction of apoptosis in cancer cells", European Journal of Pharmaceutics and Biopharmaceutics, pp. 11-21, vol. 96 (Oct. 2015).
Niemelä, "Nanoparticles as Targeting System for Cancer Treatment : From idea towards reality", in 112 pages (2019) https://urn.fi/URN:ISBN:978-952-12-3855-0.
Nienhaus et al., "Nanoparticles for biomedical applications: exploring and exploiting molecular interactions at the nano-bio interface", Mater. Today Adv., vol. 5, 100036 (Mar. 2020).

(56) References Cited

OTHER PUBLICATIONS

Nieva et al., "Viroporins: structure and biological functions", Nat. Rev. Microbiol, vol. 10(8), pp. 563-574 (2012).
Nikzamir et al., "An overview on nanoparticles used in biomedicine and their cytotoxicity", J. Drug Delivery Sci. Technol., vol. 61, 102316 (Feb. 2021).
Niles et al., "Update on in vitro cytotoxicity assays for drug development", Expert Opin. Drug Discovery, vol. 3(6), pp. 655-669 (2008).
Nishiura, "Backcalculating the Incidence of Infection with COVID-19 on the Diamond Princess", Journal of Clinical Medicine, 657 in 4 page, vol. 9 (2020).
Nisisako et al., "Synthesis of monodisperse bicolored janus particles with electrical anisotropy using a microfluidic Co-Flow system", Advanced Materials, vol. 18(9), pp. 1152-1156 (2006).
Nogrady, "How Kids' Immune System Can Evade COVID", Nature, p. 382, vol. 588 (Dec. 17, 2020).
Nooraei et al., "Virus-like particles: Preparation, immunogenicity and their roles as nanovaccines and drug nanocarriers", Journal of Nanobiotechnology, vol. 19(1), Article 59 (Feb. 2021).
Nowak-Sliwinska et al., "The chicken chorioallantoic membrane model in biology, medicine and bioengineering", Angiogenesis, pp. 779-804, vol. 17 (2014).
O'Brien et al., "Process Robustness in Lipid Nanoparticle Production: A Comparison of Microfluidic and Turbulent Jet Mixing", Molecular Pharmaceutics, vol. 20(8), pp. 4285-4296 (Jul. 2023).
Oates et al., "Role of Titanium Surface Topography and Surface Wettability on Focal Adhesion Kinase Mediated Signaling in Fibroblasts", Materials, pp. 893-907—vol. 4 (2011).
Obeid et al., "Characterisation of niosome nanoparticles prepared by microfluidic mixing for drug delivery", International Journal of Pharmaceutics: X, vol. 4, 100137 (Dec. 2022).
Obeid et al., "The impact of solvent selection on the characteristics of niosome nanoparticles prepared by microfluidic mixing", International Journal of Pharmaceutics: X, vol. 5, 100168 (Dec. 2023).
O'Brien et al., "Annexin-V and TUNEL use in monitoring the progression of apoptosis in plants", Cytom.: J. Int. Soc. Anal. Cytol., vol. 29(1), pp. 28-33 (1997).
O'Brien et al., "Mortality within 30 days of chemotherapy: a clinical governance benchmarking issue for oncology patients", British Journal of Cancer, pp. 1632-1636, vol. 95 (2006).
Oh et al., "Endocytosis and exocytosis of nanoparticles in mammalian cells", International Journal of Nanomedicine, pp. 51-63, vol. 9, Supplement I (2014).
Oh et al., "Shape-dependent cytotoxicity and proinflammatory response of poly (3, 4 ethylenedioxythiophene) nanomaterials", Small, vol. 6(7), pp. 872-879 (2010).
Oh et al., "Shape-dependent cytotoxicity of polyaniline nanomaterials in human fibroblast cells", J. Nanosci. Nanotechnol., vol. 11(5), pp. 4254-4260 (2011).
Oheim, "High-throughput microscopy must reinvent the microscope rather than speed up its functions", British Journal of Pharmacology, pp. 1-4, vol. 152 (2007).
Ohm et al., "Control of the Properties of Micrometer-Sized Actuators from Liquid Crystalline Elastomers Prepared in a Microfluidic Setup", Advanced Functional Materials, vol. 20(24), pp. 4314-4322 (2010).
Oktay et al., "DNA origami presenting the receptor binding domain of SARS-CoV-2 elicit robust protective immune response", Communications Biology, vol. 6(1), 308 (Mar. 2023).
Okuda et al., "On the size-regulation of RNA-loaded lipid nanoparticles synthesized by microfluidic device", Journal of Controlled Release, vol. 348, pp. 648-659 (Aug. 2022).
Olivera-Ugarte et al., "A nanoparticle-based COVID-19 vaccine candidate elicits broad neutralizing antibodies and protects against SARS-CoV-2 infection", Nanomedicine: Nanotechnology, Biology and Medicine, vol. 44, 102584 (Aug. 2022).
Omotuyi et al., "Benzimidazole compound abrogates SARS-COV-2 receptor-binding domain (RBD)/ACE2 interaction In vitro", Microbial Pathogenesis, vol. 176, 105994 (Mar. 2023).
Omotuyi et al., "SARS-CoV-2 Omicron spike glycoprotein receptor binding domain exhibits super-binder ability with ACE2 but not convalescent monoclonal antibody", Computers in Biology and Medicine, vol. 142, 105226 (Mar. 2022).
Onodera et al., "Inhalation of ACE2 as a therapeutic target on sex-bias differences in SARS-CoV-2 infection and variant of concern", iScience, vol. 26(8), 107470 (Aug. 2023).
Orkhan et al., "RBD and ACE2 Embedded Chitosan Nanoparticles as a Prevention Approach for SARS-COV 2", 2Biomedical Journal of Scientific & Technical Research, pp. 29193-29197 (2021) ISSN: 2574-1241, DOI: 10.26717/BJSTR.2021.37.005960.
Orrenius et al., "Cell Death Mechanisms and Their Implications in Toxicology", Toxicological Sciences, pp. 3-19, vol. 119, Issue 1 (Jan. 2011).
O'Shannessy et al., "Expression of folate receptors alpha and beta in normal and cancerous gynecologic tissues: correlation of expression of the beta isoform with macrophage markers", Journal of Ovarian Research, in 9 pages, vol. 8 (2015).
Ossowski et al., "Experimental model for quantitative study of metastasis", Cancer research, pp. 2300-2309, vol. 40 (1980).
Otsubo et al., "Human antibody recognition and neutralization mode on the NTD and RBD domains of SARS-CoV-2 spike protein", Scientific Reports, vol. 12(1), 20120 (Nov. 2022).
Ottaviani et al., "Parallel artificial membrane permeability assay: a new membrane for the fast 1480 prediction of passive human skin permeability", Journal of Medicinal Chemistry, vol. 49(13), pp. 3948-3954 (2006).
Ou et al., "Emergence of SARS-CoV-2 spike RBD mutants that enhance viral infectivity through increased human ACE2 receptor binding affinity", bioRxiv preprint doi: https://doi.org/10.1101/2020.03.15.991844.
Ou et al., "V367F mutation in SARS-CoV-2 spike RBD emerging during the early transmission phase enhances viral infectivity through increased human ACE2 receptor binding affinity", bioRxiv 2020.03.15.991844; doi: https://doi.org/10.1101/2020.03.15.991844.
Outlaw et al., "Inhibition of Coronavirus Entry In Vitro and Ex Vivo by a Lipid-Conjugated Peptide Derived from the SARS-CoV-2 Spike Glycoprotein HRC Domain", ASM Journals, mBio, e01935-20, in 14 pages, vol. 11, Issue 5 (Sep./Oct. 2020).
Owens et al., "Opsonization, biodistribution, and pharmacokinetics of polymeric nanoparticles", International Journal of Pharmaceutics, pp. 93-102, vol. 307, Issue 1 (Jan. 3, 2006).
Oxtoby et al., "Imaging plus X: multimodal models of neurodegenerative disease", Current Opinion in Neurology, pp. 371-379, vol. 30 (2017).
Ozaki et al., "Role of p53 in Cell Death and Human Cancers", Cancers, pp. 994-1013, vol. 3 (2011).
Paaby et al., "The many faces of pleiotropy", Trends in Genetics, pp. 66-73, vol. 29, Issue 2 (Feb. 1, 2013).
Paatero et al., "Analyses in zebrafish embryos reveal that nanotoxicity profiles are dependent on surface-functionalization controlled penetrance of biological membranes", Scientific Reports, in 13 pages, vol. 7, Article No. 8423 (2017).
Pace et al., "Zinc-binding cysteines: diverse functions and structural motifs", Biomolecules, pp. 419-434, vol. 4 (2014).
Padma, "An overview of targeted cancer therapy", BioMedicine, pp. 1-6, vol. 5, No. 4, Article 1 (Dec. 2015).
Palika et al., "An antiviral trap made of protein nanofibrils and iron oxyhydroxide nanoparticles", Nature Nanotechnology, pp. 918-925, vol. 16 (Aug. 2021).
Pallavicini et al., "Self-assembled monolayers of gold nanostars: a convenient tool for Near-IR photothermal biofilm eradication", Chemical Communications, pp. 1969-1971, Issue 16 (2014).
Palumbo et al., "Systemic cancer therapy: achievements and challenges that lie ahead", Frontiers in Pharmacology, pp. 1-9, vol. 4, Article 57 (May 2013).
Pan et al., "Perceptions of cruise travel during the COVID-19 pandemic: Market recovery strategies for cruise businesses in North America", Tourism Management, 104275, in 11 pages, vol. 85 (2021).
Pan et al., "Size-dependent cytotoxicity of gold nanoparticles", Small, vol. 3(11), pp. 1941-1949 (2007).

(56) References Cited

OTHER PUBLICATIONS

Panchariya et al., "Zinc2+ ion inhibits SARS-CoV-2 main protease and viral replication in vitro", bioRxiv 2021.06.15.448551; doi: https://doi.org/10.1101/2021.06.15.448551, https://www.biorxiv.org/content/10.1101/2021.06.15.448551v1.

Papa et al., "Linear and non-linear modelling of the cytotoxicity of TiO2 and ZnO nanoparticles by empirical descriptors", SAR QSAR Environ. Res., vol. 26(7-9), pp. 647-665 (2015).

Papaccio et al., "Concise Review: Cancer Cells, Cancer Stem Cells, and Mesenchymal Stem Cells: Influence in Cancer Development", Stem Cells Translational Medicine, pp. 2115-2125, vol. 6 (2017).

Papadiamantis et al., "Predicting cytotoxicity of metal oxide nanoparticles using isalos analytics platform", Nanomaterials, vol. 10(10), 2017 (Oct. 2020).

Papanikolaou et al., "From delta to Omicron: S1-RBD/S2 mutation/deletion equilibrium in SARS- CoV-2 defined variants", Gene, vol. 814, 146134 (Mar. 2022).

Papathanassis, "The growth and development of the cruise sector: A perspective article", Tourism Review, pp. 130-135, 75(1) (2019) doi: 10.1108/TR-02-2019-0037.

Papi et al., "Principles for optimization and validation of mRNA lipid nanoparticle vaccines against COVID-19 using 3D bioprinting", Nano Today, vol. 43, 101403 (Apr. 2022).

Papp et al., "Inhibition of Influenza Virus Infection by Multivalent Sialic-Acid-Functionalized Gold Nanoparticles", Small, pp. 2900-2906, vol. 6, Issue 24 (Dec. 2010).

Parisi et al., "Design and development of plastic antibodies against SARS-CoV-2 RBD based on molecularly imprinted polymers that inhibit in vitro virus infection", Nanoscale, vol. 13(40), pp. 16885-16899 (Oct. 2021).

Park et al., "Immunogenicity and protective efficacy of an intranasal live-attenuated vaccine against SARS-CoV-2", iScience, 102941 in 27 pages, vol. 24, Issue 9 (Sep. 24, 2021).

Park et al., "Lipid-based vaccine nanoparticles for induction of humoral immune responses against HIV-1 and SARS-CoV-2", Journal of Controlled Release, vol. 330(10), pp. 529-539 (Feb. 2021).

Park et al., "Non-viral COVID-19 vaccine delivery systems", Advanced Drug Delivery Reviews, vol. 169, pp. 137-151 (Dec. 2020).

Park et al., "Pharmacokinetics and biodistribution of recently-developed siRNA nanomedicines", Advanced Drug Delivery Reviews, pp. 93-109, vol. 104 (Sep. 1, 2016).

Park et al., "Self-assembled nanoplatform for targeted delivery of chemotherapy agents via affinity-regulated molecular interactions", Biomaterials, pp. 7766-7775, vol. 31, Issue 30 (Oct. 2010).

Park et al., "The effect of particle size on the cytotoxicity, inflammation, developmental toxicity and genotoxicity of silver nanoparticles", Biomaterials, vol. 32(36), pp. 9810-9817 (2011).

Parker et al., "Folate receptor expression in carcinomas and normal tissues determined by a quantitative radioligand binding assay", Analytical Biochemistry, pp. 284-293, vol. 338, Issue 2 (Mar. 2005).

Parumasivam et al., "Dry powder inhalable formulations for anti-tubercular therapy", Advanced Drug Delivery Reviews, vol. 102, pp. 83-101 (2016).

Pathakoti et al., "Using experimental data of *Escherichia coli* to develop a QSAR model forpredicting the photo-induced cytotoxicity of metal oxide nanoparticles", J. Photochem. Photobiol., B, vol. 130, pp. 234-240 (2014).

Patlolla et al., "Formulation, characterization and pulmonary deposition of nebulized celecoxib encapsulated nanostructured lipid carriers", Journal of Controlled Release, vol. 144(2), pp. 233-241 (2010).

Pattanayak et al., "Microfluidic chips: recent advances, critical strategies in design, applications and future perspectives", Microfluid. Nanofluid., vol. 25, 99 (Oct. 2021).

Pattnaik et al., "Entry inhibitors: efficient means to block viral infection", The Journal of Membrane Biology, vol. 253, 425 (Aug. 2020).

Paulos et al., "Ligand binding and kinetics of folate receptor recycling in vivo: impact on receptor-mediated drug delivery", Molecular Pharmacology, pp. 1406-1414, vol. 66, Issue 6 (Dec. 1, 2004).

Pedersen et al., "Solid lipid nanoparticles can effectively bind DNA, streptavidin and biotinylatedligands", European Journal of Pharmaceutics and Biopharmaceutics, pp. 155-162, vol. 62, Issue 2 (Feb. 2006).

Pedroso-Santana et al., "Polymeric nanoencapsulation of alpha interferon increases drug bioavailability and induces a sustained antiviral response in vivo", Materials Science and Engineering: C, vol. 116, 111260 (Nov. 2020).

Pelgrim et al., "Intratracheal administration of solutions in mice; development and validation of an optimized method with improved efficacy, reproducibility and accuracy", Journal of Pharmacological and Toxicological Methods, vol. 114, 107156 (Mar. 2022).

Peng et al., "[Clinical characteristics and outcomes of 112 cardiovascular disease patients infected by 2019-nCoV]", Zhonghua Xin Xue Guan Bing Za Zhi. 48(0): E004.

Peng et al., "Cell entry by SARS-CoV-2", Trends in Biochemical Sciences, vol. 46(10), pp. 848-860 (Jun. 2021).

Peng et al., "HSP90 inhibitor, celastrol, arrests human monocytic leukemia cell U937 at G0/G1 in thiol-containing agents reversible way", Molecular Cancer, in 13 pages, 9:79 (2010) doi: 10.1186/1476-4598-9-79.

Peng et al., "Towards developing a variant-proof SARS-CoV-2 vaccine", Cell Research, vol. 33(1), pp. 5-6 (Jan. 2023).

Pennington-Gray, "Reflections to move forward: Where destination crisis management research needs to go", Tourism Management Perspectives, pp. 136-139, vol. 25 (2018).

Pereira et al., "Origin and evolution of high throughput screening", Br. J. Pharmacol., vol. 152(1), pp. 53-61 (2009).

Perez et al., "Poly (lactic-co-glycolic acid) particles prepared by microfluidics and conventional methods. Modulated particle size and rheology", Journal of Colloid and Interface Science, vol. 441, pp. 90-97 (2015).

Pérez-Luna et al., "Molecular recognition between genetically engineered streptavidin and surface-bound biotin", Journal of the American Chemical Society, vol. 121(27), pp. 6469-6478 (1999).

Pernet, "Null hypothesis significance testing: a short tutorial", F1000Res, 2004, 4:621. doi: 10.12688/f1000research.6963.3.

Perreault et al., "Different toxicity mechanisms between bare and polymer-coated copper oxide nanoparticles in Lemna gibba", Environmental Pollution, pp. 219-227, vol. 185 (Feb. 2014).

Perrotton et al., "Microfluidic fabrication of vesicles with hybrid lipid/nanoparticle bilayer membranes", Soft Matter, vol. 15(6), pp. 1388-1395 (2019).

Pessi et al., "Controlled Expansion of Supercritical Solution: A Robust Method to Produce Pure Drug Nanoparticles With Narrow Size-Distribution", Journal of Pharmaceutical Sciences, pp. 2293-2297, vol. 105, Issue 8 (Aug. 1, 2016).

Pessi et al., "Microfluidics-assisted engineering of polymeric microcapsules with high encapsulation efficiency for protein drug delivery", International Journal of Pharmaceutics, vol. 472(1-2), pp. 82-87 (2014).

Peter et al., "The Inhibitory Effect of a Coronavirus Spike Protein Fragment with ACE2", Biophysical Journal, pp. 1001-1010, vol. 119 (Mar. 16, 2021).

Pettersen et al., "UCSF Chimera—A visualization system for exploratory research and analysis", Journal of Computational Chemistry, pp. 1605-1612, vol. 25, issue 13 (Oct. 2004).

Petti et al., "Laboratory medicine in Africa: a barrier to effective health care", Clinical Infectious Diseases, pp. 377-382, vol. 42, Issue 3 (2006).

Peuhu, "Lethal Weapons—Novel approaches for receptor-targeted cancer cell elimination", Thesis, Turku Centre for Biotechnology, University of Turku and Åbo Akademi University Department of Biosciences, Åbo Akademi University (2010).

Phan et al., "Biomimetic SARS-CoV-2 Spike Protein Nanoparticles", Biomacromolecules, vol. 24(5), pp. 2030-2041 (Mar. 2023).

Piai et al., "Structural basis of transmembrane coupling of the HIV-1 envelope glycoprotein", Nature Communications, 11:2317, in 12 pages (2020.

(56) References Cited

OTHER PUBLICATIONS

Piazzini et al., "Nanoemulsion for improving solubility and permeability of Vitex agnus-castus extract: formulation and in vitro evaluation using PAMPA and Caco-2 approaches", Drug Delivery, vol. 24(1), pp. 380-390 (2017).
Piazzini et al., "Stealth and cationic nanoliposomes as drug delivery systems to increase andrographolide BBB permeability", Pharmaceutics, vol. 10(3), 128 (2018).
Piccinini et al., "Cell counting and viability assessment of 2D and 3D cell cultures: expected reliability of the trypan blue assay", Biol. Proced. Online, vol. 19(8), pp. 1-12 (2017).
Piepenbrink et al., "Therapeutic activity of an inhaled potent SARS-CoV-2 neutralizing human monoclonal antibody in hamsters", Cell Reports Meicine, 100218 in 21 pages, vol. 2, Issue 3 (Mar. 16, 2021).
Pilkington et al., "From influenza to COVID-19: Lipid nanoparticle mRNA vaccines at the frontiers of infectious diseases", Acta Biomaterialia, vol. 131, pp. 16-40 (Sep. 2021).
Pillai, "Nanomedicines for Cancer Therapy: An Update of FDA Approved and Those under Various Stages of Development", SOJ Pharmacy & Pharmaceutical Sciences, in 13 pages, Open Access, (2014), 1. doi: 10.15226/2374-6866/1/2/00109.
Piran et al., "Dissociation rate constant of the biotin-streptavidin complex", Journal of Immunological Methods, vol. 133(1), pp. 141-143 (1990).
Piras et al., "Changes in Microtubule Phosphorylation during Cell Cycle of HeLa Cells", Proceedings of the National Academy of Sciences of the United States of America, pp. 1161-1165, vol. 72 (1975).
Pirkkala et al., "Roles of the heat shock transcription factors in regulation of the heat shock response and beyond", The FASEB Journal, pp. 1118-1131, vol. 15, Issue 7 (May 2001).
Pisil et al., "A neutralization assay based on pseudo-typed lentivirus with Sars CoV-2 spike protein in ACE2-expressing CRFK cells", Pathogens, vol. 10(2), 153 (Feb. 2021).
Pizam et al., "The Relationship Between Risk-Taking, Sensation-Seeking, and the Tourist Behavior of Young Adults: A Cross-Cultural Study", Journal of Travel Research, pp. 251-260, vol. 42, Issue 3 (2004).
Plasse et al., "A randomized, placebo-controlled pilot study of upamostat, a host-directed serine protease inhibitor, for outpatient treatment of COVID-19", International Journal of Infectious Diseases, vol. 128, pp. 148-156 (Mar. 2023).
Pokhrelet al., "Natural variants in SARS-CoV-2 Spike protein pinpoint structural and functional hotspots with implications for prophylaxis and therapeutic strategies", Scientific Reports, vol. 11, Article No. 13120 in 10 pages (2021).
Pollet et al., "Receptor-binding domain recombinant protein on alum-CpG induces broad protection against SARS-CoV-2 variants of concern", Vaccine, vol. 40(26), pp. 3655-3663 (Jun. 2022).
Pollet et al., "Recombinant protein vaccines, a proven approach against coronavirus pandemics", Advanced Drug Delivery Reviews, vol. 170, pp. 71-82 (Jan. 2021).
Pollok et al., "Interferon alpha-armed nanoparticles trigger rapid and sustained STAT1-dependent anti-viral cellular responses", Cellular Signalling, vol. 25(4), pp. 989-998 (2013).
Popat et al., "Enzyme-Responsive Controlled Release of Covalently Bound Prodrug from Functional Mesoporous Silica Nanospheres", Angewandte Chemie, International Edition, pp. 12486-12489, vol. 51, Issue 50 (Dec. 7, 2012).
Popat et al., "Mesoporous silica nanoparticles for bioadsorption, enzyme immobilisation, and delivery carriers", Nanoscale, pp. 2801-2018, vol. 3, Issue 7 (Jul. 1011).
Popowski et al., "Inhalable dry powder mRNA vaccines based on extracellular vesicles", Matter, vol. 5(9), pp. 2960-2974 (Jul. 2022).
Porotto et al., "Viral entry inhibitors targeted to the membrane site of action", Journal of Virology, vol. 84(13), pp. 6760-6768 (2010).
Porta et al., "Folic acid-modified mesoporous silica nanoparticles for cellular and nuclear targeted drug delivery", Advanced Healthcare Materials, pp. 281-286, vol. 2, Issue 2 (Feb. 2013).
Portnoff et al., "Influenza hemagglutinin nanoparticle vaccine elicits broadly neutralizing antibodies against structurally distinct domains of H3N2 HA", Vaccines, vol. 8(1), 99 (Feb. 2020).
Powell et al., "A single immunization with spike-functionalized ferritin vaccines elicits neutralizing antibody responses against SARS-CoV-2 in mice", ACS Central Science, vol. 7(1), pp. 183-199 (Jan. 2021).
Prabhakar et al., "Aspects of nanotechnology for COVID-19 vaccine development and its delivery applications", Pharmaceutics, vol. 15(2), 451 (Jan. 2023).
Pradhan et al., "A facile microfluidic method for production of liposomes", Anticancer Research, vol. 28(2A), pp. 943-947 (2008).
Pradhan et al., "A Review of Current Interventions for COVID-19 Prevention", Archives of Medical Research, pp. 363-374, vol. 51, Issue 5 (Jul. 2020).
Pradhan et al., "Recent Advancement in Nanotechnology-Based Drug Delivery System Against Viral Infections", AAPS PharmSciTech, Review Article, vol. 22(47) (Jan. 2021).
Prakash et al., "Microfluidic fabrication of lipid nanoparticles for the delivery of nucleic acids", Advanced Drug Delivery Reviews, vol. 184, 114197 (Mar. 2022).
Pramanik et al., "The rapid diagnosis and effective inhibition of coronavirus using spike antibody attached gold nanoparticles", Nanoscale Advances, vol. 3(6), pp. 1588-1596 (Mar. 2021).
Prather et al., "Reducing transmission of SARS-CoV-2", Science, pp. 1422-1424, vol. 368, No. 6498 (May 27, 2020).
Preaud et al., "Annual public health and economic benefits of seasonal influenza vaccination: a European estimate", BMC Public Health. vol. 14, 813 (2014).
Preissner et al., "Drug Cocktail Optimization in Chemotherapy of Cancer", PLoS One, e51020, in 7 pages, vol. 7, Issue 12 (Dec. 2012).
Pu et al., "Synthesis and modification of boron nitride nanomaterials for electrochemical energy storage: from theory to application", Adv. Funct. Mater., vol. 31(48), 2106315 (Aug. 2021).
Public Health England. Investigation of novel SARS-CoV-2 variant, 2020, Variant of Concern 202012/01 Technical briefing 2-28. PHE: London.
Puigmartí-Luis, "Microfluidic platforms: a mainstream technology for the preparation of crystals", Chemical Society Reviews, vol. 43(7), pp. 2253-2271 (2014).
Puranik et al., "Comparative vol. effectiveness of mRNA-1273 and BNT162b2 against symptomatic SARS-CoV-2 infection", Med, vol. 3(1), pp. 28-41 (Jan. 2022).
Puzyn et al., "Using nano-QSAR to predict the cytotoxicity of metal oxide nanoparticles", Nat. Nanotechnol., vol. 6(3), pp. 175-178 (2011).
Qi et al., "Intranasal Nanovaccine Confers Homo- and Hetero-Subtypic Influenza Protection", Small, e1703207, vol. 14, Issue 13 (Mar. 27, 2018).
Qiao et al., "Gelatin templated polypeptide co-cross-linked hydrogel for bone regeneration", Advanced Healthcare Materials, vol. 9(1), 1901239 (Dec. 2019).
Qiao et al., "Pam2CSK4-adjuvanted SARS-CoV-2 RBD nanoparticle vaccine induces robust humoral and cellular immune responses", Frontiers in Immunology, vol. 13, 992062 (Dec. 2022).
Qiao et al., "SARS-CoV-2 Mpro inhibitors with antiviral activity in a transgenic mouse model", Science, pp. 1374-1378, vol. 371 (2021).
Qiu et al., "Safe pseudovirus-based assay for neutralization antibodies against influenza A (H7N9) virus", Emerging Infectious Diseases, vol. 19(10) (Oct. 2013).
Quagliarini et al., "Microfluidic formulation of DNA-loaded multicomponent lipid nanoparticles for gene delivery", Pharmaceutics, vol. 13(8), 1292 (Aug. 2021).
Quinn et al., "Delivering nitric oxide with nanoparticles", Journal of Controlled Release, pp. 190-205, vol. 205 (May 10, 2015).
Rabi et al., "SARS-CoV-2 and Coronavirus Disease 2019: What We Know So Far", Pathogens, Mar. 20, 2020 vol. 9 p. 231.
Rabolli et al., "Influence of size, surface area and microporosity on the in vitro cytotoxic activity of amorphous silica nanoparticles in different cell types", Nanotoxicology, vol. 4(3), pp. 307-318 (2010).

(56) References Cited

OTHER PUBLICATIONS

Radic et al., "Fear and Trembling of Cruise Ship Employees: Psychological Effects of the COVID-19 Pandemic", International Journal of Environmental Research and Public Health, pp. 1-17, vol. 17 (2020).
Radic, "Towards an understanding of a child's cruise experience", Current Issues in Tourism, pp. 237-252, vol. 22, Issue 2 (2019).
Rahikainen et al., Overcoming Symmetry Mismatch in Vaccine Nanoassembly through Spontaneous Amidation, Angewandte Chemie International Edition, pp. 321-330, vol. 60 (2021).
Raja et al., "A critical review on genotoxicity potential of low dimensional nanomaterials", J. Hazard. Mater., vol. 409, 124915 (May 2021).
Rajan et al., "Silver nanoparticle ink technology: state of the art", Nanotechnology, Science and Applications, pp. 1-13, vol. 9 (2016).
Ramachandran et al., "SARS-CoV-2 infection enhances mitochondrial PTP complex activity to perturb cardiac energetics", iScience, 103722, in 24 pages, vol. 25 (Jan. 21, 2022).
Ramadan et al., "Hollow Copper Sulfide Nanoparticle-Mediated Transdermal Drug Delivery", Small, pp. 3143-3150, vol. 8 (2012).
Ramirez et al., "Potential chemotherapy side effects: what do oncologists tell parents?", Pediatric Blood & Cancer, pp. 497-502, vol. 52, Issue 4 (Apr. 2009).
Ranga et al., "Immunogenic SARS-CoV-2 Epitopes: In Silico Study Towards Better Understanding of COVID-19 Disease-Paving the Way for Vaccine Development", Vaccines, 408, in 19 pages, vol. 8 (2020).
Rannard et al., "The Selective Reaction of Primary Amines with Carbonyl Imidazole Containing Compounds: Selective Amide and Carbamate Synthesis", Organic Letters, pp. 2117-2120, vol. 2, Issue 14 (2000).
Rao et al., "Decoy nanoparticles protect against COVID-19 by concurrently adsorbing viruses and inflammatory cytokines", Proceedings of the National Academy of Sciences, vol. 117(44), p. 27141-27147 (Nov. 2020).
Rao et al., "Efficacy of a technique for exposing the mouse lung to particles aspirated from the pharynx", Journal of Toxicology and Environmental Health Part A, vol. 66(15-16), pp. 1441-1452 (2003).
Rasmussen et al., "Pan-specific prediction of peptide-MHC Class I complex stability, a correlate of T Cell Immunogenicity", Journal of Immunology, pp. 1517-1524, vol. 197, No. 4 (2016).
Rattanapisit et al., "Plant-produced recombinant SARS-CoV-2 receptor-binding domain; an economical, scalable biomaterial source for COVID-19 diagnosis", Biomaterials Translational, vol. 2(1), pp. 43-49 (Mar. 2021).
Rauf et al., "Nanoparticles in clinical trials of COVID-19: An update", International Journal of Surgery, vol. 104, 106818 (Aug. 2022).
Ray et al., "Aptamers for Targeted Drug Delivery", Pharmaceuticals (Basel), pp. 1761-1778, vol. 3 (2010).
Reboud et al., "Paper-based microfluidics for DNA diagnostics of malaria in low resource underserved rural communities" pp. 4834-4842, vol. 116, No. 11 (Mar. 12, 2019).
Ren et al., "Alterations in the human oral and gut microbiomes and lipidomics in COVID-19", BMJ, Gut Journal, pp. 1253-1265, vol. 70 (2021).
Ren et al., "Reinfection in patients with COVID-19: a systematic review", Global Health Research and Policy, vol. 7(1), Art. 12 (Apr. 2022).
Rentsch et al., "Covid-19 Testing, Hospital Admission, and Intensive Care Among 2,026,227 United States Veterans Aged 54-75 Years, 2020", medRxiv, in 32 pages, doi: https://doi.org/10.1101/2020.04.09.20059964.
Rhea et al., "The S1 protein of SARS-CoV-2 crosses the blood-brain barrier in mice", Nature Neuroscience, pp. 368-378, vol. 24 (Mar. 2021).
Rhoades et al., "Acute SARS-CoV-2 infection is associated with an increased abundance of bacterial pathogens, including Pseudomonas aeruginosa in the nose", Cell Reports, 109367, in 13 pages, vol. 36, Issue 9 (Aug. 31, 2021).
Rice et al., "Matrix stiffness induces epithelial-mesenchymal transition and promotes chemoresistance in pancreatic cancer cells", Oncogenesis, 2017, 7, e352.
Richards et al., "Polymer-Stabilized Sialylated Nanoparticles: Synthesis, Optimization, and Differential Binding to Influenza Hemagglutinins", Biomacromolecules, vol. 21(4), pp. 1604-1612 (Mar. 2020).
Ridler et al., "Picture Thresholding Using an Iterative Selection Method", IEEE Transactions on Systems, p. 311, vol. 9 (1979).
Riewe et al., "Antisolvent precipitation of lipid nanoparticles in microfluidic systems—A comparative study", International Journal of Pharmaceutics, vol. 579, 119167 (Apr. 2020).
Righeschi et al., "Enhanced curcumin permeability by SLN formulation: The PAMPA approach", LWT-Food Science and Technology, vol. 66, pp. 475-483 (2016).
Riihimäki et al., "Comparison of survival of patients with metastases from known versus unknown primaries: survival in metastatic cancer", BMC Cancer, 2013, 13:36. doi: 10.1186/1471-2407-13-36.
Ripoll et al., "Optimal self-assembly of lipid nanoparticles (LNP) in a ring micromixer", Scientific Reports, vol. 12(1), 9483 (Jun. 2022).
Ripperger et al., "Detection, prevalence, and duration of humoral responses to SARS-CoV-2 under conditions of limited population exposure", medRxiv, pp. 1-44 (2020).
Riss et al., "Cytotoxicity testing: measuring viable cells, dead cells, and detecting mechanism of cell death", In: Stoddart MJ, editor, In Mammalian Cell Viability: Methods and Protocols; Springer, pp. 103-114 (2011).
Ritchie et al., "A review of research on tourism risk, crisis and disaster management: Launching theannals of tourism research curated collection on tourism risk, crisis and disaster management", Annals of Tourism Research, 102812, vol. 79 (Nov. 2019).
Rivera-Gil et al., "The challenge to relate the physicochemical properties of colloidal nanoparticles to their cytotoxicity", Acc. Chem. Res., vol. 46(3), pp. 743-749 (2013).
Robbiani, et al., "Convergent antibody responses to SARS-CoV-2 in convalescent individuals", Nature, pp. 437-442, vol. 584 (2020) https://doi.org/10.1038/s41586-020-2456-9.
Robergs, "Lessons from Popper for science, paradigm shifts, scientific revolutions and exercise physiology", BMJ Open Sport & Exercise Medicine, 3(1):e000226. doi: 10.1136/bmjsem-2017-000226. (2017).
Robinson et al., "COVID-19 therapeutics: Challenges and directions for the future", Proceedings of the National Academy of Sciences, vol. 119(15), e2119893119 (Apr. 2022).
Robinson et al., "IPD-IMGT/HLA Database", Nucleic Acids Research, pp. D948-D955, vol. 48 (2020).
Roces et al., "Manufacturing considerations for the development of lipid nanoparticles using microfluidics", Pharmaceutics, vol. 12(11), 1095 (Nov. 2020).
Roces et al., "Translating the fabrication of protein-loaded poly (lactic-co-glycolic acid) nanoparticlesfrom bench to scale-independent production using microfluidics", Drug Delivery and Translational Research, vol. 10, pp. 582-593 (Jan. 2020).
Rodrigues et al., "Functionalizing Ferritin Nanoparticles for Vaccine Development", Pharmaceutics, 1621, in 25 pages, vol. 13 (2021).
Rodrigues et al., "Novel core (polyester)-shell (polysaccharide) nanoparticles: protein loading and surface modification with lectins", Journal of Controlled Release, vol. 92(1-2), pp. 103-112 (2003).
Rodrigues-Jesus et al., "Nano-multilamellar lipid vesicles promote the induction of SARS-CoV-2immune responses by a protein-based vaccine formulation", Nanomedicine: Nanotechnology, Biology and Medicine, vol. 45, 102595 (Sep. 2022).
Roe et al., "PTRAJ and CPTRAJ: Software for processing and analysis of molecular dynamics trajectory data", Journal of Schemical Theory and Computation, pp. 3084-3095, vol. 9 (2013).
Rose et al., "The RCSB Protein Data Bank: new resources for research and education", Nucleic Acids Research, pp. D475-D482, vol. 14 Issue D1 (Jan. 2013).
Rosenholm et al., "Amino-functionalization of large-pore mesoscopically ordered silica by a one-stephyperbranching polymerization of a surface-grown polyethyleneimine", Chemical Communications, pp. 3909-3911, Issue 37 (2006).

(56) References Cited

OTHER PUBLICATIONS

Rosenholm et al., "Cancer-cell targeting and cell-specific delivery by mesoporous silicananoparticles", Journal of Materials Chemistry, pp. 2707-2013, vol. 20, Issue 14 (2010).
Rosenholm et al., "Hyperbranching Surface Polymerization as a Tool for Preferential Functionalization of the Outer Surface of Mesoporous Silica", Chemical Materials, pp. 1126-1133, vol. 20 (2008).
Rosenholm et al., "Targeted Intracellular Delivery of Hydrophobic Agents using Mesoporous Hybrid Silica Nanoparticles as Carrier Systems", Nano Letters, pp. 3308-3311, vol. 9 (2009).
Rosenholm et al., "Targeting of Porous Hybrid Silica Nanoparticles to Cancer Cells", ACS Nano, pp. 197-206, vol. 3 (2009).
Rosenholm et al., "Towards establishing structure-activity relationships for mesoporous silica in drug delivery applications", Journal of Controlled Release, pp. 157-164, vol. 128, Issue 2 (Jun. 4, 2008).
Rosenholm et al., "Towards multifunctional, targeted drug delivery systems using mesoporous silica nanoparticles—opportunities & challenges", Nanoscale, pp. 1870-1883, vol. 2, Issue 10 (2010).
Rosenholm, J.M. et al., "Cancer-cell-specific induction of apoptosis using mesoporous silica nanoparticles as drug-delivery vectors", Small, 2010, 6(11): 1234-41. doi: 10.1002/smll.200902355.
Rosenkranz et al., "A microplate assay for the detection of oxidative products using 2-, 7-dichlorofluorescin-diacetate", J. Immunol. Methods, vol. 156(1), pp. 39-45 (1992).
Roshmi et al., "Effect of biofabricated gold nanoparticle-based antibiotic conjugates on minimum inhibitory concentration of bacterial isolates of clinical origin" Gold Bull, pp. 63-71, vol. 48 (2015) https://doi.org/10.1007/s13404-015-0162-4.
Rosqvist et al., "A low-cost paper-based platform for fast and reliable screening of cellular interactions with materials", Journal of Materials Chemistry B, pp. 1146-1156, vol. 8, No. 6 (Feb. 14, 2020).
Rosqvist et al., "Human dermal fibroblast proliferation controlled by surface roughness of two-component nanostructured latex polymer coatings", Colloids and Surfaces B: Biointerfaces, pp. 136-144, vol. 174 (Feb. 2019).
Rosqvist, "Nanostructed Polymeric Surfaces for Biological Interfaces", Thesis, Physical Chemistry, Laboratory of Molecular Science and Engineering Faculty of Science and Engineering, Åbo Akademi University (2021).
Rossi, et al., "Characteristics and outcomes of a cohort of SARS-CoV-2 patients in the Province of Reggio Emilia, Italy", 2020, medRxiv. 2020.2004.2013.20063545.
Roth et al., "Norovirus mechanisms of immune antagonism", Current Opinion in Virology, pp. 24-30, vol. 16 (Feb. 2016).
Rouaud et al., "The ACE2 receptor for coronavirus entry is localized at apical cell-cell junctions of epithelial cells", Cells, vol. 11(4), 627 (Feb. 2022).
Routhu et al., "SARS-CoV-2 RBD trimer protein adjuvanted with Alum-3M-052 protects from SARS-CoV-2 infection and immune pathology in the lung", Nature Communications, vol. 12(1), Art. 3587 (Jun. 2021).
Royal et al., "Development of a SARS-CoV-2 vaccine candidate using plant-based manufacturing and a tobacco mosaic virus-like nano-particle", Vaccines, vol. 9(11), Art. 1347 (Nov. 2021).
Rudolph et al., "Application of novel solid lipid nanoparticle (SLN)-gene vector formulations based ona dimeric HIV-1 TAT-peptide in vitro and in vivo", Pharmaceutical Research, vol. 21, pp. 1662-1669 (2004).
Rueden et al., " ImageJ2: ImageJ for the next generation of scientific image data", BMC Bioinformatics, 18(1):529. doi: 10.1186/s12859-017-1934-z. (2017).
Ruiz-Hitzky et al., "Nanotechnology responses to COVID-19", Advanced Healthcare Materials, vol. 9(19), 2000979 (Sep. 2020).
Rundle et al., "Hand hygiene during COVID-19: Recommendations from the American Contact Dermatitis Society", Journal of the American Academy of Dermatology, pp. 1730-1737, vol. 83, No. 6 (2020).
Sackmann et al., "The present and future role of microfluidics in biomedical research", Nature, vol. 507(7491), pp. 181-189 (2014).
Sader et al., "Antimicrobial activity of dalbavancin and comparators against *Staphylococcus aureus* causing pneumonia in patients with and without cystic fibrosis", International Journal of Infectious Diseases, pp. 69-71, vol. 107 (2021).
Sadiq et al., "Role of nanoparticles in tackling COVID-19 pandemic: a bio-nanomedical approach", Journal of Taibah University for Science, vol. 15(1), pp. 198-207 (Jun. 2021).
Safa, "c-FLIP, A Master Anti-Apoptotic Regulator", Experimental Oncology, pp. 176-184, vol. 34 (2012).
Safer et al., "Chitosan nanoparticles for antiviral drug delivery: a novel route for COVID-19 treatment", International Journal of Nanomedicine, vol. 16, pp. 8141-8158 (Dec. 2021).
SAGE Handbook of Mixed Methods in Social & Behavorial Research, 2nd Edition, "Mapping the Developing Landscape of Mixed Methods Research", Chapter 1, Part 1, pp. 45-68, Tashakkori et al. Editors, SAGE Publications Ltd., (2010).
Saify Nabiabad et al., "Specific delivering of RNAi using Spike's aptamer-functionalized lipid nanoparticles for targeting SARS-CoV-2: A strong anti-Covid drug in a clinical case study", Chemical Biology & Drug Design, vol. 99(2), pp. 233-246 (Oct. 2021).
Saini et al., "An Appraisal of Proliferation and Apoptotic Markers in Papillary Thyroid Carcinoma: An Automated Analysis", PLoS One, 2016, 11(2):e0148656. doi: 10.1371/journal.pone.0148656.
Salem et al., "A gold nanoparticles-based lateral flow assay utilizing baculovirus expressed recombinant nucleocapsid and receptor binding domain proteins for serodetection of IgG and IgM against SARS-CoV-2", Biotechnology Letters, vol. 44(12), pp. 1507-1517 (Nov. 2022).
Salminen et al., "Celastrol: Molecular targets of Thunder God Vine", Biochemical and Biophysical Research Communications, pp. 439-442, vol. 394, Issue 3 (Apr. 9, 2010).
Samelson, et al. "BRD2 inhibition blocks SARS-CoV-2 infection by reducing transcription of the host cell receptor ACE2", Nature Cell Biology, pp. 24-34, vol. 24 (Jan. 2022).
Sanberg et al., "Changing the academic culture: Valuing patents and commercialization toward tenure and career advancement", Proceedings of the National Academy of Sciences of the United States of America, pp. 6542-6547, vol. 111, No. 18 (May 6, 2014).
Sanches et al., "Recent advances in SARS-CoV-2 Spike protein and RBD mutations comparisonbetween new variants Alpha (B. 1.1. 7, United Kingdom), Beta (B. 1.351, South Africa), Gamma (P. 1, Brazil) and Delta (B. 1.617. 2, India)", Journal of Virus Eradication, vol. 7(3), 100054 (Sep. 2021).
Sanchez et al., "Biodegradable micro-and nanoparticles as long-term delivery vehicles for interferon-alpha", European Journal of Pharmaceutical Sciences, vol. 18(3-4), pp. 221-229 (2003).
Sanchez-Mazas, "HLA studies in the context of coronavirus outbreaks", Swiss Medical Weekly, in 5 pages, (2020).
Sandqvist et al., "Heterotrimerization of Heat-Shock Factors 1 and 2 Provides a Transcriptional Switch in Response to Distinct Stimuli", Molecular Biolgy of the Cell, pp. 1340-1347, vol. 20, (Mar. 1, 2009).
Sădulescu et al., "Therapeutic developments for SARS-CoV-2 infection-Molecular mechanisms of action of antivirals and strategies for mitigating resistance in emerging variants in clinical practice", Frontiers in Microbiology, vol. 14, 1132501 (Mar. 2023).
Sanhai et al., "Seven challenges for nanomedicine", Nature Nanotechnology, pp. 242-244, vol. 3 (2008).
Sanna et al., "Development of targeted nanoparticles loaded with antiviral drugs for SARS-CoV-2 inhibition", European Journal of Medicinal Chemistry, vol. 231, 114121 (Jan. 2022).
Santschi et al., "Non-invasive continuous monitoring of pro-oxidant effects of engineered nanoparticles on aquatic microorganisms", J. Nanobiotechnol., vol. 15(19), pp. 1-18 (2017).
Sanyang et al., "COVID-19 reinfections in The Gambia by phylogenetically distinct SARS-CoV-2variants—first two confirmed events in west Africa", The Lancet Global Health, vol. 9(7), pp. e905-e907 (Jul. 2021).
Sapp et al., "Multilayer three-dimensional filter paper constructs for the culture and analysis of aortic valvular interstitial cells", Acta Biomaterialia, pp. 199-206, vol. 13 (Feb. 2015).
Saquib et al., "Cellular and molecular toxicology of nanoparticles", Springer (2018).

(56) References Cited

OTHER PUBLICATIONS

Sarfraz et al., "Photo-thermal and cytotoxic properties of inkjet-printed copper sulfide films on biocompatible latex coated substrates", Applied Surface Science, pp. 1087-1095, vol. 435 (Mar. 2018).
Sarfraz et al., "Printed copper acetate based H2S sensor on paper substrate", Sensors and Actuators B: Chemical, pp. 868-873, vol. 173 (Oct. 2012).
Sarfraz et al., "Sub-ppm electrical detection of hydrogen sulfide gas at room temperature based on printed copper acetate-gold nanoparticle composite films", RSC Advances, pp. 13525-13529, vol. 5, Issue 18 (2015).
Sarge et al., "Activation of heat shock gene transcription by heat shock factor 1 involves oligomerization, acquisition of DNA-binding activity, and nuclear localization and can occur in the absence of stress", Molecular Cell Biology, pp. 1392-1407, vol. 13 (Mar. 1993).
Saris A, et al. "Distinct cellular immune profiles in the airways and blood of critically ill patients with COVID-19", Thorax, pp. 1010-1019, vol. 10 (Oct. 2021).
Sarode et al., "Predictive high-throughput screening of PEGylated lipids in oligonucleotide-loaded lipid nanoparticles for neuronal gene silencing", Nanoscale Advances, vol. 4(9), pp. 2107-2123 (Feb. 2022).
Sasaki et al., "Doxorubicin-induced Inhibition of Prolyl Hydroxylation during Collagen Biosynthesis in Human Skin Fibroblast Cultures Relevance to Impaired Wound Healing", Journal of Clinical Investigation pp. 1735-1741, vol. 80 (Dec. 1987).
Sato et al., "Elucidation of the physicochemical properties and potency of siRNA-loaded small-sized lipid nanoparticles for siRNA delivery", Journal of Controlled Release, vol. 229, pp. 48-57 (2016).
Satriano et al., "Surface free energy and cell attachment onto ion-beam irradiated polymer surfaces", Nuclear Instruments and Methods in Physics Research Section B: Beam Interactions with Materials and Atoms, pp. 287-293, vol. 208 (Aug. 2003).
Saunders et al., "Neutralizing antibody vaccine for pandemic and pre-emergent coronaviruses", Nature, vol. 594(7864), pp. 553-559 (May 2021).
Savjani et al., "Drug solubility: importance and enhancement techniques", ISRN Pharmaceutics, Article 195727, in 10 pages vol. 2012 (2012).
Savolainen-Kopra et al., "Single treatment with ethanol hand rub is ineffective against human rhinovirus—hand washing with soap and water removes the virus efficiently", Journal of Medical Virology, pp. 534-547, vol. 84, Issue 3 (Mar. 2012).
Sayes et al., "Comparative study of predictive computational models for nanoparticle-induced cytotoxicity", Risk Anal., vol. 30(11), pp. 1723-1734 (2010).
Schindelin et al., "Fiji: an open-source platform for biological-image analysis", Nature Methods, pp. 671-675, vol. 9 (2012).
Schindelin et al., "The ImageJ ecosystem: An open platform for biomedical image analysis", Molecular Reproduction & Development, pp. 518-529, vol. 82, Issue 7-8 (Jul.-Aug. 2015).
Schins, "Mechanisms of genotoxicity of particles and fibers", Inhalation Toxicol., vol. 14(1), pp. 57-78 (2008).
Schneider et al., "NIH Image to ImageJ: 25 years of Image Analysis". Nature Methods, pp. 671-675, vol. 9 (Jul. 2012).
Schoenmaker et al., "mRNA-lipid nanoparticle COVID-19 vaccines: Structure and stability", International Journal of Pharmaceutics, pp. 120586, in 13 pages, vol. 601 (May 15, 2021).
Schoonen et al., "High-throughput screening for analysis of in vitro toxicity", Molecular, Clinical and Environmental Toxicology, vol. 99, pp. 401-452 (2009).
Schraufnagel D.E., "The health effects of ultrafine particles", Exp. Mol. Med., vol. 52(3), pp. 311-317 (Mar. 2020).
Schubert et al., "Human serum from SARS-CoV-2-vaccinated and COVID-19 patients shows reduced binding to the RBD of SARS-CoV-2 Omicron variant", BMC Medicine, vol. 20(1), 102 (Mar. 2022).
Schuhmacher et al., "Changing R&D models in research-based pharmaceutical companies", Journal of Translational Medicine, 14:105 (2016).
Schulte et al., "Ethical and Scientific Issues of Nanotechnology in the Workplace", Environmental Health Perspectives, pp. 5-12, vol. 115, No. 1 ((Jan. 2007).
Schwegmann et al., "Host-directed drug targeting of factors hijacked by pathogens", Science Signaling, vol. 1(29) (Jul. 2008).
Scialli, "The challenge of reproductive and developmental toxicology under REACH", Regul. Toxicol. Pharmacol., vol. 51(2), pp. 244-250 (2008).
Scudellari, "The sprint to solve coronavirus protein structures—and disarm them with drugs", Nature, pp. 252-255, vol. 581 (2020).
Seaberg et al., "A rapid millifluidic synthesis of tunable polymer-protein nanoparticles", European Journal of Pharmaceutics and Biopharmaceutics, vol. 154, pp. 127-135 (Jul. 2020).
Seabra et al., "Lipid nanoparticles to counteract gastric infection without affecting gut microbiota", European Journal of Pharmaceutics and Biopharmaceutics, vol. 127, pp. 378-386 (2018).
Sedlak et al., "Direction matters: Monovalent streptavidin/biotin complex under load", Nano Letters, vol. 19(6), pp. 3415-3421 (2018).
Segura et al., "Gamma interferon loaded onto albumin nanoparticles: in vitro and in vivo activities against Brucella abortus", Antimicrobial Agents and Chemotherapy, vol. 51(4), pp. 1310-1314 (2007).
Segura et al., "Potential of albumin nanoparticles as carriers for interferon gamma", Drug Development and Industrial Pharmacy, vol. 31(3), pp. 271-280 (2005).
Seigneuric et al., "From Nanotechnology to Nanomedicine: Applications to Cancer Research", Current Molecular Medicine, pp. 640-652, vol. 10 (2010).
Sekimukai et al., "Gold nanoparticle-adjuvantes S protein induces a strong antigen-specific IgG response against severe acute respiratory syndrome-related coronavirus infection, but fails to induce protective antibodies and limit eosinophilic infiltration in lungs", Microbiology and Immunology, pp. 33-51, vol. 64, No. 1 (Jan. 2020).
Seligmann et al., "Tubulin: an example of targeted chemotherapy", Future Medicinal Chemistry, pp. 339-352, vol. 5 (2013).
Selinka et al., "Analysis of the infectious entry pathway of human papillomavirus type 33 pseudovirions", Virology, vol. 299(2), pp. 279-287 (2002).
Semerdzhiev et al., "Interactions between SARS-CoV-2 N-Protein and α-Synuclein Accelerate Amyloid Formation", . ACS Chemical Neuroscience, pp. 143-150, vol. 13 (2022).
Senut et al., "Size-dependent toxicity of gold nanoparticles on human embryonic stem cells and their neural derivatives", Small, vol. 12(5), pp. 631-646 (2015).
Seo et al., "Continuous microfluidic reactors for polymer particles", Langmuir, vol. 21(25), pp. 11614-11622 (2005).
Serra et al., "Microfluidic-assisted synthesis of polymer particles", Chemical Engineering & Technology: Industrial Chemistry-Plant Equipment-Process Engineering-Biotechnology, vol. 31(8), pp. 1099-1115 (2008).
Sevinc Ozdemir et al., "Advances in in vitro blood-air barrier models and the use of nanoparticles in COVID-19 research", Tissue Engineering Part B: Reviews, vol. 30(1) (Dec. 2023).
Seyran et al., "The structural basis of accelerated host cell entry by SARS-CoV-2", The FEBS Seyran Journal, vol. 288(17), pp. 5010-5020 (Dec. 2020).
Shaffer, "15 drugs being tested to treat COVID-19 and how they would work", Nature Medicine, doi: 10.1038/d41591-020-00019-9.
Shajahan et al., "Deducing the N- and O-glycosylation profile of the spike protein of novelcoronavirus SARS-CoV-2", Glycobiology, pp. 981-988, vol. 30, No. 12 (2020) Glycobiology, 2020, 1-20.
Shang et al., "Cell entry mechanisms of SARS-CoV-2", Proceedings of the National Academy of Sciences, vol. 117(21), pp. 11727-11734 (May 2020).
Shang et al., "Engineered nanoparticles interacting with cells: size matters", Journal of Nanobiotechnology, 12:5, in 11 pages (2014) doi: 10.1186/1477-3155-12-5.
Shang et al., "Structural basis of receptor recognition by SARS-CoV-2", Nature, pp. 221-224, vol. 581 (2020).

(56) References Cited

OTHER PUBLICATIONS

Shao et al., "Independent effect of polymeric nanoparticle zeta potential/surface charge, on their cytotoxicity and affinity to cells", Cell Proliferation, vol. 48(4), pp. 465-474 (2015).
Sharma et al., "Nanomaterials: exposure, effects and toxicity assessment", Proc. Natl. Acad. Sci., India, Sect. B, vol. 82, pp. 3-11 (2012).
Shaw et al., "90—Vaccines", Clinical Immunology (Fourth Edition), 2013, pp. 1095-1121, ISBN 9780723436911.
Shaw, "Glucose metabolism and cancer", Current Opinion in Cell Biology, pp. 598-608, vol. 18, Issue 6 (Dec. 2006).
Shaw, "Nasally delivered SARS-CoV-2 vaccines: future promise and challenges", The Lancet Respiratory Medicine, vol. 11, pp. 1038-1039 (Dec. 2023).
Shekh et al., "Molecular impacts of advanced nanomaterials at genomic and epigenomic levels", In:Sahu SC, editor, In Impact of Engineered Nanomaterials in Genomics and Epigenomics; Wiley, pp. 5-39 (May 2023).
Shen et al., "Assessment of folate receptor-β expression in human neoplastic tissues" Oncotarget, pp. 14700-14709, vol. 6, No. 16, (Jun. 10, 2015) doi: 10.18632/oncotarget.3739.
Shen et al., "Membrane wrapping efficiency of elastic nanoparticles during endocytosis: Size and shape matter", ACS Nano, vol. 13(1), pp. 215-228 (2018).
Shepherd et al., "Microfluidic formulation of nanoparticles for biomedical applications", Biomaterials, vol. 274, 120826 (Apr. 2021).
Shepherd et al., "Scalable mRNA and siRNA lipid nanoparticle production using a parallelized microfluidic device", Nano Letters, vol. 21(13), pp. 5671-5680 (Jun. 2021).
Shepherd et al., "Throughput-scalable manufacturing of SARS-CoV-2 mRNA lipid nanoparticle vaccines", Proceedings of the National Academy of Sciences, vol. 120(33), e2303567120 (Aug. 2023).
Shi et al., "RBD-mRNA vaccine induces broadly neutralizing antibodies against Omicron and multiple other variants and protects mice from SARS-CoV-2 challenge", Translational Research, vol. 248, pp. 11-21 (Oct. 2022).
Shi et al., "Structural and biochemical characteristics of mRNA nanoparticles determine anti-SARS- CoV-2 humoral and cellular immune responses", Science Advances, vol. 8(47), eabo1827 (Nov. 2022).
Shi et al., "The roles of surface chemistry, dissolution rate, and delivered dose in the cytotoxicity of copper nanoparticles", Nanoscale, vol. 9(14), pp. 4739-4750 (2017).
Shilagardi et al., "The Integral Membrane Protein ZMPSTE24 Protects Cells from SARS-CoV-2 Spike-Mediated Pseudovirus Infection and Syncytia Formation", Virology, mBio, vol. 13(5), e02543-22 (Oct. 2022).
Shin et al., "COVID-19 vaccine development and a potential nanomaterial path forward", Nature Nanotechnology, vol. 15(8), pp. 646-655 (Aug. 2020).
Shin et al., "Inhibition of ACE2-Spike Interaction by an ACE2 Binder Suppresses SARS-CoV-2 Entry", Angewandte Chemie, vol. 134(11), e202115695 (Feb. 2022).
Shin et al., "Use of metal/metal oxide spherical cluster and hydroxyl metal coordination complex for descriptor calculation in development of nanoparticle cytotoxicity classification model", SAR QSAR Environ. Res., vol. 28(11), pp. 875-888 (2017).
Shinde et al., "Efficacy of NVX-CoV2373 Covid-19 Vaccine against the B.1.351 Variant", The New England Journal of Medicine, pp. 1899-1909, vol. 384(20) (May 20, 2021).
Shockley, "Quantitative high-throughput screening data analysis: challenges and recent advances", Drug Discovery Today, vol. 20(3), pp. 296-300 (2015).
Shokoohinia et al., "Microfluidic-assisted preparation of PLGA nanoparticles for drug delivery purposes: Experimental study and computational fluid dynamic simulation", Research in Pharmaceutical Sciences, vol. 14(5), 459 (2019).
Shrader-Frechette, "Nanotoxicology and Ethical Conditions for Informed Consent", NanoEthics, pp. 47-56, vol. 1 (2007).
Shrimal et al., "A review on novel methodologies for drug nanoparticle preparation: Microfluidic approach", Chemical Engineering Research and Design, vol. 153, pp. 728-756 (Nov. 2019).
Shuchman, "Obtaining funding an age-old problem for young researchers with novel ideas", CMAJ, pp. E516-E517, vol. 190, Isue 16 (Apr. 23, 2018).
Shukla et al., "The future of toxicity testing: a focus on in vitro methods using a quantitative high-throughput screening platform", Drug Discovery Today, vol. 15(23-24), pp. 997-1007 (2010).
Sidney et al., "HLA class I supertypes: A revised and updated classification", BMC Immunology, pgs.in 15 pages, vol. 9:1 (2008).
Silva et al., "Recent trends on the development of systems for cancer diagnosis and treatment by microfluidic technology", Applied Materials Today, vol. 18, 100450 (Dec. 2020).
Silwal et al., "DNA aptamers inhibit SARS-CoV-2 spike-protein binding to hACE2 by an RBD-independent or dependent approach", Theranostics, vol. 12(12), pp. 5522-5536 (Jul. 2022).
Singanayagam et al., "ATACCC Study Investigators. Community transmission and viral load kinetics of the SARS-CoV-2 delta (B.1.617.2) variant in vaccinated and unvaccinated individuals in the UK: a prospective, longitudinal, cohort study", The Lancet Infectious Diseases, pp. 183-195, vol. 22, Issue 2 (Feb. 1, 2022).
Singh et al., "Antibody delivery for intracellular targets: emergent therapeutic potential", Bioconjugate Chemistry, vol. 30(4), pp. 1028-1041 (2019).
Singh et al., "Antiviral agents for the treatment of COVID-19: Progress and challenges", Cell Reports Medicine, vol. 3(3), 100549 (Mar. 2022).
Singh et al., "Jr Nanoparticle-based targeted drug delivery", Experimental and Molecular Pathology, pp. 215-223, vol. 86, Issue 3 (Jun. 2009).
Singh et al., "Microstructure, pathophysiology, and potential therapeutics of COVID-19: A comprehensive review", Journal of Medical Virology, vol. 93(1), pp. 275-299 (Jul. 2020).
Singh et al., "NanoGenotoxicology: The DNA damaging potential of engineered nanomaterials", Biomaterials, vol. 30(23-24), pp. 3891-3914 (2009).
Singhal, "A Review of Coronavirus Disease-2019 (COVID-19)", The Indian Journal of Pediatrics, pp. 281-286, vol. 87 (Apr. 2020).
Singhvi et al., "Polylactic acid: synthesis and biomedical applications", Journal of Applied Microbiology, pp. 1612-1626, vol. 127, Issue 6 (Dec. 2019).
Smith et al., "Novel hemagglutinin nanoparticle influenza vaccine with Matrix-M™ adjuvant induces hemagglutination inhibition, neutralizing, and protective responses in ferrets against homologous and drifted A (H3N2) subtypes", Vaccine, vol. 35(40), pp. 5366-5372 (2017).
Smith, et al., "Immunogenicity of a DNA vaccine candidate for COVID-19", Nature Communications, Article No. 2601, in 13 pages, vol. 11 92020).
Smulders et al., "Toxicity of nanoparticles embedded in paints compared with pristine nanoparticles in mice", Toxicological Sciences, vol. 141(1), pp. 132-140 (2014).
Söderberg-NaucléR, "Does reactivation of cytomegalovirus contribute to severe COVID-19 disease?", Immunity & Ageing, in 7 pages, 18:12 (2021).
Sohaebuddin et al., "Nanomaterial cytotoxicity is composition, size, and cell type dependent", Part. Fibre Toxicol., vol. 7(22), pp. 1-17 (2010).
Sohail et al., "In silico T cell epitope identification for SARS-CoV-2: Progress and perspectives", pp. 29-47, vol. 171 (Apr. 2021).
Sohrabi et al., "World Health Organization declares Global Emergency: A review of the 2019 Novel Coronavirus (COVID-19)", International Journal of Surgery, pp. 71-76, vol. 76 (Apr. 2020).
Sokolov et al., "Ferristatin II efficiently inhibits SARS-CoV-2 replication in vero cells", Viruses, vol. 14(2), 317 (Feb. 2022).
Sokolov et al., "Transport of ultrasmall gold nanoparticles (2 nm) across the blood-brain barrier in a six-cell brain spheroid model", Scientific Reports, vol. 10(1), 18033 (Oct. 2020).

(56) References Cited

OTHER PUBLICATIONS

Sokolov et al., "Ultrasmall gold nanoparticles (2 nm) can penetrate and enter cell nuclei in an in vitro 3D brain spheroid model", Acta Biomaterialia, vol. 111, pp. 349-362 (May 2020).
Solon et al., "Fibroblast Adaptation and Stiffness Matching to Soft Elastic Substrates", Biophysical Journal, pp. 44353-4461, vol. 93 (Dec. 15, 2007).
Soloviev et al., "Modelling the adsorption of proteins to nanoparticles at the solid-liquid interface", Journal of Colloid and Interface Science, vol. 605, pp. 286-295 (Jan. 2022).
Soltman et al., "Inkjet-Printed Line Morphologies and Temperature Control of the Coffee Ring Effect", Langmuir, pp. 2224-2231, vol. 24 (2008).
Song et al., "Formulation and evaluation of celastrol-loaded liposomes", Molecules, pp. 7880-7892, vol. 16 (2011).
Song et al., "Safety and immunogenicity of a SARS-CoV-2 recombinant protein nanoparticle vaccine (GBP510) adjuvanted with AS03: A randomised, placebo-controlled, observer-blinded phase 1/2 trial", EClinicalMedicine, vol. 51, 101569 (Sep. 2022).
Sönmez et al., "Determining Future Travel Behavior from Past Travel Experience and Perceptions of Risk and Safety", Journal of Travel Research, pp. 171-177, vol. 37 (1998).
Sonoke et al., "Galactose-Modified Cationic Liposomes as a Liver-Targeting Delivery System for Small Interfering RNA", Biological and Pharmaceutical Bulletin, pp. 1338-1342, vol. 34 (2011).
Southall et al., "Enabling the large-scale analysis of quantitative high-throughput screening data", In: Southall NT et al., editor, In Handbook of Drug Screening; CRC Press, pp. 442-464 (2009).
Souza et al., "A comparison of TEM and DLS methods to characterize size distribution of ceramic nanoparticles", Journal of Physics, in 5 pages, 012039, vol. 733 (2016).
Souza et al., "ACE2-derived peptides interact with the RBD domain of SARS-CoV-2 spikeglycoprotein, disrupting the interaction with the human ACE2 receptor", Journal of Biomolecular Structure and Dynamics, vol. 40(12), pp. 5493-5506 (Jan. 2021).
Sportelli et al., "Can Nanotechnology and Materials Science Help the Fight against SARS-CoV-2?",Nanomaterials (Basel), 10(4):802. doi: 10.3390/nano10040802. PMID: 32326343; PMCID: PMC7221591. (Apr. 21, 2020).
Srinivasan et al., "Structural Genomics of SARS-COV-2 Indicates Evolutionary Conserved Functional Regions of Viral Proteins", Viruses, 360, vol. 12 (Mar. 25, 2020) doi: 10.3390/v12040360.
Sriraman et al., " Barriers to Drug Delivery in Solid Tumors", Tissue Barriers, 2:e29528, in 10 pages (2014) doi: 10.4161/tisb.29528.
Srivastava et al., "Critical Review on the Toxicity of Some Widely Used Engineered Nanoparticles", Industrial & Engineering Chemistry Research, pp. 6209-6233, vol. 54 (2015).
St. Dollente Mesias et al., "Effective ACE2 peptide-nanoparticle conjugation and its binding withthe SARS-Cov-2 RBD quantified by dynamic light scattering", Chemical Communications, pp. 6979-6982, vol. 57 (2021).
Stanifer et al., "Critical Role of Type III Interferon in Controlling SARS-CoV-2 Infection in Human Intestinal Epithelial Cells", Cell Reports. 107863 in 15 pages, vol. 32, Issue 1 (Jul. 7, 2020).
Starr et al., "Complete map of SARS-CoV-2 Rbd mutations that escape the monoclonal antibody LY-CoV555 and its cocktail with LY-CoV016", Cell Reports Medicine, vol. 2(4), 100255 (Apr. 2021).
Stayton et al., "Streptavidin-biotin binding energetics", Biomolecular Engineering, vol. 16(1-4), pp. 39-44 (1999).
Steichen et al., "A review of current nanoparticle and targeting moieties for the delivery of cancer therapeutics", European Journal of Pharmaceutical Sciences: Official Journal of the European Federation for Pharmaceutical Sciences, pp. 416-427, vol. 48 (Feb. 14, 2013).
Stephan, "How Economics Shapes Science", Boston, MA: Harvard University Press, 2012a, doi: 10.1111/1475-4932.12480.
Stephan, "Research efficiency: Perverse incentives", Nature, pp. 29-31, vol. 484 (2012).
Streblow et al., "Aerosol delivery of SARS-CoV-2 human monoclonal antibodies in macaques limits viral replication and lung pathology", Nature Communications, vol. 14(1), 7062 (Nov. 2023).
Struss et al., "Paper strip whole cell biosensors: a portable test for the semiquantitative detection of bacterial quorum signaling molecules", Analytical Chemistry, pp. 4457-4463, vol. 82 (Jun. 2010).
Su et al., "Developing pan-β-coronavirus vaccines against emerging SARS-CoV-2 variants of concern", Trends in Immunology, pp. 170-172, vol. 43, Issue 3 (Mar. 1, 2022).
Subbaraman, "How Do Vaccinated People Spread Delta? What The Science Says", Nature, pp. 327-328, vol. 596 (Aug. 19, 2021).
Sudhakar, "History of Cancer, Ancient and Modern Treatment Methods", Journal of Cancer Science and Therapy, pp. 1-4, vol. 1 (Dec. 1, 2009) doi: 10.4172/1948-5956.100000e2.
Sukumaran et al., "Canonical Transient Receptor Potential Channel 2 (TRPC2) as a Major Regulator of Calcium Homeostasis in Rat Thyroid FRTL-5 Cells: Importance of Protein Kinase C δ (PKCδ) and Stromal Interaction Molecule 2 (STIM2)", Journal of Biological Chemistry, pp. 44345-44360, vol. 287 (Dec. 28, 2012).
Suman et al., "Sustainability of Coronavirus on Different Surfaces", Journal of Clinical and Experimental Hepatology, pp. 386-390, vol. 10, Issue 4 (Jul. 1, 2020).
Sun et al., "A Polysaccharide-RBD-Fc-Conjugated COVID-19 Vaccine, SCTV01A, Showed High Immunogenicity and Low Toxicity in Animal Models", Vaccines, vol. 11(3), 526 (Feb. 2023).
Sun et al., "Developing pseudovirus-based neutralization assay against omicron-included SARS-CoV-2 variants", Viruses, vol. 14(6), 1332 (Jun. 2022).
Sun et al., "Microfluidic preparation of polymer-lipid Janus microparticles with staged drug release property", Journal of Colloid and Interface Science, vol. 553, pp. 631-638 (2019).
Sun et al., "Paradigm shift in toxicity testing and modeling", AAPS J., vol. 14(3), pp. 473-480 (2012).
Sun et al., "Predictive toxicological paradigm and high throughput approach for toxicity screening of engineered nanomaterials", Int. J. Biomed. Nanosci. Nanotechnol., vol. 3(1-2), pp. 4-18 (2013).
Sun et al., "Spherical neutralizing aptamer inhibits SARS-CoV-2 infection and suppresses mutational escape", Journal of the American Chemical Society, vol. 143(51), pp. 21541-21548 (Dec. 2021).
Sun et al., "The self-assembled nanoparticle-based trimeric RBD mRNA vaccine elicits robust anddurable protective immunity against SARS-CoV-2 in mice", Signal Transduction and Targeted Therapy, vol. 6(1), 340 (Sep. 2021).
Sun et al., "A systematic analysis of FDA-approved anticancer drugs", BMC Systems Biology, vol. 11, Supplement 5, Article No. 87 (2017).
Sun et al., "Cationic nanoparticles directly bind angiotensin-converting enzyme 2 and induce acute lung injury in mice", Particle and Fibre Toxicology, vol. 12, Article No. 4 (2015).
Sun et al., "Recent Advance on Mesoporous Silica Nanoparticles-Based Controlled Release System: Intelligent Switches Open up New Horizon". Nanomaterials (Basel), pp. 2019-2053, vol. 5, No. 4 (2015).
Sun et al., "RIP-1/c-FLIPL Induce Hepatic Cancer Cell Apoptosis Through Regulating Tumor NecrosisFactor-Related Apoptosis-Inducing Ligand (TRAIL)", Medical Science Monitor, pp. 1190-1199, vol. 23 (2017).
Sun et al., "The efficacy of social distance and ventilation effectiveness in preventing COVID-19 transmission", Sustainable Cities and Society, pp. 1-10, vol. 62 (2020).
Sun, "Nanomaterial-Based Vaccine Adjuvants", Journal of Materials Chemistry B, pp. 5496-5509, vol. 4 (Sep. 7, 2016).
Sung et al., "Protein-based nanoparticle vaccines for SARS-CoV-2", International Journal of Molecular Sciences, vol. 22(24), 13445 (Dec. 2021).
Sungnak et al., "SARS-CoV-2 entry factors are highly expressed in nasal epithelial cells together with innate immune genes", Nature Medicine, pp. 681-687, vol. 26 (2020).
Suresh et al., "Cytotoxicity induced by engineered silver nanocrystallites is dependent on surface coatings and cell types", Langmuir, vol. 28(5), pp. 2727-2735 (2012).

(56) References Cited

OTHER PUBLICATIONS

Suzuki et al., "Difference in the lipid nanoparticle technology employed in three approved siRNA(Patisiran) and mRNA (COVID-19 vaccine) drugs", Drug Metabolism and Pharmacokinetics, vol. 41, 100424 (Oct. 2021).
Suzuki et al., "Lipid nanoparticles loaded with ribonucleoprotein-oligonucleotide complexes synthesized using a microfluidic device exhibit robust genome editing and hepatitis B virus inhibition", Journal of Controlled Release, vol. 330, pp. 61-71 (Dec. 2020).
Svingen, "Endocrine disruptors in a new era of predictive toxicology and dealing with the "more is different" challenge", Front. Toxicol., vol. 4, 900479 (Apr. 2022).
Sweeney et al., "Peptide-Mediated Targeting Mesoporous Silica Nanoparticles: A Novel Tool for Fighting Bladder Cancer", Journal of Biomedical Nanotechnology, pp. 232-242, vol. 13, No. 2 (2017).
Szymański et al., "Adaptation of high-throughput screening in drug discovery-toxicological screening tests", Int. J. Mol. Sci., vol. 13(1), pp. 427-452 (2012).
Szymanski et al., "Bacterial and Viral Infections", Essentials of Glycobiology [Internet], 3rd edition. Cold Spring Harbor (NY): Cold Spring Harbor Laboratory Press, Chapter 42 (2015).
Tabynov et al., "An intranasal vaccine comprising SARS-CoV-2 spike receptor-binding domain proteinentrapped in mannose-conjugated chitosan nanoparticle provides protection in hamsters", Scientific Reports, vol. 13(1), 12115 (Jul. 2023).
Tada et al., "A soluble ACE2 microbody protein fused to a single immunoglobulin Fc domain is a potent inhibitor of SARS-CoV-2 infection in cell culture", bioRxiv, pp. 1-61 (2020).
Tahir et al., "Microfluidic fabrication and characterization of Sorafenib-loaded lipid-polymer hybridnanoparticles for controlled drug delivery", International Journal of Pharmaceutics, vol. 581, 119275 (May 2020).
Tai et al., "A novel receptor-binding domain (RBD)-based mRNA vaccine against SARS-CoV-2", Cell Research, vol. 30(10), pp. 932-935 (Aug. 2020).
Tai et al., "Characterization of the receptor-binding domain (RBD) of 2019 novel coronavirus:implication for development of RBD protein as a viral attachment inhibitor and vaccine", Cellular & Molecular Immunology, vol. 17(6), pp. 613-620 (Mar. 2020).
Tai et al., "Development of a ferritin-based nanoparticle vaccine against the SARS-CoV-2 Omicron variant", Signal Transduction and Targeted Therapy, vol. 7(1), 173 (Jun. 2022).
Takahashi et al., "A low-cost paper-based synthethic biology platform for analysing gut microbiota and host biomarkers", Nature Communications, pp. 1-12, vol. 9, Article No. 3347 (2018).
Takeshita et al., "Potent neutralizing broad-spectrum antibody against SARS-CoV-2 generated from dual-antigen-specific B cells from convalescents", iScience, vol. 26(6), 106955 (May 2023).
Tamirat et al., "Deciphering the structural effects of activating EGFR somatic mutations with molecular dynamics simulation", Journal of Visualized Experiments, pp. 1-12 (2020).
Tan et al., "A COVID-19 vaccine candidate using SpyCatcher multimerization of the SARS-CoV-2 spikeprotein receptor-binding domain induces potent neutralising antibody responses", Nature Communications, pp. 1-16, vol. 12, Article No. 542 (2021).
Tang et al., "A Selective SARS-CoV-2 Host-Directed Antiviral Targeting Stress Response to Reactive Oxygen Species", ACS Central Science, vol. 9(1), pp. 109-121 (Jan. 2023).
Tang et al., "In vitro cytotoxicity of gold nanorods in A549 cells", Environ. Toxicol. Pharmacol., vol. 39(2), pp. 871-878 (2015).
Tariq et al., "Virus-like particles: Revolutionary platforms for developing vaccines against emerging infectious diseases", Frontiers in Microbiology, vol. 12, 790121 (Jan. 2022).
Tauzin et al., "Evolution of anti-RBD IgG avidity following SARS-CoV-2 infection", Viruses, vol. 14(3), 532 (Mar. 2022).
Tavakol et al., "The role of nanotechnology in current COVID-19 outbreak", Heliyon, vol. 7(4), e06841 (Apr. 2021).
Tchoryk et al., "Penetration and uptake of nanoparticles in 3D tumor spheroids", Bioconjugate Chemistry, vol. 30(5), pp. 1371-1384 (2019).
Te Velthuis et al., "Zn(2+) Inhibits Coronavirus and Arterivirus RNA Polymerase Activity In Vitro and Zinc Ionophores Block the Replication of These Viruses in Cell Culture", PLOS Pathogens, pp. 1-10, vol. 6, No. 11 (2010).
Tello et al., "Fabrication of hydrogel microspheres via microfluidics using inverse electron demand Diels-Alder click chemistry-based tetrazine-norbornene for drug delivery and cell encapsulation applications", Biomaterials Science, vol. 11, pp. 4972-4984 (Jun. 2023).
Tena et al., "Deposition of inhaled particles in the lungs", Archivos de Bronconeumologia (English Edition), pp. 240-246, vol. 48, Issue 7 (Jul. 2012).
Tennant, "Evaluation of the trypan blue technique for determination of cell viability", Transplantation, vol. 2(6), pp. 685-694 (1964).
Terada et al., "Characterization of lipid nanoparticles containing ionizable cationic lipids using design-of-experiments approach", Langmuir, vol. 37(3), pp. 1120-1128 (Jan. 2021).
Tetard et al., "Imaging nanoparticles in cells by nanomechanical holography", Nature Nanotechnology, vol. 3(8), pp. 501-505 (2008).
Thacker, "Covid-19: Researcher blows the whistle on data integrity issues in Pfizer's vaccine trial", BMJ, pp. 1-3, vol. 375, No. 2635 (2021).
Thakur et al., "Futuristic role of nanoparticles for treatment of COVID-19", Biomaterials and Polymers Horizon, vol. 1(2) (Jun. 2022).
Thakur et al., "Eps 15 homology domain containing protein of Plasmodium falciparum (PfEHD)associates with endocytosis and vesicular trafficking towards neutral lipid storage site", Biochimica et Biophysica (BBA) Acta—Molecular Cell Research, pp. 2856-2869, vol. 1853, Issue 11, Part A (2015).
The Novel Coronavirus Pneumonia Emergency Response Epidemiology Team,"Vital Surveillances: The Epidemiological Characteristics of an Outbreak of 2019 Novel Coronavirus Diseases (COVID-19)-China, 2020", China CDC Weekly, pp. 113-122, vol. 2(8) (2020).
Thi et al., "Lipid-based nanoparticles in the clinic and clinical trials: from cancer nanomedicine to COVID-19 vaccines", Vaccines, vol. 9(4), 359 (Apr. 2021).
Thiele et al., "High-Throughput Synthesis of Uniform Silver Seed Particles by a Continuous Microfluidic Synthesis Platform", Chemical Engineering & Technology, vol. 38(7), pp. 1131-1137 (2015).
Thomas et al., "Nanomaterials in the environment: from materials to high-throughput screening to organisms", ACS Nano, vol. 5(1), pp. 13-20 (2011).
Thomas et al., "STAT1: a modulator of chemotherapy-induced apoptosis", Cancer Research, pp. 8357-8364, vol. 64, Issue 22 (2004).
Thorley et al., "Mechanisms of viral entry: sneaking in the front door", Protoplasma, vol. 244, pp. 15-24 (2010).
Thorn et al., "Doxorubicin pathways: pharmacodynamics and adverse effects", Pharmacogenet Genomics, pp. 440-446, vol. 21, No. 7 (2011).
Tian et al., "Microfluidic technologies for nanoparticle formation", Lab on a Chip, vol. 22(3), pp. 512-529 (Feb. 2022).
Tian et al., "Calibrated Intervention and Containment of the COVID-19 Pandemic", arXiv, pp. 1-54 (2020).
Tinari et al., "Covid-19: Whatever happened to the Novavax vaccine?", BMJ, Dec 8, vol. 375, No. 2965 (2021).
Tirumala et al., "Novel methods and approaches for safety evaluation of nanoparticle formulations: A focus towards in vitro models and adverse outcome pathways", Front. Pharmacol., vol. 12, 612659 (Sep. 2021).
Tobjörk et al., "IR-sintering of ink-jet printed metal nanoparticles on paper", Thin Solid Films, pp. 2949-2955, vol. 520, Issue 7 (2012).
Tohme et al., "Surgery for Cancer: A Trigger for Metastases", Cancer Research, pp. 1548-1552, vol. 77, Issue 7 (2017).
Tojkander et al., "Actin stress fibers—assembly, dynamics and biological roles", Journal of Cell Science, pp. 1855-1864, vol. 125, Issue 8 (2012).
Tokiwa et al., "Biodegradability of plastics", International Journal of Molecular Sciences, pp. 3722-3742, vol. 10 (2009).

(56) References Cited

OTHER PUBLICATIONS

Tomeh et al., "Optimization of large-scale manufacturing of biopolymeric and lipid nanoparticles using microfluidic swirl mixers", International Journal of Pharmaceutics, vol. 620, 121762 (May 2022).
Tomeh et al., "Recent advances in microfluidics for the preparation of drug and gene delivery systems", Molecular Pharmaceutics, vol. 17(12), pp. 4421-4434 (Nov. 2020).
Tomoda et al., "Preparation and properties of inhalable nanocomposite particles: effects of thetemperature at a spray-dryer inlet upon the properties of particles", Colloids and Surfaces B: Biointerfaces, vol. 61(2), pp. 138-144 (2008).
Toropov et al., "Novel application of the CORAL software to model cytotoxicity of metal oxide nanoparticles to bacteria *Escherichia coli*", Chemosphere, vol. 89(9), pp. 1098-1102 (2012).
Toropova et al., "Optimal descriptor as a translator of eclectic data into prediction of cytotoxicity formetal oxide nanoparticles under different conditions", Ecotoxicol. Environ. Saf., vol. 112, pp. 39-45 (2015).
Tortorici et al., "Structural basis for human coronavirus attachment to sialic acid receptors", Nature Structural & Molecular Biology, pp. 481-489, vol. 26 (2019).
Towers et al., "Quantifying the relative effects of environmental and direct transmission of norovirus", Royal Society Open Science, pp. 1-13, vol. 5 (2018).
Tramontano et al., "Microfluidic-Assisted Production of Gastro-Resistant Active-Targeted Diatomite Nanoparticles for the Local Release of Galunisertib in Metastatic Colorectal Cancer Cells", Advanced Healthcare Materials, vol. 12(6), 2202672 (Dec. 2023).
Trimarco et al., "Cellular glycan modification by B3GAT1 broadly restricts influenza virus infection", Nature Communications, vol. 13(1), 6456 (Oct. 2022).
Trinchieri, "Interleukin-12 and the regulation of innate resistance and adaptive immunity", Nature Reviews, Immunology, pp. 133-146, vol. 3 (2003).
Trinh et al., "Quasi-SMILES-based nano-quantitative structure-activity relationship model to predictthe cytotoxicity of multiwalled carbon nanotubes to human lung cells", Chem. Res. Toxicol., vol. 31(3), pp. 183-190 (2018).
Trott et al., "Activation of heat shock and antioxidant responses by the natural product celastrol: transcriptional signatures of a thiol-targeted molecule", Molecular Biology of the Cell, pp. 1104-1112, vol. 19, No. 3 (2008).
Tsai et al., "Monoclonal Antibody-Functionalized Mesoporous Silica Nanoparticles (MSN) for Selective Targeting Breast Cancer Cells", Journal of Materials Chemistry, pp. 5737-5743, vol. 19 (2009).
Tsao et al., "HLA-A*0201 T-cell epitopes in severe acute respiratory syndrome (SARS) coronavirus nucleocapsid and spike proteins", Biochemical and Biophysical Research Communications, pp. 63-71, vol. 344, Issue 1 (2006).
Tseng et al., "A novel pseudovirus-based mouse model of SARS-CoV-2 infection to test COVID-19 interventions", Journal of Biomedical Science, vol. 28, pp. 1-8 (Apr. 2021).
Tseng et al., "Apical entry and release of severe acute respiratory syndrome-associated coronavirus in polarized Calu-3 lung epithelial cells", J. Virol., vol. 79(15), pp. 9470-9479 (2005).
Tuomisto et al., "An agent-based epidemic model REINA for COVID-19 to identify destructive policies", medRxiv, in 29 pages, doi: https://doi.org/10.1101/2020.04.09.20047498.
Ucar et al., "A nanotechnological approach in the current therapy of COVID-19: Model drug oseltamivir-phosphate loaded PLGA nanoparticles targeted with spike protein binder peptide of SARS-CoV-2", Nanotechnology, vol. 32(48), 485601 (Sep. 2021).
Umezawa et al., "Maternal inhalation of carbon black nanoparticles induces neurodevelopmental changes in mouse offspring", Particle and Fibre Toxicology, pp. 1-18, vol. 15, Article No. 36 (2018).
Unal et al., "Graphene oxide nanosheets interact and interfere with SARS-CoV-2 surface proteins and cell receptors to inhibit infectivity", Small, vol. 17(25), 2101483 (May 2021).
Underwood et al., "Challenges and approaches for particle size analysis on micrographs of nanoparticles loaded onto textile surfaces", NIST Special Publication 1200-22, pp. 1-17 (2017).
Unfried et al., "Cellular responses to nanoparticles: target structures and mechanisms", Nanotoxicology, vol. 1(1), pp. 52-71 (2007).
Upla et al., "Clustering induces a lateral redistribution of alpha 2 beta 1 integrin from membrane rafts to caveolae and subsequent protein kinase C-dependent internalization", Molecular Biology of the Cell, pp. 625-636, vol. 15, No. 2 (2004).
Uraki et al., "Host glycolipids in SARS-CoV-2 entry", Nature Chemical Biology, vol. 18(1), pp. 6-7 (Nov. 2021).
Urbano et al., "Apoptosis and the FLIP and NF-kappa B proteins as pharmacodynamic criteria for biosimilar TNF-alpha antagonists", Biologics: Targets and Therapy, pp. 211-220, vol. 8 (2014).
Urdaniz et al., "One-shot identification of SARS-CoV-2 S RBD escape mutants using yeast screening", Cell Rep, Aug. 31, 2021, 36(9):109627. doi: 10.1016/j.celrep.2021.109627. Epub Aug. 10, 2021. PMID: 34416153; PMCID: PMC8352667.
Valdes-Balbin et al., "Molecular aspects concerning the use of the SARS-CoV-2 receptor binding domain as a target for preventive vaccines", ACS Central Science, vol. 7(5), pp. 757-767 (Apr. 2021).
Valencia et al., "Microfluidic technologies for accelerating the clinical translation of nanoparticles", Nano-Enabled Medical Applications, Nanomedicine's Most Cited—vol. 2, Jenny Standford Publishing Pte. Ltd., Chapter 3, pp. 93-112 (2020).
Valencia et al., "Microfluidic technologies for accelerating the clinical translation of nanoparticles" Nature Nanotechnology, vol. 7(10), pp. 623-629 (2012).
Valencia et al., "Single-step assembly of homogenous lipid-polymeric and lipid—quantum dot nanoparticles enabled by microfluidic rapid mixing", ACS Nano, vol. 4(3), pp. 1671-1679 (2010).
Vallet-Regí et al., "Mesoporous materials for drug delivery", Angewandte Chemie International Edition, pp. 7548-7558. Vol. 46, Issue 40 (2007).
Vallet-Regi et al., "Mesoporous Silica Nanoparticles for Drug Delivery: Current Insights", Molecules, pp. 1-19, vol. 23, Issue 1 (2017).
Van De Veerdonk et al., "A guide to immunotherapy for COVID-19", Nature Medicine, vol. 28(1), pp. 39-50 (Jan. 2022).
Van Dorp et al., "Emergence of genomic diversity and recurrent mutations in SARS-CoV-2", Infection, Genetics and Evolution, pp. 1-9, vol. 83 (2020).
Van Goethem et al., "Comparative evaluation of the in vitro micronucleus test and the alkaline single cell gel electrophoresis assay for the detection of DNA damaging agents: genotoxic effects of cobalt powder, tungsten carbide and cobalt-tungsten carbide", Mutat. Res. Genet. Toxicol. Environ. Mutagen., vol. 392(1-2), pp. 31-43 (1997).
Van Grinsven et al., "Fast Convolutional Neural Network Training Using Selective Data Sampling: Application to Hemorrhage Detection in Color Fundus Images", IEEE Transactions on Medical Imaging, pp. 1273-1284, vol. 35, Issue 5 (2016).
Van Oss, "Use of the combined Lifshitz-van der Waals and Lewis acid-base approaches indetermining the apolar and polar contributions to surface and interfacial tensions and free energies", Journal of Adhesion Science and Technology, pp. 669-677, vol. 16, Issue 66 (2002).
Van Rooyen et al., "Comparison of T-cell immune responses to SARS-CoV-2 spike (S) and nucleocapsid (N) protein using an in-house flow-cytometric assay in laboratory employees with and without previously confirmed COVID-19 in South Africa: nation-wide cross-sectional study", Journal of Clinical Pathology, pp. 1-7 (2022).
Varkey et al., "α-Synuclein oligomers with broken helical conformation form lipoprotein nanoparticles", Journal of Biological Chemistry, vol. 288(24), pp. 17620-17630 (2013).
Varki et al., "Essentials of Glycobiology, Bacterial and Viral Infections", NCI Bookshelf, Fourth Edition, Cold Spring Harbor Laboratory Press, Chapter 42 (Jan. 2022).
Varki et al., "Essentials of Glycobiology [Internet], 4th edition", Cold Spring Harbor (NY): Cold Spring Harbor Laboratory Press, Chapter 42 (2022).

(56) References Cited

OTHER PUBLICATIONS

Varkouhi et al., "Endosomal Escape Pathways for Delivery of Biologicals", Journal of Controlled Release, pp. 220-228, vol. 151, Issue 3 (2011).
Vecchio et al., "Lab-on-a-chip-based high-throughput screening of the genotoxicity of engineered nanomaterials", Small, vol. 10(13), pp. 2721-2734 (2014).
Vecellio, "The mesh nebuliser: a recent technical innovation for aerosol delivery", Breathe, vol. 2(3), pp. 252-260 (2006).
Vega-Avila et al., "An overview of colorimetric assay methods used to assess survival or proliferation of mammalian cells", Proc. West. Pharmacol. Soc., vol. 54, pp. 10-14 (2011).
Venditto et al., "Cancer nanomedicines: so many papers and so few drugs!", Advanced Drug Delivery Reviews, pp. 80-88, vol. 65, Issue 1 (2013).
Venkatakrishnan et al., "Benchmarking evolutionary tinkering underlying human-viral molecular mimicry shows multiple host pulmonary-arterial peptides mimicked by SARS-CoV-2", Cell Death Discovery, pp. 1-14, vol. 6, Article No. 96 (2020).
Verdoni et al., "An outbreak of severe Kawasaki-like disease at the Italian epicentre of the SARS-CoV-2 epidemic: An observational cohort study", The Lancet, pp. 1771-1778, vol. 395, Issue 10239 (2020).
Verma et al., "Mutation informatics: SARS-CoV-2 receptor-binding domain of the spike protein", Drug Discovery Today, vol. 27(10), 103312 (Jul. 2022).
Verma et al., "Effect of Surface Properties on Nanoparticle-Cell Interactions", Small, pp. 12-21, vol. 6, Issue 1 (2010).
Verma et al., "Interactions of Peptide Coated Gold Nanoparticles with Spike Protein of the SARS-CoV- 2: A Basis for Design of a Simple and Rapid Detection Tool", ChemRxiv, pp. 1-18 (2020).
Videira et al., "Preclinical evaluation of a pulmonary delivered paclitaxel-loaded lipid nanocarrier antitumor effect", Nanomedicine: Nanotechnology, Biology and Medicine, vol. 8(7), pp. 1208-1215 (2012).
Vihervaara et al., "Transcriptional response to stress in the dynamic chromatin environment of cycling and mitotic cells", Proceedings of the National Academy of Sciences of the USA, pp. E3388-E3397, vol. 110, No. 36 (2013).
Villacé-Molinero et al., "Understanding the new post-COVID-19 risk scenario: Outlooks and challenges for a new era of tourism", Tourism Management, pp. 1-11, vol. 86 (2021).
Vita et al., "The Immune Epitope Database (IEDB): 2018 update", Nucleic Acids Research, pp. D339-D343, vol. 47, Issue D1 (2019).
Vitte et al., "Is there a predictable relationship between surface physical-chemical properties and cell behaviour at the interface?", European Cells and Materials, pp. 52-63, vol. 7 (2004).
Vivero-Escoto et al., "Mesoporous silica nanoparticles for intracellular controlled drug delivery", Small, pp. 1952-1967, vol. 6, Issue 18 (2010).
Vogel et al., "BNT162b vaccines protect rhesus macaques from SARS-CoV-2", Nature, vol. 592(7853), pp. 283-289 (Feb. 2021).
Volpatti et al., "Polymersomes decorated with the SARS-CoV-2 spike protein receptor-binding domain elicit robust humoral and cellular immunity", ACS Central Science, vol. 7(8), pp. 1368-1380 (Jul. 2021).
Von Haartman et al., "On the intracellular release mechanism of hydrophobic cargo and its relationto the biodegradation behavior of mesoporous silica nanocarriers", European Journal of Pharmaceutical Sciences, pp. 17-27, vol. 95 (2016).
Von Moos et al., "Oxidative stress induced by inorganic nanoparticles in bacteria and aquatic microalgae-state of the art and knowledge gaps", Nanotoxicology, vol. 8(6), pp. 605-630 (2014).
Voss et al., "Prevalent, protective, and convergent IgG recognition of SARS-CoV-2 non-RBD spike epitopes", Science, pp. 1108-1112, vol. 372, No. 6546 (2021).
Vrieze, J. "Suspicions grow that nanoparticles in Pfizer's COVID-19 vaccine trigger rare allergic reactions", Science (Dec. 2020).
Vu et al., "Current and future nanoparticle vaccines for COVID-19", EBioMedicine, vol. 74, 103699 (Nov. 2021).
Vuorinen et al., "Modelling aerosol transport and virus exposure with numerical simulations in relation to SARS-CoV-2 transmission by inhalation indoors", Safety Science, pp. 1-23, vol. 130 (2020).
Wagner et al., The emerging nanomedicine landscape, Nature Biotechnology, pp. 1211-1217, vol. 24 (2006).
Walker et al., "A 21st century paradigm for evaluating the health hazards of nanoscale materials?", Toxicol. Sci., vol. 110(2), pp. 251-254 (2009).
Wallis et al., "Host-directed immunotherapy of viral and bacterial infections: past, present and future", Nature Reviews Immunology, vol. 23(2), pp. 121-133 (Jun. 2023).
Walls et al., "Elicitation of broadly protective sarbecovirus immunity by receptor-binding domain nanoparticle vaccines", Cell, vol. 184(21), pp. 5432-5447 (Sep. 2021).
Walls et al., "Elicitation of potent neutralizing antibody responses by designed protein nanoparticle vaccines for SARS-CoV-2", Cell, pp. 1367-1382, vol. 183, Issue 5 (2020).
Waltz, E. "China and India approve nasal COVID vaccines", Nature, vol. 609(7927), 450 (Sep. 2022).
Wan et al., "On the Controllable Soft-Templating Approach to Mesoporous Silicates", Chemical Reviews, pp. 2821-2860, vol. 107, No. 7 (2007).
Wan et al., "Receptor Recognition by the Novel Coronavirus from Wuhan: an Analysis Based on Decade-Long Structural Studies of SARS Coronavirus", Journal of Virology, pp. 1-9, vol. 94, No. 7 (2020).
Wang et al., "A SARS-CoV-2 and influenza double hit vaccine based on RBD-conjugated inactivated influenza A virus", Science Advances, vol. 9(25), eabo4100 (Jun. 2023).
Wang et al., "Acetalated dextran based nano-and microparticles: synthesis, fabrication, and therapeutic applications", Chemical Communications, vol. 57(35), pp. 4212-4229 (May 2021).
Wang et al., "Bivalent mRNA vaccines against three SARS-CoV-2 variants mediated by new ionizable lipid nanoparticles", International Journal of Pharmaceutics, vol. 642, 123155 (Jul. 2023).
Wang et al., "Characterization of physicochemical properties of nanomaterials and their immediate environments in high-throughput screening of nanomaterial biological activity", Wiley Interdiscip. Rev. Nanomed. Nanobiotechnol., vol. 5(5), pp. 430-448 (2013).
Wang et al., "Discovery of potential small molecular SARS-CoV-2 entry blockers targeting the spike protein", Acta Pharmacologica Sinica, vol. 43(4), pp. 788-796 (Aug. 2022).
Wang et al., "Exosomes decorated with a recombinant SARS-CoV-2 receptor-binding domain as an inhalable COVID-19 vaccine", Nature Biomedical Engineering, vol. 6(7), pp. 791-805 (Jul. 2022).
Wang et al., "Ferritin nanoparticle-based SARS-CoV-2 RBD vaccine induces a persistent antibody response and long-term memory in mice", Cellular & Molecular Immunology, vol. 18(3), pp. 749-751 (Feb. 2021).
Wang et al., "Intracellular delivery of budesonide and polydopamine Co-loaded in endosomolytic poly (butyl methacrylate-co-methacrylic acid) grafted acetalated dextran for macrophage phenotype switch from M1 to M2", Advanced Therapeutics, vol. 4(1), 2000058 (Jan. 2021).
Wang et al., "Manufacturing Techniques and Surface Engineering of Polymer Based nanoparticles for Targeted Drug Delivery to Cancer", Nanomaterials, pp. 1-18, vol. 6, No. 2 ((Feb. 2016).
Wang et al., "Membrane nanoparticles derived from ACE2-rich cells block SARS-CoV-2 infection", ACS Nano, vol. 15(4), pp. 6340-6351 (Oct. 2021).
Wang et al., "Nanotechnology-facilitated vaccine development during the coronavirus disease 2019 (COVID-19) pandemic", In Exploration, vol. 2, No. 5, 20210082 (Jul. 2022).
Wang et al., "Preparation of selective organ-targeting (SORT) lipid nanoparticles (LNPs) using multiple technical methods for tissue-specific mRNA delivery", Nature Protocols, vol. 18(1), pp. 265-291 (Oct. 2023).
Wang et al., "Resistive-pulse measurements with nanopipettes: detection of Au nanoparticles and nanoparticle-bound anti-peanut IgY", Chemical Science, vol. 4(2), pp. 655-663 (2013).
Wang et al., "Skin vaccination with dissolvable microneedle patches incorporating influenza neuraminidase and flagellin protein nanoparticles

(56) References Cited

OTHER PUBLICATIONS induces broad immune protection against multiple influenza viruses", ACS Applied Bio Materials, vol. 4(6), pp. 4953-4961 (May 2021).
Wang et al., "Structural and functional basis of SARS-CoV-2 entry by using human ACE2", Cell, vol. 181(4), pp. 894-904 (Apr. 2020).
Wang et al., "Superfast and controllable microfluidic inking of anti-inflammatory melanin-like nanoparticles inspired by cephalopods", Materials Horizons, vol. 7(6), pp. 1573-1580 (Jun. 2020).
Wang et al., "Systematic in vitro nanotoxicity study on anodic alumina nanotubes with engineered aspect ratio: Understanding nanotoxicity by a nanomaterial model", Biomaterials, vol. 46, pp. 117-130 (2015).
Wang et al., "Systemic antiviral immunization by virus-mimicking nanoparticles-decorated erythrocytes", Nano Today, vol. 40, 101280 (Oct. 2021).
Wang et al., "The crystallinity and aspect ratio of cellulose nanomaterials determine their pro-inflammatory and immune adjuvant effects in vitro and in vivo", Small, vol. 15(42), 1901642 (2019).
Wang et al., "A human monoclonal antibody blocking SARS-CoV-2 infection", Nature Communications, pp. 1-6, vol. 11, Article No. 2251 (2020).
Wang et al., "ACE2 can act as the secondary receptor in the FcγR-dependent ADE of SARS-CoV-2 infection", iScience, pp. 1-20, vol. 25, Issue 1 (2022).
Wang et al., "Akt-mediated eminent expression of c-FLIP and Mcl-1 confers acquired resistance to TRAIL-induced cytotoxicity to lung cancer cells", Molecular Cancer Therapeutics, pp. 1156-1163, vol. 7, No. 5 (2008).
Wang et al., "Cetuximab-Modified Mesoporous Silica Nano-Medicine Specifically Targets EGFR-Mutant Lung Cancer and Overcomes Drug Resistance", Scientific Reports, pp. 1-10, vol. 6, Article No. 25468 (2016).
Wang et al., "Dalbavancin binds ACE2 to block its interaction with SARS-CoV-2 spike protein and is effective in inhibiting SARS-CoV-2 infection in animal models", Cell Research, pp. 17-24, vol. 31 (2020).
Wang et al., "Diverse functional autoantibodies in patients with COVID-19", Nature, pp. 283-288, vol. 595 (2021).
Wang et al., "Functional differences among the spike glycoproteins of multiple emerging severe acute respiratory syndrome coronavirus 2 variants of concern", iScience, pp. 1-22, vol. 24, No. 11 (2021).
Wang et al., "Microfabricated electrochemical cell-based biosensors for analysis of living cells in vitro", Biosensors, pp. 127-170, vol. 2 (2012).
Wang et al., "Multi-organ distant metastases confer worse disease-specific survival in differentiated thyroid cancer", Thyroid, pp. 1594-1599, vol. 24, No. 11 (2014).
Wang et al., "Thiol adsorption on and reduction of copper oxide particles and surfaces", Langmuir, pp. 3848-3857, vol. 32 (2016).
Wang, "Ordered Mesoporous Materials for Drug Delivery", Microporous and Mesoporous Materials, pp. 1-9, vol. 117, Issues 1-2 (2009).
Wannasarit et al., "A virus-mimicking pH-responsive Acetalated dextran-based membrane-active polymeric nanoparticle for intracellular delivery of antitumor therapeutics", Advanced Functional Materials, vol. 29(51), 1905352 (2019).
Watanabe et al., "Site-specific analysis of the SARS-CoV-2 glycan shield", bioRxiv, pp. 1-20 (2020).
Watkins, "Preventing a covid-19 pandemic", BMJ, pp. 1-2 (2020).
Weber et al., "Solid lipid nanoparticles (SLN) and nanostructured lipid carriers (NLC) for pulmonary application: a review of the state of the art", European Journal of Pharmaceutics and Biopharmaceutics, vol. 86(1), pp. 7-22 (2014).
Weber et al., "Structural origins of high-affinity biotin binding to streptavidin", Science, vol. 243(4887), pp. 85-88 (1989).
Weber et al., "Expression of functional folate receptors by human parathyroid cells", Surgery, pp. 1385-1393, vol. 154, Issue 6 (2013).
Wei et al., "Host-directed therapy, an untapped opportunity for antimalarial intervention", Cell Reports Medicine, vol. 2(10) (Oct. 2021).
Wei et al., "Microfluidics Fabrication of Micrometer-Sized Hydrogels with Precisely Controlled Geometries for Biomedical Applications", Advanced Healthcare Materials, vol. 11(16), 2200846 (Jun. 2022).
Wei et al., "HDL-scavenger receptor B type 1 facilitates SARS-CoV-2 entry", Nature Metabolism, pp. 1391-1400, vol. 2 (2020).
Wei et al., "Pharmacological disruption of mSWI/SNF complex activity restricts SARS-CoV-2 infection", Nat. Genet., vol. 55(3), pp. 471-483 (Mar. 2023).
Weibel et al., "Mechanism of Zn Particle Oxidation by H2O and CO2 in the Presence of ZnO", Chemistry of Materials, pp. 6486-6495, vol. 26 (2014).
Weidenbacher et al., "A ferritin-based COVID-19 nanoparticle vaccine that elicits robust, durable, broad-spectrum neutralizing antisera in non-human primates", Nature Communications, vol. 14(1), 2149 (Apr. 2023).
Weinstain et al., "Real-time monitoring of drug release", Chemical Communications, vol. 46(4), pp. 553-555 (2010).
Weiskopf et al., "Phenotype of SARS-CoV-2-specific T-cells in COVID-19 patients with acute respiratory distress syndrome", medRxiv, pp. 1-29 (2020).
Weiss et al., "Toward Nanotechnology-Enabled Approaches against the COVID-19 Pandemic", ACS Nano, pp. 6383-6406, vol. 14 (2020).
Wenzlik et al., "Preparation of cholesteric particles from cellulose derivatives in a microfluidic setup", Soft Matter, vol. 7(6), pp. 2340-2344 (2011).
Westerheide et al., "Celastrols as Inducers of the Heat Chock Response and Cytoprotection", Journal of Biological Chemistry, vol. 279, No. 53, pp. 56053-56060 (2004).
Westerheide et al., "Stress-inducible regulation of heat shock factor 1 by the deacetylase SIRT1", Science, pp. 1063-1066, vol. 323, Issue 5917 (2009).
Whisenant et al., "Blocking Coronavirus 19 Infection via the SARS-CoV-2 Spike Protein: Initial Steps", ACS Medicinal Chemistry Letters, pp. 1076-1078, vol. 11 (2020).
Whitaker et al., "Variant-specific symptoms of COVID-19 in a study of 1,542,510 adults in England", Nature Communications, vol. 13(1), 6856 (Nov. 2022).
Whitehouse, "Handbook of Surface and Nanometrology", Taylor & Francis, Institute of Physics Publishing Bristol and Philadelphia, 1st edition, in 1128 pages, [1st upload of 2 uploads (663 pages)] (2002).
Whitehouse, "Handbook of Surface and Nanometrology", Taylor & Francis, Institute of Physics Publishing Bristol and Philadelphia, 1st edition, in 1128 pages, [2nd upload of 2 uploads (465 pages)] (2002).
Whitehouse, "Handbook of Surface and Nanometrology", Second Edition, CRC Press, in 978 pages (2011).
Whitehouse, "Handbook of Surface and Nanometrology (second edition)", CRC Press, Coventry, UK (2011).
Whitesides, "The origins and the future of microfluidics", Nature, vol. 442, pp. 368-373 (2006).
Wicki et al., "Nanomedicine in cancer therapy: challenges, opportunities, and clinical applications", Journal of Controlled Release, pp. 138-157, vol. 200 (2015).
Widge et al., "An influenza hemagglutinin stem nanoparticle vaccine induces cross-group 1 neutralizing antibodies in healthy adults", Science Translational Medicine, vol. 15(692), eade4790 (Apr. 2023).
Wilbrandt, "The significance of the structure of a membrane for its selective permeability", Journal of General Physiology, pp. 933-965, vol. 18, No. 6 (1935).
Willett et al., "SARS-CoV-2 Omicron is an immune escape variant with an altered cell entry pathway", Nature Microbiology, vol. 7(8), pp. 1161-1179 (Jul. 2022).
Williams, "The Williams Dictionary of Biomaterials" (1999).
Willyard, "Coronavirus Blood-Clot Mystery Intensifies", Nature, p. 250, vol. 581 (May 21, 2020).
Wilson et al., "Transforming early pharmaceutical assessment of genotoxicity: applying statistical learning to a high throughput, multi end point in vitro micronucleus assay", Sci. Rep., vol. 11(1), 2535 (Jan. 2021).

(56) References Cited

OTHER PUBLICATIONS

Winfree et al., "Quantitative large-scale three-dimensional imaging of human kidney biopsies: a bridge to precision medicine in kidney disease", Nephron, vol. 140(2), pp. 134-139 (2018).
Winfree et al., "Quantitative three-dimensional tissue cytometry to study kidney tissue and resident immune cells", Journal of the American Society of Nephrology (JASN), vol. 28(7), 2108 (2017).
Wischke, "Concepts for efficient preparation of particulate polymer carrier systems by droplet-based microfluidics", International Journal of Pharmaceutics, vol. 584, 119401 (Jun. 2020).
Witzigmann et al., "Optimization-by-design of hepatotropic lipid nanoparticles targeting the sodium-taurocholate cotransporting polypeptide", Elife, vol. 8, e42276 (2019).
Wong et al., "Direct force measurements of the streptavidin-biotin interaction", Biomolecular Engineering, vol. 16(1-4), pp. 45-55 (2019).
Wong et al., "DNA vaccination against respiratory influenza virus infection", Vaccine, vol. 19(17-19), pp. 2461-2467 (2001).
Wong et al., "Mechanisms of drug release in nanotherapeutic delivery systems", Chemical Reviews, vol. 115(9), pp. 3388-3432 (2015).
Wong et al., "Mechanisms and implications of dual-acting methotrexate in folate-targeted nanotherapeutic delivery", International Journal of Molecular Sciences, pp. 1772-1790, vol. 16 (2015).
Woods et al., "In vivo biocompatibility, clearance, and biodistribution of albumin vehicles for pulmonary drug delivery", Journal of Controlled Release, vol. 210, pp. 1-9 (2015).
World Health Organization, "Mental health and psychosocial considerations during the COVID-19 outbreak", WHO Ref No. WHO/2019-nCoV/MentalHealth/2020.1 (Mar. 2020).
Wu et al., "Direct and indirect genotoxicity of graphene family nanomaterials on DNA—A review", Nanomaterials (Basel), vol. 11(11), 2889 (Oct. 2021).
Wu et al., "Engineering soluble monomeric streptavidin with reversible biotin binding capability", Journal of Biological Chemistry, vol. 280(24), pp. 23225-23231 (2005).
Wu et al., "Enhanced prevention of breast tumor metastasis by nanoparticle-delivered vitamin E in combination with interferon-gamma", Advanced Healthcare Materials, vol. 9(6), 1901706 (Feb. 2020).
Wu et al., "A new coronavirus associated with human respiratory disease in China", Nature, pp. 265-269, vol. 579 (2020).
Wu et al., "Effect of surface roughness on the initial response of MC3T3-E1 cells cultured on polished titanium alloy", Bio-medical Materials and Engineering, pp. 155-164, vol. 26 (2015).
Wu et al., "Paper as a scaffold for cell cultures: Teaching an old material new tricks", MRS Communications, pp. 1-14, vol. 8, No. 1 (2018).
Wu, "Progress and concept for COVID-19 vaccine development", Biotechnology Journal, vol. 15(6) (Apr. 2020).
Wuertz et al., "A SARS-CoV-2 spike ferritin nanoparticle vaccine protects hamsters against Alpha and Beta virus variant challenge", NPJ Vaccines, vol. 6(1), 129 (Oct. 2021).
Wut et al., "Crisis management research (1985-2020) in the hospitality and tourism industry: A review and research agenda", Tourism Management, p. 104307, vol. 85 (2021).
Xia et al., "A bioengineered pseudovirus nanoparticle displaying SARS-CoV 2 RBD fully protects micefrom mortality and weight loss caused by SARS-CoV 2 challenge", Biotechnology Journal, vol. 18(10), Art. 2300130 (Jun. 2023).
Xia et al., "Bioengineered pseudovirus nanoparticles displaying the HA1 antigens of influenza viruses for enhanced immunogenicity", Nano Research, vol. 15(5), pp. 4181-4190 (Jan. 2022).
Xia et al., "A streptavidin linker layer that functions after drying", Langmuir, vol. 20(9), pp. 3710-3716 (2004).
Xiao et al., "A dual-responsive mesoporous silica nanoparticle for tumor-triggered targeting drug delivery", Small, pp. 591-598, vol. 10, Issue 3 (2014).
Xiao, "CuS nanoparticles: clinically favorable materials for photothermal applications?", Nanomedicine, pp. 373-375, vol. 9, No. 3 (2014).
Xie et al., "Effect of PLGA as a polymeric emulsifier on preparation of hydrophilic protein-loaded solid lipid nanoparticles", Colloids and Surfaces B: Biointerfaces, vol. 67(2), pp. 199-204 (2008).
Xie et al., "Copper sulfide nanocrystals with tunable composition by reduction of covellite nanocrystals with Cu+ ions", Journal of the American Chemical Society, pp. 17630-17637, vol. 135 (2013).
Xie et al., "Nanoparticle-based theranostic agents", Advanced Drug Delivery Review, pp. 1064-1079, vol. 62, No. 11 (2010).
Xie et al., "Nanoscale transformations in covellite (CuS) nanocrystals in the presence of divalent metal cations in a mild reducing environment", Chemistry of Materials, pp. 7531-7537, vol. 27 (2015).
Xie, "A novel Monte Carlo simulation procedure for modelling COVID-19 spread over time", Scientific Reports, pp. 1-9, vol. 10, Article 13120 (2020).
Xing et al., "Comparison of three quantification methods for the TZM-bl pseudovirus assay for screening of anti-HIV-1 agents", Journal of Virological Methods, vol. 233, pp. 56-61 (2016).
Xiong et al., "Cytotoxicity of metal-based nanoparticles: from mechanisms and methods of evaluation to pathological manifestations", Adv. Sci., vol. 9(16), 2106049 (Mar. 2022).
Xiong et al., "Robust neutralization assay based on SARS-CoV-2 S-protein-bearing vesicularstomatitis virus (VSV) pseudovirus and ACE2-overexpressing BHK21 cells", Emerging Microbes & Infections, vol. 9(1), pp. 2105-2113 (Dec. 2020).
Xu et al., "Dual-targeting cyclic peptides of receptor-binding domain (RBD) and main protease (Mpro)as potential drug leads for the treatment of SARS-CoV-2 infection", Frontiers in Pharmacology, vol. 13, 1041331 (Oct. 2022).
Xu et al., "Generation of monodisperse particles by using microfluidics: control over size, shape, and composition", Angewandte Chemie, vol. 117(5), pp. 734-738 (2005).
Xu et al., "Microfluidic controllable synthesis of monodispersed sulfur nanoparticles with enhanced antibacterial activities", Chemical Engineering Journal, vol. 398, 125293 (Oct. 2020).
Xu et al., "Nanotechnology for the management of COVID-19 during the pandemic and in the post-pandemic era", National Science Review, vol. 9(10), nwac124 (Jun. 2022).
Xu et al., "Nanotechnology-based delivery of CRISPR/Cas9 for cancer treatment", Adv. Drug Delivery Rev., vol. 176, 113891 (Sep. 2021).
Xu et al., "Preparation of monodisperse biodegradable polymer microparticles using a microfluidic flow-focusing device for controlled drug delivery", Small, vol. 5(13), pp. 1575-1581 (2009).
Xu et al., "Transmission routes of Covid-19 virus in the Diamond Princess Cruise ship", medRxiv Apr. 9, 2020,.20059113; doi: https://doi.org/10.1101/2020.04.09.20059113.
Xu et al., "Fabrication of nanoperforated ultrathin TiO2 films by inkjet printing", Journal Materials Research, pp. 2151-2160, vol. 30, No. 14 (2015).
Xu et al., "Nanobodies from camelid mice and llamas neutralize SARS-CoV-2 variants", Nature, pp. 278-282, vol. 595 (2021).
Xu et al., "The ACE2/Angiotensin-(1-7)/Mas Receptor Axis: Pleiotropic Roles in Cancer", Frontiers in Physiology, pp. 1-8, vol. 8, Article 276 (2017).
Xu, et al., "Lessons and suggestions to travelers and cruise ships in the fight against COVID-19", QJM: An International Journal of Medicine, pp. 153-154, vol. 114, Issue 2 (2020).
Yadavali et al., "Silicon and glass very large scale microfluidic droplet integration for terascale generation of polymer microparticles", Nature Communications, vol. 9(1), 1222 (2018).
Yaghmur et al., "Recent advances in drug delivery applications of cubosomes, hexosomes, and solid lipid nanoparticles", Acta Pharmaceutica Sinica B, vol. 11(4), pp. 871-885 (Apr. 2021).
Yamagishi et al., "Descriptive study of COVID-19 outbreak among passengers and crew on Diamond Princess cruise ship, Yokohama Port, Japan, Jan. 20 to Feb. 9, 2020", Euro Surveillance, pp. 1-8, vol. 25, No. 23 (2020).
Yamahata et al., "Preparation for Quarantine on the Cruise Ship Diamond Princess in Japan due to COVID-19", JMIR Public Health and Surveillance, e18821, in 8 pages, vol. 6, No. 2 (2020).
Yamamoto et al., "The anticoagulant nafamostat potently inhibits SARS-CoV-2 S protein-mediated fusion in a cell fusion assay

(56) References Cited

OTHER PUBLICATIONS system and viral infection in vitro in a cell-type-dependent manner", Viruses, vol. 12(6), 629 (Jun. 2020).
Yamashiro et al., A case of water intoxication with prolonged hyponatremia caused by excessive water drinking and secondary SIADH:, Case Reports in Nephrology and Urology, pp. 147-152, vol. 3, No. 2 (2013).
Yan et al., "A SARS-CoV-2 nanoparticle vaccine based on chemical conjugation of loxoribine and SpyCatcher/SpyTag", International Journal of Biological Macromolecules, vol. 253, Part 5, 127159 (Dec. 2023).
Yan et al., "COVID-19 vaccines: a review of the safety and efficacy of current clinical trials", Pharmaceuticals, vol. 14(5), 406 (Apr. 2021).
Yan et al., "Microfluidic strategy for coating and modification of polymer-bonded nano-HNS explosives", Chemical Engineering Journal, vol. 428, 131096 (Jan. 2022).
Yan et al., "Targeted cancer therapies", Chinese Journal of Cancer, pp. 1-4, vol. 30, No. 1 (2011).
Yang et al., "Safety and immunogenicity of a recombinant tandem-repeat dimeric RBD-based protein subunit vaccine (ZF2001) against COVID-19 in adults: two randomised, double-blind, placebo-controlled, phase 1 and 2 trials", The Lancet Infectious Diseases, vol. 21(8), pp. 1107-1119 (Aug. 2021).
Yang et al., "A microfluidic method to synthesize transferrin-lipid nanoparticles loaded with siRNA LOR-1284 for therapy of acute myeloid leukemia", Nanoscale, vol. 6(16), pp. 9742-9751 (2014).
Yang et al., "A vaccine targeting the RBD of the S protein of SARS-CoV-2 induces protective immunity", Nature, vol. 586, pp. 572-577 (Jul. 2020).
Yang et al., "An optimized and robust SARS-CoV-2 pseudovirus system for viral entry research", Journal of Virological Methods, vol. 295, 114221 (Sep. 2021).
Yang et al., "Cationic nanoparticles directly bind angiotensin-converting enzyme 2 and induce acutelung injury in mice", Particle and Fibre Toxicology, Biomed central, London, p. 4, vol. 12, No. 1 (Mar. 7, 2015).
Yang et al., "Fabricated technology of biomedical micro-nano hydrogel", Biomedical Technology, vol. 2, pp. 31-48 (Jun. 2023).
Yang et al., "Ice-inspired lubricated drug delivery particles from microfluidic electrospray for osteoarthritis treatment", ACS Nano, vol. 15(12), pp. 20600-20606 (Dec. 2021).
Yang et al., "Macrophages participate in local and systemic inflammation induced by amorphous silica nanoparticles through intratracheal instillation", International Journal of Nanomedicine, vol. 11, pp. 6217-6228 (2016).
Yang et al., "Molecular interaction and inhibition of SARS-CoV-2 binding to the ACE2 receptor", Nature Communications, vol. 11(1), 4541 (Sep. 2020).
Yang et al., "PLGA porous microspheres dry powders for codelivery of afatinib-loaded solid lipidnanoparticles and paclitaxel: novel therapy for EGFR tyrosine kinase inhibitors resistant nonsmall cell lung cancer", Advanced Healthcare Materials, vol. 8(23), 1900965, (Oct. 2019).
Yang et al., "SCORe: SARS-CoV-2 Omicron Variant RBD-Binding DNA Aptamer for Multiplexed Rapid Detection and Pseudovirus Neutralization", Analytical Chemistry, vol. 94(37), pp. 12683-12690 (Aug. 2022).
Yang et al., "Tumor microenvironment-responsive dual drug dimer-loaded pegylated bilirubin nanoparticles for improved drug delivery and enhanced immune-chemotherapy of breast cancer", Advanced Functional Materials, vol. 29(32), 1901896 (2019).
Yang et al., "Angiotensin II Receptor Blockers and Angiotensin-Converting Enzyme Inhibitors Usage is Associated with Improved Inflammatory Status and Clinical Outcomes in COVID-19 Patients With Hypertension", medRxiv, (2020).
Yang et al., "Angiotensin-converting enzyme 2 (ACE2) mediates influenza H7N9 virus-induced acute lung injury", Scientific Reports, p. 1, vol. 4 (2014).
Yang et al., "Molecular interaction and inhibition of SARS-CoV-2 binding to the ACE2 receptor", Nature Communications, pp. 1-10 (2020).
Yang et al., "Non-invasive administration of AAV to target lung parenchymal cells and develop SARS-CoV-2-susceptible mice", Molecular Therapy, pp. 1994-2004, vol. 30, Issue 5 (2022).
Yang et al., "Structural basis for clonal diversity of the human T-cell response to a dominant influenza virus epitope", Journal of Biological Chemistry, pp. 18618-18627, vol. 292, Issue 45 (2017).
Yao et al., "Human H-ferritin presenting RBM of spike glycoprotein as potential vaccine of SARS-CoV-2", bioRxiv, 05.25 15618; doi: https://doi.org/10.1101/2020.05.25.115618 (2020).
Yasamineh et al., "An overview on nanoparticle-based strategies to fight viral infections with a focus on COVID-19", Journal of Nanobiotechnology, vol. 20(440) (Oct. 2022).
Ye et al., "Biotinylation of TiO2 nanoparticles and their conjugation with streptavidin", Langmuir, vol. 23(10), pp. 5630-5637 (2007).
Ye et al., "Cryo-EM structure of a SARS-CoV-2 omicron spike protein ectodomain", Nature Communications, vol. 13(1), 1214 (Mar. 2022).
Yeh et al., "Novel protein-loaded chondroitin sulfate-chitosan nanoparticles: Preparation and characterization", Acta Biomaterialia, vol. 7(10), pp. 3804-3812 (2011).
Yeh et al., "Requirement for Casper (c-FLIP) in regulation of death receptor-induced apoptosis and embryonic development", Immunity, pp. 633-642, vol. 12, Issue 6 (2000).
Yi et al., "Jigsaw puzzle of SARS-CoV-2 RBD evolution and immune escape", Cellular & Molecular Immunology, vol. 19, pp. 848-851 (Jun. 2022).
Yin et al., "Co-delivery of doxorubicin and interferon-γ by thermosensitive nanoparticles for cancer immunochemotherapy", Molecular Pharmaceutics, vol. 15(9), pp. 4161-4172 (2018).
Yin et al., "Effects of aspect ratio (AR) and specific surface area (SSA) on cytotoxicity and phototoxicity of ZnO nanomaterials", Chemosphere, vol. 124, pp. 116-121 (2015).
Yin et al., "The effects of particle size and surface coating on the cytotoxicity of nickel ferrite", Biomaterials, vol. 26(29), pp. 5818-5826 (2005).
Ying et al., "A high throughput methodology for continuous preparation of monodispersed nanocrystals in microfluidic reactors", Chemical Engineering Journal, vol. 135(3), pp. 209-215 (2008).
Ylösmäki et al., "Novel personalized cancer vaccine platform based on Bacillus Calmette-Guèrin", Journal for Immunotherapy of Cancer, e002707, pp. 1-13, vol. 9, No. 7 (2021).
Yogev et al., "Genome wide screen of RNAi molecules against SARS-CoV-2 creates a broadly potent prophylaxis", bioRxiv. 488010; doi: https://doi.org/10.1101/2022.04.12.488010 (Posted Apr. 12, 2022).
You et al., "Streptavidin-coated Au nanoparticles coupled with biotinylated antibody-based bifunctionallinkers as plasmon-enhanced immunobiosensors", ACS Applied Nano Materials, vol. 3(2), pp. 1900-1909 (Jan. 2020).
Younis et al., "Ultra-small lipid nanoparticles encapsulating sorafenib and midkine-siRNA selectively-eradicate sorafenib-resistant hepatocellular carcinoma in vivo", Journal of Controlled Release, vol. 331, pp. 335-349 (Mar. 2021).
Yu et al., "Ad26.COV2.S and SARS-CoV-2 spike protein ferritin nanoparticle vaccine protect againstSARS-CoV-2 Omicron BA. 5 challenge in macaques", Cell Reports Medicine, vol. 4(4), 101018 (Mar. 2023).
Yu et al., "Deletion of the SARS-CoV-2 spike cytoplasmic tail increases infectivity in pseudovirus neutralization assays", Journal of Virology, vol. 95(11) (May 2021).
Yu et al., "Optimization of inhalable liposomal powder formulations and evaluation of their in vitro drug delivery behavior in Calu-3 human lung epithelial cells", International Journal of Pharmaceutics, vol. 586, 119570 (Jun. 2020).
Yu et al., "Design of Nanoparticle-Based Carriers for Targeted Drug Delivery", Journal of Nanomaterials, pp. 1-15, vol. 2016 (2016).
Yu et al., "Inhaled budesonide for COVID-19 in people at high risk of complications in the community inthe UK (Principle): a randomised, controlled, open-label, adaptive platform trial", The Lancet, pp. 843-855, vol. 398, Issue 10303 (2021).

(56) References Cited

OTHER PUBLICATIONS

Yu et al., "Inkjet printed surface enhanced Raman spectroscopy array on cellulose paper" Analytical Chemistry, pp. 9626-9630, vol. 82, No. 23 (2010).
Yu, et al., "Auger parameters for sulfur-containing compounds using a mixed aluminum-silver excitation source", Journal of Electron Spectroscopy Related Phenomena, pp. 159-166, vol. 50, Issue 2 (1990).
Yuan et al., "A bivalent nanoparticle vaccine exhibits potent cross-protection against the variants of SARS-CoV-2", Cell Reports, vol. 38(3) (Dec. 2021).
Yuan et al., "Antitumor activity of tripterine via cell-penetrating peptide-coated nanostructured lipidcarriers in a prostate cancer model", International Journal of Nanomedicine, pp. 4339-4350, vol. 8, Issue 1 (2013).
Yuan et al., "Mechanistic study of the covalent loading of paclitaxel via disulfide linkers for controlled drug release", Langmuir, pp. 734-743, vol. 29, No. 2 (2013).
Yue et al., "Surface Charge Affects Cellular Uptake and Intracellular Trafficking of Chitosan-Based Nanoparticles", Biomacromolecules, pp. 2440-2446, vol. 12, No. 7 (2011).
Zahradník et al., "SARS-CoV-2 variant prediction and antiviral drug design are enabled by RBD in vitro evolution", Nature Microbiology, vol. 6(9), pp. 1188-1198 (Aug. 2021).
Zambaux et al., "Preparation and characterization of protein C-loaded PLA nanoparticles", Journal of Controlled Release, vol. 60(2-3), pp. 179-188 (1999).
Zeisser-Labouèbe et al., "Screening of nanoparticulate delivery systems for the photodetection of cancer in a simple and cost-effective model", Nanomedicine (Lond), pp. 135-143, vol. 4, No. 2 (2009).
Zeng et al., "Scalable production of therapeutic protein nanoparticles using flash nanoprecipitation", Advanced Healthcare Materials, vol. 8(6), 1801010 (2019).
Zeng et al., "Hypertension in patients hospitalized with COVID-19 in Wuhan, China: A single-center retrospective observational study", medRxiv, pp. 1-31 (2020).
Zenker et al., "The coronavirus pandemic—A critical discussion of a tourism research agenda", Tourism Management, p. 104164, vol. 81 (2020).
Zha et al., "Development of a vaccine against SARS-CoV-2 based on the receptor-binding domain displayed on virus-like particles", Vaccines (Basel), vol. 9, 395 (Apr. 2021).
Zhai et al., "Comparison of severe acute respiratory syndrome coronavirus 2 spike protein binding to ACE2 receptors from human, pets, farm animals, and putative intermediate hosts", J. Virol., vol. 94(15), 00831-20 (Jul. 2020).
Zhai et al., "Lipid-PEG conjugates sterically stabilize and reduce the toxicity of phytantriol-based lyotropic liquid crystalline nanoparticles", Langmuir, vol. 31(39), pp. 10871-10880 (2015).
Zhang et al., "A nanomaterial targeting the spike protein captures SARS-CoV-2 variants and promotes viral elimination", Nature Nanotechnology, vol. 17(9), pp. 993-1003 (Aug. 2022).
Zhang et al., "A thermostable mRNA vaccine against COVID-19", Cell, vol. 182(5), pp. 1271-1283 (Jul. 2020).
Zhang et al., "Carboxymethyl chitosan nanoparticles loaded with Ctenopharyngodon idella interferon-γ2 (CiIFN-γ2) enhance protective efficacy against bacterial infection in grass carp", Aquaculture, vol. 572, 739554 (Jul. 2023).
Zhang et al., "Continuous, safe and large-scale preparation of insensitive high-energy TATB/HMX composite particles by microfluidic self-assembly technology", Chemical Engineering Science, vol. 264, 118160 (Dec. 2022).
Zhang et al., "Controlled Interfacial Polymer Self-Assembly Coordinates Ultrahigh Drug Loading and Zero-Order Release in Particles Prepared under Continuous Flow", Advanced Materials, vol. 35, 2211254 (Feb. 2023).
Zhang et al., "Development of Peptide and Protein Microparticles for Diabetes Therapy: From Fabrication to In Vivo Evaluation", Doctoral Thesis, University of Helsinki (Helsingin yliopisto), http://hdl.handle.net/10138/347105 (Aug. 2022).
Zhang et al., "Effect of different adjuvants on immune responses elicited by protein-based subunit vaccines against SARS-CoV-2 and its delta variant", Viruses, vol. 14(3), 501 (Feb. 2022).
Zhang et al., "Effect of size, shape, and surface modification on cytotoxicity of gold nanoparticles to human HEp-2 and canine MDCK cells", J. Nanomater., vol. 2012, 375496 (2012).
Zhang et al., "Enhanced immunogenicity induced by mRNA vaccines with various lipid nanoparticlesas carriers for SARS-CoV-2 infection", Journal of Materials Chemistry B, vol. 11(31), pp. 7454-7465 (Jul. 2023).
Zhang et al., "Fabrication of a multifunctional nano-in-micro drug delivery platform by microfluidic templated encapsulation of porous silicon in polymer matrix", Advanced Materials, vol. 26(26), pp. 4497-4503 (2014).
Zhang et al., "Host-Directed Virus-Mimicking Particles Interacting with the ACE2 Receptor Competitively Block Coronavirus SARS-CoV-2 Entry", Nano Letters, vol. 24 (2024).
Zhang et al., "Improvement of a SARS-CoV-2 vaccine by enhancing the conjugation efficiency of theimmunogen to self-assembled nanoparticles", Cellular & Molecular Immunology, vol. 18(8), pp. 2042-2044 (Jul. 2021).
Zhang et al., "Inhibiting phase transfer of protein nanoparticles by surface camouflage—A versatile and efficient protein encapsulation strategy", Nano Letters, vol. 21(22), pp. 9458-9467 (Nov. 2021).
Zhang et al., "Inhibition of Pathogen Adhesion by Bacterial Outer Membrane-Coated Nanoparticles". Angewandte Chenie International Edition, pp. 11404-11408, vol. 58, Issue 33 (Aug. 12, 2019).
Zhang et al., "Mechanism of a COVID-19 nanoparticle vaccine candidate that elicits a broadly neutralizing antibody response to SARS-CoV-2 variants", Science Advances, vol. 7(43), eabj3107 (Oct. 2021).
Zhang et al., "Microfluidic encapsulation of prickly Zinc-Doped copper oxide nanoparticles with VD1142 modified spermine acetalated dextran for efficient cancer therapy", Advanced Healthcare Materials, vol. 6(11), 1601406 (2017).
Zhang et al., "Microfluidic synthesis of hybrid nanoparticles with controlled lipid layers: understanding flexibility-regulated cell-nanoparticle interaction", ACS Nano, vol. 9(10), pp. 9912-9921 (2015).
Zhang et al., "Molecular mechanism of interaction between SARS-CoV-2 and host cells and interventional therapy", Signal Transduction and Targeted Therapy, vol. 6(1), 233 (Jun. 2021).
Zhang et al., "Mosaic RBD Nanoparticles Elicit Protective Immunity Against Multiple Human Coronaviruses in Animal Models", Advanced Science, vol. 11(9), Art. 2303366, pp. 1-13 (Dec. 2023).
Zhang et al., "Photothermal-responsive nanosized hybrid polymersome as versatile therapeutics codelivery nanovehicle for effective tumor suppression", Proceedings of the National Academy of Sciences, vol. 116(16), pp. 7744-7749 (2019).
Zhang et al., "Preparation and characterization of water-soluble chitosan nanoparticles as protein delivery system", Journal of Nanomaterials, vol. 2010, Article 898910 (2009).
Zhang et al., "Preparation of itraconazole nanoparticles by anti-solvent precipitation method using acascaded microfluidic device and an ultrasonic spray drier", Chemical Engineering Journal, vol. 334, pp. 2264-2272 (2018).
Zhang et al., "Rapid Detection of SARS-CoV-2 Spike RBD Protein in Body Fluid: Based on Special Calcium Ion-Mediated Gold Nanoparticles Modified by Bromide Ions", The Journal of Physical Chemistry Letters, vol. 14(1), pp. 88-94 (Dec. 2022).
Zhang et al., "Rapid development of an updated mRNA vaccine against the SARS-CoV-2 Omicron variant", Cell Research, vol. 32(4), pp. 401-403 (Feb. 2022).
Zhang et al., "Shape dependent cytotoxicity of PLGA-PEG nanoparticles on human cells", Sci. Rep., vol. 7(1), p. 7315 (2017).
Zhang et al., "Size-dependent endocytosis of nanoparticles", Adv. Mater. (Deerfield Beach, Fla.), vol. 21(4), pp. 419-424 (2009).
Zhang et al., "Surface Adsorption-Mediated Ultrahigh Efficient Peptide Encapsulation with a Precise Ratiometric Control for Type 1 and 2 Diabetic Therapy", Small, vol. 18(15), 2200449 (Apr. 2022).

(56) References Cited

OTHER PUBLICATIONS

Zhang et al., "Understanding the excitation wavelength dependence and thermal stability of the SARS-CoV-2 receptor-binding domain using surface-enhanced raman scattering and machine learning", ACS Photonics, vol. 9(9), pp. 2963-2972 (Sep. 2022).
Zhang et al., "Use of metal oxide nanoparticle band gap to develop a predictive paradigm for oxidative stress and acute pulmonary inflammation", ACS Nano, vol. 6(5), pp. 4349-4368 (2012).
Zhang et al., "A platform incorporating trimeric antigens into self-assembling nanoparticles reveals sars-cov-2-spike nanoparticles to elicit substantially higher neutralizing responses than spike alone", Scientific Reports, vol. 10, Article No. 18149 (2020).
Zhang et al., "Advances in developing ACE2 derivatives against SARS-CoV-2", Lancet Microbe. vol. 4(5), pp. e369-e378 (May 2023).
Zhang et al., "Altered energy metabolism in cancer: a unique opportunity for therapeutic intervention", Cancer Biology & Therapy, pp. 81-89, vol. 14, No. 2 (2013).
Zhang et al., "Association of Inpatient Use of Angiotensin Converting Enzyme Inhibitors and Angiotensin II Receptor Blockers with Mortality Among Patients With Hypertension Hospitalized With COVID-19", Circulation Research, pp. 1671-1681, vol. 126, No. 12 (2020).
Zhang et al., "Enhanced radiation sensitivity in prostate cancer by gold-nanoparticles", Clinical and Investigative Medicine, pp. E160-E167 (2008).
Zhang et al., "Enhancement of oral bioavailability of tripterine through lipid nanospheres: preparation, characterization, and absorption evaluation", Journal of Pharmaceutical Sciences, pp. 1711-1719, vol.103, Issue 6 (2014).
Zhang et al., "Inhalable nanocatchers for SARS-CoV-2 inhibition", Proceedings of the National Academy of Sciences of the United States of America, pp. 1-9, vol. 118, No. 29 (2021).
Zhang et al., "Nanoparticles That Reshape the Tumor Milieu Create a Therapeutic Window for Effective T-cell Therapy in Solid Malignancies", Cancer Research, pp. 3718-3730, vol. 78, Issue 13 (2018).
Zhang et al., "Self-assembly in the ferritin nano-cage protein superfamily", International Journal of Molecular Sciences, pp. 5406-5421, vol. 12, No. 8 (2011).
Zhang et al., "Site-specific N-glycosylation Characterization of Recombinant SARS-CoV-2 Spike Proteins", bioRxiv, pp. 1-37 (2020).
Zhang et al., "Zeta potential: a surface electrical characteristic to probe the interaction of nanoparticles with normal and cancer human breast epithelial cells", Biomedical Microdevices, pp. 321-328, vol. 10 (2008).
Zhao et al., "A safe and convenient pseudovirus-based inhibition assay to detect neutralizing antibodies and screen for viral entry inhibitors against the novel human coronavirus MERS-CoV", Virology Journal, vol. 10(1) (2013).
Zhao et al., "Cellular uptake, intracellular trafficking, and cytotoxicity of nanomaterials", Small, vol. 7(10), p. 1322-1337 (2011).
Zhao et al., "Cytotoxicity of hydroxyapatite nanoparticles is shape and cell dependent", Arch. Toxicol., vol. 87(6), pp. 1037-1052 (2012).
Zhao et al., "Glycyrrhizic acid nanoparticles as antiviral and anti-inflammatory agents for COVID-19 treatment", ACS Applied Materials & Interfaces, vol. 13(18), pp. 20995-21006 (Apr. 2021).
Zhao et al., "Long-term stability and protection efficacy of the RBD-targeting COVID-19 mRNA vaccine in nonhuman primates", Signal Transduction and Targeted Therapy, vol. 6(1), 438 (Dec. 2021).
Zhao et al., "Microfluidic platform for preparation and screening of narrow size-distributed nanoscale explosives and supermixed composite explosives", Industrial & Engineering Chemistry Research, vol. 57(39), pp. 13191-13204 (2018).
Zhao et al., "Microfluidic synthesis of barcode particles for multiplex assays", Small, vol. 11(2), pp. 151-174 (2015).
Zhao et al., "Omicron SARS-CoV-2 mutations stabilize spike up-RBD conformation and lead to a non-RBM-binding monoclonal antibody escape", Nature Communications, vol. 13(1), 4958 (Aug. 2022).
Zhao et al., "Microwave-induced polyol-process synthesis of copper and copper oxide nanocrystals with controllable morphology", European Journal of Inorganic Chemistry, pp. 4072-4080, No. 20 (2004).
Zhao et al., "Systematically benchmarking peptide-MHC binding predictors: From synthetic to naturally processed epitopes", PLoS Computational Biology, pp. 1-28, vol. 14 (2018).
Zheng et al., "Neutralization assay with SARS-CoV-1 and SARS-CoV-2 spike pseudotyped murine leukemia virions", Virology Journal, vol. 18(1) (Jan. 2021).
Zheng et al., "Recent advances in drug release monitoring", Nanophotonics, vol. 8(3), pp. 391-413 (2019).
Zheng et al., "Novel antibody epitopes dominate the antigenicity of spike glycoprotein in SARS-CoV-2 compared to SARS-CoV", Cellular & Molecular Immunology, pp. 536-538, vol. 17, No. 5 (2020).
Zhigaltsev et al., "Bottom-up design and synthesis of limit size lipid nanoparticle systems with aqueous and triglyceride cores using millisecond microfluidic mixing", Langmuir, vol. 28(7), pp. 3633-3640 (2012).
Zhou et al., "Vitrified collagen-based conjunctival equivalent for ocular surface reconstruction", Biomaterials, vol. 35(26), pp. 7398-7406 (2014).
Zhou et al., "A chelator-free multifunctional [64Cu]CuS nanoparticles platform for simultaneous micto-PET/CT imaging and photothermal ablation therapy", Journal of American Chemical Society, pp. 15351-15358, vol. 132, No. 43 (2010).
Zhou et al., "A pneumonia outbreak associated with a new coronavirus of probable bat origin", Nature, pp. 270-273, vol. 579 (2020).
Zhou et al., "Effects of human mobility restrictions on the spread of COVID-19 in Shenzhen, China: a modelling study using mobile phone data", The Lancet Digit Health, pp. e417-e424, vol. 2, No. 8 (2020).
Zhou et al., "Interferon-$\alpha$2b Treatment for COVID-19", Frontiers in Immunology, pp. 1-6, vol. 11, No. 1061 (2020).
Zhou et al., "Mesoporous silica nanoparticles for drug and gene delivery", Acta Pharmaceutica Sinica B, pp. 165-177, vol. 8, No. 2 (2018).
Zhu et al., "A universal bacteriophage T4 nanoparticle platform to design multiplex SARS-CoV-2 vaccine candidates by CRISPR engineering", Science Advances, vol. 7(37) (Sep. 2021).
Zhu et al., "Applications of nanomaterials as vaccine adjuvants", Hum. Vaccines Immunother., vol. 10(9), pp. 2761-2774 (2014).
Zhu et al., "Long-range enhancement of N501Y-endowed mouse infectivity of SARS-CoV-2 by the non-RBD mutations of Ins215KLRS and H655Y", Biology Direct, vol. 17(1) (Jun. 2022).
Zhu et al., "Safety and efficacy of the intranasal spray SARS-CoV-2 vaccine dNS1-RBD: a multicentre,randomised, double-blind, placebo-controlled, phase 3 trial", The Lancet Respiratory Medicine, vol. 11(12), pp. 1075-1088 (Dec. 2023).
Zhu et al., "Safety and immunogenicity of a live-attenuated influenza virus vector-based intranasal SARS-CoV-2 vaccine in adults: randomised, double-blind, placebo-controlled, phase 1 and 2 trials", The Lancet Respiratory Medicine, vol. 10(8), pp. 749-760 (Aug. 2022).
Zhu et al., "Surface De-PEGylation controls nanoparticle-mediated siRNA delivery in vitro and in vivo", Theranostics, vol. 7(7), pp. 1990-2002 (2017).
Zhu et al., "Acute toxicities of six manufactured nanomaterial suspensions to Daphnia magna", Journal of Nanoparticle Research, pp. 67-75, vol. 11, No. 1 (2009).
Zhu et al., "Trophic transfer of TiO2 nanoparticles from Daphnia to zebrafish in a simplified freshwater food chain" Chemosphere, pp. 928-933, vol. 79, Issue 9 (2010).
Zhuk et al., "Advances in the Chemistry of Polyethyleneimine (Polyaziridine)", Russian Chemical Review, pp. 515-527, vol. 34, No. 7 (1965).

(56) References Cited

OTHER PUBLICATIONS

Zijlstra et al., "A quantitative analysis of rate-limiting steps in the metastatic cascade using human-specific real-time polymerase chain reaction", Cancer Research, pp. 7083-7092, vol. 62 (2002).
Zipeto et al., "HLA-C and HIV-1: Friends or foes?" Retrovirology, pp. 1-9, vol. 9, Issue 39 (2012).
Zoqlam et al., "Evaluation of the benefits of microfluidic-assisted preparation of polymeric nanoparticles for DNA delivery", Materials Science and Engineering: C, vol. 127, 112243 (Aug. 2021).
Zou et al., "Tapping the Chinese market: An examination of Chinese tourists' images and constraints towards cruising", Tourism Review international, pp. 347-364, vol. 21, Issue 4 (2017).
Zuber et al., "COVID 19: challenges for virologists in the food industry", Microbial Biotechnology, pp. 1689-1701, vol. 13, Issue 6 (2020).
Zumla et al., "Host-directed therapies for infectious diseases: current status, recent progress, and future prospects", The Lancet Infectious Diseases, vol. 16(4), pp. e47-e63 (2016).
Zumla et al., "Reducing mortality from 2019-nCoV: host-directed therapies should be an option", The Lancet, vol. 395(10224), pp. e35-e36 (Feb. 2020).
Zwicke et al., "Utilizing the folate receptor for active targeting of cancer nanotherapeutics." Nano Reviews, pp. 1-12, vol. 3, Issue 1 (2012).
Abdool Karim et al., "New SARS-CoV-2 Variants-Clinical, Public Health, and Vaccine Implications", The New England Journal of Medicine, vol. 384(19), pp. 1866-1868 (Mar. 2021).
An et al., "A protein vaccine of RBD integrated with immune evasion mutation shows broad protection against SARS-CoV-2", Signal Transduction and Targeted Therapy, vol. 9(301), pp. 1-12 (Nov. 2024).
Barnes et al., "SARS-CoV-2 neutralizing antibody structures inform therapeutic strategies", Nature, vol. 588, Art. 7839, pp. 682-687 (Oct. 2020).
Carabelli et al., "SARS-CoV-2 variant biology: immune escape, transmission and fitness", Nature Review Microbiology., vol. 21(3), pp. 162-177 (Mar. 2023).
Chen et al., "Resistance of SARS-CoV-2 variants to neutralization by monoclonal and serum-derived polyclonal antibodies", Nature Medicine, vol. 27(4), pp. 717-726 (Apr. 2021).
Dai et al., "Viral targets for vaccines against COVID-19", Nature Reviews, Immunology, vol. 21(2), pp. 73-82 (Feb. 2021).
Dickey et al., "Design of the SARS-CoV-2 RBD vaccine antigen improves neutralizing antibody response", Science Advances, vol. 8(37), pp. 1-12 (Sep. 2022).
Editorial, "Let's talk about lipid nanoparticles", Nature Reviews Materials, vol. 6(2), p. 99 (Feb. 2021).
Formica et al., "On a highway to the brain: A review on nose-to-brain drug delivery using nanoparticles", Applied Materials Today, vol. 29, pp. 1-23 (Jun. 2022).
Hamasaki et al., "Platelet-Activating Factor Raises Airway and Vascular Pressures and InducesEdema in Lungs Perfused with Platelet-Free Solution", Am. Rev. Respir. Dis., vol. 129(5), pp. 742-746 (May 1984).
Harvey et al., "SARS-CoV-2 variants, spike mutations and immune escape", Nature Reviews, Microbiology, vol. 19(7), pp. 409-424 (Jul. 2021).
Heinz et al., "Distinguishing features of current COVID-19 vaccines: knowns and unknowns of antigen presentation and modes of action", NPJ Vaccines, vol. 6, Art. 104, pp. 1-13 (Aug. 2021).
Hutchinson et al., "Nanoparticle display of prefusion coronavirus spike elicits S1-focused cross-reactive antibody response against diverse coronavirus subgenera", Nature Communications, vol. 14, Art. 6195, pp. 1-11 (Oct. 2023).
Islam et al., "Comparative effectiveness over time of the mRNA-1273 (Moderna) vaccine and the BNT162b2 (Pfizer-BioNTech) vaccine", Nature Communications, vol. 13, Art. 2377, pp. 1-7 (May 2022).
Katira et al., "Adverse Heart-Lung Interactions in Ventilator-induced Lung Injury", American Journal of Respiratory and Critical Care Medicine, vol. 196(11), pp. 1411-1421 (Dec. 2017).
Kleanthous et al., "Scientific rationale for developing potent RBD-based vaccines targeting COVID-19", NPJ Vaccines, vol. 6, Art. 128, pp. 1-10 (Oct. 2021).
Li et al., "COVID-19 vaccine development: milestones, lessons and prospects", Signal Transduction and Targeted Therapy, vol. 7(146), pp. 1-32 (May 2022).
Liang et al., "RBD trimer mRNA vaccine elicits broad and protective immune responses against SARS-CoV-2 variants", iScience, vol. 25, Art. 104043, pp. 1-29 (Apr. 2022).
Liu et al., "Physicochemical properties affecting the fate of nanoparticles in pulmonary drug delivery", Drug Discovery Today, vol. 25(1), pp. 150-159 (Jan. 2020).
Liu et al., "RBD-Fc-based COVID-19 vaccine candidate induces highly potent SARS-CoV-2 neutralizing antibody response", Signal Transduction and Targeted Therapy, vol. 5(282), pp. 1-10 (Nov. 2020).
Liu et al., "Virus-mimicking nanosystems: from design to biomedical applications", Royal Society of Chemistry, vol. 52, pp. 8481-8499 (Nov. 2023).
Luo et al., "The immunodominance of RBD antigen of delta variant as vaccine candidate against SARS-CoV-2 infection", Journal Medical Virology, vol. 95, pp. 1-3 (Nov. 2022).
Lyngse et al., "Increased transmissibility of SARS-CoV-2 lineage B.1.1.7 by age and viral load", Nature Communications, vol. 12, Art. 7251, pp. 1-8 (Dec. 2021).
Mabrouk et al., "Advanced materials for SARS-CoV-2 Vaccines", Advanced Materials, vol. 34, Art. 2107781, pp. 1-17 (Dec. 2021).
Oladunni et al., "Lethality of SARS-CoV-2 infection in K18 human angiotensin-converting enzyme 2 transgenic mice", Nature Communications, vol. 11, Art. 6122, pp. 1-17 (Nov. 2020).
Puranik et al., "Comparative effectiveness of mRNA-1273 and BNT162b2 against symptomatic SARS-CoV-2 infection", Med, vol. 3, pp. 28-41 (Dec. 2021).
Radvak et al., "SARS-CoV-2 B.1.1.7 (alpha) and B.1.351 (beta) variants induce pathogenic patterns in K18-hACE2 transgenic mice distinct from early strains", Nature Communications, vol. 12(6559), pp. 1-15 (Nov. 2021).
Ren et al., "Characterization of SARS-CoV-2 Variants B.1.617.1 (Kappa), B.1.617.2 (Delta), and B 1.618 by Cell Entry and Immune Evasion", mBio, American Society for Microbiology, vol. 13(2), pp. 1-12 (Apr. 2022).
Sankhala et al., "Diverse array of neutralizing antibodies elicited upon Spike Ferritin Nanoparticle vaccination in rhesus macaques", Nature Communications, vol. 15(200), pp. 1-19 (Jan. 2024).
Sun et al., "The self-assembled nanoparticle-based trimeric RBD mRNA vaccine elicits robust anddurable protective immunity against SARS-CoV-2 in mice", Signal Transduction and Targeted Therapy, vol. 6(340), pp. 1-11 (Sep. 2021).
Tartof et al., "Effectiveness of mRNA BNT162b2 COVID-19 vaccine up to 6 months in a large integrated health system in the USA: a retrospective cohort study", The Lancet, vol. 398, pp. 1407-1416 (Oct. 2021).
Thomas et al., "Safety and Efficacy of the BNT162b2 mRNA Covid-19 Vaccine through 6 months", The New England Journal of Medicine, vol. 385, pp. 1761-1773 (Sep. 2021).
Wan et al., "Pathogen-Mimicking Nanoparticles Based on Rigid Nanomaterials as an Efficient Subunit Vaccine Delivery System for Intranasal Immunization", Advanced Healthcare Materials, vol. 13, pp. 1-14 (Jun. 2024).
Zang et al., "Yeast-produced RBD-based recombinant protein vaccines elicit broadly neutralizing antibodies and durable protective immunity against SARS-CoV-2 infection", Cell Discovery, vol. 7(71), pp. 1-16 (Aug. 2021).
Zhan, et al., "B.1.617.2 (Delta) Variant of SARS-CoV-2: features, transmission and potential strategies", International Journal of Biological Sciences, vol. 18(5), pp. 1844-1851 (Feb. 2022).
Zhang et al., "Controlled Interfacial Polymer Self-Assembly Coordinates Ultrahigh Drug Loading and Zero-Order Release in Particles Prepared under Continuous Flow", Advanced Materials, vol. 35, Art. 2211254, pp. 1-16 (Feb. 2023).

(56) References Cited

OTHER PUBLICATIONS

Zhang et al., "Nanoparticle-liver interactions: Cellular uptake and hepatobiliary elimination", Journal of Controlled Release, vol. 240, pp. 332-348 (Jan. 2016).
Zhang et al., "Surface Adsorption-Mediated Ultrahigh Efficient Peptide Encapsulation with a Precise Ratiometric Control for Type 1 and 2 Diabetic Therapy", Small, vol. 18, Art. 2200449, pp. 1-12 (Mar. 2022).
Zhou et al., "Evidence of escape of SARS-CoV-2 variant B.1.351 from natural and vaccine-induced sera", Cell, vol. 189, pp. 2348-2361 (Apr. 2021).
U.S. Appl. No. 17/684,341 U.S. Pat. No. 11,564,892, filed Mar. 1, 2022, Virus-Like Particles for Preventing the Spreading and Lowering the Infection Rate of Viruses.
U.S. Appl. No. 18/152,930, U.S. Pat. No. 12,144,898, filed Jan. 11, 2023, Virus-Like Particles for Preventing the Spreading and Lowering the Infection Rate of Viruses.
U.S. Appl. No. 18/936,852, filed Nov. 4, 2024, Virus-Like Particles for Preventing the Spreading and Lowering the Infection Rate of Viruses.
U.S. Appl. No. 17/735,010, filed May 2, 2022, Methods for Lowering the Infection Rate of Viruses.
U.S. Appl. No. 17/735,019, filed May 2, 2022, Particles for Stimulating an Imiviune Response Against Viral Infections.
U.S. Appl. No. 18/544,302 U.S. Pat. No. 12,194,157, filed Dec. 18, 2023, Carrier for Targeted Delivery to a Host.
U.S. Appl. No. 18/544,302 U.S. Pat. No. 12,194,157, filed Dec. 18, 2023, Methods of Targeted Delivery to a Host Using a Carrier.
U.S. Appl. No. 18/907,374, filed Oct. 4, 2024, Carrier for Lowering The Infection Rate of Bacteria.
U.S. Appl. No. 17/735,019, filed May 2, 2022, Particles for Stimulating an Iivimune Response Against Viral Infections.
U.S. Appl. No. 18/544,302, filed Dec. 18, 2023, Virus-Like Particles for Preventing the Spreading and Lowering the Infection Rate of Viruses.
Annex to Form PCT/ISA/206 issued in PCT application No. PCT/US2024/045709, dated Dec. 16, 2024.
Gong et al., "Liquid-Phase and Ultrahigh-Frequency-Acoustofluidics-Based Solid-Phase Synthesis of Biotin-Tagged 6' /3'—Sialyl-N-Acetylglucosamine by Sequential One-Pot Multienzyme System", Catalysts, vol. 10, No. 11, p. 1347, (Nov. 2020).
Ran et al., "Microfluidic self-assembly of a combinatorial library 1-29 of single- and dual-ligand liposomes forin vitroandin vivotumor targeting", European Journal of Pharmaceutics and Biopharmaceutics, Elsevier Science Publishers B.V., Amsterdam, NL, vol. 130, No. 15, pp. 1-10, (Jun. 2018).
Pérez-Alonso et al., "Glycan-Silica Nanoparticles as Effective Inhibitors for Blocking Virus Infection, ACS Appl. Mater. Interfaces", vol. 17, pp. 10292-10304 (Feb. 2025).

XXXXXXXXXXXXXXXXXXXXXXXXXXXXXXXXXXXXXXXXXXXXXXXXXXXXRVQPTESIVRFPNITNLCPFGEVFNATRFASVYAWNRKRISN 1 10 20 30 40 50 60 70 80 90

Signal Sequence | Tag | Spacer | Region: 319.......SARS-CoV-2 RBD.........................

CVADYSVLYNSASFSTFKCYGVSPTKLNDLCFTNVYADSFVIRGDEVRQIAPGQTGKIAD 100 110 120 130 140 150

.............................................................SARS-CoV-2 RBD............................

YNYKLPDDFTGCVIAWNSNNLDSKVGGNYNYLYRLFRKSNLKPFERDISTEIYQAGSTPC 160 170 180 190 200 210

.............................................................SARS-CoV-2 RBD............................

NGVEGFNCYFPLQSYGFQPTNGVGYQPYRVVVLSFELLHAPATVCGPKKSTNLVKNKCVNF 220 230 240 250 260 270

.............................................................SARS-CoV-2 RBD............................541

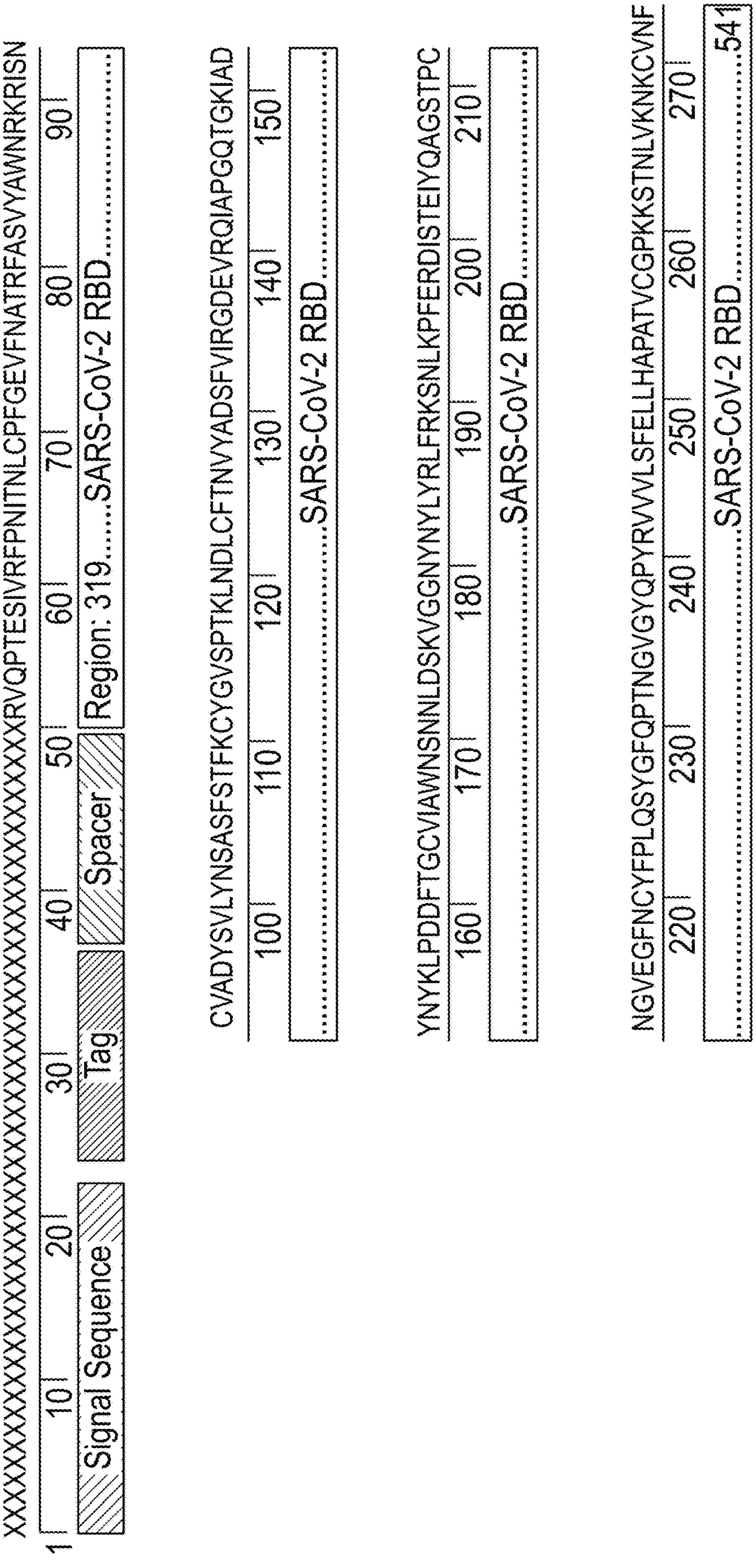

FIG. 7

METHODS OF TARGETED DELIVERY TO A HOST USING A CARRIER

CROSS-REFERENCE TO RELATED APPLICATIONS

This application is a continuation of U.S. patent application Ser. No. 18/544,302, filed Dec. 18, 2023, which is a continuation-in-part (CIP) of U.S. patent application Ser. No. 18/152,930, filed Jan. 11, 2023, which is a continuation of U.S. patent application Ser. No. 17/684,341, filed Mar. 1, 2022 and issued as U.S. Pat. No. 11,564,892 on Jan. 31, 2023, which is a continuation-in-part (CIP) of PCT Application PCT/FI2021/050259, filed Apr. 9, 2021 and published on Oct. 14, 2021 as PCT Publ. WO 2021/205077, which claims priority to Finnish Application Nos. 20205382, filed Apr. 9, 2020 and 20215182, filed Feb. 19, 2021; and also claims priority to U.S. provisional application No. 63/433,755, which was filed Dec. 19, 2022. The contents of each of the aforementioned applications are incorporated by reference herein in their entireties and made part of the present application.

INCORPORATION BY REFERENCE OF MATERIAL IN SEQUENCE LISTING

This application incorporates by reference the material within the Sequence Listing contained in the following XML file being submitted concurrently herewith: File name: FICU.002P5C1_Replacement_SEQ_LIST.XML; created on Feb. 28, 2025 and is 10,456 bytes in size.

BACKGROUND

Field

The present application pertains to the field of pharmaceutical products, biologics, medical devices, over-the-counter drugs and consumer products preventing or reducing the spread of pathogens or other disease-causing agents, factors or sources, such as, for example, coronaviruses (e.g., the Severe Acute Respiratory Syndrome Coronavirus 2 (SARS-CoV-2)), influenzas and viruses causing respiratory infection, diarrhea, common cold, cytokine storm, general discomfort and/or death, bacteria, other pathogens and the like. More specifically, the present application relates to nano- and/or micromaterials-based carriers, such as mimetic nano- and/or micromaterials-based carriers, synthesized to minimize the spread of pathogens and infectious agents (e.g., viruses (e.g., influenzas, rhinoviruses, noroviruses, respiratory syncytial virus (RSV), SARS-CoV-2, future strains and/or types of coronaviruses derived thereof, etc.), bacteria, parasites, antigens, prions, mold, fungi, toxins, poisons, and allergens), and/or other disease-causing agents, factors and/or sources.

The present application also relates to combinatory tailored treatments of an active pharmaceutical ingredient ("API") loaded inside a carrier system capable of delivering the drug specifically to target cells and/or tissues (e.g., targeted drug/material delivery). More specifically this application pertains to the fabrication and use of man-made materials in the nano- and/or microscale that would, at least partially, saturate and bind to receptors, proteins and/or macromolecules at the cellular level in order to prevent and/or minimize (or reduce the likelihood of) pathogen binding, in particular, for example, novel coronaviruses binding and entry to the host target cells and/or tissues by competitive inhibition. In some embodiments, the targeted drug and/or other material delivery includes using a carrier to at least partially alter, inhibit and/or otherwise impact disease onset and/or progression. This can be accomplished by, in part, the carrier binding to a target site (e.g., a receptor, a protein, a macromolecule, etc.). Once carriers bind to host cells, they can enter said host cells (e.g., by endocytosis). Accordingly, the drug and/or other contents of the carrier can be advantageously provided to host cell (e.g., target host cells) with lower or less impact on other host cells. The carrier As a result, in some arrangements, an enhanced therapy can be provided by targeting particular cells of a host and being able to deliver specific drugs and/or other components to said cells. The carriers can increase the therapeutic window of drugs and/or other components loaded to (e.g., within) and/or otherwise provided with the carrier. In some embodiments, the drugs and/or other components provided with the carrier have low solubility and/or permeability and/or are prone to aggregate and be rendered non or less efficacious (e.g., when not using a carrier as a delivery vehicle to the subject's anatomy).

The present application further relates to a medical device or delivery device capable of releasing (e.g., on-demand, specific amounts of) the synthesized carrier system to targeted tissue or tissues susceptible to, for example, coronaviruses. In some embodiments, for example, such a device includes an inhalation device, e.g., meter dose, dry inhaler, nebulization, ultrasonication, nose or mouth drops, or a nasal spray for the respiratory tract. In some arrangements, the device includes tailored orally ingestible tablets or solutions for the gastrointestinal tract, a topically administrable cream or ointment intended to be applied to a subject's skin and/or an injectable substance intended to be applied subcutaneously, intravenously, intraperitoneally or otherwise injected and/or administered using, at least in part, for example, high pressure or laser.

Further, the present application relates to synthesized materials (e.g., carriers, nanoparticles, etc.) that are configured to bind to pathogen co-receptors and/or natural occurring carriers (e.g., high-density lipoprotein receptors in the blood and other secondary receptors, such as, for instance, the FcγR for, at least partially, preventing the infectious agent for entering the host cell). Therefore, according to some embodiments, the carrier system described herein is configured to reduce the likelihood of infection of host cells by blocking receptors and/or other binding sites/features of host cells to which viruses and/or other pathogens may bind (e.g., for entry into host cells), and by delivering immune stimulating properties to target cell populations, by having protrusions at the surface of the carrier that mimics-naturally occurring epitopes found at the pathogen.

Further, the present application relates to synthesized materials that have the capacity and ability of binding and encapsulating pathogens or pathogens co-receptors and natural occurring carriers for, at least partially, immobilizing and neutralizing the infectious agent for disrupting the infectious agent. Therefore, according to some embodiments, the carrier system described herein is configured to reduce the likelihood of infection of host cells by (1) blocking receptors and/or other binding sites/features of host cells to which viruses and/or other pathogens may bind (e.g., for entry into host cells), (2) delivering immune stimulating properties to target cell populations, and/or (3) immobilizing viruses and/or other pathogens by attracting virus and/or other pathogens (e.g., so such viruses and/or other pathogens are unable to bind to host cells).

Further, the present application relates to synthesized materials (e.g., carriers) that are configured to present and/or otherwise include epitopes capable of eliciting and/or configured to elicit an immunological response towards viruses and/or other pathogens. Therefore, according to some embodiments, the carriers disclosed herein are configured to be used as, for and/or in a vaccination (e.g., to have a vaccination-type effect) at target cell populations where the said epitopes can elicit an advantageous response. For example, in some embodiments, the epitopes can elicit a B cell response generating specific antibodies and/or T cell response priming and mounting a possible cytotoxic T-cell response against a virus and/or other pathogens. Accordingly, in some embodiments, one or more of the carrier systems described herein are configured to reduce the likelihood of infection of host cells by at least partially blocking receptors and/or other binding sites/features of host cells to which viruses and/or other pathogens may bind (e.g., for entry into host cells) and/or to provide immune stimulating properties to target cell populations (e.g., by mounting an efficient immunologic reaction).

Background

Different pathogens (e.g., viruses, bacterium, parasites, etc.) prefer environments typical of their specific niche inside the host tissues. For example, Escherichia. Coli prefers to colonize the intestine, whereas tuberculosis residues in the lungs of its host [1]. Malaria-bearing mosquitos may infect their human host by biting, allowing parasites to enter the blood stream and travel to the liver of the subject for maturation [2]. For the pathogens to colonize and replicate at their specific environments and tissues, they need to infect and/or inoculate their host [1-4]. At the cellular level, this mechanism of entry starts by the pathogen binding or getting in proximity of the host cell where specific receptors, macromolecules and/or proteins protruding at the cell membrane facilitates the endocytosis of the infectious agent. If the specific route of entry is known, such knowledge can be used for creating a man-made object that can allosterically hinder the specific pathogens entry by competitive inhibition [5]. For example, by creating a carrier (e.g., nanoparticle), such as a mimetic nanoparticle, of similar size, surface chemistry and charge as the pathogen of interest, it is possible to saturate and block the specific receptors at the host cells hindering the pathogens entry. Another possibility includes synthetizing man-made materials (e.g., carriers) that would efficiently bind to the pathogen of interest encapsulating and immobilizing the infectious agent, thereby minimizing the possible entry to the host. Another possibility includes synthetizing man-made materials (e.g., carriers) that would efficiently bind to the pathogen, such as the novel coronavirus and/or co-receptor of interest, thereby immobilizing the infectious agent and reducing the likelihood (e.g., minimizing) the possible spread of the disease further inside the body and/or reducing the likelihood (e.g., preventing) entry to the host.

In some embodiments, by creating a carrier (e.g., nanoparticle), such as a mimetic nanoparticle, of similar size, surface chemistry and/or charge as the pathogen of interest, it is possible to saturate and block the specific receptors at the host cells, hindering the pathogen's entry. Another possibility includes synthesizing man-made materials (e.g., carriers) that would efficiently bind to the pathogen co-receptor of interest, thereby at least partially hindering the infectious agent and reducing the likelihood (e.g., minimizing) the possible spread of the disease further inside the body and/or reducing the likelihood (e.g., preventing) entry to the host.

Viruses use components derived from their host for cell entry. For example, the SARS-CoV-2 virus that causes a respiratory infection called COVID-19 is decorated by glycoprotein spikes at the surface of the viral particle. These glycoproteins have high affinity for the human angiotensin converting enzyme 2 (ACE-2) allowing for specific internalization of the virus in the epithelial cells of the respiratory tract, possible intestinal tract and/or another tract or system of a subject where there is high expression of its target receptor [3,4]. Thus, potentially allowing for tailored molecules to be used for intervention of the SARS-CoV-2 virus enter to its human host. In bacterium it has been shown that surface topography together with surface charge greatly influences adhesion that modulates bacterial growth [6]. Using nanostructured surfaces, it could be possible to control bacterial adhesion and growth that could be used in medical applications for preventing infections. Plasmodium falciparum, which is the human Malaria parasites, uses dynamin like Eps15 homology domain-containing proteins for hijacking the endocytosis pathways important for infecting more erythrocytes in its host [2].

For example, the novel coronavirus SARS-CoV-2 that causes a respiratory infection called Coronavirus Disease 2019 (COVID-19), are decorated by glycoprotein spikes at the surface of the viral particle having high affinity for specific receptor(s). SARS-CoV-2, SARS-CoV and MERS-CoV belong to the betacoronavirus genus having a genome size of approximate 30 kilobases encoding both structural and non-structural proteins. Structural proteins include the envelope (E) protein, spike (S) glycoprotein, the nucleocapsid (N) protein and the membrane (M) protein, whereas to the non-structural proteins belong, for example, the RNA-dependent RNA polymerase. The spike (S) glycoproteins decorated on coronaviruses consist of a homotrimeric transmembrane protein, each 180 kDa monomer comprising two functional subunits S1 and S2, whereas the S1 unit consists of two domains: N-terminal domain (NTD) and C-terminal domain (CTD). Depending on the coronavirus type, either the NTD or CTD of S1 is used as the receptor binding domain (RBD) capable of binding to specific receptors at the host cell surface. Each of SARS-CoV-2 and SARS-CoV utilizes the CTD as its RBD for the human angiotensin converting enzyme 2 (ACE2) allowing for specific internalization of the virus in the epithelial cells of the respiratory tract and possible intestine where there is high expression of its target receptor [3,4,6]. However, due to the novel amino acid sequence and structure of SARS-CoV-2. the affinity for the ACE2 receptor is significantly higher compared to SARS-CoV [6,7]. In both of the aforementioned coronaviruses, the RBD forms a concave surface that contains a ridge loop that has the ability to bind to the receptor binding motif, which is the outer surface of the human ACE2 receptor at its N-terminal helix. In SARS-CoV, this loop contains a three-residue motif proline-proline-alanine, and these prolines repeats makes the ridge loop to make a sharp and short turn. SARS-CoV-2 has a four-residue motif of glycine-valine/glutamine-glutamate/threonine-glycine that give rise to two bulkier residues and two flexible glycine residues that creates a different and compact conformation, allowing the viral loop to be closer to the ACE2 receptors N-terminal helix forming additional hydrogen bonds between the loop and the human receptor resulting in a stronger binding [6]. The S2 subunit from the S protein is necessary for viral fusion with the host cellular membrane mediated by proteolytic cleavage by the human transmembrane serine protease 2 (TMPRSS2), leading to the internalization of SARS-CoV-2, enabling viral replication inside its host cell [7]. The inhibitory effect of RBD spike fragment hexapeptide 438YKYRYL443 (SEQ ID No: 1) of the SARS-CoV-2 has been estimated to have the highest affinity for ACE2 when compared to another known coronavirus derived hexapeptides. The specific hexapeptide YKYRYL (SEQ ID No: 1) carries the dominant binding amino acid sequence that binds to ACE2 with a high affinity of KD=46 μM. However, the simulation gives rise to potential alternative synthetic hexapeptide variants YKYNYI (SEQ ID No: 2) and YKYNYL (SEQ ID No: 3) with even stronger binding affinity towards the ACE2 receptor which is highly conserved among different mammalian organisms allowing transmission from animals to humans and vice versa [8]. Furthermore, some amino acid sequences from viruses such as SARS-COV-2, have been shown to induce predominantly B cell response whereas other have been shown to induce predominantly T cell response. For example, but not limited to epitopes from SARS-CoV-2 spike protein: 1220FIAGLIAIV1228, 17VLLFLAFVV25, 20FLAFVVFLL28, 204VLAWLYAAV212 and 184VLWAHGFEL192 that stimulates at least partly the T cell response. Whereas for example but not limited to epitopes from SARS-CoV-2 spike protein: 287DAVDCALDPLSETKCTLKSFTVEKGIYQTSN317, 524VCGPKKSTNLVKNKCVNFNFNGLTGTGVLTESNKKFLPFQQFGRDIADTTDAVRDPQTLEILDITPC SFGGVSVI598, 601GTNTSNQVAVLYQDVNCTEVPVAIHADQLTPTWRVYSTGS640, 802FSQILPDPSKPSKRSFIE819, 888FGAGAALQIPFAMQMAYRFNGI909, that stimulates at least partly the B cell response. There are variations among human populations and the animal kingdom regarding the ACE2 receptor in terms of expression levels and polymorphisms that could influence the susceptibility of SARS-CoV-2 and outcome of COVID-19 disease [6-10]. Thus, potentially allowing for tailored molecules to be used for intervention of the SARS-CoV-2 virus enter to its human and animal hosts.

In the context of this specification, both ACE2 and ACE-2 may be understood as referring to human angiotensin converting enzyme 2.

Influenza, rhinoviruses, coronaviruses, respiratory syncytial virus (RSV) and noroviruses are non-limiting examples of viruses causing respiratory infection, diarrhea, common cold, cytokine storm, general discomfort, death and/or other symptoms or ailments. For example, influenza virus is a negative-sense, single-stranded RNA that causes a respiratory infection commonly called the “flu” which affects millions of individuals annually and causes thousands of deaths and millions of hospitalizations. The flu viral envelope is decorated with the fusion protein hemagglutinin (HA) that binds to the host sialic acid receptors and neuraminidase (NA), an enzyme located at the viral surface that cleaves the glycosidic bonds of the monosaccharide sialic acid, aiding in penetrating the host mucus and enabling the escape of newly formed viral particles. The size of influenza virus particles is around 80-120 nm, which is quite close to the size of coronaviruses. However, influenzas differ by having two main proteins on the surface, i.e., HA and NA, whereas coronaviruses only have the spike proteins protruding on the surface. To further complicate matters, there are currently 17 different HA proteins and 10 different NA proteins that have been characterized. It is these different combinations of proteins that give influenzas their subtype names. For example, the sequence homology of the HA2 subunit compared to the other HA subtypes is around 51-80%, whereas the HA1 subunit has an 34% to 59% sequence homology, rendering different genetic and protein varieties between the influenza subtypes. Combining the genetic variation with the potential protein combination of these viruses contributes to the immune evasive properties of influenzas, rendering efficacious vaccination development to a difficult task. This limited protection against influenzas, induced by vaccination, is listed by the Center for Disease Control (CDC) as follows, “flu vaccination reduces the risk of flu illness by between 40% and 60% among the overall population.” Therefore, there exists a significant need for developing anti-viral compounds and broad immune stimulating influenza vaccines in order to mitigate the spreading of the flu.

Rhinoviruses is one category of other major causative agents for the common cold, and there is currently no efficient vaccination against these types of viruses. Human Rhinoviruses (HRV) belong to the picornavirus family and are positive-sense, single-stranded ribonucleic acid (RNA) viruses that have an icosahedral symmetry with a particle size of around 30 nm. The viral capsid is composed of four main proteins: VP1, VP2, VP3, and VP4, whereas the VP4 protein is located inside of the virus anchoring the genetic information to the capsid structure. There are over 150 different serotypes of HRVs with the two most common types being HRV-A and HRV-B that uses the intercellular adhesion molecule-1 (ICAM-1) as the cell receptor for entering the host. However, some of the HRV serotypes use heparin sulfate proteoglycan as an additional receptor, and there are around 10 serotypes that use low-density lipoprotein as the cell receptor. Additionally, a new serotype of HRVs that arose in 2002 was given the name HRV-C, having a route of cell entry still remains elusive rendering rhinoviruses to a difficult task to mitigate.

Respiratory syncytial virus (RSV) belongs to the family of paramyxoviridae viruses and are negative-sense, single-stranded RNA viruses that usually cause a mild cold in most healthy humans. However, for infants, the elderly and/or other humans that are immunocompromised or otherwise susceptible to disease, the RSV can cause a more serious disease such as bronchiolitis and pneumonia, oftentimes leading to hospitalization. The RSVs have an average size of around 200 nm and contain three membrane proteins: 1) the host receptor attachment protruding glycoprotein (G), 2) the fusion protein (F), and 3) a short hydrophobic (SH) protein that forms a ion channel. RSVs can be further divided into two groups, A and B, depending on the reaction with monoclonal antibodies directed against the F and G proteins. The A group is the most prevalent circulating virus, and the largest genetic divergence is associated with the gene encoding for the G protein, rendering this protein to the most variable protein of the virus. This diverse variation of proteins explains, at least partially, why no effective vaccination against RSV currently exists on the market. Noroviruses (NoV) belong to the family Caliciviridae, which are genetically a diverse group of single-stranded positive-sense RNA that are non-enveloped viruses that cause an infection commonly called gastroenteritis or “stomach flu,” giving sudden onset of vomiting, diarrhea and other symptoms, which are often relatively severe. The most common symptoms for norovirus include nausea, vomiting, stomach pain or cramps, diarrhea, fever and/or muscle pain, with early symptoms usually beginning about 12 to 48 hours after exposure to the virus. Such symptoms can last up to several days. Infected individuals may continue to shed noroviruses in their feces for several weeks after recovery, thereby transmitting the disease, without knowing, to other individuals. The norovirus consists of an ~7.7-kb RNA genome with three open reading frames (ORFs), where ORF1 encodes a polyprotein precursor which is processed into several non-structural proteins, and where the two other ORFs encode the major (VP1) and minor (VP2) capsid proteins. The viral particles are around 27-30 nm in diameter having an icosahedral symmetry where the viral capsid is built of 90 dimers consisting of VP1, each protein having a shell (S) domain and a protruding (P) domain connected by a flexible linker. The S domain is responsible for the assembly of the virus capsid shell encapsulating the viral genome and is highly conserved domain of the VP1 protein. The P domain, on the other hand, is more variable and includes a P1 and a P2 subdomain. The P1 subdomain binds the S domain with the P2 domain, and the P2 subdomain contains the host receptor binding site which is also a target for neutralizing antibodies. The norovirus enters its host by binding to cell-associated glycans located on the cell membranes, including sialic acid and histo-blood group antigens. Then soluble cofactors facilitate viral binding to its host receptor. For murine norovirus (MNoVv), the receptor is a CD300lf an immunoglobulin (Ig) domain-containing membrane protein, whereas for the feline calicivirus (FCV), the receptor is a feline junctional adhesion molecule A (fJAM-A). However, the receptor for the human norovirus (HNoV) remains elusive. Taking together the highly variable P2 domain in combination of the VP1 protein's ability to inhibit cytokine induction and VP2 protein's capability of regulating antigen presentation and the complex transmission routes makes noroviruses challenging pathogens to combat.

Although vaccines can be effective in protecting against infectious agents, they often take significant time and resources to develop. For example, effective vaccines that can safely be administered to patients require many clinical tests that need to be performed before approval. Secondly, vaccinations only work if the correct antigens for the specific pathogen are being administered with sufficient immunological reaction, creating an immunity for the specific disease [11]. For example, seasonal influenza strains normally vary from one year to the next, and the vaccines usually contain only a few epitopes of different influenza strains, thereby rendering the creation of some vaccinations to an educated guess work.

A vaccination's efficacy is based on, at least in part, administering to the subject a composition comprising epitopes that mimic specific antigens of the said pathogen of interest. Once inside the host, these compositions containing epitopes can be internalized by cells of the host and then at least partly presented via the viral antigen presentation pathway of the immune system. In humans, such an antigen presenting pathway is named human leukocyte antigen (HLA) system and comprises of major histocompatibility complex (MHC) I and II. MHC I pathways can be crucial in stimulating the immune responses in which CD8+ cytotoxic T cells are primed for eliminating virus-infected cells, while the MHC II class is responsible for presenting antigens from the virus or epitopes from an vaccination composition that primes and stimulates B cells in producing antibodies against that specific antigen.

Anti-viral medicine can also be effective against viral infections if treated correctly. However, these medications often interrupt viral DNA or RNA replication machinery, and thus, it is not always plausible to use such medicines as a proactive drug. Unfortunately, these compounds can be harmful for the patient if used under prolonged periods [12]. Antibiotics are effective against the spread of bacteria by disrupting their cell division and/or the synthesis of the proteoglycan-based cell wall [1]. Formulating the most efficient antibiotic depends on if the target bacterium is gram positive (having a cell wall) or gram negative (lacking a cell wall). Recently, there have been numerous cases were multi-resistant bacteria have emerged that are not responding to traditional antibiotics. In these cases, broad spectrum antibiotics have been used to combat infection. However, such strong cocktails of antibiotics can take their toll on the patient and potentially can give rise to more antibiotic resistance bacteria [1]. Therefore, there is an unmet need of developing medications, such as over-the-counter (OTC) drugs and consumer products, that can be used for preventing or reducing the likelihood of the spread of pathogens, including mutating novel coronaviruses, using proactive purposes and having minimal or minor side effects. Also, the use of tailored medicine using carriers (e.g., nanomaterials) loaded with an active pharmaceutical ingredient (API) for both inhibiting the endocytosis of the target pathogen, in particular viruses, as well as stopping the replication of already infected cells and/or tissues.

In addition, according to some embodiments, the immune response includes cytokines produced by the host such as Interferons (IFNs) that have potent or substantially potent antiviral effects. These cytokines are part of the first line of defense against viral infections and have important roles in immunosurveillance. There are two different classes of interferons: type I IFNs and type II IFN. There are many type I interferons, including for example interferon alpha (IFN-α), interferon beta (IFN-β) and interferon epsilon (IFN-ω) whereas there is only one type II interferon named interferon gamma (IFN-γ). Interferon (IFN)-gamma is a critical antiviral mediator central to the elimination of viruses from the host and could be used as an immune modulating drug.

In addition, according to some embodiments, part of the immune response includes activation of innate immune system by the particle (e.g., carrier). Where the particle contains component or components capable at least partly to target dendritic cells (DCs) to aid in the antigen presenting pathway to inform the immune response what to fight against such as invasive pathogens and/or cancerous cells while. The component loaded into or onto the particle can at least partly activate macrophages by engaging for example, pattern-recognition receptors such as Toll-like receptor or receptors (TRL) that is part of the interferon type I secretion pathway.

Protein and proteasome inhibitors show great potential as these compounds can specificity bind and allosterically hinder the enzymatic reaction by binding to the active site blocking the target molecules interaction with the enzyme [13]. However, one of the major drawbacks of proteasome inhibitors is their instability and possible low solubility. Further, due to their high specificity, such molecules often only show efficacy to only a few or one specific enzyme per drug molecule.

Monoclonal antibodies have been used since 1986. The first such drug approved by the FDA was Orthoclone OKT3, which is used for reducing kidney rejection after transplantation. Monoclonal antibodies that are used in cancer therapeutics include trastuzumab (Herceptin), which is a drug that binds to the human epidermal growth factor receptor 2 (HER2) slowing down the growth of malignant HER2 positive breast cancer cells [14]. The major limitation of antibody-based therapeutics is that these proteins are foreign. For example, such therapeutics are produced in mice or other animals so when they are introduced to patients, they can invoke an immunologic reaction, potentially giving adverse reaction of the treatment.

Cells of multicellular organisms, such as humans and animals, need to maintain their cellular homeostasis, which can be a delicate balance or equilibrium that is constantly challenged by disease-causing agents. Disease is more likely to occur when this balance or equilibrium is disrupted or otherwise impacted by one or more disease-causing agents.

In some embodiments, disease causing agents, factors and/or sources include, without limitation, include a pathogen, an infectious agent and/or any other type of disease-causing agent or source, such as, for example, and without limitation, viruses (e.g., SARS-CoV-2 viruses, other coronaviruses, influenza viruses, rhinoviruses, noroviruses, respiratory syncytial viruses (RSV), other viruses that impact the respiratory system, any other type of viruses, etc.), bacteria, parasites (e.g., worms), protozoa, microorganisms, prions, fungi (e.g., molds), allergens, antigens, toxins, poisons (e.g., venoms, pollutants, etc.), carcinogens, compounds or molecules (e.g., organic, inorganic, etc.), chemical agents (e.g., naturally-occurring, synthetic or man-made, etc.), radiation (e.g., electromagnetic radiation, radioactive compounds/materials, other radiation, etc.), enzymes or proteins, regulatory elements and/or substances (e.g., hormones, enzymes, other proteins, DNA/RNA repair elements or agents, replication machinery, chaperone machinery, other host-producing elements or substances, etc.), inflammatory agents, elements or substances and/or the like. Pathogens, infectious agents or other types of disease-causing agents or sources can be internal and/or external to the host's cells.

In some embodiments, internal disease-causing agents, factors and/or sources include, by way of example, enzymes and proteins responsible for correcting or otherwise impacting the cellular homeostasis within the cells. For instance, the disease-causing agents can include DNA-repair machinery enzymes, which are proteins that correct or adjust genetic material, and/or protein folding machinery, which can refold or otherwise adjust incorrectly folded or aggregated proteins. However, in some cases, unwanted changes can occur in such repair machinery, which can result in one or more diseases. For example, in some arrangements, chemical agents, carcinogens and/or radiation can result in mutations to genetic code. This can lead to accumulation of cells and other unwanted results because, for example, repair machinery of cells has become faulty or otherwise impaired, causing diseases or other health issues, such as cancer, immune disorders, etc. In some embodiments, mutations arising from internal or external agents can cause other changes in the cellular homeostasis, leading to, by way of example, excessive cell removal that may cause neurodegenerative diseases, such as, for instance, Huntington's disease and Alzheimer's disease, degenerative disorders of organs (e.g., liver cirrhosis, muscular dystrophies, etc.) and/or any other disease, disorder or other health issue.

Nanomedicine shows great potential in the field of targeted drug delivery, where nanotechnology and medicine are combined for the development of personalized diagnostics, as well as the treatment and prevention of different diseases. In some arrangements, nanomaterials or other carriers include man-made and/or naturally occurring objects with dimensions between 0.2 nm to 100 nm. The physical properties of such materials can be drastically different compared to their bulk counterpart. For example, nanomaterials can be more reactive on both biological and chemical substances due to higher surface area to volume ratio. Functionalized nanoparticles have shown to be able to target specific cell types opening the possibility of targeted drug delivery lowering the off-target effects [15]. Combing these different fields, it would be possible to develop a carrier (e.g., a synthetic particle or object) that mimics (e.g., partially, completely, etc.) the pathogen or pathogens of interest (e.g., viruses, bacteria, other pathogens, etc.) in order to hinder the spread of the disease by competitive inhibition. Further, such carriers can be used to advantageously deliver the appropriate API, drug, molecule and/or other substance or material (e.g., as provided in one or more portions of this specification) to the target tissues with increased efficacy and minimal or reduced side effects. For example, by utilizing such targeting strategies, it is possible to create a carrier that can deliver one or more materials to specific cell populations. In some embodiments, carriers can be loaded with or otherwise include different active molecules used in treating diseases caused by disruptions in the cellular homeostasis.

SUMMARY

According to some embodiments, a synthetic carrier comprises a particle forming a core and having a maximum size in at least one dimension in a nanometer or a micrometer range, and a functionalized surface configured to bind to target areas of cell surfaces of the host, wherein the functionalized surface comprises protruding features that include targeting moieties, wherein the protruding features at least partially mimic protrusions of a disease-causing agent or source, wherein at least one component is loaded into or onto or otherwise included with the carrier, wherein the carrier is configured to bind to specific areas of the host cells for targeted delivery of the at least one component to the host, and wherein the carrier is configured to assist with a treatment of a disease or adverse impact caused by the pathogen or other disease-causing agent or source.

According to some embodiments, the target areas comprise at least one of a receptor, a target molecule, an amino acid and a nucleotide.

According to some embodiments, the disease-causing agent or source comprises a pathogen. In one embodiment, the pathogen comprises a virus (e.g., a coronavirus, a SARS-CoV-2 virus, an influenza virus, a rhinovirus, a norovirus, a respiratory syncytial virus (RSV) and a virus that impacts the respiratory system, another type of virus, etc.).

According to some embodiments, the carrier is made, at least in part, using a bottom-up method or a top-down method of fabrication.

According to some embodiments, the disease causing agent or source comprises one or more of the following: an infectious agent, a pathogen, a virus, a bacterium, a parasite, an antigen, a protein, a prion, a mold, a fungus, a toxin, a poison and an allergen.

According to some embodiments, the carrier is used for personalized treatment or personalized diagnostics related to a disease, infection or allergic reaction or other condition caused by the disease-causing agent or source.

According to some embodiments, the at least one component comprises at least one of the following: an API, a drug, a protein, an amino acid, RNA, DNA and a molecule.

According to some embodiments, the carrier is configured to be delivered to the host using an inhalation device, an aerosol, a spray, a drop, a tablet, a cream, an ointment, an injection or an intravenous administration.

According to some embodiments, the carrier is configured to be delivered to the host using a dispensing device, the dispensing device comprising an inhalation device configured to deliver the carrier to at least a portion of the host's respiratory tract.

According to some embodiments, a method of providing treatment of a host comprises binding a carrier to cell structures of the host to reduce a likelihood of a disease-causing agent or source binding to said cell structures, thereby to at least partially inhibiting the disease-causing agent or source from binding to said cell structures, wherein the carrier comprises a core and a surface functionalized on the core, wherein the functionalized surface is configured to bind to target areas of the cell structures of the host, wherein at least one component is loaded into or onto or otherwise included with the carrier, the carrier being configured for targeted delivery of the at least one component to the host, and wherein the carrier is configured to assist with a treatment of a disease or adverse impact caused by the pathogen or other disease-causing agent or source.

According to some embodiments, a size of the carrier is in the nanometer to micrometer range.

According to some embodiments, the disease-causing agent or source comprises a pathogen. In one embodiment, the pathogen comprises a virus (e.g., a coronavirus, a SARS-CoV-2 virus, an influenza virus, a rhinovirus, a norovirus, a respiratory syncytial virus (RSV) and a virus that impacts the respiratory system, another type of virus, etc.).

According to some embodiments, the carrier is made, at least in part, using a bottom-up method or a top-down method of fabrication.

According to some embodiments, the disease causing agent or source comprises one or more of the following: an infectious agent, a pathogen, a virus, a bacterium, a parasite, an antigen, a protein, a prion, a mold, a fungus, a toxin, a poison and an allergen.

According to some embodiments, the carrier is used for personalized treatment or personalized diagnostics related to a disease, infection or allergic reaction or other condition caused by the disease-causing agent or source.

According to some embodiments, the at least one component comprises at least one of the following: an API, a drug, a protein, an amino acid, RNA, DNA and a molecule.

According to some embodiments, the carrier is configured to be delivered to the host using an inhalation device, an aerosol, a spray, a drop, a tablet, a cream, an ointment, an injection or an intravenous administration.

According to some embodiments, the carrier is configured to be delivered to the host using a dispensing device, the dispensing device comprising an inhalation device configured to deliver the carrier to at least a portion of the host's respiratory tract.

According to some embodiments, a method of providing treatment of a host comprises binding a carrier to cell structures of cells of the host to reduce a likelihood of an agent binding to said cell structures to at least partially inhibits the agent from binding to said cell structures, wherein the carrier comprises a core and a surface functionalized on the core, wherein the functionalized surface bind to target areas of cell structures of the host's cells, and wherein the carrier is to be used as targeted treatment for one or more disease, infections or allergic reactions caused by a disease-causing agent or source.

According to some embodiments, a synthetic carrier comprises a particle forming a core and having a maximum size in at least one dimension in a nanometer or a micrometer range and a functionalized surface capable of binding to target areas of cell surfaces of the host, wherein the functionalized surface features contain targeting moieties protruding from the surface, wherein the protruding surface features at least partially physically mimic naturally-occurring protrusions of the pathogen, wherein the carrier is loaded into or onto with an additive, wherein the carrier is configured to bind to specific areas of the host cells for targeted delivery; the one or more diseases, infections or allergic reactions, and wherein the carrier is to be used as targeted treatment for one or more disease, infections or allergic reactions caused by a disease-causing agent or source.

According to some embodiments, the target areas of the host's cells comprise a receptor, a target molecule, an amino acid and/or a nucleotide.

According to some embodiments, the disease-causing agent or source comprises a pathogen. In some embodiments, the pathogen comprises a virus (e.g., a coronavirus, a SARS-CoV-2 virus, an influenza virus, a rhinovirus, a norovirus, a respiratory syncytial virus (RSV), another virus that impacts the respiratory system, any other type of virus, etc.).

According to some embodiments, the carrier is made, at least in part, using a bottom-up method or a top-down method of fabrication.

According to some embodiments, the disease causing agent or source comprises one or more of the following: an infectious agent, a chemical agent, a pathogen, a virus, a bacterium, a parasite, an antigen, a protein, a prion, a mold, a fungus, a toxin, a poison or an allergen, enzyme, electromagnetic radiation, carcinogens, molecules, hormones, inflammation, other agents, etc.

According to some embodiments, the carrier is used for personalized diagnostics, treatment and/or prevention of one or more diseases, infections or allergic reactions.

According to some embodiments, the one or more diseases, infections or allergic reactions comprises at least one of the following: autoimmunity, inflammation, cancer, diseases caused by imbalance of hormones, neurological disorders, muscle dystrophies, cystic fibrosis, diabetes, rheumatoid arthritis, systemic lupus erythematosus, etc.

According to some embodiments, wherein the carrier further comprises at least one additional component, the at least one additional component comprises at least one of: an API, a drug, a protein, an amino acid, RNA, DNA and a molecule.

According to some embodiments, the carrier is configured to be delivered to the host using an inhalation device, an aerosol, a spray, an eye drop, a tablet, a cream, an ointment or an injection. In some embodiments, the carrier is configured to be delivered to the host using a dispensing device, the dispensing device comprising an inhalation device configured to deliver the carrier to at least a portion of the host's respiratory tract.

According to some embodiments, a method of reducing the spread of infection by a target pathogen in a host comprises binding a carrier to a target areas of the host's cells to reduce a likelihood that the target pathogen binds to the target areas, thereby blocking at least some of the target areas, and providing a gained advantage to the host's immune system to fight a disease caused by the target pathogen, wherein providing the gained advantage comprises decorating the carrier with epitopes to be used as a vaccination at target cell populations.

According to some embodiments, a method of reducing the onset and/or spread of infection by a target pathogen in a host comprises binding a carrier to a target areas of the host's cells to reduce a likelihood that the target pathogen binds to the target areas, and creating an advantage to the host's immune system to fight a disease caused by the target pathogen, wherein creating the advantage comprises decorating the carrier with epitopes or targeting ligands.

According to some embodiments, the target areas of the host's cells comprise a receptor, a target molecule, an amino acid, a nucleotide and/or the like.

According to some embodiments, the carrier comprises a core and a functionalized surface. In some arrangements, the functionalized surface comprises features that mimic surface properties of the target pathogen. In some embodiments, the features comprise protruding structures (e.g., peptide structures in the form of protein spikes, other protruding structures, etc.).

According to some embodiments, the carrier further comprises at least one of an API, a drug, a protein, an amino acid, RNA, DNA, a molecule and/or the like, wherein the at least one of an API, a drug, a protein, an amino acid, RNA, DNA, a molecule and/or the like is configured to reduce the spread of the target pathogen or is configured to hinder replication of the target pathogen inside the host.

According to some embodiments, the carrier further comprises a compound configured to hinder replication of the target pathogen. In some embodiments, the compound comprises an anti-pathogenic compound, an anti-viral compound, an anti-microbial compound and/or any other compound or substance.

According to some embodiments, the target pathogen comprises a virus (e.g., SARS-CoV-2, a coronavirus, influenzas, rhinoviruses, noroviruses, respiratory syncytial virus (RSV), etc.).

According to some embodiments, the carrier is configured to resemble the target pathogen.

According to some embodiments, the carrier can be loaded to a medical device capable of releasing an amount of the carrier to specific tissue of the host. In some embodiments, the specific tissue of the host comprises the host's upper or lower respiratory tract.

According to some embodiments, a carrier for reducing a likelihood of a pathogen binding to cell structures of a host comprises a core having an exterior surface, a plurality of surface features extending from the exterior surface of the core, wherein the surface features are configured to bind to target areas of cell structures of the host, wherein binding of the carrier to at least one of the target areas of cell structures of the host is configured to at least partially block the pathogen from binding to said target areas as a result of competitive inhibition, and wherein the surface features at least partially physically mimic naturally-occurring protrusions of the pathogen, and wherein the surface features are configured to comprise immune stimulating properties, wherein a size of the carrier is in the nanometer to micrometer range (e.g., in the nanometer or micrometer range).

According to some embodiments, a carrier for reducing a likelihood of a pathogen or other disease-causing agent binding to cell structures of a host comprises a core having an exterior surface, a plurality of surface features extending from the exterior surface of the core, wherein the surface features are configured to bind to target areas of cell structures of the host, wherein binding of the carrier to at least one of the target areas of cell structures of the host is configured to at least partially block the pathogen from binding to said target areas as a result of competitive inhibition, and wherein the surface features at least partially physically mimic naturally-occurring protrusions of the pathogen, and wherein the surface features are configured to comprise immune stimulating properties. The carrier further comprises a plurality of binding sites along the exterior surface, wherein the binding sites are configured to attract at least one portion of the pathogen, wherein the binding sites are configured to at least partially mimic binding sites of the cell structures of the host, wherein the binding sites are recognizable by the pathogen or other disease-causing agent and are able to be bound by the pathogen or agent, thereby at least partially immobilizing the pathogen and reducing the likelihood of the pathogen binding to target areas of cell structures of the host, and wherein a size of the carrier is in the nanometer to micrometer range (e.g., in the nanometer or micrometer range).

According to some embodiments, the pathogen comprises a virus. In some embodiments, the virus includes one or more of the following: a coronavirus, SARS-CoV-2 virus, an influenza virus, a rhinovirus, a norovirus, a respiratory syncytial virus (RSV), another virus that impacts the respiratory system and any other type of virus.

According to some embodiments, the pathogen comprises a bacterium, a parasite, an antigen, a prion, a mold, a fungus or an allergen.

According to some embodiments, the naturally-occurring protrusions of the pathogen comprise proteins at the surface of the viral exterior.

According to some embodiments, the carrier is sized, shaped or otherwise configured to reach targeted portions of the host that are susceptible to infection by the pathogen. In some embodiments, the targeted portions of the host that are susceptible to infection by the pathogen comprise the lungs or other area of the host's upper or lower respiratory tract. In some embodiments, the carrier is configured to be delivered via the respiratory tract of the host to the targeted portions of the host that are susceptible to infection by the pathogen.

According to some embodiments, the carrier comprises at least one coating that improves a binding affinity of the carrier to the pathogen relative to a binding affinity of the cell structures of the host to the pathogen.

According to some embodiments, the carrier further comprises at least one component positioned at least partially on and/or within carrier. In some embodiments, the at least one component comprises a pharmaceutical agent (e.g., API). In some embodiments, the pharmaceutical agent comprises at least one of an anti-viral compound, an adjuvant, a nucleic acid and an RNA or DNA sequence. In several embodiments, the adjuvant is selected from the group consisting of potassium alum, aluminum hydroxide, aluminum phosphate, calcium phosphate hydroxide, paraffin oil, peanut oil, inactivated bacteria and/or bacterial products from *Bordetella pertussis*, inactivated bacteria and/or bacterial products from *Mycobacterium bovis*, inactivated bacterial toxoids, monophosphoryl lipid A, saponins (e.g., QS-21), soybean derivatives, senegaroot derivatives, interleukin (IL) 1, IL2, IL12, squalene or squalene-containing compounds, MF59, AS03, and combinations thereof.

According to some embodiments, a carrier for reducing a likelihood of a pathogen or other disease-causing agent binding to cell structures of a host comprises a core, surface features extending from an exterior surface of the core, wherein the surface features are configured to bind to target areas of cell structures of the host to at least partially block the pathogen or other agent from binding to said target areas as a result of competitive inhibition, and wherein the surface features comprise immune stimulating properties.

According to some embodiments, a carrier for reducing a likelihood of a pathogen or other disease-causing agent binding to cell structures of a host comprises a core, surface features extending from an exterior surface of the core, wherein the surface features are configured to bind to target areas of cell structures of the host to at least partially block the pathogen or other agent from binding to said target areas as a result of competitive inhibition, and wherein the surface features comprise immune stimulating properties. The carrier further comprises a plurality of binding sites along the exterior surface, wherein the binding sites are configured to attract at least one portion of the pathogen or other agent, wherein the binding sites are configured to at least partially mimic binding sites of the host, and wherein the binding sites are recognizable by the pathogen or other agent and are able to be bound by the pathogen or other agent, thereby at least partially immobilizing the pathogen or other agent and reducing the likelihood of the pathogen or other agent binding to target areas of cell structures of the host.

According to some embodiments, the pathogen or other disease-causing agent comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus.

According to some embodiments, the pathogen comprises a bacterium, a parasite, an antigen, a prion, a mold, a fungus or an allergen.

According to some embodiments, the carrier is sized, shaped and otherwise configured to reach targeted portions of the host that are susceptible to infection by the pathogen, the targeted portions of the host that are susceptible to infection by the pathogen comprise the lungs or other area of the host's respiratory tract.

According to some embodiments, the carrier is configured to be delivered via a respiratory tract of the host to the targeted portions of the host that are susceptible to infection by the pathogen or other disease-causing agent.

According to some embodiments, the carrier further comprises at least one component positioned at least partially on and/or within carrier (e.g., an anti-viral compound, a nucleic acid, an adjuvant, an RNA or DNA sequence and another pharmaceutical agent, etc.).

In some embodiments, additional adjuvants, other additives and/or modifications to the carriers, adjuvants, particles and/or objects can be used. Examples of adjuvants include, by way of example and without limitation, mineral salts (e.g., aluminum hydroxide, magnesium hydroxide, etc.), cytokines and/or chemokines (e.g., GM-CSF, Type I IFN-alpha, IL-12, etc.), modified microbial antigens (e.g., LT and CT derivatives, monophosphoryl lipid A (MPL), etc.), immunostimulatory oligonucleotides (e.g., CpG motifs), oil emulsions (e.g., MF59, 25 AS02, AS03, Mantanide ISA-51, ISA-720, AF03, etc.), liposomes (e.g., AS01, AS015, etc.), particulate adjuvants (e.g., virosomes, AS04, ISCOMS) and/or any other materials. In some embodiments, such additives and/or modification can help enhance the immunogenic reaction to said carriers, adjuvants, particles and/or objects.

In one embodiment, the additives of the carriers, adjuvants, particles and/or objects include one or more of the following, for example and without limitation, a preservative (e.g., thimerosal, 2-phenoxyethanol, etc.), a stabilizer (e.g., sorbitol, sucrose, glycerol, trehalose, gelatin, urea, etc.), a surfactant (e.g., polysorbate 80, polysorbate 20, etc.) and/or any other enhancing component or other additive.

According to some embodiments, a carrier for reducing a likelihood of a pathogen binding to cell structures of a host comprises a core, surface features extending from an exterior surface of the core, wherein the surface features are configured to bind to target areas of cell structures of the host to at least partially block the pathogen from binding to said target areas as a result of competitive inhibition, and a plurality of binding sites along the exterior surface, thereby at least partially reducing the likelihood of the pathogen binding to target areas of cell structures of the host. According to some embodiments, the pathogen comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus.

According to some embodiments, a carrier for reducing a likelihood of a pathogen or other disease-causing agent binding to cell structures of a host comprises a core, surface features extending from an exterior surface of the core, wherein the surface features are configured to bind to target areas of cell structures of the host to at least partially block the pathogen or other agent from binding to said target areas as a result of competitive inhibition, and a plurality of binding sites along the exterior surface, wherein the binding sites are configured to attract at least one portion of the pathogen or other agent, wherein the binding sites are recognizable by the pathogen or other agent and are able to be bound by the pathogen or other agent, thereby at least partially immobilizing the pathogen or other agent and reducing the likelihood of the pathogen or other agent binding to target areas of cell structures of the host. According to some embodiments, the pathogen comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus.

According to some embodiments, the pathogen or other disease-causing agent comprises a bacterium, a parasite, an antigen, a prion, a mold, a fungus or an allergen. According to some embodiments, the carrier is sized, shaped and otherwise configured to reach targeted portions of the host that are susceptible to infection and/or other impact by the pathogen or other disease-causing agent, the targeted portions of the host that are susceptible to infection and/or other impact by the pathogen or other agent comprise the lungs or other area of the host's respiratory tract. According to some embodiments, the carrier is configured to be delivered via a respiratory tract of the host to the targeted portions of the host that are susceptible to infection or other impact by the pathogen or other agent. According to some embodiments, the carrier further comprises or is accompanied by (e.g., delivered before, with, or after the carrier) at least one component positioned at least partially on and/or within carrier (e.g., an anti-viral compound, a nucleic acid, an RNA or DNA sequence and another pharmaceutical agent (such as an adjuvant), etc.).

According to some embodiments, a method of reducing a spread of pathogens or other disease-causing agents within a host comprises at least partially blocking pathogens or other agents from binding to said target areas as a result of competitive inhibition by delivering a carrier to the host, wherein the carrier comprises a core, surface features extending from an exterior surface of the core, and a plurality of binding sites along the exterior surface, and at least partially immobilizing pathogens or other agents and reducing the likelihood of pathogens or other agents binding to target areas of cell structures of the host by binding the carrier to at least one of the pathogens or agents, wherein the surface features are configured to bind to target areas of cell structures of the host, wherein the surface features at least partially physically mimic naturally-occurring protrusions of the pathogen or other agent, wherein the surface features are configured to comprise immune stimulating properties.

According to some embodiments, a method of reducing a spread of pathogens within a host comprises at least partially blocking pathogens from binding to said target areas as a result of competitive inhibition by delivering a carrier to the host, wherein the carrier comprises a core, surface features extending from an exterior surface of the core, and a plurality of binding sites along the exterior surface, and reducing the likelihood of pathogens binding to target areas of cell structures of the host by competitive inhibition, wherein the surface features at least partially physically mimic naturally-occurring protrusions of the pathogen, wherein the surface features are configured to comprise immune stimulating properties to be delivered to target cell populations and subsequently mounting an efficient immunologic reaction, wherein the binding sites are configured to attract at least one portion of the pathogen, wherein the binding sites are configured to at least partially mimic binding sites of the cell structures of the host, and wherein, and wherein the binding sites are recognizable by the pathogen and are able to be bound by the pathogen.

According to some embodiments, a method of reducing a spread of pathogens within a host comprises at least partially blocking pathogens from binding to said target areas as a result of competitive inhibition by delivering a carrier to the host, wherein the carrier comprises a core, surface features extending from an exterior surface of the core, and a plurality of binding sites along the exterior surface, where the exterior surface at least partially includes specific set of epitopes capable of eliciting an immunological response towards viruses and/or other pathogens.

According to some embodiments, the carrier system described herein is configured to be used as a vaccination at target cell populations where the said epitopes can elicit a B cell response generating specific antibodies and/or T cell response priming and mounting a possible cytotoxic T-cell response against virus and/or other pathogens. Therefore, according to some embodiments, the carrier system described herein is configured to reduce the likelihood of infection of host cells by (1) blocking receptors and/or other binding sites/features of host cells to which viruses and/or other pathogens may bind (e.g., for entry into host cells), (2) delivering immune stimulating properties to target cell populations and by mounting an efficient. In several embodiments, the carrier system is utilized with an adjuvant to enhance the development of an immune response to the virus and/or other pathogens. The adjuvant may be organic or inorganic, depending on the embodiment. In several embodiments, the adjuvant is selected from the group consisting of potassium alum, aluminum hydroxide, aluminum phosphate, calcium phosphate hydroxide, and combinations thereof. An oil, such as paraffin oil or peanut oil may be used in some embodiments. Inactivated bacteria and/or bacterial products may be used in some embodiments, such as *Bordetella pertussis, Mycobacterium bovis*, or inactivated bacterial toxoids, including monophosphoryl lipid A. Plant-derived adjuvants can also be used in some embodiments, such as saponins (e.g., QS-21), soybean derivatives, senega-root derivatives and the like. Cytokines, such as interleukin (IL) 1, IL2 and/or IL12 can be used in some embodiments.

Squalene or squalene-containing adjuvants may also be used, such as MF59 and/or AS03, depending on the embodiment. In some embodiments, additives, preservatives and/or other materials can be used, such as, for example, thimerosal and 2-phenoxyethanol, stabilizers (e.g., sorbitol, sucrose, trehalose, glycerol, purified gelatin, urea, etc.), surfactants (e.g., polysorbate 80, polysorbate 20, etc.) and/or the like.

According to some embodiments, the pathogen comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus.

According to some embodiments, the pathogen comprises a bacterium, a parasite, an antigen, a prion, a mold, a fungus or an allergen.

According to some embodiments, the carrier is sized, shaped and otherwise configured to reach targeted portions of the host that are susceptible to infection by the pathogen, the targeted portions of the host that are susceptible to infection by the pathogen comprise the lungs or other area of the host's respiratory tract.

According to some embodiments, the carrier is configured to be delivered via a respiratory tract of the host to the targeted portions of the host that are susceptible to infection by the pathogen.

According to some embodiments, the carrier further comprises at least one component positioned at least partially on and/or within carrier (e.g., an anti-viral compound, a nucleic acid, an RNA or DNA sequence and another pharmaceutical agent, such as an adjuvant, etc.).

According to some embodiments, a carrier for reducing a likelihood of a pathogen or other disease-causing agent binding to cell structures of a host, the carrier comprising a core having an exterior surface, a plurality of surface features extending from the exterior surface of the core, wherein the surface features are configured to bind to target areas of cell structures of the host, wherein binding of the carrier to at least one of the target areas of cell structures of the host is configured to at least partially block the pathogen or other agent from binding to said target areas as a result of competitive inhibition, wherein the surface features are configured to at least partially physically mimic naturally-occurring protrusions of the pathogen or other agent, and wherein the surface features are configured to comprise immune stimulating properties, and a plurality of binding sites along the exterior surface, thereby at least partially reducing the likelihood of the pathogen binding to target areas of cell structures of the host, and wherein a maximum cross-sectional dimension of the carrier in at least one dimension is in the nanometer to micrometer range (e.g., in the nanometer or micrometer range).

According to some embodiments, a carrier for reducing a likelihood of a pathogen or other disease-causing agent binding to cell structures of a host, the carrier comprising a core having an exterior surface, a plurality of surface features extending from the exterior surface of the core, wherein the surface features are configured to bind to target areas of cell structures of the host, wherein binding of the carrier to at least one of the target areas of cell structures of the host is configured to at least partially block the pathogen or other agent from binding to said target areas as a result of competitive inhibition, wherein the surface features are configured to at least partially physically mimic naturally-occurring protrusions of the pathogen or other agent, and wherein the surface features are configured to comprise immune stimulating properties, and a plurality of binding sites along the exterior surface, wherein the binding sites are configured to attract at least one portion of the pathogen or other agent, wherein the binding sites are configured to at least partially mimic binding sites of the cell structures of the host, wherein the binding sites are recognizable by the pathogen or other agent and are able to be bound by the pathogen or other agent, thereby at least partially immobilizing the pathogen or other agent and reducing the likelihood of the pathogen or other agent binding to target areas of cell structures of the host, and wherein a maximum cross-sectional dimension of the carrier in at least one dimension is in the nanometer to micrometer range (e.g., in the nanometer or micrometer range).

It is an aim of the present application to control and hinder (e.g., slow or prevent) the spread of pathogens and other infectious agents, e.g., viruses, bacteria, parasites, antigens, proteins, prions, toxins, allergens, other substances that are foreign and/or potentially harmful and the like. Specifically, the application provides ways of targeting viruses, such as, for example, influenzas, rhinoviruses, noroviruses, respiratory syncytial virus (RSV), coronaviruses (e.g., SARS-CoV-2, future mutated strains derived from a coronavirus, etc.) and the like, that could otherwise give rise to disease, infections or allergic reactions in the host.

It is an aim of the inventions disclosed herein to decrease the risk of infection (or at least decrease the spread of infection if a host has been infected) by a pathogen or pathogens. As such, various embodiments disclosed herein can be helpful combatting infection and any resulting symptoms and other consequences (e.g., respiratory infection, diarrhea, common cold, cytokine storm, other inflammatory reactions, general discomfort, intubation, other symptoms, death, etc.). Accordingly, various embodiments disclosed herein are configured to, at least partially, resist and otherwise combat the effects of contracting the COVID-19 disease caused by SARS-CoV-2 (e.g., via entry of the virus into a host for a temporary or prolonged duration), to give a targeted treatment for the specific disease caused by the infectious agent, to provide one or more additional benefits or advantages, etc.

Further, it is an aim of the inventions disclosed in the present application to provide a method for preventing the spreading and/or for lowering the infection rate of pathogens, such as SARS-CoV-2, influenzas, rhinoviruses, noroviruses, respiratory syncytial viruses (RSVs) and/or the like, by, at least in part, competitive inhibition using synthesized carriers (e.g., nanomaterials, particles, objects, etc.).

Thus, in one aspect, the inventions disclosed herein include carriers (e.g., synthesized nano- or micro sized materials) that mimic, at least partially, the pathogen or pathogens of interest, such as coronaviruses (e.g., SARS-CoV-2), influenzas, rhinoviruses noroviruses, respiratory syncytial viruses (RSVs) and other viruses (e.g., viruses capable of causing respiratory infection) using surface functionalization to hinder or otherwise lower the likelihood of the infectious agent entering the host. In some embodiments, carriers can be used to target pathogens other than viruses, including without limitation, bacteria, parasites, antigens, prions, mold, fungi, toxins, poisons, and allergens. In some embodiments, this is accomplished, at least in part, by competitive inhibition (e.g., at the cellular level).

It is another aim of the inventions disclosed in the present application to create a carrier (e.g., man-made particle, object, material, etc.) that efficiently binds to the pathogen(s) of interest (e.g., coronavirus) and/or circulating co-receptors (e.g., high-density lipoprotein (HDL) receptor in the blood and other secondary receptors such as the FcγR that affects SARS-CoV-2 infection dynamics by antibody-mediated enhancement (ADE)). Thus, in some embodiments, the carrier at least partially binds to the pathogen or other infectious agent co-receptor of the host and at least partly hinders the receptor mediated viral entry. In some embodiments, the carrier is configured to at least partially inhibit the infectious agent's reproduction capabilities by including appropriate API, thereby reducing the spread of said host organism. In some embodiments, the carriers immune stimulating protrusions make it easier for the host body to identify, engulf and/or eliminate the pathogen and/or pathogen infected cell, resulting in elimination or neutralization of the infectious agent.

It is another aim of the inventions disclosed in the present application to create a carrier (e.g., man-made particle, object, material, etc.) that efficiently binds to the pathogen(s) of interest (e.g., coronavirus) and/or circulating co-receptors (e.g., high-density lipoprotein (HDL) receptor in the blood and other secondary receptors such as the FcγR that affects SARS-CoV-2 infection dynamics by antibody-mediated enhancement (ADE)). Thus, in some embodiments, the carrier at least partially encapsulates and/or immobilizes the pathogen or other infectious agent and at least partly hinders the receptor mediated viral entry. In some embodiments, the carrier is configured to at least partially inhibit the infectious agent's reproduction capabilities, thereby reducing the spread of said host organism. In some embodiments, the carrier makes it easier for the host body to identify, engulf and/or filter the macromolecule holding the pathogen, resulting in elimination or neutralization of the infectious agent.

A synthetic carrier can be used to at least partially prevent or reduce infection of a host by one or more pathogens, such as, for example, influenzas, rhinoviruses, noroviruses, respiratory syncytial viruses (RSVs), corona viruses (e.g., SARS-CoV-2), other viruses or pathogens. In some embodiments, the carrier is configured to bind to target areas of cell surfaces of a host. For example, the carrier can bind to ACE2 receptors, TMPRSS2 receptors, sialic acid, histo-blood group antigens, ICAM-1, IGF1R receptors, intracellular or extracellular receptors, other receptors, or combination of receptors and/or any other portion of the cell structures of the host that may be susceptible to the pathogen. According to some embodiments, a carrier is formed by biocompatible particles having a maximum size in at least one dimension in the nanometer or micrometer range (e.g., a core of the carrier includes a maximum size in at least one dimension in the nanometer or micrometer range). Further, a functionalized surface can be formed on or along a core of the carrier that is capable of binding to said target areas of the cell surfaces of the host to at least temporarily and/or at least partially block the target areas, thereby, at least partially, preventing or minimizing pathogen binding and internalization. Accordingly, the risk of the host being infected or contracting a disease caused by said pathogen, such as a virus, can be beneficially reduced.

In an aspect, the present application provides for loading of synthetic particles (e.g., carriers) with API or molecules, such as for example and without limitation, Celastrol, anti-viral drugs, Zinc and/or immune stimulating molecules such as, for example, Interferon-Gamma modulators alternatively administering RNA vectors encoding Interferon-Gamma producing said protein in the host, anti-viral compounds that prevent the spread of (and/or hinder the replication of) the targeted pathogen or pathogens (e.g., coronavirus, influenzas, rhinovirus, noroviruses, respiratory syncytial virus, etc.) inside the host body and/or the like.

In some embodiments, particles (e.g., carriers) having prophylactic properties include interfering and/or modulating nucleotides, such as for example and without limitation, RNA interference (RNAi), microRNA (miRNA), short hairpin RNA or small hairpin RNA (shRNA), small interfering RNA (siRNA), long non-coding RNA (lncRNA), small nucleolar RNA (snoRNA), Piwi-interacting RNA (piRNA). Such carrier embodiments can help prevent or reduce the spread of (and/or hinder the replication of) the targeted pathogen or pathogens (e.g., coronavirus, influenzas, rhinovirus, noroviruses, respiratory syncytial virus, etc.) inside the host body and/or the like.

It is another aim of the inventions disclosed in the present application to provide a medical device capable of delivering the synthetized carrier, particle, object or other material (e.g., on-demand by the patient or other user). Therefore, in some embodiments, the carrier can be administered to the anatomy by the subject or patient, making the carrier capable of self-administration. For example, in some embodiments, such a medical device comprises an inhalation device, an aerosol, a spray, eye or oral drops, an intravenous injection, a tablet, a topically applicable cream, an ointment or other material.

It is another aim of the inventions disclosed in the present application to provide a medical countermeasure similar to that of chelating agents used in toxifications of metal complexes (e.g., arsenic poisoning, snake venoms, mold toxins, etc.) [16]. In some embodiments, the present inventions provide a functionalized nanomaterial or carrier, which, in some configurations, is effectively an antidote capable of binding toxic components of a specific virus to larger entities that can be metabolized, degraded or secreted from the body and/or capable of binding to viral co-receptors inside the host to minimize or otherwise reduce potential spreading inside the organism [15]. The antidote (e.g., nanomaterial or other carrier) can be inhaled, orally ingested or administered through intravenous injection and/or any other delivery method or technology (e.g., inhalation, ingestion, topical application, etc.), as desired or required.

It is another aim of the inventions in the present application to provide a medical countermeasure similar to that of chelating agents used in toxifications of metal complexes (e.g., arsenic poisoning, snake venoms, mold toxins and the like). In some embodiments, the present inventions provide a carrier (e.g., a functionalized nanomaterial) that acts as an antidote, and is advantageously capable of binding toxic metal complexes, toxins, poisons and/or the like to larger entities that can be metabolized, degraded and/or secreted/otherwise removed from the body [15]. The antidote (e.g., carrier or nanomaterial) could be inhaled, orally ingested, administered to the host using intravenous injection and/or any other delivery method or technology.

In some embodiments, a carrier (e.g., a functionalized nanoparticle) is loaded, coated and/or decorated with an API and/or RNA/DNA and/or other molecules or materials capable of binding to cell structures of the host (e.g., receptors of the host's cell structures) and delivering its cargo or contents to targeted cell population. Beneficially, this can at least partially block or otherwise limit entry of a specific pathogen, such as, for example, influenzas, rhinoviruses, noroviruses, respiratory syncytial viruses, coronaviruses and other viruses causing infection (e.g., in the respiratory tract or other anatomical location). Further the use of such carriers can advantageously provide the capability of releasing certain materials (e.g., APIs, therapeutics, other molecules, etc.) to the host thereby minimizing or at least reducing the spread of the infectious agent.

According to some embodiments, the present application discloses a carrier (e.g., a polymeric or protein/peptide functionalized nano and/or micro particle) that is loaded with one or more anti-viral molecules capable of binding to one or more receptors and/or other portions of a host cell structure (e.g., ACE2 and/or TMPRSS2 receptors, sialic acid, histo-blood group antigens, ICAM-1, IGF1R receptors, other receptors in humans that at least partially hinder (e.g., allosterically hinder) the targeted virus or other pathogen (e.g., influenza, rhinovirus, norovirus, respiratory syncytial virus, SARS-CoV-2 or another corona virus) from binding to its target receptor). As a result, the risk of infecting the host can be reduced, e.g., for a limited or prolonged duration.

Certain advantages are obtainable as a result of the present inventions, as carriers (e.g., nanoparticles, other particles or objects, etc.) can be synthetized using different materials and/or functionalized (or otherwise configured) with virtually endless combinations of features and/or functionality. In some embodiments, the carriers include mesoporous silica nanoparticles (MSNs) or other inorganic silica-based materials which have shown great potential for targeted drug delivery. For example, MSNs can have tunable ordered repetitive mesostructures of pores that can be loaded with different drugs and/or other components or materials. In some arrangements, such carriers or particles can be synthesized in various sizes, shapes and/or other configurations, as desired or required for its particular purpose or application. Furthermore, inorganic silica materials, such as MSNs, are safe, biocompatible, stable, customizable and versatile. For instance, inorganic silica materials have been given a Generally Recognized As Safe (GRAS) designation by the FDA as silica degrades in aqueous solution to silicic acid and gets excreted or otherwise removed (e.g., via the urine), and is, therefore, considered biocompatible [15]. In some embodiments, since MSNs and other inorganic silica-based materials have been proved to be a versatile delivery vehicle with beneficial features and properties (e.g., improved stability, large surface area, tunable pore sizes and volumes, capable easy encapsulation of drugs, proteins, biogenic molecules, etc.), they are well suited to be used in carriers.

In some embodiments, the carriers comprise lipid-based micelles (e.g., forming the cores of the carriers). Such carriers can be provided by synthetizing, for example, cholesterol based lipid particles decorated with SARS-CoV-2 spike protein fragments that bind both to ACE2 and TMPRSS2 as well as to cholesterol and its high-density lipoprotein (HDL) scavenger receptor B type 1 (SR-B1) and/or FcγR receptor. These co-receptors can facilitate ACE2-dependent entry of the carrier (e.g., the envisioned nanoparticle) loaded with one or more selected APIs for combating a targeted disease (e.g., COVID-19 disease). In some embodiments, advantageously, by creating a carrier (e.g., a nanoparticle and/or microparticle) that competes with the spike protein-HDL interaction, the ability of SARS-CoV-2 for ACE2-mediated internalization is lowered and viral entry to host cells is blocked and replication hindered.

In some embodiments, the carriers comprise solid lipid particles synthetized by microfluidics and/or protein-based particles such as ferritin-based particles that self-assembly decorated or conjugated with viral mimicking protrusion capable of both binding to the target receptor and stimulating the host immune system against the said virus.

In some embodiments, carriers comprise quantum nanoparticles (e.g., as a core). Such quantum particles or carriers once decorated or otherwise provided with the desired surface features (e.g., SARS-CoV-2 or other viral spike protein receptor binding domain (RBD)) can be capable of binding to ACE2 receptors, other receptors and/or other binding sites of the host cell structure. Accordingly, such carriers can be internalized (e.g., by ACE2-GFP HEK293T cells after a certain time period, for example, approximately 3 hours), thereby validating that it is possible to produce man-made virus-like particles that efficiently bind and are internalized by target cells. Furthermore, protein-lipid entities, such as Dalbavancin, an antibiotic, can bind to the ACE2 receptor (or another receptor or binding site) to prevent or reduce the likelihood that the targeted pathogen (e.g., SARS-CoV-2) is able to enter its host via intervening viral-receptor interactions.

In some arrangements, carriers (e.g., nano-sized and/or micro-sized materials) are synthesized that mimic (e.g., accurately, approximately) the targeted pathogen by using, for example, the known size, morphology, surface properties and/or other properties of the infectious agent. Thus, a man-made carrier (e.g., particle, object) can be produced that at least partially hinders or otherwise mitigates the spread of the disease caused by the target infectious agent (e.g., virus, bacterium, other pathogen) by competitive inhibition. In some embodiments, such man-made carriers (e.g., particles, materials, etc.) are configured to (i) bind to receptors or other binding sites of host cell structures, thereby blocking the attachment of pathogens to such receptors or binding sites and preventing (or lowering the likelihood of) the infectious agent from entry into the cell structure, and (ii) the mimicking protrusion of the carrier elicits and immune response against said infectious agent. Accordingly, the carrier embodiments disclosed herein and equivalents thereof provide two possible approaches to reducing infection of a host's cells, and as such, have immense potential in different applications in medicine, drug development, medical devices, consumer, sanitation products and/or the like.

In some arrangements, carriers (e.g., nano-sized and/or micro-sized materials) are synthesized that mimic (e.g., accurately, approximately) the targeted pathogen by using, for example, the known size, morphology, surface properties and/or other properties of the infectious agent. Thus, a man-made carrier (e.g., particle, object) can be produced that at least partially hinders or otherwise mitigates the spread of the disease caused by the target infectious agent (e.g., virus, bacterium, other pathogen) by competitive inhibition. In some embodiments, such man-made carriers (e.g., particles, materials, etc.) are configured to (i) bind to receptors or other binding sites of host cell structures, thereby blocking the attachment of pathogens to such receptors or binding sites and preventing (or lowering the likelihood of) the infectious agent from entry into the cell structure and/or (ii) bind to the infectious agent itself thus immobilizing the threat caused by the infection agent. Accordingly, the carrier embodiments disclosed herein and equivalents thereof provide two possible approaches to reducing infection of a host's cells, and as such, have immense potential in different applications in medicine, drug development, medical devices, consumer, sanitation products and/or the like.

According to some embodiments, it is possible to synthetize nano-sized and/or micro-sized materials (e.g., carriers, particles, objects) that mimic, at least partially, targeted viruses or other pathogens (e.g., SARS-CoV-2 virus, the spread of which resulted in a global epidemic starting in 2020, pandemic strain/type of the influenzas, rhinoviruses, noroviruses, respiratory syncytial viruses, coronaviruses (including mutated forms thereof) derived from SARS-CoV-2, other viruses, other pathogens, etc.) by using the known size, morphology, surface properties and/or other characteristics or properties of the targeted virus or other pathogen. Thus, carriers (e.g., man-made particles or objects) can beneficially hinder or at least slow the spread of the disease by competitive inhibition.

In some embodiments, such carriers (e.g., man-made materials) are designed and otherwise configured to bind to surface receptors, co-receptors and/or other binding sites of a host cell structure, and thereby blocking, at least partially, the entry of the virus or other pathogen. In some arrangements, in addition to binding to host cell structures (and thus at least partially blocking or preventing the attachment of a pathogen to said host cell structures) and by immune stimulating the host of said pathogen, carriers are configured to simultaneously administer or otherwise deliver APIs and/or other materials. Such APIs and/or other materials delivered to target cells and tissues can be configured to create an environment that is hostile to viral replication and that provides a synergistic approach to the host. Such carriers and the associated methods of treatment can have immense potential in different applications in medicine, drug development, medical devices, consumer products and the like. In some embodiments, for instance, adding Zinc ions, Celastrol Cannabinols, anti-viral molecules, other APIs and/or other substances or materials to the nanoparticle or other carrier, it would be possible to create an environment for at least partially arresting the viral replication cycle inside host cells (e.g., cells that are expressing ACE2 receptors or other targeted receptors on their cell surface).

In some embodiments, such carriers (e.g., man-made materials) are designed and otherwise configured to bind to surface receptors, co-receptors and/or other binding sites of a host cell structure, and thereby blocking, at least partially, the entry of the virus, other pathogen or other disease-causing agent. In some arrangements, in addition to binding to host cell structures (and thus at least partially blocking or preventing the attachment of a pathogen to said host cell structures) and/or immobilizing the pathogen or other agent by binding to the pathogen or other agent itself, carriers are configured to simultaneously administer or otherwise deliver APIs and/or other materials. Such APIs and/or other materials delivered to target cells and tissues can be configured to create an environment that is hostile to replication (e.g., viral replication) and that provides a synergistic approach to the host. Such carriers and the associated methods of treatment can have immense potential in different applications in medicine, drug development, medical devices, consumer products and the like. In some embodiments, for instance, adding Zinc ions, Celastrol Cannabinols, anti-viral molecules, other APIs and/or other substances or materials to the nanoparticle or other carrier, it would be possible to create an environment for at least partially arresting the viral replication cycle inside host cells (e.g., cells that are expressing ACE2 receptors or other targeted receptors on their cell surface).

In some embodiments, a carrier (e.g., a synthetic nanoparticle and/or microparticle) can be used to reduce the spread of influenzas, rhinoviruses, noroviruses, respiratory syncytial viruses (RSVs), coronaviruses (e.g., SARS-CoV-2, other derived coronaviruses), other viruses that cause symptoms such as respiratory infection, diarrhea, common cold, cytokine storm, general discomfort, serious illness, death and/or any other viruses or other pathogens. To that end, in some embodiments, the synthetic particles or other carriers can be manufactured to match, imitate, emulate or substantially match, imitate or emulate one or more characteristics or other properties of one or more targeted pathogens (such as, for example, influenzas, rhinoviruses, noroviruses, respiratory syncytial viruses (RSVs), coronaviruses (e.g., SARS- CoV-2 virus) and/or any other viruses or other pathogens). More specifically, according to some arrangements, the particle or carrier is preferably fabricated to a size of around 10 to 200 nm, for example 50 to 150 nm (such as around 100 to 120 nm), 10 to 200 nm, 10 to 100 nm, 100 to 200 nm, 50 to 200 nm, 10 to 150 nm, values between the foregoing values and ranges).

Further, in some embodiments, the carriers can be coated with similar amino acids and peptides as the targeted virus and/or other pathogen. For example, in some embodiments, the carrier can contain glycoprotein spike proteins, other protrusions, similar molecules and/or other surface features. In some embodiments, such features of the carrier can be configured to mimic or substantially mimic certain surface features of the viral envelope. More specifically, in some embodiments, the particle is preferably fabricated to a size of around 100-120 nm and coated with similar amino acids and peptides as the virus contains, for example, glycoprotein spikes, protrusions and/or other features at the viral surface or similar molecules that mimic the surface of the viral envelope. In some embodiments, the carrier (e.g., particle or object) is fabricated to a size of around 100 nm (e.g., 80 to 120 nm, 90 to 110 nm, 100 nm, values between the foregoing, etc.) and is coated with similar amino acids and peptides as the targeted virus or other pathogen (e.g., glycoprotein spikes and/or protrusions at the viral surface or similar molecules that mimic the surface of the viral envelope). In more specific embodiments, the carrier (e.g., object or particle) is fabricated to a size of around 0.2 to 100 nm and coated with similar amino acids and peptides as the virus contains e.g., protrusions at the viral surface.

Further, in some embodiments, carriers are coated and/or otherwise functionalized with amino acids and/or peptides similar to those of a targeted virus and/or other pathogen for targeted drug delivery. The carrier can be loaded with one or more materials, such as, for example, an API, a drug, a protein, an amino acid, RNA, DNA, a molecule and/or the like (e.g., any other materials disclosed in this specification). In some embodiments, the carrier (loaded with one or more materials) is configured to provide a targeted treatment for a specific disease or other health issue caused by the disease causing agent or other agent. In some arrangements, the carrier is configured to release one or more materials loaded on and/or within the carrier to target cells with reduced off-target effects or impacts.

In some embodiments, carriers (e.g., man-made materials) that mimic, at least partially, certain features and/or other aspects of a targeted virus and/or other pathogen for targeted drug delivery can increase the drug accumulation at target tissue with minimal or reduced off-target effects or other impacts. This can be due to, at least in part, the carrier having an enhanced or "high" uptake in specific cells that have the specific receptors to which the carrier binds. In some embodiments, the binding of the carrier is partly due to the functionalization properties enabling binding to the target receptor that initiates the endocytosis of the carrier that can be loaded with specific APIs. In some embodiments, such a specific endocytosis at targeted tissues increases the therapeutic window and improves the therapeutic index of the specific API. Many APIs and/or other components have relatively poor solubility and/or permeability that makes such compounds difficult to administer to the host. Using a carrier that can be loaded with APIs and/or other components that mimic or substantially mimic, at least partially, a pathogen to be used as an "trojan horse" could increase the therapeutic window of such compounds. The targeting embodiments disclosed herein or variation thereof can be classified in to either active or passive targeting. Passive targeting commonly refers to non-functionalized carriers (e.g., particles, objects, etc.) that usually accumulate in the liver and spleen for clearance. Whereas active targeting commonly refers to functionalized carriers (e.g., particles, objects, etc.) that enable active uptake of carriers at target site. Functionalizing carriers surfaces with an active targeting ligand can, in some embodiments, improve or otherwise enhance drug accumulation at the target site and lower drug accumulation at unwanted off-target sites. In some embodiments, this can minimize or reduce possible side effects.

In some embodiments, carriers (e.g., man-made materials) that mimic, at least partially, certain features and/or other aspects of a targeted virus and/or other pathogen for targeted drug delivery can be loaded into or onto with additional components, API, drug, chemicals, protein, peptides or any combination thereof. The loading degree depends on the material used in the carrier for example silica based carriers with mesopores can be loaded inside the pores with hydrophobic drugs. Whereas polymer based carriers are capable of being loaded with hydrophilic drugs such as Poly(Lactic Acid) based micelles. Whereas lipid based particles such as solid lipid particles can be loaded with either hydrophobic components in the lipid components or hydrophilic components inside the particle hollow core.

In some embodiments, the amount of one or more additional components (e.g., APIs, drugs, chemicals, proteins, peptides, other materials and/or any combination thereof, etc.) loaded into or onto the carrier is 0.1 to 40 percent by weight (% weight or % wt) of the carrier (e.g., 0.1 to 40, 0.1 to 5, 5 to 10, 0.1 to 10, 10 to 20, 20 to 30, 30 to 40, 10 to 40, 10 to 30, 15 to 40, 20 to 40, 30 to 40, 5 to 30%, values between the foregoing ranges and values, etc.). In some embodiments, the core comprises a lipid core, which in some embodiments, allows for a greater "loading" of a carrier with an additional component. In some embodiments, the carrier is configured to be loaded with more than 5% by weight of one or more component relative to the carrier (e.g., at least 5%, at least 10%, at least 15%, at least 20%, at least 25%, at least 30%, at least 40%, at least 50%, more than at least 50%, values between the foregoing, etc.).

Next, certain embodiments will be described in more detail.

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

FIG. 7 shows an example of a SARS-CoV-2 spike RBD expression construct. Different expression cassettes (shown as the XXX region) can be used for expressing the desired construct e.g., influenza H7 haemagglutinin (indicated as "Signal sequence"), Tag, spacer, and SARS-CoV-2 RBD.

DETAILED DESCRIPTION

Figure 1:
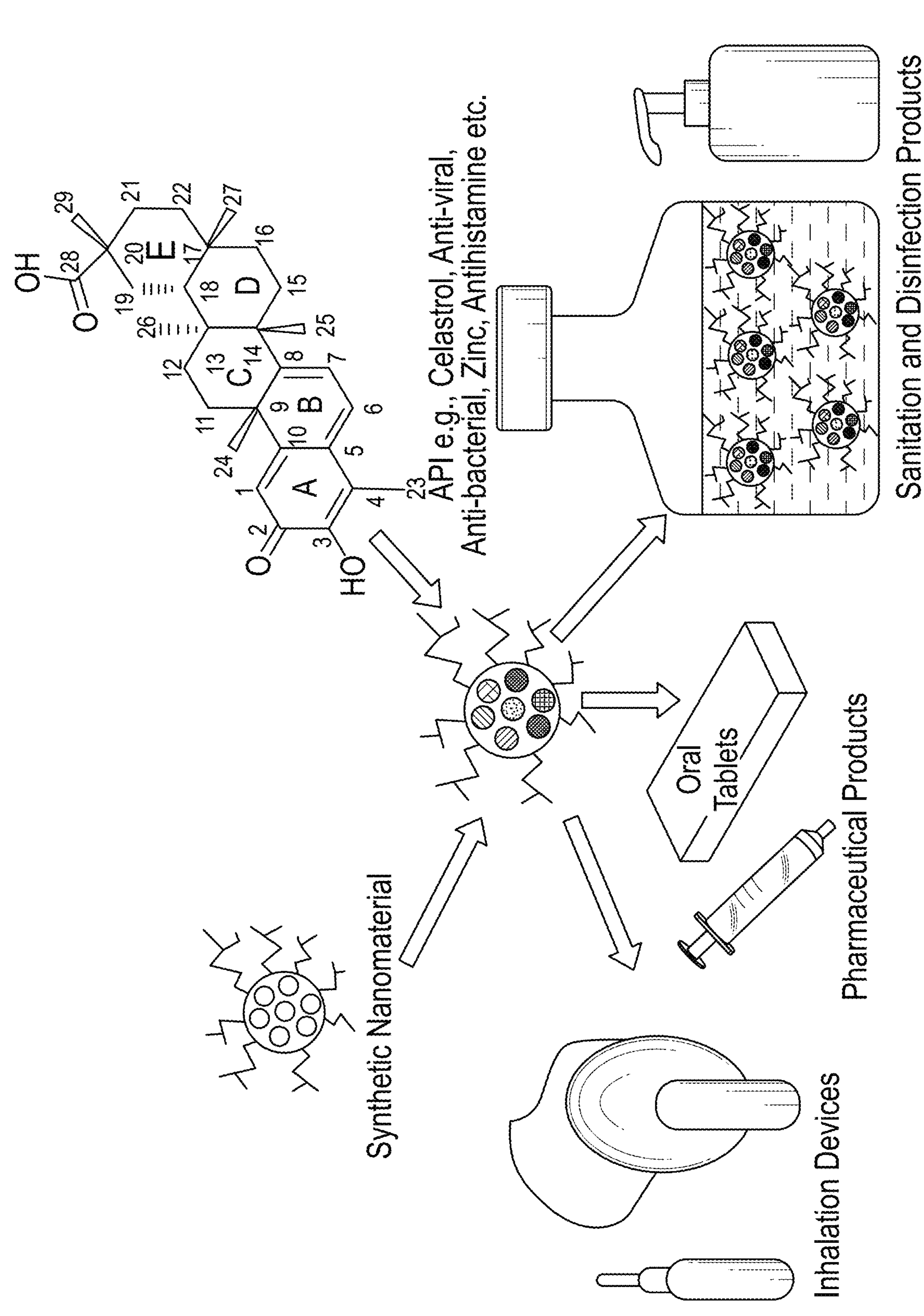
FIG. 1 is a schematic depiction of different applications of synthetized nanomaterials according to some embodiments of the present technology.

In the present context, the term "around" means, when used in connection with numerical values, that a variation of ±25%, in particular ±20%, for example ±10%, or ±5%, of the exact value is included by a literal reading of that value.

In the present context, the term "about" means, when used in connection with numerical values, that a variation of ±25%, in particular ±20%, for example ±10%, or ±5%, of the exact value is included by a literal reading of that value.

The term "polymer" is used herein in a broad sense and refers to materials, compounds, amino acids and proteins characterized by repeating moieties or units.

The term "functionalization" is used herein in a broad sense and refers to conjugating, coating, covalently and/or otherwise adding (e.g., allosterically adding) materials, compounds, drugs, amino acids and/or proteins to the synthetized particle or object.

The term "biocompatible" refers herein to "the ability of a material to perform with an appropriate host response in a specific application" (e.g., William's definition) [19].

The term "therapeutic window" as used herein, refers to the dosage range between a minimum effective therapeutic concentration and the minimum toxic concentration.

The term "therapeutic index" (also referred to as therapeutic ratio) as used herein, is a quantitative measurement of the relative safety of a drug. The ratio of the dose that exerts toxicity in 50% of the population (TD50) divided by the dose that exerts a therapeutic response (ED50) in 50% of the population (TI=TD50/ED50). For clarification, a higher therapeutic index is preferable to a lower one for API, drugs and components to be given to the host, as it means, for example, a greater likelihood of successful outcomes (e.g., with respect to combating an infection, a disease, etc.).

Nanomaterials and nanomedicine can be classified according to the targeting strategies used, which can include, for instance, active or passive targeting. In some embodiments, passive targeting utilizes non-functionalized particles for accumulation in organs and tissues that are responsible for clearance of foreign objects such as macrophages, e.g., in the liver, spleen, etc. In some arrangements, tumor microenvironments typically show an enhanced permeability and retention effect (EPR), which can be a consequence of leaky and fenestrated blood vessels around tumors. Active targeting, on the other hand, uses a targeting ligand or functionalization that enhances the accumulation of the carrier at target site [15].

There are virtually endless functionalization possibilities by covalently attaching, adhering, saturating or binding (e.g., allosterically binding) molecules, polymers, proteins, amino acids, compounds and/or drugs onto the nanomaterial for achieving active targeting. One of the major advantages of functionalizing a smaller molecule to a larger entity, e.g., proteins, epitopes, amino acid sequences or hydrophobic molecules to a nanomaterial, is to increase the combined objects stability and/or solubility and/or possible minimize the unwanted immunologic reaction [15].

Described herein are carriers (e.g., fabricated nanomaterials or other carriers) used for inhibiting or improving the ability to inhibit, at least partially, pathogen entry of certain pathogens or other unwanted organisms, in particular coronaviruses (e.g., SARS-CoV-2), influenzas, rhinoviruses, noroviruses, respiratory syncytial viruses and other viruses causing respiratory infection to the host organism. Accordingly, such nanomaterials or other carriers can be advantageously used to limit or reduce the replication and spread of a disease or virus.

Embodiments disclosed herein have capabilities of carrying or otherwise delivering or providing anti-pathogenic pharmaceuticals or other materials, such as anti-viral drugs, in the carrier (e.g., nanomaterial) to reduce the replication and growth of the infectious agent.

As discussed, any of the carrier embodiments disclosed herein can be configured to deliver or otherwise provide one or more materials to cells of a subject, such as, for example, drugs, pharmaceuticals, APIs, viscosity modulators, antihistamines, immunosuppressors other molecules, compounds, substances, materials, etc. to give targeted treatment for one or more specific diseases, disorders and/or other health issues (e.g., caused by a pathogen, other disease causing agent, etc.).

Embodiments disclosed herein pertain to the fabrication of man-made (e.g., fabricated) carriers or materials (e.g., in the nano- and/or microscale) that are configured to at least partially saturate and bind to receptors, proteins and/or macromolecules at the cellular level in order to reduce the likelihood (e.g., prevent) and reduce (e.g., minimize) pathogens or other disease-causing agents (e.g., coronavirus) binding to and/or entering into receptors and/or target tissues of the host. In some embodiments, the synthesized carrier (e.g., nanomaterial) can be stored and loaded onto a medical device capable of releasing (e.g., on-demand, specific amounts) the synthesized carrier system to specific tissue. Such medical devices or other devices or systems include, without limitation, inhalation devices, oral tablets, injectable substances, lotions or creams and/or any other device, system or component, as desired or required.

In one aspect or embodiment, a synthetic carrier, particle or object is configured to at least partially hinder or impede the spread of the COVID-19 disease by competitive inhibition and to deliver an API, drug or molecule to targeted cells and/or tissues with increased or improved efficacy. In some embodiments, the use of such carriers, particles or objects is configured to have few or minimal side effects for creating a hostile environment for the virus or other targeted pathogen. According to some arrangements, the carrier or particle (e.g., the mimetic nanoparticle) is functionalized with, in one non-limiting example, hexapeptide resembling that of the RBD from SARS-CoV-2. This can, according to some embodiments, allow high binding affinity to the ACE2 receptor at the lining of the respiratory system, thus blocking, at least partially, a route (e.g., a primary route) of infection. In some embodiments, this approach virtually eliminates the problem associated with mutations of the viral strain, because the specific target is the human receptor and not the constantly evolving coronavirus. This may be especially significant, for instance, in light of the impactful SARS-CoV-2 mutations that have appeared starting in 2021 and beyond, which have and will have a significant impact on the state of world health. In some embodiments, alternatively or simultaneously, ACE2 receptor binding moieties or antibodies designed to bind and immobilize the virus at specific sites can be used.

Therefore, in some embodiments, as noted above and discussed in greater detail herein, carriers (e.g., particles, obstacles, etc.) are configured to prevent or reduce the likelihood of infection by pathogens or other disease-causing agents using one or more principles or mechanisms. For example, in some arrangements, the carriers are sized, shaped and otherwise configured to prevent or reduce the likelihood of negative health impacts (e.g., pathogen infection) by competitive inhibition (e.g., blocking receptors).

In another aspect or embodiment, a carrier (e.g., a synthetic particle or object) is configured to deliver its "cargo" or content to targeted cell population (e.g., for targeted treatment of a disease, disorder, ailment or other health issue, to target specific pathogens and/or disease-causing agents or sources, etc.). For example, in some arrangements, the carrier comprises a core material that can be "loaded" or otherwise provided with (e.g., into or onto) drugs, API and/or other molecules or materials. Such substances provided in and/or on the carrier can be targeted with higher efficacy to specific cells and tissues using, for example, functionalization (e.g., protrusions that are capable of binding to host cell structures such as receptors that facilitates carrier uptake at said cells enabling targeted therapeutics). Thus, potentially, the therapeutic effect of the drug can be improved, increased or otherwise enhanced, e.g., by accumulating the local dosage in specific cells, reducing at least some side-effects of the drug (e.g., by reducing off-target effect in unwanted cells and/or the like).

Therefore, in some embodiments, as noted above and discussed in greater detail herein, carriers can be "loaded" or otherwise provided with (e.g., into or onto) one or more of the following: a drug, an API, a mineral, another molecule or material used to at least partially reduce or alleviate symptoms, the progression, discomfort and/or other issues caused by an disease causing agent or source. In some embodiments, disease causing agents or sources include, but are not limited to, viruses (e.g., SARS-CoV-2 viruses, other coronaviruses, influenza viruses, rhinoviruses, noroviruses, respiratory syncytial viruses (RSV), other viruses that impact the respiratory system, any other type of viruses, etc.), bacteria, parasites (e.g., worms), protozoa, microorganisms, prions, fungi (e.g., molds), allergens, antigens, toxins, poisons (e.g., venoms, pollutants, etc.), carcinogens, compounds or molecules (e.g., organic, inorganic, etc.), chemical agents (e.g., naturally-occurring, synthetic or man-made, etc.), radiation (e.g., electromagnetic radiation, radioactive compounds/materials, other radiation, etc.), enzymes or proteins, regulatory elements and/or substances (e.g., hormones, enzymes, other proteins, DNA/RNA repair elements or agents, replication machinery, chaperone machinery, other host-producing elements or substances, etc.), inflammatory agents, elements or substances and/or the like. In some embodiments, the disease caused by the disease-causing agents or sources include, by way of example, inflammation local or systemic or both, neurodegenerative diseases, autoimmune diseases (e.g., psoriatic arthritis, rheumatoid arthritis (RA), Sjögren's syndrome, Systemic lupus erythematosus (e.g., Lupus, SLE), cancer (e.g., bladder cancer, breast cancer, colon cancer, rectal cancer, endometrial cancer, kidney cancer, leukemia, liver cancer, lung cancer, melanoma, Non-Hodgkin lymphoma, pancreatic cancer, prostate cancer, thyroid cancer, any other type of cancer, etc.), muscle dystrophies, cystic fibrosis, diabetes, rheumatoid arthritis, diseases caused by imbalance of hormones (e.g., hormone imbalance, infertility, acne, metabolism, thyroid disease, etc.) and/or any other type of disease, ailment, syndrome and/or condition.

In some embodiments, the carrier is loaded with or otherwise comprises one or more materials (as noted in the preceding paragraph and/or other portions of this specification) that the carrier can advantageously deliver to target tissues, cells and/or areas or portions of the subject's anatomy with increased efficacy and with reduced side effects. This can help create an environment in which disease progression or other negative health issue is at least partially haltered or otherwise attenuated. As noted herein, in some arrangements, the size of the carrier (e.g., the particle or object) is similar or substantially similar to the size of the virus or other pathogen or other disease-causing agent being targeted. For example, a diameter or other cross-sectional dimension of the carrier can be 50% to 200% (e.g., 50-200, 50-100, 50-150, 50-200, 100-150, 150-200%, values and ranges between the foregoing, etc.) of the diameter or other cross-sectional dimension of a targeted pathogen and/or agent (e.g., influenza, other virus or pathogen, other disease-causing agent or source, etc.).

The following tables provide certain non-limiting examples of materials that can be delivered to portions of a subject's anatomy using a carrier for targeted treatment (e.g., for combatting the effects or other impacts of certain pathogens or disease-causing agents or sources, to help with the symptoms and/or other impacts of a disease, disorder or other health-related issue, etc.). The information included in the tables below (and/or information included in other portions of the application) is not intended to be inclusive of all possible uses of the embodiments disclosed herein. Accordingly, there may be additional and/or different particles or carriers, anatomical locations, diseases and/or conditions, purposes, advantages and/or benefits, modes of delivery and/or the like that exist which are not explicitly listed herein. Further, it should be understood that a particular carrier or set of carriers can be used to target more than one disease and/or condition, to provide more than one purpose, benefit and/or advantage and/or the like. Relatedly, a carrier can be delivered (e.g., simultaneously, non-simultaneously, etc.) to more than one anatomical location.

| Target delivery location of carrier (at least in part) | Disease/condition that is at least partially prevented, treated, combatted and/or otherwise impacted to benefit a recipient (not intended to be exhaustive of all diseases/conditions) | Other purposes/benefits/advantages (not intended to be exhaustive of all purposes/benefits/advantages) |
|---|---|---|
| Lungs/respiratory tract (e.g., upper respiratory tract, lower respiratory tract, etc.) | Infection by pathogens | Therapeutic, preventative/prophylactic, vaccine |
| Intravascular system | Infection by pathogens | Therapeutic, preventative/prophylactic, vaccine |
| Tissues (e.g., muscle, fat, connective tissues, bones, skin, etc.) | Infection by pathogens | Therapeutic, preventative/prophylactic, vaccine |
| Organs (e.g., solid organs (e.g., liver, pancreas, spleen, kidneys, adrenal glands, etc.), hollow organs (e.g., stomach, intestines, gallbladder, bladder, rectum, etc.), etc.) | Infection by pathogens | Therapeutic, preventative/prophylactic, vaccine |
| Lungs/respiratory tract (e.g., upper respiratory tract, lower respiratory tract, etc.) | Cancer (e.g., caused by mutating agents and/or mutations in the germline) | Therapeutic, preventative/prophylactic, vaccine |
| Intravascular system | Cancer (e.g., caused by mutating agents and/or mutations in the germline) | Therapeutic, preventative/prophylactic, vaccine |
| Tissues and connective organs | Cancer (e.g., caused by mutating agents and/or mutations in the germline) | Therapeutic, preventative/prophylactic, vaccine |
| Organs (e.g., solid organs (e.g., liver, pancreas, spleen, kidneys, adrenal glands, etc.), hollow organs (e.g., stomach, intestines, gallbladder, bladder, rectum, etc.), etc.) | Cancer (e.g., caused by mutating agents and/or mutations in the germline) | Therapeutic, preventative/prophylactic, vaccine |
| Lungs/respiratory tract (e.g., upper respiratory tract, lower respiratory tract, etc.) | Cellular imbalances and/or deficiencies | Therapeutic, preventative/prophylactic, vaccine |
| Intravascular system | Cellular imbalances and/or deficiencies | Therapeutic, preventative/prophylactic, vaccine |
| Tissues: muscle, fat, connective tissues, bones, skin, etc. | Cellular imbalances and/or deficiencies | Therapeutic, preventative/prophylactic, vaccine |
| Organs (e.g., solid organs (e.g., liver, pancreas, spleen, kidneys, adrenal glands, etc.), hollow organs (e.g., stomach, intestines, gallbladder, bladder, rectum, etc.), etc.) | Cellular imbalances and/or deficiencies | Therapeutic, preventative/prophylactic, vaccine |
| Lungs/respiratory tract (e.g., upper respiratory tract, lower respiratory tract, etc.) | Fibrosis, other scars and aggregates, etc. | Therapeutic, preventative/prophylactic, vaccine |
| Intravascular system | Fibrosis, other scars and aggregates, etc. | Therapeutic, preventative/prophylactic, vaccine |
| Tissues (e.g., muscle, fat, connective tissues, bones, skin, etc.) | Fibrosis, and other scars and aggregates, etc. | Therapeutic, preventative/prophylactic, vaccine |
| Organs (e.g., solid organs (e.g., liver, pancreas, spleen, kidneys, adrenal glands, etc.), hollow organs (e.g., stomach, intestines, gallbladder, bladder, rectum, etc.), etc.) | Fibrosis, other scars and aggregates, etc. | Therapeutic, preventative/prophylactic, vaccine |

-continued

| | | |
|---|---|---|
| Lungs/respiratory tract (e.g., upper respiratory tract, lower respiratory tract, etc.) | Metabolic disorders or diseases | Therapeutic, preventative/prophylactic, vaccine |
| Intravascular system | Metabolic disorders or diseases | Therapeutic, preventative/prophylactic, vaccine |
| Tissues (muscle, fat, connective tissues, bones, skin, etc.) | Metabolic disorders or diseases | Therapeutic, preventative/prophylactic, vaccine |
| Organs (e.g., solid organs (e.g., liver, pancreas, spleen, kidneys, adrenal glands, etc.), hollow organs (e.g., stomach, intestines, gallbladder, bladder, rectum, etc.), etc.) | Metabolic disorders or diseases | Therapeutic, preventative/prophylactic, vaccine |
| Material (either alone or with one or more other material(s)) | | |
| Anti-pathogenic | Infection (e.g., viral infection, bacterial infection, infection caused by other pathogens, microorganisms or sources, etc.) | Therapeutic, preventative/prophylactic, vaccine |
| Anti-Viral | Infection (e.g., viral infection) | Therapeutic, preventative/prophylactic, vaccine |
| Anti-bacterial | Infection (e.g., bacterial infection) | Therapeutic, preventative/prophylactic, vaccine |
| Anti-parasitic | Infection (e.g., parasitic infection) | Therapeutic, preventative/prophylactic, vaccine |
| Anti-fungal | Infection (e.g., fungal infection) | Therapeutic, preventative/prophylactic, vaccine |
| Minerals, vitamins and/or supplements | Infection (e.g., viral infection, bacterial infection, infection caused by other pathogens, microorganisms or sources, etc.) | Therapeutic, preventative/prophylactic, vaccine |
| Minerals, vitamins and/or supplements | Cellular imbalances | Therapeutic, preventative/prophylactic, vaccine |
| Minerals, vitamins and/or supplements, etc. | Deficiencies | Therapeutic, preventative/prophylactic, vaccine |
| Dilating drugs, nitro glycerin, vasodilating beta blockers, etc. | Hypoxemia-caused conditions and/or diseases | Therapeutic, preventative/prophylactic, vaccine |
| Immune modulating drugs, viscosity modulators, bronchodilators, etc. | Fibrosis, other scars, obstructions and aggregates, etc. | Therapeutic, preventative/prophylactic, vaccine |
| Cancer drugs and medications, chemotherapy, hormone therapy, immunotherapy, pain killers, immune modulating drugs, etc. | Cancer | Therapeutic, preventative/prophylactic, vaccine |
| Neurodegenerative drugs, protein aggregation modulating drugs, chaperons, etc. | Neurodegenerative disorders and diseases | Therapeutic, preventative/prophylactic, vaccine |
| Metabolic steroids, metabolic drugs, insulin, etc. | Help prevent, cure and/or otherwise treat or target metabolic disorders | Therapeutic, preventative/prophylactic, vaccine |

In another aspect or embodiment, a carrier (e.g., a synthetic particle or object) is configured to hinder, at least partially, the spread of influenza or the "flu" by competitive inhibition of virus entry. As noted above, in some arrangements, the size of the carrier (e.g., the particle or object) is similar or substantially similar to the size of the virus or other pathogen being targeted. For example, a diameter or other cross-sectional dimension of the carrier can be 50% to 200% (e.g., 50-200, 50-100, 50-150, 50-200, 100-150, 150-200%, values and ranges between the foregoing, etc.) of the diameter or other cross-sectional dimension of influenza or other targeted virus or pathogen.

In some embodiments, the carrier is loaded with or otherwise comprises an API, drug, molecule and/or other materials to be delivered to target cells and tissues with increased efficacy and with minimal or reduced side effects, while creating a hostile environment for the virus. However, in other arrangements, the carrier (e.g., particle or object) does not contain any API, drug or other molecule that is intended to be delivered to targeted cells and tissues. Even in such embodiments, the carriers or particles can be configured to reduce the likelihood of infection (e.g., by preventing the actual virus from binding to and infecting targeted cells of the host). This can be accomplished by, at least in part, blocking receptors (or other binding sites or portions) of host cells. The mimetic carrier or particle can be functionalized with, for example and without limitation, protein fragments resembling HA and NA binding moiety. In such embodiments, high binding affinity to the host sialic acid receptors at the lining of the respiratory system if facilitated, thereby at least partially blocking a route (e.g., the primary route) of infection. Additionally, in some embodiments, the protrusions are at least partially capable of electing or configured to elect an immune response against said pathogen.

In another aspect, a carrier (e.g., a synthetic particle or object) mimics (or is configured or adapted to mimic), for example, Rhinoviruses in order to hinder, at least partially, the spread of the major causative agent of the common cold by competitive inhibition. In some embodiments, the appropriate API, drug or molecule is delivered to target cells and tissues with increased efficacy and with minimal or reduced side effects while creating a hostile environment for the virus. The mimetic particle (e.g., carrier) can be functionalized with, for example, but not limited to, VP1 and VP2 capsid protein allowing high binding affinity to the ICAM-1 and other related receptors at the lining of the respiratory system. Thus, the primary route of infection can be, at least partially, blocked. Additionally, in some embodiments, the protrusions are at least partially capable of electing or configured to elect an immune response against said pathogen.

In another aspect, a carrier (e.g., a synthetic particle or object) mimics (or is configured to mimic), at least approximately or substantially, respiratory syncytial virus (RSV) in order to hinder, at least partially, the spread of influenza or the "flu," a respiratory disease, by competitive inhibition. In some embodiments, with the use of such carriers, the appropriate (e.g., desired, required, etc.) API, drug or molecule is delivered to target cells and tissues with increased efficacy and with minimal or reduced side effects while creating a hostile environment for the virus. The envisioned carrier (e.g., mimetic particle or object) functionalized with, for example and without limitation, receptor attachment protruding glycoprotein (G) allowing high binding affinity to the IGF1R receptor at the lining of the respiratory system. Accordingly, such a carrier can be configured to block, at least partially, the primary route of infection. Additionally, in some embodiments, the protrusions are at least partially capable of electing or configured to elect an immune response against said pathogen.

In another aspect, a carrier (e.g., a synthetic particle or object) mimics or is configured or adapted to mimic) Noroviruses. In such embodiments, the carrier can hinder, at least partially, the spread of "stomach flu" a gastroenteritis disease by competitive inhibition. In some embodiments, with the use of such carriers, the appropriate (e.g., desired, required, etc.) API, drug or molecule is delivered to the target cells and tissues with increased efficacy and with minimal or reduced side effects while creating a hostile environment for the virus. The carrier (e.g., the envisioned mimetic particle) functionalized with, for example and without limitation, VP1 containing the P2 subdomain allowing high binding affinity to the including sialic acid and histo-blood group antigens at the lining of the respiratory system. Thus, the carriers can block, at least partially, the primary route of infection. Additionally, in some embodiments, the protrusions are at least partially capable of electing or configured to elect an immune response against said pathogen.

FIG. 1 schematically shows some non-limiting applications of synthetized carriers (e.g., nanomaterials, objects, particles, etc.) according to some embodiments of the present technology. Thus, by way of an example, the carrier (e.g., nanomaterial) can be loaded with one or more active pharmaceutical ingredients (API), such as, e.g., Celastrol, Zinc, anti-viral compounds, Interferon-Gamma modulators, etc., and then used in inhalation devices, oral tablets or injectables, or other devices or tools of administering the carriers, to name just a few. Such nanomaterials and/or micromaterials can be used to hinder, at least partially, the entry of novel coronaviruses within host cells, thereby reducing or minimizing the spreading of the disease.

Embodiments disclosed herein allow for decreasing the risk of a pathogen or pathogens, such as coronaviruses, influenzas, rhinoviruses, other viruses causing respiratory infection (e.g., SARS-CoV-2), entering its host for a temporary or prolonged duration. Accordingly, such embodiments can advantageously give a targeted treatment for the specific disease caused by the infectious agent.

In a first embodiment, a synthetic carrier is provided, which comprises biocompatible particles having a maximum size in at least one dimension in the nanometer or micrometer range. In some embodiments, said maximum size in at least one dimension is 10 to 500 nanometers (e.g., 10 to 500, 10 to 50, 10 to 100, 50 to 100, 1 to 100, 100 to 200, 200 to 300, 300 to 400, 400 to 500, 200 to 400 nanometers, values and ranges between the foregoing, etc.). In some embodiments, such carriers form or include a core and include a functionalized surface capable of binding to target areas of cell surfaces of a host. Advantageously, such binding can at least temporarily block the target areas to prevent or minimize pathogens (e.g., influenzas, rhinoviruses, coronaviruses including but not limited to SARS-CoV-2, other viruses causing respiratory infection, thereby reducing the risk of the host contracting the disease caused by the pathogen (e.g., the COVID-19 disease, diarrhea, respiratory infections, common cold, etc.).

In one embodiment, a carrier (e.g., a synthetic carrier) comprises biocompatible particles having a maximum size in at least one dimension in the nanometer or micrometer range. In some embodiments, said maximum size in at least one dimension is 10 to 500 nanometers (e.g., 10 to 500, 10 to 50, 10 to 100, 50 to 100, 1 to 100, 100 to 200, 200 to 300, 300 to 400, 400 to 500, 200 to 400 nanometers, values and ranges between the foregoing, etc.). In some embodiments, such carriers comprise (e.g., include or form) a core and a functionalized surface configured to at least partially bind to target areas of cell surfaces of a host. Advantageously, such carriers can be utilized for targeted drug delivery.

As used herein, the term "host" means, but is not necessarily limited to, an individual mammal, in particular a human or an animal.

Figure 2:
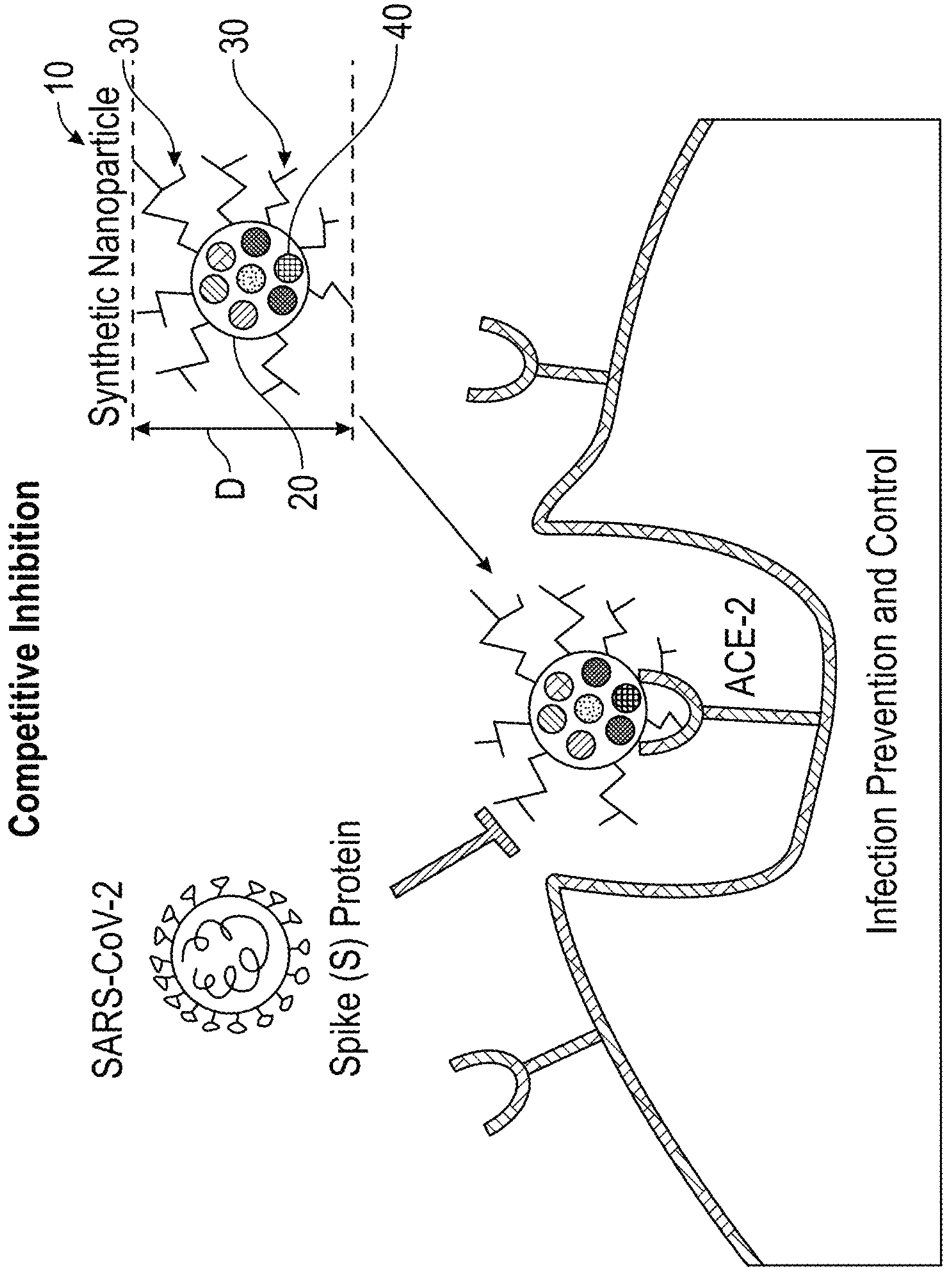
FIG. 2 is a schematic depiction of infection prevention and control by competitive inhibition using synthetic nanoparticles according to some embodiments of the present technology.

As schematically illustrated in FIG. 2, in some embodiments, the carrier 10 comprises a core 20 and a plurality of surface features 30 related to the core. As disclosed herein, the surface features can include protrusions that resemble or mimic, at least partially, spike proteins or other protrusions or features of a target virus or other pathogen. With continued reference to FIG. 2, the carrier 10 can be "loaded" or otherwise provided with one or more materials or other substances (e.g., APIs, other pharmaceuticals or agents, etc.) 40. As disclosed herein, such materials 40 can be delivered by the carrier to or near the site of a targeted virus or other pathogen for improved treatment (e.g., therapeutic treatment, infection prevention or mitigation, etc.).

In some embodiments, the synthetic carrier comprises a "nano" material which can be of nano- or micrometer or larger size. In some arrangements, the synthetic carrier has a size in at least one dimension which is in the nanometer scale. In some arrangements, the synthetic carrier has a size in at least one dimension which is in the micrometer scale. For example, such a size in at least one dimension is schematically depicted in FIG. 2 as dimension D. In other embodiments, the carrier has a size in at least one dimension that is outside the nanometer or micrometer range, as desired or required. For instance, the carrier can have a size in at least one dimension which is smaller than one nanometer (e.g., in the picometer range or smaller) or greater than one millimeter, depending on the targeted pathogen or other factors. The nanomaterial or other synthetic carrier can be formed as a particle, spheroid, cubical, cigar-shaped, elongated, triangle, sharp and pointy, a sheet and film and/or any configuration or shape.

According to some embodiments, a maximum cross-sectional dimension of the core 20 of the carrier 10 is 10% to 1000% (e.g., 10 to 1000, 500 to 1000, 10 to 500, 50 to 150, 10 to 300, 100 to 500, 10 to 100, 75 to 125%, values between the foregoing, etc.) of a maximum cross-sectional dimension of the pathogen (e.g., virus, bacterium, other pathogen, etc.).

In some embodiments, the synthetic carrier has a maximum size in at least one dimension which is smaller than 2500 μm (e.g., less than 2500 μm, less than 2000 μm, less than 1500 μm, less than 1000 μm, less than 500 μm, less than 100 μm, less than 50 μm, less than values between the foregoing, etc.). In one embodiment, the material has a maximum size in at least one dimension which is smaller than 10 μm (e.g., less than 10 μm, less than 5 μm, less than 1 μm, less than values between the foregoing, etc.). In one embodiment, the material in particular nanomaterial has a maximum size in at least one dimension which is smaller than 1000 nm, in particular smaller than around 500 nm or around 100 nm or smaller than around 10 nm or smaller than around 0.2 nm.

In one embodiment, the synthetic carrier is biocompatible. For example, according to some arrangements, such a material is configured to cause no reaction or only a minor unwanted reaction in the end-user (e.g., toxicity, off-target effects, etc.).

Generally, in some embodiments, the carriers disclosed herein are synthetic, which is used interchangeably with "synthesized" to denote that they are man-made or non-natural.

Embodiments of the carriers comprise organic or inorganic materials, protein based, ferritin protein particles, lipid droplets, micelles, solid lipids, or any combination of these.

The synthetic material can be selected from inorganic and organic, monomeric and polymeric materials capable of forming biocompatible nano- or micro-sized particles as explained herein.

Examples of materials for the carriers comprise one or more of the following: synthetic polymers (e.g., thermoplastic or thermosetting materials, such as polyolefins, polyesters, including biodegradable polyesters (e.g., polylactides, polycaprolactones, etc.), polyamides, polyimides, polynitriles, etc.). Further non-limiting examples of possible materials include, for example and without limitation, silica, polysiloxanes, silicone materials which optionally may contain organic and metal residues, and/or the like. In some embodiments, silica particles are preferred, but not in all embodiments.

According to some embodiments, the carrier comprises amino acids, proteins, salts and minerals and/or similar molecules or materials, as desired or required.

In one embodiment, the material, which forms the core structure of the carrier, is manufactured or otherwise obtained using one or more of the following: 3D printing, microfluidics, sol-gel methods (e.g., bottom-up methods or top-down methods of fabrication), genetically engineered organism producing specific proteins or amino acids that can either self-assembly such as ferritin protein particles or conjugate to larger entities any other method or technique, and/or combinations thereof.

In one embodiment, the core material comprises one or more materials, such as, for example, mesoporous silica nanoparticles with ordered mesostructures of pores. Such pores can be loaded with different drugs. The most common methods for drug loading to particles is either by physical adsorption using a highly saturated drug solution (e.g., a hydrophobic solvent such as cyclohexane with a hydrophobic drug) or an aqueous solution for water-soluble drugs. In some embodiments, loading further includes covalently conjugating the molecule to the particle surface using, for example, thiol chemistry and/or attracting the cargo molecule by having a different charge than the particle (e.g., particles having a positive charge which will allow loading of negatively charged drug, RNA/DNA molecules).

The carriers (e.g., particles or objects) disclosed herein can be synthetized in various sizes and shapes. In one embodiment, the material forming the core of the carrier contains pores with diameters between 1 and 75 nm, such as, for example, 2 to 50 nm, 2.5 to 30 nm, 2 to 5.5 nm, other values or ranges within the foregoing. In some embodiments, determining the hydrodynamic size using dynamic light scattering (DLS) makes it possible to confirm redispersibility of particle. In some arrangements, the morphology and particle diameter can be measured by either scanning electron microscope (SEM) or transmission electron microscopy (TEM). In order to determine surface area, pore size and pore volume, N2-sorption measurements can be used. The size and volume of the of the mesopores can be detected using small angle X-ray (SAXRD), according to some embodiments. The drug loading is, in some embodiments, measured by Thermogravimetric analysis (TGA) and alternatively or additionally measured by UV/vis spectroscopy measurements at a wavelength of 425 nm. Any alternative method or technology of forming the carriers and/or determining measurements can be used, either in addition to or in lieu of those disclosed herein, as desired or required.

In one embodiment, the core material comprises mesoporous silica nanoparticles (MSNs).

In one embodiment, the material compromises a nanoparticle core with coated targeting ligands with a possibility of (or configured to allow for) loading the particle with API, drugs, molecules, proteins and amino acids, RNA or DNA and compounds of interest.

In one embodiment, the material compromises a nanoparticle core and/or microparticle core with coated and/or functionalized targeting ligands with a possibility of (or configured to allow for) loading the particle into or onto with API, drugs, molecules, proteins and amino acids, RNA or DNA and compounds of interest.

Thus, in one embodiment, a nano and/or micro sized particle for example solid lipid particle (e.g., palmitate-based or stearylamine and the matrix lipid Compritol) having a net positive charge can be decorated/coated with negative molecules, such as RNA or DNA encoding for example interferon gamma for targeted delivery.

Thus, in one embodiment, the nanomaterial compromises a core particle or object functionalized with targeting moieties, drugs, amino acids, protein or any combination thereof, such as hybrid materials containing but not limited to 1,2-Dioleoyl-3-trimethylammonium propane (DOTAP), Cholesterol (Chol), Dioleoylphosphatidylethanolamine (DOPE) and/or 1,2-Distearoyl-sn-glycero-3-phosphorylethanolamine (DSPE), polyethylene glycol (PEG) (e.g., DOTAP:Chol:DOPE:PEG or DOTAP:Chol:DSPE:PEG) loaded with, for example and without limitation, RNA and/or DNA. In some embodiments, the object is preferably loaded with an active substance, drug or API.

In some embodiments of the present application and the technologies disclosed herein, two ways of synthetizing nanomaterials or other carriers are in particular employed. These include the top-down and the bottom-up approach or hybrid approach where some of the particle components are done with one approach and another component with another approach. In other embodiments, however, carriers can be synthesized or otherwise manufactured using other methods or approaches, as desired or required.

In the top-down approach, for example, the building materials have larger dimensions than the final product, which means that the materials undergo physical stresses, such as, e.g., grinding, milling etc., in order to be reduced in size. This process can lead to surface imperfections that could give rise to some variations in the final product that affect particle distribution in the host and binding kinetics.

In some embodiments, the bottom-up method starts by using smaller building blocks in solution transforming gradually to the final product, which can provide a more cost-efficient way of producing nanomaterials and/or micromaterials. Common bottom-up methods include, for example, co-precipitation, template synthesis and sol-gel method where the building blocks are often copolymers, colloids and liquid crystals and self-assembling components such as ferritin protein particles.

The carrier or particle system comprising of a core and functionalization can be characterized, in some arrangements, using Scanning electron microscopy and/or electron microscopy to confirm the size, monodispersity, morphology and non-agglomerated state of the particles. In some embodiments, to find (e.g., accurately, approximately) the amount of drug loading in the particle if the drug is fluorescent, particles can be dispersed in ethanol for complete drug elution. The concentration of drug can be determined by UV/vis spectroscopy measurements at a wavelength of 425 nm, for example with Celastrol. In some embodiments, from such measurements, the drug loading amount can be calculated or approximated. The mesoscopic ordering of the particles can be detected by powder-XRD using a Kratky compact small-angle system or similar X-ray diffraction (XRD) methods. In some embodiments, the hydrodynamic size of the particles can be determined by dynamic light scattering, and the mesoporosity by nitrogen sorption measurements. Thermogravimetric analysis can be used in order to estimate the amount of Polyethyleneimines (PEI), sugar motifs, folic acid (FA) or methotrexate (MTX) or other organic content functionalized to the particle. In some embodiments, thermogravimetric analysis can be used to estimate the amount of organic contact or other molecule and/or drug content functionalized to the particle.

In one embodiment, inhibiting the spread of the virus SARS-CoV-2, influenza, rhinovirus, other viruses causing respiratory infection and/or any other virus includes using a carrier (e.g., a mesoporous silica nanoparticle, lipid nanoparticle, protein-based nanoparticle or any combination thereof with similar size as the virus). In some embodiments, such nanoparticles or other carriers are configured to be strategically provided or otherwise administered to a host in one or more ways (e.g., via inhalation, oral ingestion, intravenous injection, topical application, etc.), as desired or required. In some arrangements, the carriers (e.g., nanoparticles) include a size of 1 to 200 nm (e.g., 1 to 200, 10 to 120, 50 to 100, 90 to 110, 100 nm, values between the foregoing ranges, etc.). In some embodiments, the carriers include a size of 0.01 to 1000 nm (e.g., 0.01 to 1000, 10 to 1000, 50 to 1000, 100 to 1000, 1 to 500, 500 to 1000, 200 to 800, 400 to 600 nm, values between the foregoing ranges, etc.). In some embodiments, the carriers include a size of 0.2 to 100 nm (e.g., 0.2 to 100, 1 to 10, 2 to 20, 5 to 50, 10 to 100 nm, values between the foregoing ranges, etc.). Further, the nanoparticles can be fabricated using the bottom-up sol-gel method or top-down method.

A carrier in accordance with any of the embodiments disclosed herein can be configured to mitigate or otherwise reduce the progression of one or more diseases, disorders and/or other health-related symptoms, complications or other issues caused by one or more disease-causing agents or sources. The carrier can include a nanoparticle, a mesoporous silica nanoparticle, lipid nanoparticle, protein-based nanoparticle or any combination thereof). The carrier can include a similar or substantially similar size as the target pathogen or other disease-causing agent or source. The carrier can further include protrusions and/or other surface features, which can mimic, at least in part, protrusions and/or surface features of the targeted pathogen or disease-causing agent or source. In some embodiments, as discussed throughout this application, the carrier is configured to be strategically provided or otherwise administered to a host in one or more ways (e.g., via inhalation, oral ingestion, intravenous injection, topical application, etc.), as desired or required. In some arrangements, a diameter or other cross-sectional dimension of the carriers (e.g., nanoparticles) is 1 to 200 nm (e.g., 1 to 200, 10 to 120, 50 to 100, 90 to 110, 100 nm, values between the foregoing ranges, etc.). In some embodiments, the diameter or other cross-sectional dimension of the carriers is 0.01 to 1000 nm (e.g., 0.01 to 1000, 10 to 1000, 50 to 1000, 100 to 1000, 1 to 500, 500 to 1000, 200 to 800, 400 to 600 nm, values between the foregoing ranges, etc.). In some embodiments, the diameter or other cross-sectional dimension of the carrier is 0.2 to 100 nm (e.g., 0.2 to 100, 1 to 10, 2 to 20, 5 to 50, 10 to 100 nm, values between the foregoing ranges, etc.). The diameters or cross-sectional dimensions provided above can be the maximum diameter or cross-sectional dimension of the carrier. Alternatively, the diameters or other cross-sectional dimensions of the carrier can be the average or mean diameter or cross-sectional dimension of the carrier. Further, the carrier can be fabricated using the bottom-up (e.g., sol-gel) method or top-down method.

In some embodiments, by using known viral genetic information, such as known viral (e.g., coronaviral, influenza viral, rhinoviral and/or other viral, etc.) genetic information, it is possible to produce similar peptides present in targeted viruses. For example, peptides or other structures can be similar or substantially similar to those found in viral glycoprotein spikes and/or protein protrusions, thus, in some arrangements, mimicking (e.g., at least substantially or approximately) at least some of the viral surface properties that assist with the binding of the carrier to certain receptors (e.g., ACE2 N-terminal helix or sialic acid, histo-blood group antigens, ICAM-1, IGF1R, other target receptors ACE2, etc.). In some arrangements, the carrier can include amino acid sequences found in the viral receptor binding domain (RBD) or the viral receptor binding motif (RBM) in the S protein, HA or NA or VP other decorated proteins that could be used or functionalizing the particle with similar (e.g., substantially similar) or identical peptides. Alternatively or additionally, the carrier's ability to at least partially inhibit entry of viruses can be enhanced by including organic polymers as part of the protrusion (e.g., of cationic polyamidoamine dendrimer (PAMAM)) or by predicting an amino acid sequence or polymer for producing a surface coating which is similar in surface charge as the viral surface or by attaching targeting motifs which are known to bind to the target receptor allowing selective internalization in target cells [6-9,20].

In one embodiment, the carriers disclosed in the present application or variations thereof comprise mesoporous silica particles. In some embodiments, such carriers preferably include a spherical or substantially spherical form or shape. In some arrangements, the particles or other carriers are provided with a plurality of protruding (e.g., relative to a spherical or substantially spherical core) peptide structures in the form of protein spikes or protein fragments/protrusions on their surfaces. In some embodiments, each of the particles include 5 to 500 protruding peptide structures (e.g., 5 to 500, 0 to 100, 100 to 200, 200 to 300, 300 to 400, 400 to 500, 100 to 500, 200 to 500, 300 to 500, 0 to 200, 0 to 300, 0 to 400, 0 to 500, values between the foregoing ranges and values, etc.). In some embodiments, each of the particles include 1 to 1000 protruding peptide structures (e.g., 1 to 1000, 0 to 100, 100 to 200, 200 to 300, 300 to 400, 400 to 500, 100 to 500, 200 to 500, 300 to 500, 100 to 600, 200 to 600, 300 to 600, 400 to 600, 500 to 600, 100 to 700, 200 to 700, 300 to 700, 400 to 700, 500 to 700, 600 to 700, 100 to 800, 200 to 800, 300 to 800, 400 to 800, 500 to 800, 600 to 800, 700 to 800, 100 to 900, 200 to 900, 300 to 900, 400 to 900, 500 to 900, 600 to 900, 700 to 900, 800 to 900, 100 to 1000, 200 to 1000, 300 to 1000, 400 to 1000, 500 to 1000, 600 to 1000, 700 to 1000, 800 to 1000, 900 to 1000, 0 to 200, 0 to 300, 0 to 400, 0 to 500, 0 to 600, 0 to 700, 0 to 800, 0 to 900, 0 to 1000, values between the foregoing ranges and values, etc.).

In one embodiment, the surface features or other members that protrude from a core of the carrier (e.g., spikes) have a length of about 1 to 200 nm (e.g., 1 to 200, 1 to 100, 2 to 80, 5 to 50, 20 to 100, 50 to 100, 100 to 200 nm, values between the foregoing, etc.). In some embodiments, the surface features or other members that protrude from a core of the carrier (e.g., spikes) have a length of 0.2 to 100 nm (e.g., 0.2 to 100, 1 to 10, 2 to 20, 5 to 50, 10 to 100 nm, values between the foregoing ranges, etc.). In some embodiments, the length includes the actual length of a spike or other protrusion is the total liner length of such a spike or protrusion. However, in other embodiments, the length includes the distance from the spherical or other core of the carrier to the outermost radial distance of the protrusion.

In some embodiments, allowing the carrier (e.g., synthetic particle) to compete with viral particles, such as coronaviruses (e.g., the SARS-CoV-2 virus, variants thereof, etc.), influenzas, rhinoviruses, Respiratory Syncytial Viruses (RSVs), noroviruses, other viruses, etc.) for the same receptor and/or other binding site or portion of a host cell (e.g., ACE2, sialic acid, histo-blood group antigens, ICAM-1, IGF1R receptor, etc.) can function as a hindrance and/or other obstacle (e.g., allosteric regulation or hinder, other competitive or non-competitive inhibition, etc.) for the viral particle to bind to the receptor or other site or portion. This can advantageously minimize or reduce the likelihood of endocytosis of the virus or other pathogen, thereby lowering the risk of infecting the host cell.

One embodiment of the principle of competitive inhibition is schematically illustrated in FIG. 2. As shown, by way of an example, in some embodiments, a host receptor (e.g., ACE2) is responsible for mediating the SARS-CoV-2 infection responsible for coronavirus disease 19 (e.g., COVID-19). In some configurations, by binding carriers (e.g., the novel synthetic nanoparticles, other particles, objects, etc.) to that reception site (e.g., receptor), to the specific host receptors motifs and/or other any other site or portions of the host cell, infection (e.g., caused by the SARS-CoV-2 viruses, other viruses, etc.) can be advantageously prevented, controlled and/or otherwise mitigated.

With continued reference to FIG. 2, by way of an example, a host receptor (e.g., ACE2) responsible for mediating the infection resulting in a specific disease is generally depicted (schematically). In some embodiments, by binding a carrier (e.g., a novel synthetic particle, object, etc.) to that specific area or to the specific host receptors motifs, the infection caused by the specific virus, viruses and/or other pathogen can be prevented and controlled (e.g., the likelihood of infection can be reduced or otherwise mitigated, etc.). The competitive inhibition can be utilized against different viruses and/or other pathogens (such as, for example and without limitation, influenzas, rhinoviruses, RSVs, noroviruses, other respiratory and gastrointestinal viruses, other viruses or pathogens, etc.).

Based on, for example, the foregoing, in an embodiment, carriers (e.g., synthetic nanoparticles, other particles, etc.) are selected such that they resemble, at least partially, coronaviruses (e.g., SARS-CoV-2), influenzas, rhinoviruses, noroviruses, other common cold viruses and/or any other viruses or pathogens, as desired or required. In some embodiments, preferably, synthetic nanoparticles are enhanced or otherwise optimized, at least partially, for competitive inhibition. For example, the particle morphology, size, surface properties and/or any other properties or features of such particles can be modified to achieve higher (or otherwise improve) affinity for the target receptor angiotensin converting enzyme 2 (ACE2) and/or TMPRSS2, sialic acid, histo-blood group antigens, ICAM-1, IGF1R or other target receptors. Thus, the binding affinity for the specific receptor can be advantageously increased, thereby blocking the internalization of the viral envelope more efficiently and potentially prolonging the gained viral protection [8-10].

A carrier system as described herein, wherein the carrier (e.g., synthetic nanoparticle, other particle or object, etc.) resembling a targeted virus (e.g., the SARS-CoV-2, other corona or spiked viruses, influenza, rhinoviruses, noroviruses, other common cold viruses, etc.) can be enhanced or optimized for personalized medicine as variations and mutations in individuals might give rise to slightly different target receptors. Thus, the surface properties and functionalization of the carrier can be changed to match or substantially match the individual properties (e.g., mutations or variations) in target receptors and/or other binding sites or locations of a host cell for tailored therapies.

Figure 4A:
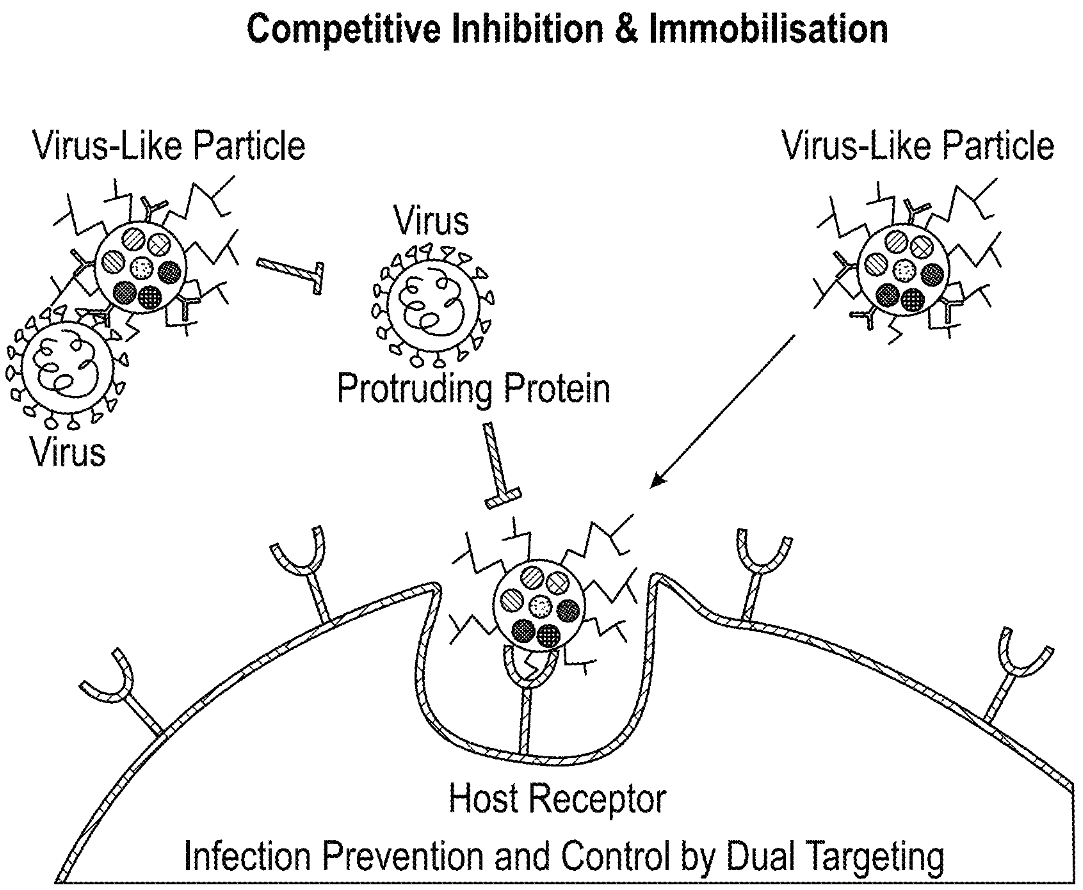
FIG. 4A is a schematic depiction of dual targeting strategy compromising both immobilization of an infectious agent and by infection prevention and control by competitive inhibition functionalized nanomaterials according to some embodiments of the present technology.
Figure 4B:
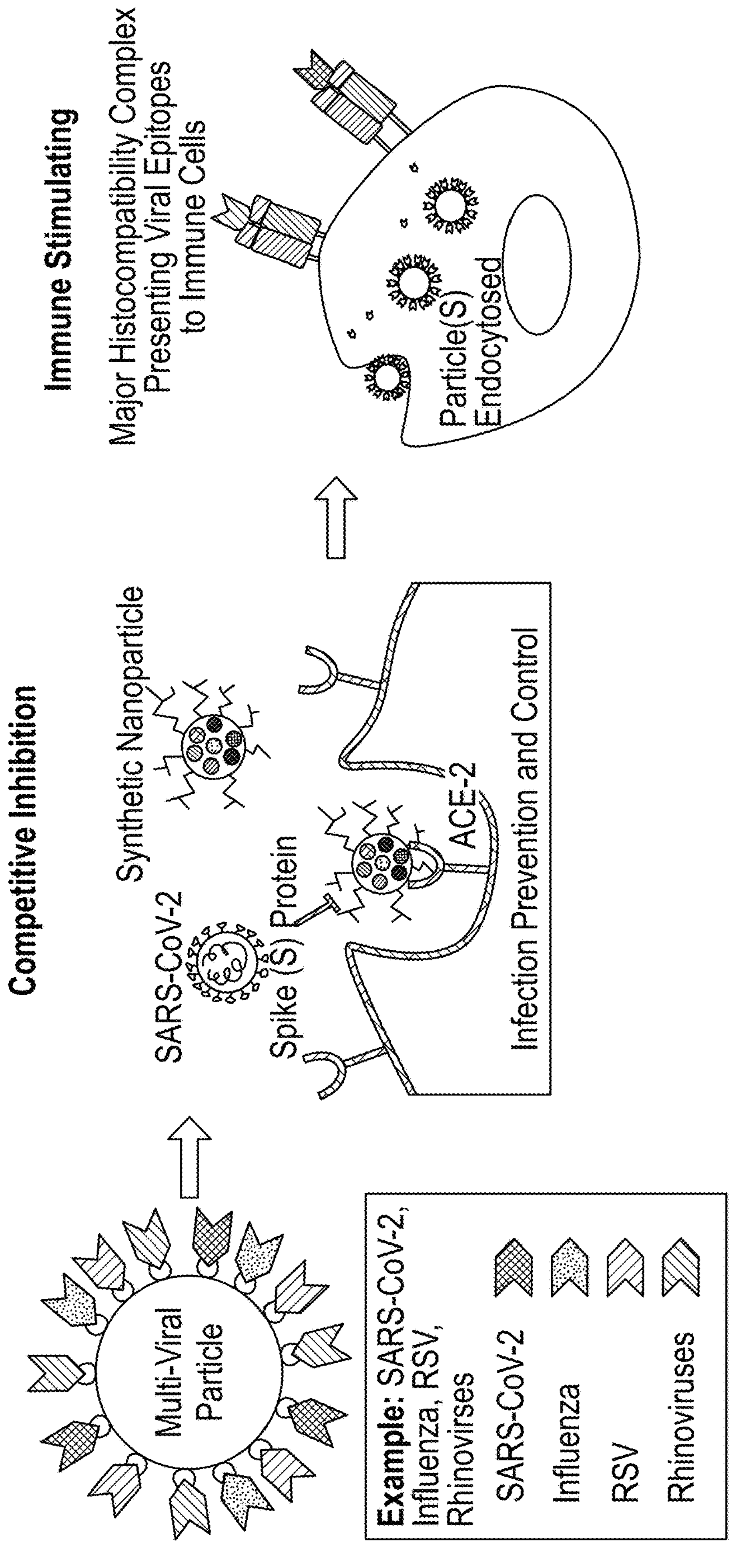
FIG. 4B is a schematic depiction of multi-viral targeting strategy compromising multiple epitopes of different pathogens capable of electing an broad immunologic reaction and by infection prevention and control by competitive inhibition functionalized nanomaterials according to some embodiments of the present technology.

One embodiment of a targeted and/or personalized medicine is schematically illustrated in FIGS. 4A and 4B. As depicted, by way of an example, by designing a carrier (e.g., synthetic nanoparticle, other particle or object, etc.) that has features that resemble the selected or targeted virus or other pathogen (e.g., SARS-CoV-2, other corona or spiked viruses, influenzas, rhinoviruses, noroviruses, other common cold viruses, etc.). For example, the synthetic particles or other carriers can include spike protein fragments, protein protrusions, other protrusions, other surface features and/or any other feature or property. Accordingly, it is possible for targeted drug delivery at (e.g., at, to, near, etc.) host cells that are susceptible for the virus and/or other pathogen. In some embodiments, as discussed herein, the carrier can include (e.g., can be "loaded" or otherwise provided with) one or more drugs and/or other compounds, substances and/or materials (for example, anti-viral compounds, zinc, immune modulating drugs (e.g., Celastrol, other interferon-gamma or stimulating molecules, penicillium, Dalbavancin or other anti-bacterial compounds, drugs intended to combat virus-related pneumonia, voriconazole, isavuconazole, drugs intended to combat viral-associated pulmonary aspergillosis, anti-fungal compounds, etc.) and/or the like, as desired or required by a particular application or use.

In some embodiments, a synthetic particle or other carrier is configured to be used for targeted and/or personalized medicine. For example, in some embodiments, the carrier's targeted therapy possibilities improve the therapeutic index of the API, drug, component and/or other material loaded into or onto the carrier. In some embodiments, the carrier improves the therapeutic index of the API, drug, component and/or other material by 1 to 1000 (e.g., 1 to 1000, 0 to 100, 100 to 200, 200 to 300, 300 to 400, 400 to 500, 100 to 500, 200 to 500, 300 to 500, 100 to 600, 200 to 600, 300 to 600, 400 to 600, 500 to 600, 100 to 700, 200 to 700, 300 to 700, 400 to 700, 500 to 700, 600 to 700, 100 to 800, 200 to 800, 300 to 800, 400 to 800, 500 to 800, 600 to 800, 700 to 800, 100 to 900, 200 to 900, 300 to 900, 400 to 900, 500 to 900, 600 to 900, 700 to 900, 800 to 900, 100 to 1000, 200 to 1000, 300 to 1000, 400 to 1000, 500 to 1000, 600 to 1000, 700 to 1000, 800 to 1000, 900 to 1000, 0 to 200, 0 to 300, 0 to 400, 0 to 500, 0 to 600, 0 to 700, 0 to 800, 0 to 900, 0 to 1000, values between the foregoing ranges and values, etc.), vis-à-vis, for example, delivering the same or equivalent amount of a material or component (e.g., API, drug, etc.) to the host without using the carrier as a delivery tool (e.g., a targeted delivery tool or mechanism). The therapeutic index (and the likelihood of successfully combatting a pathogen or other agent) is improved relative to no carrier or same API/other component that is delivered without a carrier (e.g., ingested, injected, crème, etc.). In some embodiments, delivery using a carrier in accordance with any of the embodiments disclosed herein or equivalents thereof increases or otherwise improves or enhances solubility and/or permeability of the drug. For example, the solubility and/or permeability of the component being delivered to the host using the carrier can be improved by 0.1 to 50% (e.g., 0.1 to 5, 5 to 10, 10 to 20, 20 to 30, 30 to 40, 40 to 50, 0.1 to 50, 1 to 20, 1 to 50, 20 to 50, 10 to 40%, values between the foregoing, etc.), more than 50% (e.g., 50 to 60, 60 to 70, 70 to 80, 80 to 100, 50 to 100%, values between the foregoing, greater than 100%, greater than 200%, etc.), relative to, for example, the same or similar component delivered by other means (e.g., via ingestion, injection, droplets, lotions, etc.).

In some embodiments, the synthetic particle or other carrier comprises (e.g., is provided with) a coating and/or functionalization that has higher affinity towards the receptor favoring the binding of the synthetic particle or other carrier than the viral one (e.g., the virus, other pathogenic or infectious agent or member, etc.).

In one embodiment, for example, the synthetic particle or other carrier comprises an amino acid sequence that is similar to that of the said viral protrusion having affinity for the same target receptor as the pathogen thus having competition for the same receptor.

In one embodiment, for example, the synthetic particle or other carrier is further optimized for improved binding to said host receptor in order to achieve improved blocking effect by competitive inhibition to the said pathogen.

In one embodiment, for example, the synthetic particle or other carrier having coating and/or functionalization of epitopes similar to that of the pathogen of interest in order to give a vaccination at target cell population.

According to some embodiments, the synthetic particle or other carrier is decorated and/or loaded with immunogenic epitopes of the pathogen or pathogens of interest for the targeted cell populations to present the said epitopes to B and/or T cells in order to elicit an immunological response towards said pathogen or pathogens. In some embodiments, this advantageously results in the infected cells to be hindered and/or eliminated by the host's immune system.

In some embodiments, by way of example, the synthetic particle (e.g., carrier) is decorated and/or loaded with polypeptide protrusions containing epitopes from several different pathogens of interest to be used in the composition of a particle-based vaccine composition. The carrier protrusions, which can include both B cell stimulating and/or T cell stimulating epitopes, can be configured to comprise a specific sequence obtained from the amino-acid sequence of the protein of interest (e.g., derived from a coronavirus, SARS-CoV-2 virus, an influenza virus, a rhinovirus, a norovirus, a respiratory syncytial virus (RSV), another virus that impacts the respiratory system, any other type of virus, etc.).

In some embodiments, for example, the synthetic particle or other carrier is decorated and/or loaded with a selected and isolated nucleic acid molecules (e.g., RNA or DNA) having a nucleic acid sequence that encodes a specific polypeptide sequence. Such a sequence can include both B cell stimulating and/or T cell stimulating epitopes that include specific sequences. In some embodiments, the sequences are obtained from the amino-acid sequence (e.g., complete sequence) of the protein of interest (e.g., derived from a coronavirus, SARS-CoV-2 virus, an influenza virus, a rhinovirus, a norovirus, a respiratory syncytial virus (RSV), another virus that impacts the respiratory system, any other type of virus, etc.).

In one embodiment, the synthetic particle or other carrier is configured to prevent or at least partially hinder the ability of the SARS-CoV-2 pathogen to infect and/or replicate in the host (e.g., human, animal, etc.).

In some arrangements, the synthetic particle or carrier is synthesized using different materials and functionalization in order to match or substantially match the optimal or beneficial properties to be administered to target cell populations (e.g., hydrophobic or hydrophilic properties, depending on the intended use).

In one embodiment, for example, silica (e.g., stable organic silica) is used as the core material that could exhibit a blocking effect that, optionally after modification of the particle, could be prolonged for hours, days or longer as it takes time for silica nanoparticles to degrade in aqueous conditions similar to the environment of the human body.

In one embodiment, for example, solid lipid particles (e.g., fabricated by a bottom-up method using microfluidics) are used as the core material for the carrier to be further coated, functionalized and/or loaded into or onto with API, epitopes, proteins, RNA/DNA, anti-virals and immune stimulating compounds such as Celastrol, interferon gamma.

In one embodiment, for example, self-assembling protein particles produced by genetically-engineered bacterial or mammalian cells producing proteins or protein fragments, such as ferritin heavy or light chain, are used as the core material for the carrier. Such particles can be further functionalized and/or loaded into or onto other molecules, epitopes, API, epitopes, proteins, RNA/DNA, anti-virals and immune stimulating compounds such as Celastrol, interferon gamma.

According to some embodiments, the administration route of a carrier depends on the tissue that the virus has invaded. For example, if the virus or other targeted pathogen resides in the upper or lower respiratory tract, it may be preferred to use an inhalation device for administering the carriers (e.g., synthetic particles) with a desired dosage. In some arrangements, such an inhalation device can allow a desired (e.g., optimal, effective, etc.) dosage of a carrier to be provided to a targeted anatomical location on demand.

In one embodiment, there is provided an inhalation device which compromises a container (e.g., a small plastic container) with dried carriers (e.g., synthetic particles, objects, etc.) like that of a dry powder inhaler or as a meter dose inhaler where the carriers (e.g., particles) are sprayed from the inhaler as an aerosol, as an vaporizer creating a fine mist of particles and solution, as an nasal spray dispersed in an aqueous solution and/or in any other form or configuration or hybrid form, as desired or required.

In some embodiments, for improving or enhancing (e.g., maximizing) the coverage of the upper respiratory tract, an inhalation mask is used. As a result, the entry of carriers (e.g., particles) into the nasal cavity and lower respiratory tract (where epithelial cells expressing ACE2, sialic acid, histo-blood group antigens, ICAM-1, IGF1R or other receptors that may also reside) can be enhanced or otherwise improved, thereby lowering (e.g., minimizing) the risk of being infected by the virus or other pathogen, at least temporarily.

In embodiments where the viral infection is (or would be) in the gastrointestinal tract, a tablet, an orally ingestible liquid and/or any other ingestible material is the preferred route of administration of the carrier to the host or subject. The synthetic particles or other carriers of such orally administered compositions can advantageously temporarily protect, at least partially, the end-user from infection by the virus (e.g., orally, via fecal-oral transmission, etc.).

In some embodiments, the carrier (e.g., nanomaterial, other particle or object, etc.) can also be fabricated and configured to have a high or a favorable affinity for the pathogen, thus, at least partially, encapsulating and immobilizing the threat of infection e.g., coating or functionalizing the particle with molecules that has high binding affinity towards the pathogen. Accordingly, such carriers could be used in disinfecting products (e.g., cleaning solution, hand sanitizer products, disinfecting wipes, etc.).

Figure 3A:
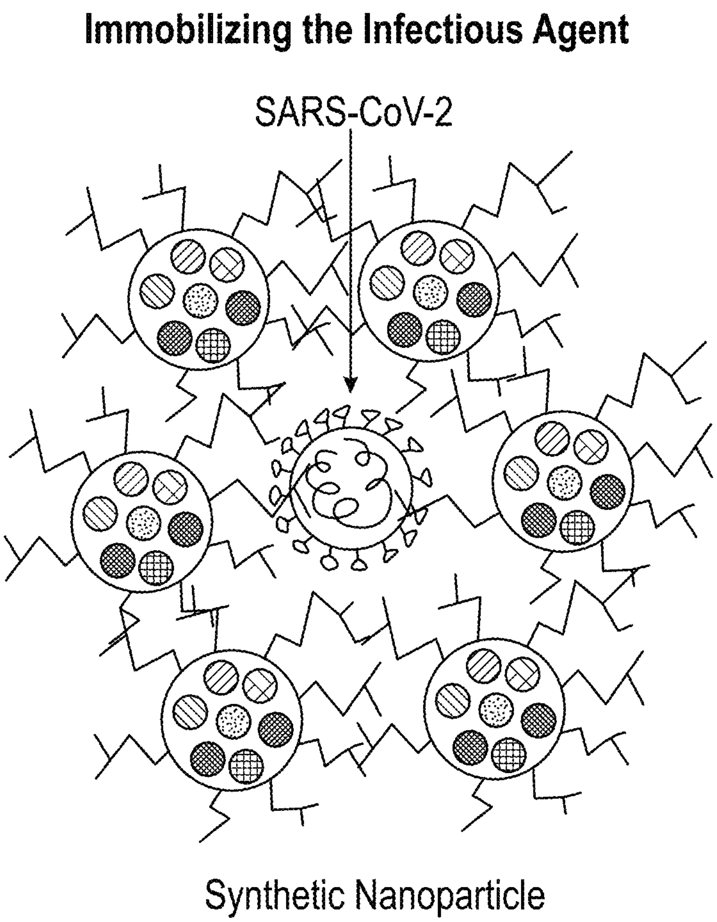
FIG. 3A is a schematic depiction of immobilization of an infectious agent by functionalized nanomaterials according to some embodiments of the present technology.

FIG. 3A shows, schematically and by way of an example, utilization of carriers (e.g., nanoparticles, other particles or objects, etc.) coated and/or otherwise provided with peptides resembling the binding motif of the target receptor, such as, e.g., ACE-2, sialic acid, histo-blood group antigens, ICAM-1, IGF1R or other receptors that the specific or targeted virus or other pathogen uses. For example, such targeted viruses or other pathogens include, without limitation or restrictions, coronaviruses (e.g., SARS-CoV-2), influenzas, rhinoviruses, noroviruses and other common cold viruses and/or the like. In some embodiments, as discussed throughout this application, the carriers are configured to encapsulate and/or immobilize the virus and/or other pathogen, thus minimizing or otherwise reducing the risk of the virus and/or other pathogen infecting the host.

Figure 3B:
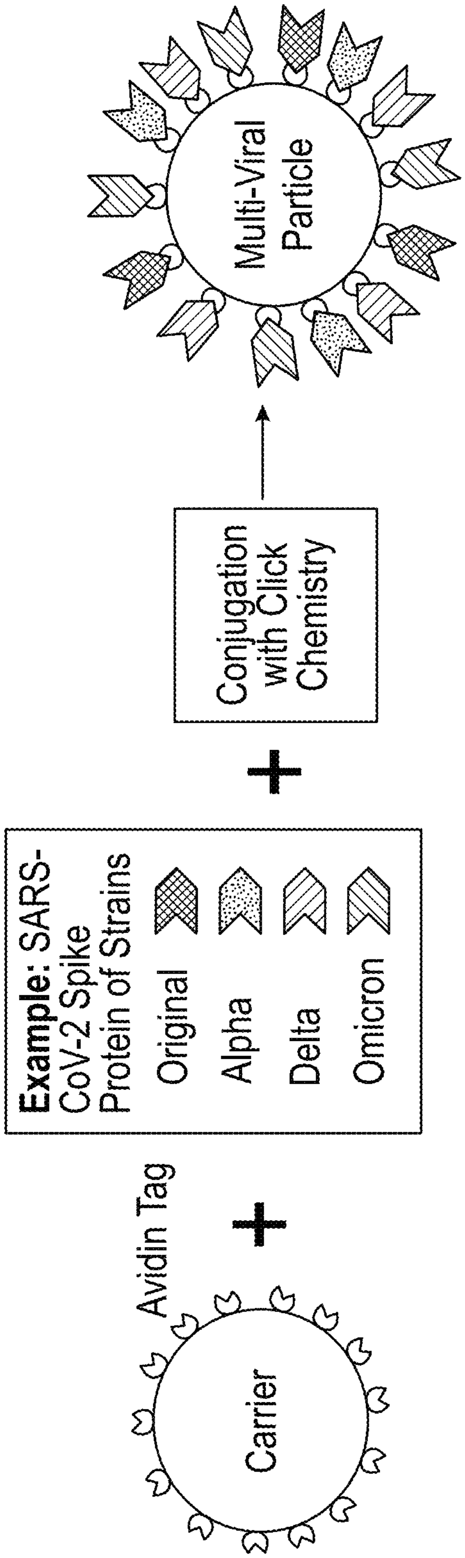
FIG. 3B is a schematic depiction of the carrier having protrusions mimicking several amino acids sequences of different viruses or viral strains capable of both binding to targeted receptor and/or receptors, blocking viral entry, and/or functioning as an vaccination at targeted cell population.

FIG. 3B shows, schematically and by way of an example, utilization of carriers (e.g., nanoparticles, other particles or objects, etc.) coated and/or otherwise provided with peptides (epitopes) resembling the naturally occurring protrusions of the pathogen or pathogens capable of binding to targeted receptor and/or receptors, blocking viral entry and functioning as a vaccine for targeted cell populations. For example, such targeted viruses or other pathogens can include, without limitation or restrictions, coronaviruses (e.g., SARS-CoV-2), influenzas, rhinoviruses, noroviruses and other common cold viruses and/or the like. In some embodiments, as discussed throughout this application, the carriers are configured to at least partially hinder viral or pathogen spread and elicit an protective immune response against said virus and/or other pathogen, thus minimizing or otherwise reducing the risk of viral or other pathogenic infection within the host.

In some embodiments, the carrier (e.g., nanomaterial, other particle or object, etc.) can also be fabricated to have high or favorable affinity for the receptor and co-receptor. Thus, the carrier can be configured to bind to multiple receptors (e.g., receptors that various pathogens use for cell entry). Further, as noted herein, the synthetic particle or other carrier can be provided with a coating or similar layering or component that has higher or otherwise favorable or improved affinity towards the receptor favoring the binding of the carrier (e.g., synthetic particle). This can allow or otherwise facilitate the carrier to be used in a multiple targeting approach (e.g., further reducing (e.g., minimizing) the risk of contracting said disease or diseases (e.g., viral or pathogenic infection and the diseases originating therefrom)).

FIGS. 4A and 4B schematically shows, by way of an example only, utilization of nanoparticles or other carriers coated (or otherwise provided) with peptides resembling the binding motif of a viral protrusion protein, such as, for example, the spike protein from the SARS-CoV-2 or other coronaviruses, Hemagglutinin (HA) and Neuraminidase (NA) proteins from influenza A virus, etc. combined with peptides resembling the binding motif of host receptors (e.g., ACE2, sialic acid, histo-blood group antigens, ICAM-1, IGF1R or other receptors) of the subject. As a result, the carriers can advantageously be provided with dual targeting strategies, thereby minimizing or reducing the risk of viruses or other pathogens infecting the host.

According to some embodiments, the carrier (e.g., nanomaterial, particle or object, etc.) can be fabricated or otherwise configured to have high or favorable affinity for the targeted pathogen(s) (e.g., virus(es) circulating co-receptors e.g., high-density lipoprotein (HDL) scavenger receptor B type 1 (SR-B1), thus immobilizing the treat which could be used as an antidote preventing further spreading of the virus in the said host.

Figure 5:
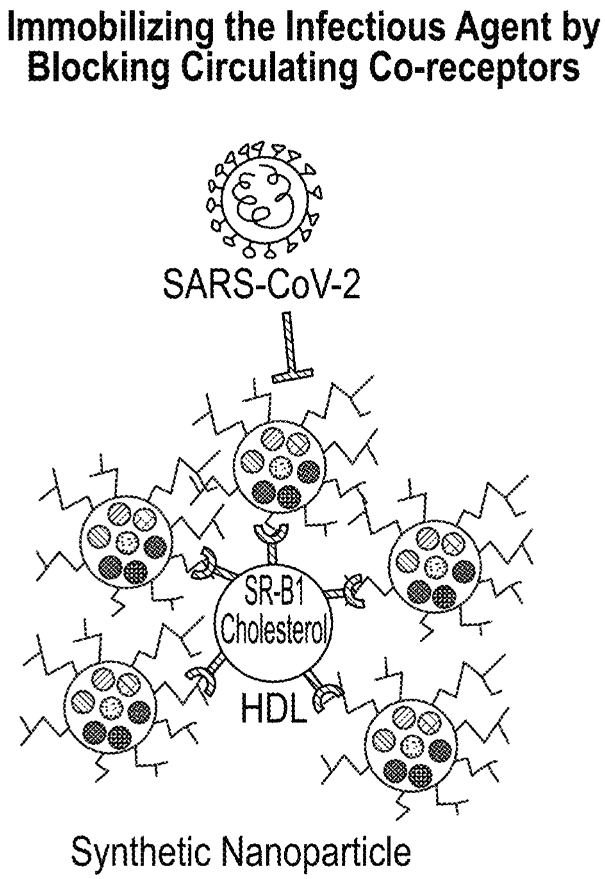
FIG. 5 schematic depiction of utilization of nanoparticles coated with peptides resembling the binding motif of the spike protein from the SARS-CoV-2 virus for binding and blocking co-receptor and as a consequence decrease the virus mobility, thus minimizing the risk of the virus's infecting the host cells or infecting the host to other organs.
Figure 6:
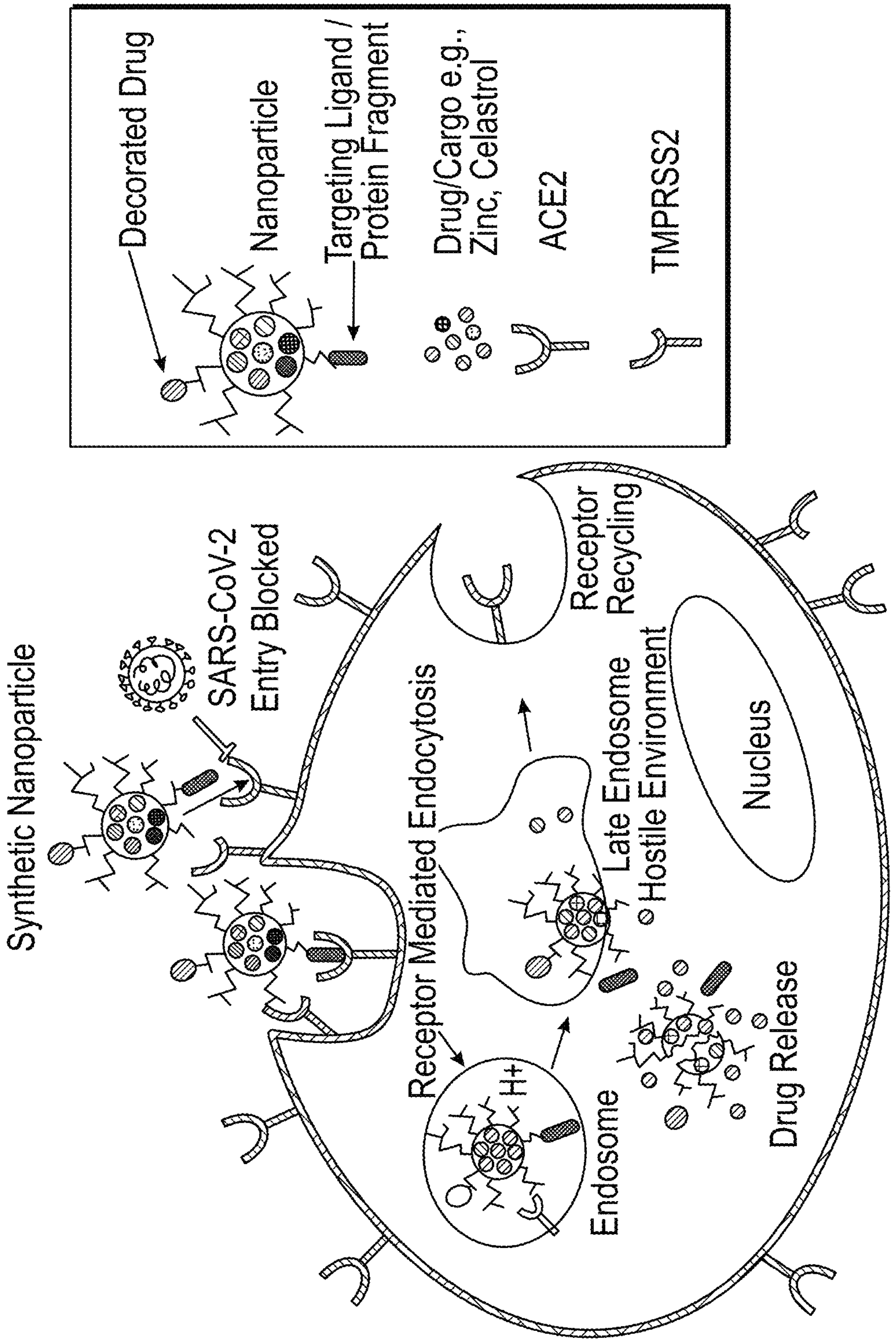
FIG. 6 is a schematic depiction of functionalized nanoparticles mimicking SARS-CoV-2 to be used as targeted intervention and therapy against COVID-19 and other respiratory diseases according to some embodiments of the present technology.

FIG. 5 schematically shows, by way of an example, utilization of nanoparticles or other carriers coated (and/or otherwise provided) with peptides resembling the binding motif of the spike protein from a coronavirus (e.g., the SARS-CoV-2 virus) for at least partially binding to the co-receptor. As a consequence of such carriers within the host, the mobility of the virus can be advantageously decreased, thus minimizing or otherwise reducing the risk of the targeted virus or other pathogen infecting the host or spreading the viral infection inside the said host (e.g., spread to other organs or locations of the host).

Based on, for example, the above, the following represents non-limiting embodiments of the present technology:

A carrier (e.g., synthetized carrier in the nano- or microscale or any other object that has the capacity of saturating and binding to target receptors, proteins and/or macromolecules for example but not limited to ACE2, sialic acid, histo-blood group antigens, ICAM-1, IGF1R or other receptors at the surface of cells that prevents and minimize pathogen, such as influenzas, rhinoviruses, RSVs, noroviruses, coronaviruses (e.g., SARS-CoV-2), other viruses causing respiratory infection, binding and entry to the host lowering the risk of contracting the specific disease, such as COVID-19 disease, diarrhea, common cold, cytokine storm, death or generally discomfort or a combination thereof.

A carrier (e.g., a synthetized carrier in the nano- or microscale or any other object that has the capacity of binding and encapsulating the pathogen of interest, thus immobilizing, at least partially, the pathogens' ability to bind and entry to the host, thereby lowering the risk of contracting the specific infectious agent).

A carrier (e.g., a carrier as above), wherein the core structure of the carrier is obtained (e.g., manufactured, fabricated, etc.), at least in part, by 3D printing, microfluidics, supercritical solution method, sol-gel method, other bottom-up and/or top-down method of fabrication self-assembling components and/or any other method or technology.

A carrier (e.g., as provided above and/or herein), where the core material is made of or comprises, however not limited to, organic or inorganic components, lipid droplets, micelles, cholesterol, amino acids, proteins, salts and minerals or other molecules.

One embodiment comprises lipid-based micelles made by, for example, cholesterol decorated with SARS-CoV-2 spike protein fragments and/or other protrusions that bind both to host receptor sites or other portions of the host cell (e.g., ACE2, TMPRSS2, etc.) and to cholesterol and its high-density lipoprotein (HDL) scavenger receptor B type 1 (SR-B1) that would facilitate ACE2-dependent entry of the nanoparticle and/or microparticle loaded with selected API for combating COVID-19 disease or other disease resulting from infection by a virus or other pathogen. In some embodiments, the cholesterol recognition amino acid consensus (CRAC) motifs near the inverted cholesterol recognition motif (CARC) have been proven to bind with SARS-CoV-2 S1 subunit and this HDL complex enhances viral entry to host cells facilitating replication [17]. Therefore, by creating a carrier (e.g., nanoparticle, other particle or object, etc.) that would compete with this spike protein-HDL interaction would potentially lower the ability of SARS-CoV-2 (or the targeted pathogen for ACE2-mediated (or other receptor-mediated) internalization, at least partially blocking viral entry to host cells and at least partially hindering replication. In one arrangements, this co-receptor incarceration could be blocked by decorating the nanoparticle with spike protein fragments from CARC-CRAC region of SARS-CoV-2 preferably but not limited to 129KKKKVCEFQFCNDPFLGVYYHKNNKKKK150 (SEQ ID No: 4) together with other amino acids for example the RBD spike fragment hexapeptide 438YKYRYL443 (SEQ ID No: 1) that binds to the ACE2 receptor creating a nanoparticle capable of blocking viral-host interaction on multiple positions loaded with selected API for targeted therapeutics (e.g., Celastrol, Zinc, ITX 5601, etc.). [8,15-18].

One embodiment comprises the use of simultaneous inhibiting of multiple receptors by multiple targeting approaches, where the carrier (e.g., mimetic particle) includes protrusions (e.g., located on or along an outer surface of the carrier, extending from the outer surface, etc.) that are similar or substantially similar to those of the target virus or viruses. Such protrusions can include, for example, spike proteins, HA and NA or VP that would bind to the specific host receptor for inhibiting viral entry by competitive inhibition, etc. In some embodiments, the carrier (e.g., virus-like particle) also includes surface protrusions that mimic epitopes selected from said viruses for eliciting an immune response against said viruses.

According to one embodiment comprises the use of simultaneous targeting of multiple receptors by multiple targeting approaches, where the carrier (e.g., mimetic particle) includes protrusions (e.g., located on or along an outer surface of the carrier, extending from the outer surface, etc.) that are similar or substantially similar to those of the target virus or viruses. Such protrusions can include, for example, spike proteins, HA and NA or VP that would bind to the specific host receptor for inhibiting viral entry by competitive inhibition, etc. In some embodiments, the carrier (e.g., virus-like particle) also includes drugs, API or other molecules for targeted delivery to the host.

Another embodiment comprises the use of simultaneous inhibiting and immobilizing by dual targeting approaches, where the carrier (e.g., mimetic particle) has protrusions on the outer surface that are similar to those of the virus, for example, spike protein, HA and NA or VP that would bind to the specific host receptor for inhibiting viral entry by competitive inhibition. In some embodiments, the carrier (e.g., virus-like particle) also includes surface protrusions that mimic the host component (e.g., ACE2, silicid sialic acid, histo-blood group antigens, ICAM-1, IGF1R receptors, and/or antibodies such as the monoclonal antibody bebtelovimab, etc.).

Another embodiment comprises using self-assembling recombinant protein-based nanoparticle constructs, such as, for example, SpyTag/SpyCatcher system and ferritin-based constructs [23]. Where the constructs are expressed in *E. Coli*; the proteins are purified and then assembled like a two-component "superglue" into virus-like particles (VLPs) conjugated with the selected antigens, viral epitopes or fragments [24]. The carrier could be assembled using the SpyTag/SpyCatcher system or ferrtin (heavy or light chain) based particle core and then conjugated, coated and/or functionalized with the selected SARS-CoV-2 spike protein or selected hexapeptide 438YKYRYL443 derived thereof or peptides from the CARC-CRAC region or other proteins of interest. Several studies show that it is possible to construct such a VLP using SARS-CoV-2 spike protein (RBD) candidate combined with SpyCatcher technology and ferritin based particle systems [24, 25]. The selected studies using RBD-SpyVLP demonstrate that the construct is easily producible and scalable, and that the final product is thermally stable even at room temperature for several weeks [25]. The SARS-CoV-2 RBD conjugated to SpyCatcher-mi3 nanoparticle (abbreviated: RBD-mi3 NP) shows higher binding affinity for the ACE2 receptor than viral RBD monomers detected using Biolayer interferometry (BLI) kinetic assays [24]. Therefore, it appears possible to develop mimetic nanoparticles or other carriers for preventing the spreading and lowering the infection rate of novel coronaviruses with higher affinity then the RBD monomer.

The synthetic carrier or nanoparticle may comprise or be decorated with a polypeptide or protein having an amino acid sequence of the ACE2 binding sequence and/or the SARS-CoV-2 spike protein RBD or a fragment thereof. In an embodiment, the amino acid sequence of the ACE2 binding sequence and/or the SARS-CoV-2 spike protein RBD or a fragment thereof is optimized, for example such that it has a higher binding affinity for the ACE2 receptor and enhanced blocking properties that of the spike protein of the coronavirus interaction compared to the corresponding, unmodified spike protein sequence (SEQ ID No: 5). By optimizing the amino acid sequence of the ACE2 binding sequence and/or the SARS-CoV-2 spike protein RBD or a fragment thereof it is possible achieve even higher binding affinity for example with combining hexapeptides 438YKYRYL443 (SEQ ID No: 1) or 438YKYNYL443 (SEQ ID No: 3) with the optimized spike protein sequence.

In a carrier as above, according to some embodiments, the core or core material may be made of, for example, self-assembling virus-like protein nanoparticles that can be saturated with different drugs. These particles can be synthesized in various sizes and shapes.

A carrier as above, where the core material is made of, for example, mesoporous silica nanoparticles with ordered mesostructures of pores that can be loaded with different drugs and that these particles can be synthetized in various sizes and shapes.

A carrier as above, wherein the core material is functionalized with one or several of the following: amino acids, epitopes, peptides or proteins and/or protein fragments, chemical agents, active pharmaceutical ingredients (API), organic or inorganic polymers or molecules.

A functionalized carrier as above, wherein the carrier with its functionalization provides a method of specifically bind to receptors, proteins and macromolecules at the cellular level in order to prevent and minimize pathogen entry to the host target tissues by competitive inhibition.

A functionalized carrier as above, wherein the carrier with its functionalization provides a method of specifically bind to receptors, proteins and macromolecules at the cellular level in order to prevent and minimize SARS-CoV-2, influenzas, rhinoviruses, respiratory syncytial virus, norovirus and other viruses causing respiratory infection entry to the host target receptors by competitive inhibition.

A carrier system as above, wherein the carrier with its functionalization provides a method of loading drugs, API, molecules, peptides inside or onto the carrier system.

A carrier system as above, where the functionalized and drug loaded carrier system can be used for targeted drug delivery of anti-pathogenic, anti-viral or anti-microbial compounds in order to decrease the growth of the infectious agent.

A carrier system as above, where the functionalized and drug loaded carrier system can be used for targeted drug delivery of, anti-viral compounds in order to decrease the replication rate of the coronavirus.

A carrier system as above, wherein the synthetic nanoparticle resembling the SARS-CoV-2 virus is loaded into or onto the nanoparticle for further enchanting the anti-viral properties of the invention. For example, Zinc which has been shown to reduce viral replication in its host cells, can be employed [21]. Also, viscosity modulators, antihistamines, Celastrol and/or immunosuppressors can be used in the COVID-19 disease for minimizing the cytokine storm that potentially is dangerous to some patients [18,21,22].

A carrier system as above, wherein the synthetic nanoparticle resembling the SARS-CoV-2, influenzas, rhinoviruses and other viruses causing respiratory infection is loaded with proteome inhibitors or new molecular entities developed in the future for efficiently deliver the compounds in the target tissues with minimal off-target effects.

A carrier system as above, wherein the synthetic nanoparticle is decorated with molecules that has high affinity towards the SARS-CoV-2 virus or influenzas, rhinoviruses and viruses causing respiratory infection e.g., proteins resembling that of the ACE-2, sialic acid, histo-blood group antigens, ICAM-1, IGF1R receptor or any other pathogen of interest in order to bind and immobilize the infectious agent preventing or minimizing the potential risk of host entry.

A carrier system as above, wherein the synthetic nanoparticle resembling the SARS-CoV-2 virus, or any other pathogen for example influenzas, rhinoviruses and viruses causing respiratory infection is decorated with epitopes to be used as a vaccination at target cell populations.

A carrier system as above, wherein the carrier system is loaded, stored or dispersed in a device or vessel capable of on-demand release of the carrier to the end-user. Therefore, in some embodiments, the carrier can be administered to the anatomy by the subject or patient, making the carrier capable of self-administration.

A carrier system as above, wherein the carrier system is loaded inside a dispenser such as an inhalation device, tablet, injectable substance, cream or ointment.

A carrier system as above, wherein the man-made materials are used to immobilize specific pathogens by adding the synthetic material in sanitation products and disinfectants.

A carrier system as above for minimizing the spread of diverse pathogens by binding to the target molecule in the hos body or binding to the infectious agent itself and potently inhibit the spread of the disease. Furthermore, as a combination treatment listen in the preceding embodiments hindering the replication of the infectious agent together with giving the immune system in the host a gained advantage to fight the disease similar to vaccines or immunoregulating drugs.

In further embodiments, the present invention is thus directed to a method for preparing a synthetic nanomaterial comprising a core object, particle, sheet, film or spheroid, tringle, star shaped, said object also compromising a coating or functionalization of organic polymers, amino acids proteins or molecules mimicking the surface of the pathogen, such as the coronavirus of interest, e.g., SARS-CoV-2 and future variants alternatively influenzas, rhinoviruses and other viruses causing respiratory infection. FIG. 7 exemplifies how the SARS-CoV-2 spike protein, and variation thereof, may be produced using a vector for producing the specific protein construct to be conjugated to the virus-like nanoparticle or synthetic carrier.

Producing a man-made material that has the capability of mimicking the pathogen of interest that has the capability of competing with the pathogen of interest for the same host target molecule, receptor, amino acid or nucleotide. Alternatively, in some embodiments, producing a material that has the capability of binding and immobilizing the pathogen of interest minimizing the possible infection in its host. However, in other embodiments, such immobilization is not required or necessary.

Producing a man-made material that has the capability of mimicking the coronavirus of interest, e.g., SARS-CoV-2, influenzas, rhinoviruses and other viruses causing respiratory infection that has the capability of competing with the virus for the same host target molecule, receptor, amino acid or nucleotide e.g., ACE2 and/or TMPRSS2, sialic acid, histo-blood group antigens, ICAM-1, IGF1R receptors.

One embodiment comprises the steps of:

a) providing a core material, e.g., a nano- and/or micro-material including nanoparticles, microparticles or any other object as disclosed herein;
b) coating or functionalizing the core material with molecules, polymers, amino acids, proteins, API, drugs or other material as disclosed herein;
c) loading the object with compounds, molecules, drugs, API, DNA or RNA etc.;

d) coating a second protective or functional layer on top of the object in particular for increasing its resistance that could be important in extreme environments such as the acidic environment in the stomach; and e) providing a small device, medical device, inhalation device or aerosol, sanitation product or consumer product that on-demand will release the containing synthetic material, particle or object for administration.

FIG. 7 shows an example of a SARS-CoV-2 spike RBD (receptor-binding domain) expression construct. Different expression cassettes (shown as the XXX region) can be used for expressing the desired construct e.g., influenza H7 haemagglutinin (indicated as "Signal sequence"), Tag, spacer, and SARS-CoV-2 RBD (using amino acid region 319 to 541, depicted in SEQ ID No: 5; PUBMED 32015508 [26]; the full amino acid sequence of the surface glycoprotein of SARS-CoV-2 is shown in in SEQ ID No: 6). The spike protein construct can be further optimized for ACE2 receptor interaction using other known amino acid sequences from SARS-CoV-2 variants such as but not limited to Alpha (B.1.1.7), Beta (B.1.351), Gamma (P.1), Delta (B.1.617.2), Omicron (B.1.1.529) and/or predicted amino acids or amino acid substitutions e.g., V367F [27], W436R, and/or N354D/D364Y.

FIG. 7 exemplifies how a spike protein, and variation thereof, or other viral protein, may be produced using a vector for producing the specific protein construct to be conjugated to the virus-like nanoparticle or synthetic man-made carrier. In an embodiment, the synthetic carrier or synthetic nanoparticle comprises and/or is coated with a peptide, a polypeptide or a protein having an amino acid sequence comprising (or consisting of) a sequence as set forth in any one of SEQ ID Nos. 1, 2, 3, 4, 5 and/or 6. In a further embodiment, the synthetic carrier or synthetic nanoparticle comprises and/or is coated with a polypeptide or a protein having an amino acid sequence comprising (or consisting of) a sequence as set forth in SEQ ID No. 5 and/or 6, wherein the sequence optionally comprises one or more amino acid substitutions. The one or more amino acid substitutions may be selected from (but are not limited to) V367F, W436R, and/or N354D/D364Y or other amino acid substitutes consisting of new coronavirus variants of concern (VOC) having higher affinity for the target receptor (table 1). To be used against contracting the COVID-19 disease and to release and shorten the disease progression and duration.

The following represent non-limiting embodiments of the present technology. The following is a non-exclusive list of embodiments, and as such, should not be seen to limit, in any way, the various inventions disclosed herein.

1. A method of preventing or reducing pathogen binding to target areas of cell surfaces of a host selected from mammals, comprising providing administering to the mammal a carrier comprising biocompatible particles having a maximum size in at least one dimension in the nanometer or micrometer range, forming a core, and further having a functionalized surface capable of binding to said target areas of said cell surfaces to at least temporarily block said target areas to prevent or minimize pathogen binding and thus, reducing the risk of the host contracting a disease caused by said pathogen.

2A. The method according to embodiment 1, wherein the carrier has the capacity of functioning as a targeted vaccination minimizing the pathogens' ability to bind and entry to the host lowering the risk of contracting the specific infectious agent.

2B. The method according to embodiment 1, wherein the carrier has the capacity of binding and encapsulating the pathogen, thus immobilizing the pathogens' ability to bind and entry to the host lowering the risk of contracting the specific infectious agent.

3. The method according to embodiment 1 or 2, wherein the core structure of the carrier is being obtained by 3D printing, microfluidics, sol-gel method or other bottom-up and/or top-down method of fabrication.

4. The method according to any of embodiments 1 to 3, wherein the core material comprises organic or inorganic components, lipid droplets, amino acids, proteins, salts and minerals or other molecules or wherein the core material comprises mesoporous silica nanoparticles, in particular mesoporous silica particles with ordered mesostructures of pores that preferably are capable of being loaded with drugs.

5A. The method according to any of embodiments 1 to 4, wherein the core material is functionalized with substance selected from the group consisting of amino acids, epitopes, peptides, proteins and/or protein fragments, chemical agents, active pharmaceutical ingredients (API), organic or inorganic polymers or molecules and combinations thereof.

5B. The method according to any of embodiments 1 to 4, wherein the core material is functionalized with substance selected from the group consisting of peptides, proteins such as antibodies, chemical agents, active pharmaceutical ingredients (API), organic or inorganic polymers or molecules and combinations thereof.

6. The method according to any of embodiments 1 to 5, wherein the carrier functionalized for specifically binding to receptors, proteins and macromolecules at the cellular level in order to prevent and minimize pathogen entry to the host target tissues by competitive inhibition.

7. The method according to any of embodiments 1 to 6, wherein the synthetic nanoparticle and/or microparticle is used for reducing the spread of SARS-CoV-2 virus or other viruses that causes a respiratory infection, diarrhea, common cold, influenzas or generally discomfort or a combination thereof.

8. The method according to any of embodiments 1 to 7, wherein said synthetic nanoparticle has a 3D-configuration generally matching the characteristics of the SARS-CoV-2 virus or other viruses that causes a respiratory infection, diarrhea, common cold, influenzas or generally discomfort or a combination thereof., in particular the particle is fabricated to a size of around 100 nm and coated with similar amino acids as the glycoprotein spikes or protruding proteins at the surface of the viral particle or similar molecules that mimic the surface of the viral envelope.

9. The method according to any of embodiments 1 to 8, wherein said synthetic nanoparticle resembles the SARS-CoV-2 virus, influenza viruses, rhinoviruses, common cold viruses and/or noroviruses or is optimized for competitive inhibition.

10. The method according to any of embodiments 1 to 9, wherein the synthetic carrier exhibits a modified particle morphology, size or surface properties to achieve increased affinity for the target receptor angiotensin converting enzyme 2 (ACE-2), compared with the SARS-CoV-2 virus, and/or other viruses that causes a respiratory infection, diarrhea, common cold, in particular for increasing the binding affinity for the specific receptor e.g., silicid sialic acid, histo-blood group antigens, ICAM-1, IGF1R blocking the internalization of the viral envelope more efficiently and potentially prolonging the gained viral protection.

11. The method according to any of embodiments 1 to 10, wherein said synthetic nanoparticle resembling the SARS- CoV-2 virus, influenza viruses, rhinoviruses, common cold viruses and/or noroviruses is adapted for personalized medicine.

12. The method according to any of embodiments 1 to 11, wherein said the synthetic nanoparticle resembling the SARS-CoV-2 virus, influenza viruses, rhinoviruses, common cold viruses and/or noroviruses is loaded into or onto the nanoparticle for further enhancing the anti-viral properties.

13. The method according to any of embodiments 1 to 12, wherein said synthetic nanoparticle resembling the SARS-CoV-2 virus, influenza viruses, rhinoviruses, common cold viruses and/or noroviruses is loaded with vehicles or proteome inhibitors for efficiently delivering the compounds in the target tissues with minimal off-target effects.

14. The method according to any of embodiments 1 to 13, wherein the synthetic nanoparticle is decorated with molecules that have high affinity towards the SARS-CoV-2 virus or any other pathogen of interest such as influenza viruses, rhinoviruses, common cold viruses and/or noroviruses in order to bind and immobilize the infectious agent preventing or minimizing the potential risk of host entry.

15. The method according to any of embodiments 1 to 14, wherein the synthetic nanoparticle resembling the SARS-CoV-2 virus or any other pathogen such as influenza viruses, rhinoviruses, common cold viruses and/or noroviruses is coated or decorated with epitopes to be used as a vaccination at target cell populations.

16. The method according to any of embodiments 1 to 15, wherein the carrier is loaded, stored or dispersed in a device or vessel capable of on-demand release of the carrier to the end-user. In some embodiments, the carrier is configured to be administered to the anatomy by the subject or patient, making the carrier capable of self-administration.

17. The method according to any of embodiments 1 to 16, wherein the carrier system is loaded inside a dispenser such as an inhalation device, tablet, injectable substance, cream or ointment.

18. The method according to any of embodiments 1 to 17, wherein the man-made materials is used for immobilizing specific pathogens by adding the synthetic material in sanitation products and disinfectants.

19. The method according to any of embodiments 1 to 18 for preventing or reducing pathogen binding to target areas of cell structures of a host according to any one of the preceding embodiments, wherein said method comprises minimizing the spread of diverse pathogens by binding to the target molecule in the hos body or binding to the infectious agent itself and potently inhibit the spread of the disease.

The following embodiments are disclosed. The following is a non-exclusive list of embodiments, and as such, should not be seen to limit, in any way, the various inventions disclosed herein.

1. A synthetic carrier for use in a method of preventing or reducing pathogen binding to target areas of cell surfaces of a host, said carrier comprising biocompatible particles having a maximum size which, in at least one dimension, is in the nanometer or micrometer range, forming a core, and further having a functionalized surface capable of binding to said target areas of said cell surfaces so as to at least temporarily block said target areas to prevent or minimize pathogen binding and, thus, reducing the risk of the host contracting a disease caused by said pathogen.

2A. The synthetic carrier for use in a method of preventing or reducing pathogen binding to target areas of cell structures of a host according to embodiment 1, said carrier having the capacity of eliciting an protective immunological reaction against said pathogen thus at least partially hindering the ability of the pathogen to bind to and enter the host, thereby lowering the risk of contracting the specific infectious agent and the related disease.

2B. The synthetic carrier for use in a method of preventing or reducing pathogen binding to target areas of cell structures of a host according to embodiment 1, said carrier having the capacity of binding and encapsulating the pathogen, thus immobilizing the pathogens' ability to bind and entry to the host lowering the risk of contracting the specific infectious agent.

3. The synthetic carrier for use in a method of preventing or reducing pathogen binding to target areas of cell structures of a host according to embodiment 1 or 2, wherein said core structure of the carrier is being obtained by 3D printing, microfluidics, sol-gel method or other bottom-up and/or top-down method of fabrication.

4. The synthetic carrier for use in a method of preventing or reducing pathogen binding to target areas of cell structures of a host according to any one of embodiments 1 to 3, wherein the core material comprises organic or inorganic components, lipid droplets, amino acids, proteins, salts and minerals or other molecules.

5. The synthetic carrier for use in a method of preventing or reducing pathogen binding to target areas of cell structures of a host according to any one of the preceding embodiments, wherein the core material comprises inorganic silica nanoparticles, in particular mesoporous silica particles, such particles preferably having ordered mesostructures of pores that preferably are capable of being loaded with drugs.

6A. The synthetic carrier for use in a method of preventing or reducing pathogen binding to target areas of cell structures of a host according to any one of the preceding embodiments, wherein said core material is functionalized with substance selected from the group consisting of amino acids, epitopes, peptides, proteins or fragments of proteins, chemical agents, active pharmaceutical ingredients (API), organic or inorganic polymers or molecules and combinations thereof.

6B. The synthetic carrier for use in a method of preventing or reducing pathogen binding to target areas of cell structures of a host according to any one of the preceding embodiments, wherein said core material is functionalized with substance selected from the group consisting of peptides, proteins such as antibodies, chemical agents, active pharmaceutical ingredients (API), organic or inorganic polymers or molecules and combinations thereof.

7. The synthetic carrier for use in a method of preventing or reducing pathogen binding to target areas of cell structures of a host according to any one of the preceding embodiments, wherein said the carrier with its functionalization is used for specifically binding to receptors, proteins and macromolecules at the cellular level in order to prevent and minimize pathogen entry to the host target tissues by competitive inhibition.

8. The synthetic carrier for use in a method of preventing or reducing pathogen binding to target areas of cell structures of a host according to any one of the preceding embodiments, said method comprising loading drugs, API, molecules, peptides inside or onto the carrier system.

9. The synthetic carrier for use in a method of preventing or reducing pathogen binding to target areas of cell structures of a host according to any one of the preceding embodiments, comprising a functionalized and drug loaded carrier, said carrier being used for targeted drug delivery of anti-pathogenic, anti-viral or anti-microbial compounds in order to decrease the growth of the pathogen, such as infectious agent.

10. The synthetic carrier for use in a method of preventing or reducing pathogen binding to target areas of cell structures of a host according to any one of the preceding embodiments, wherein said synthetic nanoparticle and/or microparticle is used for reducing the spread of SARS-CoV-2 virus or other viruses that causes a respiratory infection, diarrhea, common cold, influenzas or generally discomfort or a combination thereof.

11. The synthetic carrier for use in a method of preventing or reducing pathogen binding to target areas of cell structures of a host according to any one of the preceding embodiments, wherein said synthetic nanoparticle has a 3D-configuration generally matching the characteristics of the SARS-CoV-2 virus or influenza viruses, rhinoviruses, common cold viruses and/or noroviruses, in particular the particle is fabricated to a size of around 100 nm and coated with similar amino acids as the glycoprotein spikes or other protruding proteins at the surface of the viral particle or similar molecules that mimic the surface of the viral envelope and thus binds to the same target receptor as the virus.

12. The synthetic carrier for use in a method of preventing or reducing pathogen binding to target areas of cell structures of a host according to any one of the preceding embodiments, wherein said synthetic nanoparticle resembles the SARS-CoV-2 virus or influenza viruses, rhinoviruses, common cold viruses and/or noroviruses or is optimized for competitive inhibition.

13. The synthetic carrier for use in a method of preventing or reducing pathogen binding to target areas of cell structures of a host according to embodiment 12, wherein the synthetic carrier exhibits a modified particle morphology, size or surface properties to achieve increased affinity for the target receptor angiotensin converting enzyme 2 (ACE-2) compared with the SARS-CoV-2 virus or influenza viruses, rhinoviruses, common cold viruses and/or noroviruses, in particular for increasing the binding affinity for the specific receptor e.g., silicid sialic acid, histo-blood group antigens, ICAM-1, IGF1R blocking the internalization of the viral envelope more efficiently and potentially prolonging the gained viral protection.

14. The synthetic carrier for use in a method of preventing or reducing pathogen binding to target areas of cell structures of a host according to any one of the preceding embodiments, wherein said synthetic nanoparticle resembling the SARS-CoV-2 virus, or influenza viruses, rhinoviruses, common cold viruses and/or noroviruses is adapted for personalized medicine.

15. The synthetic carrier for use in a method of preventing or reducing pathogen binding to target areas of cell structures of a host according to any one of the preceding embodiments, wherein said the synthetic nanoparticle resembling the SARS-CoV-2 virus or influenza viruses, rhinoviruses, common cold viruses and/or noroviruses is loaded into or onto the nanoparticle for further enhancing the anti-viral properties.

16. The synthetic carrier for use in a method of preventing or reducing pathogen binding to target areas of cell structures of a host according to any one of the preceding embodiments, wherein said synthetic nanoparticle resembling the SARS-CoV-2 virus, or influenza viruses, rhinoviruses, common cold viruses and/or noroviruses is loaded with vehicles or proteome inhibitors for efficiently delivering the compounds in the target tissues with minimal off-target effects.

17A. The synthetic carrier for use in a method of preventing or reducing pathogen binding to target areas of cell structures of a host according to any one of the preceding embodiments, wherein said synthetic nanoparticle is decorated with molecules that mimics naturally occurring protrusion of SARS-CoV-2 virus or any other pathogen of interest for example influenza viruses, rhinoviruses, common cold viruses and/or noroviruses in order to bind to target receptor of said host and thus preventing or minimizing the potential risk of the infectious agent entry to host.

17B. The synthetic carrier for use in a method of preventing or reducing pathogen binding to target areas of cell structures of a host according to any one of the preceding embodiments, wherein said synthetic nanoparticle is decorated with molecules that have high affinity towards the SARS-CoV-2 virus or any other pathogen of interest for example influenza viruses, rhinoviruses, common cold viruses and/or noroviruses in order to bind and immobilize the infectious agent preventing or minimizing the potential risk of host entry.

18. The synthetic carrier for use in a method of preventing or reducing pathogen binding to target areas of cell structures of a host according to any one of the preceding embodiments, wherein said synthetic nanoparticle resembling the SARS-CoV-2 virus or any other pathogen for example or influenza viruses, rhinoviruses, common cold viruses and/or noroviruses is coated or decorated with epitopes to be used as a vaccination at target cell populations making the administration potentially easier for the end user e.g., inhalation compared to intra muscular injection used in traditional vaccinations.

19. The synthetic carrier for use in a method of preventing or reducing pathogen binding to target areas of cell structures of a host according to any one of the preceding embodiments, wherein said carrier is loaded, stored or dispersed in a device or vessel capable of on-demand release of the carrier to the end-user.

20. The synthetic carrier for use in a method of preventing or reducing pathogen binding to target areas of cell structures of a host according to any one of the preceding embodiments, wherein said carrier system is loaded inside a dispenser such as an inhalation device, tablet, injectable substance, cream or ointment.

21. The synthetic carrier for use in a method of preventing or reducing pathogen binding to target areas of cell structures of a host according to any one of the preceding embodiments, wherein said the man-made materials is used for immobilizing specific pathogens by adding the synthetic material in sanitation products and disinfectants.

22. The synthetic carrier for use in a method of preventing or reducing pathogen binding to target areas of cell structures of a host according to any one of the preceding embodiments, wherein said method comprises minimizing the spread of diverse pathogens by binding to the target molecule in the hos body or binding to the infectious agent itself and potently inhibit the spread of the disease.

23. Method of producing a synthetic carrier according to any of embodiments 1 to 22, comprising the steps of a) providing a core material, e.g., a nano- and/or micro-material including nanoparticles, microparticles or any other object as disclosed herein;
b) coating or functionalizing the core material with molecules, polymers, amino acids, proteins, API, drugs or other material as disclosed herein;
c) loading the object with compounds, molecules, drugs, API, DNA or RNA etc.;

d) coating a second protective and/or functional layer on top of the object in particular for increasing its resistance that could be important in extreme environments such as the acidic environment in the stomach; and providing a small device, medical device, inhalation device or aerosol, sanitation product or consumer product that on-demand will release the containing synthetic material, particle or object for administration.

The following embodiments are non-limiting representative configurations of the present technology. The following is a non-exclusive list of embodiments, and as such, should not be seen to limit, in any way, the various inventions disclosed herein.

1. A method of preventing or reducing pathogen binding, in particular of preventing or reducing binding of SARS-CoV-2 or influenza viruses, rhinoviruses, common cold viruses and/or noroviruses and viral strains thereof, to target areas of cell surfaces of a host selected from mammals, comprising providing administering to the mammal a carrier comprising biocompatible particles having a maximum size in at least one dimension in the nanometer or micrometer range, forming a core, and further having a functionalized surface capable of binding to said target areas of said cell surfaces to at least temporarily block said target areas to prevent or minimize pathogen binding and thus, reducing the risk of the host contracting a disease caused by said pathogen.

2. The method according to embodiment 1, wherein the carrier has the capacity of binding and encapsulating the pathogen, thus immobilizing the pathogens' ability to bind and entry to the host lowering the risk of contracting the specific infectious agent.

3A. The method according to embodiment 1 or 2, wherein the carrier has the capacity of at least partly hindering (e.g., preventing) pathogens from binding and entering host cells, wherein the carrier is capable of binding to several said target areas of cell surfaces to at least temporarily and/or partially block viral entry, thereby giving the carrier dual targeting strategies and at least partially (e.g., partially, significantly, etc.) hindering the ability of one or more target pathogens to bind to and/or enter the host. In some embodiments, such carriers lower the risk of contracting the specific infectious agent.

3B. The method according to embodiment 1 or 2, wherein the carrier has the capacity of binding and encapsulating the pathogen thus immobilizing the pathogens' ability to bind and enter the host and capable of binding to said target areas of said cell surfaces to at least temporarily block viral entry, thus having dual targeting strategies thus significantly hinder the pathogens' ability to bind and entry to the host lowering the risk of contracting the specific infectious agent.

4. The method according to embodiment 1 to 3, wherein the core structure of the carrier is being obtained by 3D printing, microfluidics, sol-gel method or other bottom-up and/or top-down method of fabrication.

5. The method according to any of embodiments 1 to 4, wherein the core material comprises organic or inorganic components, lipid droplets, amino acids, proteins, salts and minerals or other molecules or wherein the core material comprises mesoporous silica nanoparticles, in particular mesoporous silica particles with ordered mesostructures of pores that preferably are capable of being loaded with drugs.

6A. The method according to any of embodiments 1 to 5, wherein the core material is functionalized with substance selected from the group consisting of amino acid, epitopes, peptides, proteins and/or fragments of proteins, chemical agents, active pharmaceutical ingredients (API), organic or inorganic polymers or molecules and combinations thereof.

6B. The method according to any of embodiments 1 to 5, wherein the core material is functionalized with substance selected from the group consisting of peptides, proteins such as antibodies, chemical agents, active pharmaceutical ingredients (API), organic or inorganic polymers or molecules and combinations thereof.

7. The method according to any of embodiments 1 to 6, wherein the carrier functionalized for specifically binding to receptors, proteins and macromolecules at the cellular level in order to prevent and minimize pathogen entry to the host target tissues by competitive inhibition.

8. The method according to any of embodiments 1 to 7, wherein the synthetic nanoparticle and/or microparticle is used for reducing the spread of SARS-CoV-2 virus or other viruses that causes a respiratory infection, diarrhea, common cold, influenzas or generally discomfort or a combination thereof.

9. The method according to any of embodiments 1 to 8, wherein said synthetic nanoparticle has a 3D-configuration generally matching the characteristics of the SARS-CoV-2 virus or other viruses that causes a respiratory infection, diarrhea, common cold, influenzas or generally discomfort or a combination thereof, in particular the particle is fabricated to a size of around 100 nm and coated with similar amino acids as the glycoprotein spikes at the surface of the viral particle or similar molecules that mimic the surface of the viral envelope.

10. The method according to any of embodiments 1 to 9, wherein said synthetic nanoparticle resembles the SARS-CoV-2 virus or other viruses that causes a respiratory infection, diarrhea, common cold, influenzas or generally discomfort or a combination thereof, or is optimized for competitive inhibition.

11. The method according to any of embodiments 1 to 10, wherein the synthetic carrier exhibits a modified particle morphology, size or surface properties to achieve increased affinity for the target receptor angiotensin converting enzyme 2 (ACE2) compared with the SARS-CoV-2 virus or other viruses that causes a respiratory infection, diarrhea, common cold, influenzas or generally discomfort or a combination thereof, in particular for increasing the binding affinity for the specific receptor e.g., silicid sialic acid, histo-blood group antigens, ICAM-1, IGF1R blocking the internalization of the viral envelope more efficiently and potentially prolonging the gained viral protection.

12. The method according to any of embodiments 1 to 11, wherein said synthetic nanoparticle resembling the SARS-CoV-2 virus or other viruses that causes a respiratory infection, diarrhea, common cold, influenzas or generally discomfort or a combination thereof. is adapted for personalized medicine.

13. The method according to any of embodiments 1 to 12, wherein said the synthetic nanoparticle resembling the SARS-CoV-2 virus or other viruses that causes a respiratory infection, diarrhea, common cold, influenzas or generally discomfort or a combination thereof. is loaded into or onto the nanoparticle for further enhancing the anti-viral properties.

14. The method according to any of embodiments 1 to 13, wherein said synthetic nanoparticle resembling the SARS-CoV-2 virus or other viruses that causes a respiratory infection, diarrhea, common cold, influenzas or generally discomfort or a combination thereof is loaded with vehicles or proteome inhibitors for efficiently delivering the compounds in the target tissues with minimal off-target effects.

15. The method according to any of embodiments 1 to 14, wherein the synthetic nanoparticle is decorated with molecules that have high affinity towards the SARS-CoV-2 virus or any other pathogen of interest for example influenzas, rhinoviruses and viruses causing respiratory infection in order to bind and immobilize the infectious agent preventing or minimizing the potential risk of host entry.

16. The method according to any of embodiments 1 to 15, wherein the synthetic nanoparticle resembling the SARS-CoV-2 virus or any other pathogen for example influenzas, rhinoviruses and viruses causing respiratory infection is coated or decorated with epitopes to be used as a vaccination at target cell populations.

17. The method according to any of embodiments 1 to 16, wherein the carrier is loaded, stored or dispersed in a device or vessel capable of on-demand release of the carrier to the end-user.

18. The method according to any of embodiments 1 to 17, wherein the carrier system is loaded inside a dispenser such as an inhalation device, tablet, injectable substance, cream or ointment.

19. The method according to any of embodiments 1 to 18, wherein the man-made materials is used for immobilizing specific pathogens by adding the synthetic material in sanitation products and disinfectants.

20. The method according to any of embodiments 1 to 19 for preventing or reducing pathogen binding to target areas of cell structures of a host according to any one of the preceding embodiments, wherein said method comprises minimizing the spread of diverse pathogens by binding to the target molecule in the hos body or binding to the infectious agent itself and potently inhibit the spread of the disease.

The following embodiments are disclosed. The following is a non-exclusive list of embodiments, and as such, should not be seen to limit, in any way, the various inventions disclosed herein.

1. A synthetic carrier for use in a method of preventing or reducing binding of a pathogen to target areas of cell structures of a host, said carrier comprising biocompatible particles having a maximum size in at least one dimension in the nanometer or micrometer range, forming a core, and further having a functionalized surface, which preferably mimics that of the pathogen capable of binding to said target areas of said cell surfaces to at least temporarily block said target areas to prevent or minimize pathogen binding and thus, reducing the risk of the host contracting a disease caused by said pathogen.

2. The synthetic carrier for use in a method of preventing or reducing pathogen binding to target areas of cell structures of a host according to embodiment 1, wherein the pathogen is a coronavirus, in particular SARS-CoV-2 or viral strains derived thereof.

3. The synthetic carrier for use in a method of preventing or reducing pathogen binding to target areas of cell structures of a host according to embodiment 1, wherein the cell structures are selected from ACE2 and TMPRSS2 receptors and combinations thereof.

4A. The synthetic carrier for use in a method of preventing or reducing pathogen binding to target areas of cell structures of a host according to embodiment 1 or 2, said carrier having the capacity of binding to the pathogen's co-receptors (e.g., high-density lipoprotein (HDL) scavenger receptor B type 1 (SR-B1), thus at least partially hindering the ability of the pathogens to bind and enter the host. Advantageously, this can lower the risk of contracting the specific infectious agent and the disease resulting therefrom.

4B. The synthetic carrier for use in a method of preventing or reducing pathogen binding to target areas of cell structures of a host according to embodiment 1 or 2, said carrier having the capacity of binding and encapsulating the pathogens co-receptors e.g., high-density lipoprotein (HDL) scavenger receptor B type 1 (SR-B1), thus immobilizing the pathogens' ability to bind and entry to the host lowering the risk of contracting the specific infectious agent.

5. The synthetic carrier for use in a method of preventing or reducing pathogen coronaviruses, such as SARS-CoV-2, binding to target areas of cell structures of a host according to any of embodiments 1 to 3, wherein said core structure of the carrier is being obtained by 3D printing, microfluidics, sol-gel method or other bottom-up and/or top-down method of fabrication, and wherein the core material comprises organic or inorganic components, lipid droplets, amino acids, proteins, salts and minerals or other molecules.

6. The synthetic carrier for use in a method of preventing or reducing pathogen, in particular coronaviruses binding to target areas of cell structures of a host according to any one of the preceding embodiments, wherein the core material comprises inorganic silica nanoparticles, in particular mesoporous silica particles, such particles preferably having ordered mesostructures of pores that preferably are capable of being loaded with drugs.

7A. The synthetic carrier for use in a method of preventing or reducing coronaviruses binding to target areas of cell structures of a host according to any one of the preceding embodiments, wherein said core material is functionalized with substance selected from the group consisting of amino acids, epitopes, peptides, proteins and/or fragments of proteins, chemical agents, active pharmaceutical ingredients (API), organic or inorganic polymers or molecules and combinations thereof, and wherein said carrier with its functionalization is preferably used for specifically binding to receptors, proteins and macromolecules at the cellular level in order to prevent and minimize novel coronaviruses such as SARS-CoV-2 entry to the host target cells by competitive inhibition.

7B. The synthetic carrier for use in a method of preventing or reducing coronaviruses binding to target areas of cell structures of a host according to any one of the preceding embodiments, wherein said core material is functionalized with substance selected from the group consisting of peptides, proteins such as antibodies, chemical agents, active pharmaceutical ingredients (API), organic or inorganic polymers or molecules and combinations thereof, and wherein said carrier with its functionalization is preferably used for specifically binding to receptors, proteins and macromolecules at the cellular level in order to prevent and minimize novel coronaviruses such as SARS-CoV-2 entry to the host target cells by competitive inhibition.

8. The synthetic carrier for use in a method of preventing or reducing coronaviruses binding to target areas of cell structures of a host according to any one of the preceding embodiments, said method comprising loading drugs, API, molecules, peptides inside or onto the carrier system, wherein the carrier preferably comprises a functionalized and drug loaded carrier, said carrier being used for targeted drug delivery of anti-viral in order to decrease the replication of the virus inside the host cell.

9. The synthetic carrier for use in a method of preventing or reducing coronaviruses binding to target areas of cell structures of a host according to any one of the preceding embodiments, wherein said synthetic nanoparticle and/or microparticle is used for reducing the spread of SARS-CoV-2 or other coronaviruses strains and/or types derived from the SARS-CoV-2 that causes a respiratory infection, diarrhea, common cold, cytokine storm, death or generally discomfort or a combination thereof.

10. The synthetic carrier for use in a method of preventing or reducing coronaviruses binding to target areas of cell structures of a host according to any one of the preceding embodiments, wherein said synthetic nanoparticle has a 3D-configuration generally matching the characteristics of the SARS-CoV-2 virus or future variants thereof, in particular the particle is fabricated to a size of around 100-120 nm and coated with similar amino acids as the glycoprotein spikes at the surface of the viral particle or similar molecules that mimic the surface of the viral envelope e.g., spike protein and thus binds to the same target receptor as the virus.

11. The synthetic carrier for use in a method of preventing or reducing coronaviruses binding to target areas of cell structures of a host according to any one of the preceding embodiments, wherein said synthetic nanoparticle resembles the SARS-CoV-2 virus or is optimized for competitive inhibition, wherein preferably the synthetic carrier exhibits a modified particle morphology, size or surface properties to achieve increased affinity for the target receptor ACE2 and/or TMPRSS2, compared with the SARS-CoV-2 virus, in particular for increasing the binding affinity for the specific receptor blocking the internalization of the viral envelope more efficiently and potentially prolonging the gained viral protection.

12. The synthetic carrier for use in a method of preventing or reducing coronaviruses binding to target areas of cell structures of a host according to any one of the preceding embodiments, wherein said synthetic nanoparticle resembling the SARS-CoV-2 virus is adapted for personalized medicine.

13. The synthetic carrier for use in a method of preventing or reducing coronavirus binding to target areas of cell structures of a host according to any one of the preceding embodiments, wherein said synthetic nanoparticle resembling the SARS-CoV-2 virus is adapted for personalized medicine in the case of ACE2 receptor polymorphism or different animal host organisms for achieving receptor interaction.

14. The synthetic carrier for use in a method of preventing or reducing coronaviruses binding to target areas of cell structures of a host according to any one of the preceding embodiments, wherein said synthetic nanoparticle resembling the SARS-CoV-2 virus is loaded into or onto the nanoparticle for further enhancing the anti-viral properties, or wherein said synthetic nanoparticle resembling the SARS-CoV-2 virus is loaded with vehicles or proteome inhibitors for efficiently delivering the compounds in the target cell and tissues with minimal off-target effects.

15. The synthetic carrier for use in a method of preventing or reducing coronaviruses binding to target areas of cell structures of a host according to any one of the preceding embodiments, wherein said carrier is loaded, stored or dispersed in a device or vessel capable of on-demand release of the carrier to the end-user, wherein said carrier system is preferably loaded inside a dispenser such as an inhalation device, tablet, injectable substance, cream or ointment.

16. The synthetic carrier for use in a method of preventing or reducing coronaviruses binding to target areas of cell structures of a host according to any one of the preceding embodiments, wherein said synthetic nanoparticle is a self-assembling recombinant protein-based nanoparticle construct, such as a SpyTag/SpyCatcher system 17. Method of producing a synthetic carrier according to any of embodiments 1 to 16, comprising the steps of a) providing a core material, e.g., a nano- and/or micro-material including nanoparticles, microparticles or any other object as disclosed herein;
b) coating or functionalizing the core material with molecules, polymers, amino acids, proteins, API, drugs or other material as disclosed herein;
c) loading the object with compounds, molecules, drugs, API, DNA or RNA etc.;
d) coating a second protective and/or functional layer on top of the object in particular for increasing its resistance that could be important in extreme environments such as the acidic environment in the stomach; and providing a small device, medical device, inhalation device or aerosol, sanitation product or consumer product that on-demand will release the containing synthetic material, particle or object for administration.

It will be obvious to a person skilled in the art that, as the technology advances, the inventive concept can be implemented in various ways. The invention and its embodiments are not limited to the examples described above but may vary within the scope of the claims.

REFERENCES

1. Szymanski C M, Schnaar R L, Aebi M. Bacterial and Viral Infections. 2017. In: Varki A, Cummings R D, Esko J D, et al., editors. Essentials of Glycobiology [Internet]. 3rd edition. Cold Spring Harbor (NY): Cold Spring Harbor Laboratory Press; 2015-2017. Chapter 42. Available from: https://www.ncbi.nlm.nih.gov/books/NBK453060/
2. Thakur V, Asad M, Jain S, Hossain M E, Gupta A, Kaur I, Rathore S, Ali S, Khan N J, Mohmmed A. Eps15 homology domain containing protein of Plasmodium falciparum (PfEHD) associates with endocytosis and vesicular trafficking towards neutral lipid storage site. Biochim Biophys Acta. 2015 November; 1853(11 Pt A):2856-69. doi: 10.1016/j.bbamcr.2015.08.007.
3. Lin Li, Ting Sun, Yufei He, Wendong Li, Yubo Fan, Jing Zhang. Epitope-based peptide vaccines predicted against novel coronavirus disease caused by SARS-CoV-2. bioRxiv 2020.02.25.965434
4. Ahmed S F, Quadeer A A, Mckay M R. Preliminary Identification of Potential Vaccine Targets for the COVID-19 Coronavirus (SARS-CoV-2) Based on SARS-CoV Immunological Studies. Viruses. 2020 Feb. 25; 12(3).
5. Larry R. Engelking, Chapter 6—Enzyme Kinetics. Editor (s): Larry R. Engelking, Textbook of Veterinary Physiological Chemistry (Third Edition). Academic Press, 2015, Pages 32-38, ISBN 9780123919090.
6. Shang J, Ye G, Shi K, Wan Y, Luo C, Aihara H, Geng Q, Auerbach A, Li F. Structural basis of receptor recognition by SARS-CoV-2. Nature. 2020 May; 581(7807):221-224. doi: 10.1038/s41586-020-2179-y. Epub 2020 Mar. 30. PMID: 32225175; PMCID: PMC7328981.
7. Ranga V, Niemelä E, Tamirat M Z, Eriksson J E, Airenne T T, Johnson M S. Immunogenic SARS-CoV-2 Epitopes: In Silico Study Towards Better Understanding of COVID-19 Disease-Paving the Way for Vaccine Development. Vaccines (Basel). 2020 Jul. 23; 8(3):408. doi: 10.3390/vaccines8030408. PMID: 32717854; PMCID: PMC7564651.

8. Peter E K, Schug A. The Inhibitory Effect of a Coronavirus Spike Protein Fragment with ACE2. Biophys J. 2020 Aug. 27:S0006-3495(20)30670-6. doi: 10.1016/j.bpj.2020.08.022. Epub ahead of print. PMID: 32941783; PMCID: PMC7451127.
9. Devaux C A, Rolain J M, Raoult D. ACE2 receptor polymorphism: Susceptibility to SARS-CoV-2, hypertension, multi-organ failure, and COVID-19 disease outcome. J Microbiol Immunol Infect. 2020 June; 53(3):425-435. doi: 10.1016/j.jmii.2020.04.015. Epub 2020 May 6. PMID: 32414646; PMCID: PMC7201239.
10. Lam S D, Bordin N, Waman V P, Scholes H M, Ashford P, Sen N, van Dorp L, Rauer C, Dawson N L, Pang C S M, Abbasian M, Sillitoe I, Edwards S J L, Fraternali F, Lees J G, Santini J M, Orengo C A. SARS-CoV-2 spike protein predicted to form complexes with host receptor protein orthologues from a broad range of mammals. Sci Rep. 2020 Oct. 5; 10(1):16471. doi: 10.1038/s41598-020-71936-5. PMID: 33020502; PMCID: PMC7536205.
11. Alan R. Shaw, Mark B. Feinberg, 90—Vaccines, Editor (s): Robert R. Rich, Thomas A. Fleisher, William T. Shearer, Harry W. Schroeder, Anthony J. Frew, Cornelia M. Weyand, Clinical Immunology (Fourth Edition), 2013, Pages 1095-1121, ISBN 9780723436911.
12. Clercq E D, Li G, Approved Antiviral Drugs over the Past 50 Years, Clinical Microbiology Reviews Jun. 2016, 29 (3) 695-747; DOI: 10.1128/CMR.00102-15.
13. Dou Q P, Zonder J A. Overview of proteasome inhibitor-based anti-cancer therapies: perspective on bortezomib and second generation proteasome inhibitors versus future generation inhibitors of ubiquitin-proteasome system. Curr Cancer Drug Targets. 2014; 14(6):517-36.
14. Liu J K. The history of monoclonal antibody development-Progress, remaining challenges and future innovations. Ann Med Surg (Lond). 2014 Sep. 11; 3(4):113-6.
15. Niemelä E. Nanoparticles as Targeting System for Cancer Treatment: From idea towards reality. Åbo Akademi Univeristy. Painosalama. ISBN:978-952-12-3855-0.
16. Flora G, Mittal M, Flora S J S, 26—Medical Countermeasures-Chelation Therapy, Editor(s): Flora S J S, Handbook of Arsenic Toxicology, Academic Press, 2015, Pages 589-626, ISBN 9780124186880.
17. Wei C, Wan L, Yan Q, Wang X, Zhang J, Yang X, Zhang Y, Fan C, Li D, Deng Y, Sun J, Gong J, Yang X, Wang Y, Wang X, Li J, Yang H, Li H, Zhang Z, Wang R, Du P, Zong Y, Yin F, Zhang W, Wang N, Peng Y, Lin H, Feng J, Qin C, Chen W, Gao Q, Zhang R, Cao Y, Zhong H. HDL-scavenger receptor B type 1 facilitates SARS-CoV-2 entry. Nat Metab. 2020 Nov. 26. doi: 10.1038/s42255-020-00324-0. Epub ahead of print. PMID: 33244168.
18. Caruso F, Singh M, Belli S, Berinato M, Rossi M. Interrelated Mechanism by Which the Methide Quinone Celastrol, Obtained from the Roots of Tripterygium wilfordii, Inhibits Main Protease 3CLpro of COVID-19 and Acts as Superoxide Radical Scavenger. Int J Mol Sci. 2020 Dec. 4; 21(23):9266. doi: 10.3390/ijms21239266. PMID: 33291769; PMCID: PMC7731079.
19. The Williams dictionary of Biomaterials, Williams D F, 1999, ISBN 0-85323-921-5
20. Sun Y, Guo F, Zou Z, et al. Cationic nanoparticles directly bind angiotensin-converting enzyme 2 and induce acute lung injury in mice. Part Fibre Toxicol. 2015; 12:4. Published 2015 Mar. 7.
21. te Velthuis A J, van den Worm S H, Sims A C, Baric R S, Snijder E J, van Hemert M J. Zn(2+) inhibits coronavirus and arterivirus RNA polymerase activity in vitro and zinc ionophores block the replication of these viruses in cell culture. PLoS Pathog. 2010 Nov. 4; 6(11):e1001176.
22. Shaffer L. 15 drugs being tested to treat COVID-19 and how they would work. Nature Medicine. doi: 10.1038/d41591-020-00019-9
23. Bruun T U J, Andersson A C, Draper S J, Howarth M. Engineering a Rugged Nanoscaffold to Enhance Plug-and-Display Vaccination. ACS Nano. 2018 Sep. 25; 12(9):8855-8866. doi: 10.1021/acsnano.8b02805. Epub 2018 Jul. 26. PMID: 30028591; PMCID: PMC6158681.
24. Yin-Feng Kang, Cong Sun, Zhen Zhuang, Run-Yu Yuan, Qing-Bing Zheng, Jiang-Ping Li, Ping-Ping Zhou, Xin-Chun Chen, Xiao Zhang, Xiao-Hui Yu, Xiang-Wei Kong, Qian-Ying Zhu, Miao Xu, Nan-Shan Zhong, Yi-Xin Zeng, Guo-Kai Feng, Chang-Wen Ke, Jin-Cun Zhao, Mu-Sheng Zeng. Rapid development of SARS-CoV-2 receptor binding domain-conjugated nanoparticle vaccine candidate.bioRxiv 2020.11.03.366138; doi:https://doi.org/10.1101/2020.11.03.366138
25. Tan T K, Rijal P, Rahikainen R, Keeble A H, Schimanski L, Hussain S, Harvey R, Hayes J W P, Edwards J C, McLean R K, Martini V, Pedrera M, Thakur N, Conceicao C, Dietrich I, Shelton H, Ludi A, Wilsden G, Browning C, Zagrajek A K, Bialy D, Bhat S, Stevenson-Leggett P, Hollinghurst P, Tully M, Moffat K, Chiu C, Waters R, Gray A, Azhar M, Mioulet V, Newman J, Asfor A S, Burman A, Crossley S, Hammond J A, Tchilian E, Charleston B, Bailey D, Tuthill T J, Graham S P, Duyvesteyn H M E, Malinauskas T, Huo J, Tree J A, Buttigieg K R, Owens R J, Carroll M W, Daniels R S, McCauley J W, Stuart D I, Huang K A, Howarth M, Townsend A R. A COVID-19 vaccine candidate using SpyCatcher multimerization of the SARS-CoV-2 spike protein receptor-binding domain induces potent neutralising antibody responses. Nat Commun. 2021 Jan. 22; 12(1):542. doi: 10.1038/s41467-020-20654-7. PMID: 33483491; PMCID: PMC7822889.
26. Wu F, Zhao S, Yu B, Chen Y M, Wang W, Song Z G, Hu Y, Tao Z W, Tian J H, Pei Y Y, Yuan M L, Zhang Y L, Dai F H, Liu Y, Wang Q M, Zheng J J, Xu L, Holmes E C, Zhang Y Z. A new coronavirus associated with human respiratory disease in China. Nature. 2020 March; 579 (7798):265-269. doi: 10.1038/s41586-020-2008-3. Epub 2020 Feb. 3. Erratum in: Nature. 2020 April; 580(7803): E7. PMID: 32015508; PMCID: PMC7094943.
27. Ou J, Zhou Z, Dai R, Zhao S, Wu X, Zhang J, Lan W, Cui L, Wu J, Seto D, Chodosh J, Zhang G, Zhang Q. V367F mutation in SARS-CoV-2 spike RBD emerging during the early transmission phase enhances viral infectivity through increased human ACE2 receptor binding affinity. bioRxiv 2020.03.15.991844; doi:https://doi.org/10.1101/2020.03.15.991844

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions disclosed herein should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods summarized above and set forth in further detail below describe certain actions taken by a practitioner; however, it should be understood that they can also include the instruction of those actions by another party. The methods summarized above and set forth in further detail below describe certain actions taken by a user (e.g., a professional in some instances); however, it should be understood that they can also include the instruction of those actions by another party. Thus, actions such as "delivering" include "instructing delivering." The ranges disclosed herein also encompass any and all overlap, sub-ranges, and combinations thereof. Language such as "up to," "at least," "greater than," "less than," "between," and the like includes the number recited. Numbers proceeded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A method of delivery of at least one component to a host, the method comprising:
   - introducing the at least one component to the host using a carrier, the carrier comprising a maximum size in at least one dimension in a nanometer or a micrometer range;
   - wherein the carrier comprises a core and a functionalized surface configured to increase a binding affinity of the carrier to target cells of the host;
   - wherein the carrier is configured to attach to target cells of the host; and
   - wherein the at least one component is configured to be delivered and released to target cells of the host using the carrier; and
   - delivering the at least one component to target cells of the host to assist with a prevention or a treatment of a disease or other adverse condition.

2. The method of claim 1, wherein target areas comprise at least one of a receptor, a target molecule, an amino acid and a nucleotide.

3. The method of claim 1, wherein the functionalized surface comprises at least one of a targeting moiety, an amino acid, a protein and a drug.

4. The method of claim 3, wherein the at least one of a targeting moiety, an amino acid, a protein and a drug is added to the carrier covalently, allosterically, via conjugation or via coating.

5. The method of claim 1, wherein the functionalized surface comprises an amino acid sequence of a receptor binding motif configured to bind to target cells.

6. The method of claim 1, wherein the at least one component comprises at least one of the following: an API, a drug, a protein, an amino acid, RNA, DNA and a molecule.

7. The method of claim 1, wherein the carrier is used for personalized treatment or personalized diagnostics.

8. The method of claim 1, wherein the carrier is configured to be delivered to the host using an inhalation device.

9. The method of claim 1, wherein the carrier is configured to be delivered to the host using an aerosol, a spray, a drop, a tablet, a cream, an ointment, an injection or an intravenous administration.

10. The method of claim 1, wherein the carrier is configured to deliver genetic information to assist the host with a prevention or a treatment of the disease or other adverse condition.

11. A method of delivery of at least one component to a host, the method comprising:
    - introducing at least one component within the host using a carrier, the carrier comprising a maximum size in at least one dimension in a nanometer or a micrometer range;
    - wherein the carrier comprises a core and a functionalized surface configured to increase a binding affinity of the carrier to target tissue of the host;
    - wherein the functionalized surface is configured to specifically bind to target tissue of the host; and
    - wherein the at least one component is configured to be delivered to target tissue of the host using the carrier; and
    - delivering the at least one component to target tissue of the host.

12. The method of claim 11, wherein the functionalized surface comprises at least one of a targeting moiety, an amino acid, a protein and a drug.

13. The method of claim 12, wherein the at least one of a targeting moiety, an amino acid, a protein and a drug is added to the carrier covalently, allosterically, via conjugation or via coating.

14. The method of claim 11, wherein the functionalized surface comprises an amino acid sequence of a receptor binding motif configured to bind to target cells.

15. The method of claim 11, wherein target tissue comprises at least one of a receptor, a target molecule, an amino acid and a nucleotide.

16. The method of claim 11, wherein the at least one component comprises at least one of the following: an API, a drug, a protein, an amino acid, RNA, DNA and a molecule.

17. The method of claim 11, wherein the carrier is used for personalized treatment or personalized diagnostics.

18. The method of claim 11, wherein the carrier is configured to be delivered to the host using an inhalation device.

19. The method of claim 11, wherein the carrier is configured to be delivered to the host using an aerosol, a spray, a drop, a tablet, a cream, an ointment, an injection or an intravenous administration.

* * * * *

SEQUENCE LISTING

```
Sequence total quantity: 7
SEQ ID NO: 1            moltype = AA  length = 6
FEATURE                 Location/Qualifiers
source                  1..6
                        mol_type = protein
                        organism = SARS-CoV-2
SEQUENCE: 1
YKYRYL                                                                6

SEQ ID NO: 2            moltype = AA  length = 6
FEATURE                 Location/Qualifiers
REGION                  1..6
                        note = Potential alternative synthetic hexapeptide variant
source                  1..6
                        mol_type = protein
                        organism = synthetic construct
SEQUENCE: 2
YKYNYI                                                                6

SEQ ID NO: 3            moltype = AA  length = 6
FEATURE                 Location/Qualifiers
REGION                  1..6
                        note = Potential alternative synthetic hexapeptide variant
source                  1..6
                        mol_type = protein
                        organism = synthetic construct
SEQUENCE: 3
YKYNYL                                                                6

SEQ ID NO: 4            moltype = AA  length = 28
FEATURE                 Location/Qualifiers
source                  1..28
                        mol_type = protein
                        organism = SARS-CoV-2
SEQUENCE: 4
KKKKVCEFQF CNDPFLGVYY HKNNKKKK                                        28

SEQ ID NO: 5            moltype = AA  length = 223
FEATURE                 Location/Qualifiers
source                  1..223
                        mol_type = protein
                        organism = SARS-CoV-2
SEQUENCE: 5
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                    223

SEQ ID NO: 6            moltype = AA  length = 1273
FEATURE                 Location/Qualifiers
source                  1..1273
                        mol_type = protein
                        organism = SARS-CoV-2
SEQUENCE: 6
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
```

-continued

```
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 7           moltype = AA  length = 272
FEATURE                Location/Qualifiers
REGION                 1..272
                       note = Synthetic
VARIANT                1..49
                       note = MISC_FEATURE - Different Expression Cassette -
                        Signal Sequence - Tag - Spacer; X is any amino acid
source                 1..272
                       mol_type = protein
                       organism = synthetic construct
SEQUENCE: 7
XXXXXXXXXX XXXXXXXXXX XXXXXXXXXX XXXXXXXXXX XXXXXXXXXR VQPTESIVRF  60
PNITNLCPFG EVFNATRFAS VYAWNRKRIS NCVADYSVLY NSASFSTFKC YGVSPTKLND  120
LCFTNVYADS FVIRGDEVRQ IAPGQTGKIA DYNYKLPDDF TGCVIAWNSN NLDSKVGGNY  180
NYLYRLFRKS NLKPFERDIS TEIYQAGSTP CNGVEGFNCY FPLQSYGFQP TNGVGYQPYR  240
VVVLSFELLH APATVCGPKK STNLVKNKCV NF                               272
```